US012630556B2

(12) United States Patent
Breitenbucher et al.

(10) Patent No.: US 12,630,556 B2
(45) Date of Patent: *May 19, 2026

(54) SUBSTITUTED [1,2,4]TRIAZOLO[1,5-A]PYRIMIDIN-7-YL COMPOUNDS AS PDE2 INHIBITORS

(71) Applicant: Dart Neuroscience, LLC, Dallas, TX (US)

(72) Inventors: James Breitenbucher, Escondido, CA (US); Graeme Freestone, San Diego, CA (US); Laurent Gomez, San Diego, CA (US); Robert Lemus, Escondido, CA (US); Kiev Ly, San Diego, CA (US); Margaret McCarrick, San Diego, CA (US); William Vernier, Vista, CA (US); Troy Vickers, San Diego, CA (US)

(73) Assignee: Dart NeuroScience LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/613,695

(22) Filed: Mar. 22, 2024

(65) Prior Publication Data

US 2025/0092047 A1 Mar. 20, 2025

Related U.S. Application Data

(63) Continuation of application No. 17/850,668, filed on Jun. 27, 2022, now abandoned, which is a continuation of application No. 17/455,405, filed on Nov. 17, 2021, now abandoned, which is a continuation of application No. 16/694,869, filed on Nov. 25, 2019, now Pat. No. 11,186,582, which is a continuation of application No. 15/905,672, filed on (Continued)

(51) Int. Cl.

| | |
|---|---|
| ***C07D 487/04*** | (2006.01) |
| ***A61K 31/519*** | (2006.01) |
| ***A61P 25/18*** | (2006.01) |
| ***A61P 25/22*** | (2006.01) |
| ***A61P 25/24*** | (2006.01) |
| ***A61P 25/28*** | (2006.01) |
| ***C07D 519/00*** | (2006.01) |
| ***C12Q 1/50*** | (2006.01) |

(52) U.S. Cl.

CPC .......... *C07D 487/04* (2013.01); *A61K 31/519* (2013.01); *A61P 25/18* (2018.01); *A61P 25/22* (2018.01); *A61P 25/24* (2018.01); *A61P 25/28* (2018.01); *C07D 519/00* (2013.01); *C12Q 1/50* (2013.01)

(58) Field of Classification Search

CPC .................................................... C07D 487/04

See application file for complete search history.

(56) References Cited

U.S. PATENT DOCUMENTS

| | | | |
|---|---|---|---|
| 4,447,438 | A | 5/1984 | Ledelec et al. |
| 4,938,949 | A | 7/1990 | Borch et al. |

(Continued)

FOREIGN PATENT DOCUMENTS

| | | | |
|---|---|---|---|
| CN | 103391941 | A | 11/2013 |
| RU | 2097382 | C1 | 11/1997 |

(Continued)

OTHER PUBLICATIONS

Preedy, M. E. (Cardiovascular Drugs and Therapy, 2020, 34, pp. 401-417).*

Sadek et al. (International Journal of Molecular Sciences, 2020, 21, pp. 1-29).*

Chan et al. (Circulation Research, 2017, 13-16).*

CAS Database Registry Nos. 2012:1381754-80-8; 1381750-79-3; 1381747-28-9; 1381743-97-0; "Methanone, . . . "; Entered Jul. 5, 2012; 2 pages.

CAS Database Registry Nos. 2010:1240215-31-9; 1240208-98-3; 1240201-99-3; 1240195-90-7; 1240195-65-6; 1340181-24-1; 1240169-61-2; 1240166-99-7; 1240166-22-6; 1240153-22-3; 1240128-18-0; 1240115-42-7; 1240102-95-7; 1240093-87-1; 1240091-60-4; "Methanone, . . . "; Entered Sep. 7/8, 2010; 8 pages.

(Continued)

*Primary Examiner* — Susanna Moore

(74) *Attorney, Agent, or Firm* — Knobbe, Martens, Olson & Bear, LLP

(57) ABSTRACT

The invention provides a chemical entity of Formula (I):

(I)

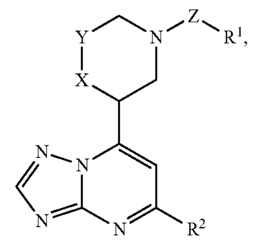

wherein $R^1$, $R^2$, X, Y and Z have any of the values described herein, and compositions comprising such chemical entities; methods of making them; and their use in a wide range of methods as disclosed herein, including metabolic and reaction kinetic studies; detection and imaging techniques; radioactive treatments; modulating and treating disorders mediated by PDE2 activity; treating neurological disorders, CNS disorders, dementia, neurodegenerative diseases, and trauma-dependent losses of function; treating stroke, including cognitive and motor deficits during stroke rehabilitation; facilitating neuroprotection and neurorecovery; enhancing the efficiency of cognitive and motor training, including animal skill training protocols; and treating peripheral disorders, including hematological, cardiovascular, gastroenterological, and dermatological disorders.

9 Claims, No Drawings

Related U.S. Application Data

Feb. 26, 2018, now Pat. No. 10,501,465, which is a continuation of application No. 15/306,069, filed as application No. PCT/US2015/027102 on Apr. 22, 2015, now Pat. No. 9,932,345.

(60) Provisional application No. 61/983,387, filed on Apr. 23, 2014.

(56) References Cited

U.S. PATENT DOCUMENTS

| | | | |
|---|---|---|---|
| 5,478,825 | A | 12/1995 | Reiter et al. |
| 6,573,263 | B2 | 6/2003 | Niewöhner et al. |
| 6,998,402 | B2 | 2/2006 | Niewöhner et al. |
| 7,410,963 | B2 | 8/2008 | Abarghaz et al. |
| 7,671,050 | B2 | 3/2010 | Schmidt et al. |
| 7,851,472 | B2 | 12/2010 | Schmidt et al. |
| 7,868,015 | B2 | 1/2011 | Tully et al. |
| 7,947,731 | B2 | 5/2011 | Tully et al. |
| 8,106,047 | B2 | 1/2012 | Schmidt et al. |
| 8,598,155 | B2 | 12/2013 | Helal et al. |
| 9,932,345 | B2 | 4/2018 | Breitenbucher et al. |
| 10,239,882 | B2 | 3/2019 | Allan et al. |
| 10,501,465 | B2 | 12/2019 | Breitenbucher et al. |
| 11,186,582 | B2 | 11/2021 | Breitenbucher et al. |
| 2007/0112006 | A1 | 5/2007 | Schiemann et al. |
| 2008/0188525 | A1 | 8/2008 | Hallam et al. |
| 2009/0053140 | A1 | 2/2009 | Scott et al. |
| 2011/0082137 | A1 | 4/2011 | Giovannini et al. |
| 2012/0214791 | A1 | 8/2012 | Helal et al. |
| 2016/0159808 | A1 | 6/2016 | Kawasaki et al. |

FOREIGN PATENT DOCUMENTS

| | | |
|---|---|---|
| WO | WO 2002/064211 | 8/2002 |
| WO | WO 2004/044234 | 5/2004 |
| WO | WO 2004/108136 | 12/2004 |
| WO | WO 2005/041957 | 5/2005 |
| WO | WO 2005/054246 | 6/2005 |
| WO | WO 2008/117943 | 10/2008 |
| WO | WO 2009/152825 | 12/2009 |
| WO | WO 2010/054253 | 5/2010 |
| WO | WO 2010/054260 | 5/2010 |
| WO | WO 2011/011312 | 1/2011 |
| WO | WO 2012/080729 | 6/2012 |
| WO | WO 2012/104293 | 8/2012 |
| WO | WO 2012/114222 | 8/2012 |
| WO | WO 2012/168817 | 12/2012 |
| WO | WO 2013/000924 | 1/2013 |
| WO | WO 2013/034755 | 3/2013 |
| WO | WO 2013/034758 | 3/2013 |
| WO | WO 2013/034761 | 3/2013 |
| WO | WO 2016/073424 | 5/2016 |
| WO | WO 2015/012328 | 3/2017 |

OTHER PUBLICATIONS

CAS Database Registry Nos. 2010:1214610-92-0; 1214601-85-0; 1214591-56-6; 1214486-88-0; 1214427-36-7; "Methanone, . . . "; Entered Mar. 25, 2010; 3 pages.

CAS Database Registry Nos. 2007:958707-04-5; 958706-09-7; 958706-04-2; 958618-14-9; 958596-27-5; 958586-25-9; 958585-88-1; 958583-82-9; 958583-78-3; "Methanone structures"; Entered Dec. 18/19, 2007; 6 pages.

Chan et al., Phosphodiesterase 2 as a therapeutic target for heart failure: Is Upregulation an option? Circ Res. Jan. 6, 2017;120(1): 13-16.

Preedy M.E.J., Cardiac Cyclic Nucleotide Phosphodiesterases: Roles and therapeutic potential in heart failure. Cardio Drugs Ther., Jun. 2020;34:401-417.

Sadek et al., Therapeutic implications for PDE2 and cGMP/cAMP mediated crosstalk in cardiovascular diseases. Int J Mol Sciences. Oct. 10, 2020;21(20):7462 in 29 pages.

Stella et al., Prodrugs: Some thoughts and current issues. J Pharm Sci (2010), 99(12):4755-4765.

International Search Report and Written Opinion dated Sep. 14, 2015 for International Application No. PCT/US2015/027102, filed Apr. 22, 2015.

* cited by examiner

SUBSTITUTED [1,2,4]TRIAZOLO[1,5-A]PYRIMIDIN-7-YL COMPOUNDS AS PDE2 INHIBITORS

CROSS REFERENCE TO RELATED APPLICATIONS

Any and all priority claims identified in the Application Data Sheet, or any correction thereto, are hereby incorporated by reference under 37 CFR 1.57. For example, this application is a continuation of U.S. application Ser. No. 16/694,869, filed on Nov. 25, 2019, which is a continuation of U.S. application Ser. No. 15/905,672, filed on Feb. 26, 2018, which is a continuation of U.S. application Ser. No. 15/306,069 having a 371(c)(1) date of Oct. 21, 2016 which is a U.S. National Phase of International Application No. PCT/US2015/027102, filed on Apr. 22, 2015 and published on Oct. 29, 2015 as WO 2015/164508, which claims the benefit of U.S. Provisional Application No. 61/983,387, filed on Apr. 23, 2014, which is incorporated herein by reference in its entirety.

BACKGROUND

Field

The present invention relates to certain substituted [1,2,4]triazolo[1,5-a]pyrimidinyl compounds and derivatives of such compounds; pharmaceutical compositions containing them; methods of making them; and their use in various methods, including the inhibition of PDE2, and the treatment of one or more disorders, including neurological disorders, psychotic disorders, dementia, and other conditions and diseases involving PDE2.

Description of the Related Technology

The mammalian phosphodiesterases (PDEs) are a group of closely related enzymes divided into 11 families (PDE1-11) based on substrate specificity, inhibitor sensitivity and more recently, on sequence homology. The 11 families are coded by 21 genes, providing several of the families with multiple members. All mammalian PDEs share a conserved catalytic domain located in the COOH-terminal portion of the protein. In GAF-containing PDEs, one or both GAFs can provide dimerization contacts. In addition, one of the GAFs in each of these proteins provides for allosteric cGMP binding (PDE2, PDE5, PDE6, PDE11), allosteric cAMP binding (PDE10), and regulation of catalytic site functions (PDE2, PDE5, PDE6). The other families of PDEs have unique complements of various subdomains (UCR, NHR, PAS, membrane association) that contribute to regulation of activity. PDEs 1, 2, 3, and 4 are expressed in many tissues, whereas others are more restricted. The homology between families, suggests that it may be possible to develop selective inhibitors for each of these subtypes. Numerous studies have highlighted a role for PDEs generally, in modulating intracellular signaling pathways that regulate many physiological processes, including those underling neural plasticity, cognition, and memory (Menniti et al., 2006, *Nat Rev Drug Discov.* 5, 660-670). In particular, PDEs play an important role in intracellular signal transduction pathways involving the second messengers, cAMP and cGMP (phosphodiesterase 2 and 10 inactivate both cAMP and cGMP. These cyclic nucleotides function as ubiquitous intracellular signaling molecules in all mammalian cells. PDE enzymes hydrolyze cAMP and cGMP by breaking phosphodiester bonds to form the corresponding monophosphates (Bender and Beavo, *Pharmacol. Rev.*, 2006, 58(3), 488-520). PDE activities are modulated in coordination with adenylyl cyclase (AC) and guanylyl cyclase (GC) activities through direct effectors and feedback pathways, thereby maintaining cAMP and cGMP levels within optimum ranges for responsiveness to signals. The ability of extracellular signals to modulate the intracellular concentration of cyclic nucleotides allows cells to respond to external stimuli across the boundary of the cell membrane.

The cyclic nucleotide signaling cascades have been adapted to respond to a host of transduction systems including G-protein coupled receptors (GPCRs) and voltage and ligand gated ion channels. Cyclic nucleotides transmit their signal in the cell through a variant of tertiary elements. The best described of these are cAMP dependent protein kinase (PKA) and cGMP dependent protein kinase (PKG). The binding of the cyclic nucleotide to each enzyme enables the phosphorylation of downstream enzymes and proteins functioning as effectors or additional elements in the signaling cascade. Of particular importance to memory formation is cAMP activation of PKA which phosphorylates cAMP response element-binding protein (CREB). pCREB is an activated transcription factor, which binds to specific DNA loci and initiates transcription of multiple genes involved in neuronal plasticity. Both in vitro and in vivo studies have associated alterations in cyclic nucleotide concentrations with biochemical and physiological process linked to cognitive function (Kelly and Brandon, *Progress in Brain Research,* 2009, 179, 67-73; Schmidt, *Current Topics in Medicinal Chemistry,* 2010, 10, 222-230). Signal intensity and the levels of coincident activity at a synapse are established variables that can result in potentiation of transmission at a particular synapse. Long term potentiation (LTP) is the best described of these processes and is known to be modulated by both the cAMP and cGMP signaling cascades.

PDE2 inhibitors have been shown to enhance long term potentiation of synaptic transmission and to improve memory acquisition and consolidation in the object recognition and in the social recognition tests in rats. PDE2 inhibitors have also been shown to display activity in forced swim test and light/dark box models; and to show anxiolytic-like effects in elevated plus-maze, hole-board and open-field tests; and to prevent stress-induced changes in apoptosis and behaviour (Boess et al., *Neuropharmacology,* 2004, 47 (7) 1081-92; Masood et al. *J. Pharmacol. Exp. Ther.* 2009, 331, 690-699). Additionally, it is reported that a selective PDE2 inhibitor is efficacious in the novel object recognition test, the social recognition test and the T-maze, an animal model of working memory (Rutten et al., *Eur. J. Neurosci.,* 2007, 558(1-3), 107-112). Moreover, PDE2 inhibitors appear beneficial in reducing oxidative stress-induced anxiety, supporting their use in treating anxiety in psychiatric disorders and neurodegenerative disorders that oxidative stress, such as Alzheimer's disease, Parkinson's disease and multiple sclerosis. (Masood et al., *J. Pharmacol. Exp. Ther.,* 2008, 326, 369-379).

Such observations highlight the interest in inhibiting PDEs, including PDE2, as a therapeutic target for numerous disorders and in cognitive enhancement. Various small-molecule PDE2 enzyme inhibitors have been reported e.g., substituted triazolopyrazines (H. Lundbeck A/S, Intl. Pat. Appl. Publ. WO2013/034755, Mar. 14, 2013 and Intl. Pat. Appl. Publ. WO2013/034758, Mar. 14, 2013), pyridine compounds (H. Lundbeck A/S, Intl. Pat. Appl. Publ. WO2013/034761, Mar. 14, 2013), 1-aryl-4-methyl-[1,2,4]triazolo[4,3-a]quinoxalines (Janssen Pharmaceutica NV, Intl. Pat. Appl. Publ. WO2013/000924, Jan. 3, 2013), pyrazolopyrimidines (Pfizer Inc., Intl. Pat. Appl. Publ. WO2012/168817, Dec. 13, 2012), imidazo[5,1-f][1,2,4]triazines (Pfizer Inc., U.S. Pat. No. 8,598,155, Aug. 23, 2012), (1,2,4)triazolo[4,3-a]quinoxalines (Boehringer Ingelheim International GmbH, Intl. Pat. Appl. Publ. WO2012/104293, Aug. 9, 2012), quinolinones (Merck Sharp & Dohme Corp., Intl. Pat. Appl. Publ. WO2011/011312, Jan. 27, 2011), imidazo[5,1-c][1,2,4]benzotriazines (Biotie Therapies GmbH, Intl. Pat. Appl. Publ. WO2010/054260, May 14, 2010), triazines (Biotie Therapies GmbH, Intl. Pat. Appl. Publ. WO2010/054253, May 14, 2010), triazolophthalazines (Altana Pharma AG, U.S. Pat. No. 8,106,047, Jul. 13, 2006; U.S. Pat. No. 7,671,050, Jul. 13, 2006; U.S. Pat. No. 7,851,472, Mar. 9, 2006), benzo[1,4]diazepin-2-ones (Neuro3d, U.S. Pat. No. 7,410,963, Jun. 29, 2005), oxindoles (Pfizer Products Inc., Intl. Pat. Appl. Publ. WO2005/041957, May 12, 2005), and imidazotriazinones (Bayer AG, U.S. Pat. No. 6,573,263, Jun. 27, 2002 and EP Pat. 1,363, 912, Sep. 5, 2002).

However, there remains a need for potent PDE2 inhibitors with desirable pharmaceutical properties, such as potency, exposure, selectivity, and side effect profile. The present invention addresses these and other needs in the art by disclosing substituted [1,2,4]triazolo[1,5-a]pyrimidin-7-yl compounds as potent and well-tolerated PDE2 inhibitors.

SUMMARY

Some embodiments provide a chemical entity of Formula (I):

(I)

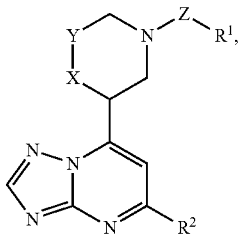

wherein

X is —$CH_2$— or —O—;

Y is —$CH_2$— or —$CF_2$—;

Z is —$CH_2$— or —C(═O)—;

$R^1$ is a member selected from the group consisting of:

(a) phenyl unsubstituted or substituted with one, two, three four or five $R^a$ members;

where $R^a$ is each independently selected from the group consisting of: —H, -halo, —$C_{1-6}$alkyl, —$C_{1-6}$haloalkyl, —$C_{1-6}$alkoxy, —$C_{1-6}$haloalkoxy, —CN, —N($C_{1-6}$alkyl)$_2$, —$SF_5$, —$C_{3-6}$cycloalkyl, -pyrrolidine, -morpholine, -piperidine, -pyrazole, -furan, -imidazole, -thiophene, -thiazole, -pyridine, and -phenyl, wherein phenyl is unsubstituted or substituted with one, two, three, four or five $R^b$ members;

where $R^b$ is each independently selected from the group consisting of: —H, —Cl and —F; or optionally two adjacent $R^a$ members come together to form a ring, optionally unsubstituted or substituted with one or more members independently selected from: —H, -halo, —$C_{1-6}$alkyl or —$C_{1-6}$alkoxy;

(b) monocyclic or bicyclic heteroaromatic ring each unsubstituted or substituted with one, two, three or four $R^c$ members;

where $R^c$ is each independently selected from the group consisting of: —H, -halo, —$C_{1-6}$alkyl, —$C_{1-4}$haloalkyl, —$C_{1-4}$alkoxy, —N($C_{1-6}$alkyl)$_2$, —($C_{1-6}$alkyl) cycloalkyl, -cyclopropyl, -morpholine, -pyrrolidine, -4-chlorophenoxy, and -phenyl optionally unsubstituted or substituted with -halo, —$C_{1-6}$alkyl or —$C_{1-4}$alkoxy; and (c) heterocycloalkyl ring optionally unsubstituted or substituted with one or more —H, —F, or —$OCH_3$; and $R^2$ is —$C_{1-6}$alkyl optionally substituted with five fluoro members.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I). In a specific aspect, the chemical entity is a compound of Formula (I), or a pharmaceutically acceptable salt thereof.

In certain embodiments, the compound of Formula (I) is a compound selected from those species described or exemplified in the detailed description below.

Some embodiments provide pharmaceutical compositions for treating a disease, disorder, or medical condition mediated by PDE2 activity, comprising an effective amount of at least one chemical entity selected from compounds of Formula (1), pharmaceutically acceptable salts of compounds of Formula (I), pharmaceutically acceptable prodrugs of compounds of Formula (I), and pharmaceutically active metabolites of Formula (I).

Pharmaceutical compositions according to the embodiments may further comprise one or more pharmaceutically acceptable excipients.

Some embodiments provide a method of treating a subject suffering from or diagnosed with a disease, disorder, or medical condition mediated by PDE2 activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

Chemical entities of compounds of Formula (I) are useful in wide range of methods. Isotopically-labeled compounds and prodrugs can be used in metabolic and reaction kinetic studies, detection and imaging techniques, and radioactive treatments. In certain embodiments, the chemical entities can be used to inhibit PDE2, in particular; to treat a disorder mediated by PDE2, in particular; to enhance neuronal plasticity; to treat neurological disorders, including neurodegenerative disorders, cognitive disorders, and cognitive deficits associated with central nervous system (CNS) disorders; to facilitate neuroprotection and neurorecovery; and to treat peripheral disorders, including infectious, hematological, cardiovascular, gastroenterological, and dermatological diseases. In certain embodiments, the chemical entities are also useful as augmenting agents to enhance the efficiency of cognitive and motor training, including animal skill training protocols. The embodiments may be further directed to the general and specific embodiments defined, respectively, and by the independent and dependent claims appended hereto, which are incorporated by reference herein.

DETAILED DESCRIPTION

The invention may be more fully appreciated by reference to the following description, including the examples. Unless otherwise defined, all technical and scientific terms used herein have the same meaning as commonly understood by one of ordinary skill in the art.

Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

ABBREVIATIONS

The specification includes numerous abbreviations, whose meanings are listed in the following Table:

TABLE 1

| Abbreviation | Definition |
|---|---|
| ACN | Acetonitrile |
| AIBN | Azobisisobutyronitrile |
| BINAP | 2,2'-Bis(diphenylphosphino)-1,1'-binaphthyl |
| BOC or $Boc_2O$ | tert-Butoxycarbonyl or Di-tert-butyl dicarbonate |
| CELITE ® | Diatomaceous earth |
| CDI | 1,1'-Carbonyldiimidazole |
| m-CPBA | meta-Chloroperoxybenzoic acid |
| DAST | Diethylaminosulfur trifluoride |
| DBU | 1,8-Diazabicyclo[5.4.0]undec-7-ene |
| DCC | Dicyclohexylcarbodiimide |
| DCM | Dichloromethane |
| Deoxo-Fluor ® | Bis(2-methoxyethyl)aminosulfur trifluoride |
| DIPEA | N,N-Ethyl-diisopropylamine or N,N-Diisopropyl-ethyl amine |
| DMA | N,N-Dimethylacetamide |
| DMAP | 4-Dimethylamino pyridine |
| DMF | N,N-Dimethylformamide |
| DMSO | Dimethylsulfoxide |
| DPEphos | Bis[(2-diphenylphosphino)phenyl] ether |
| dppf | 1,1'-Bis(diphenylphosphino)ferrocene |
| EDCI | N-(3-Dimethylaminopropyl)-N'-ethylcarbodiimide hydrochloride |
| EtOAc, or EA | Ethyl Acetate |
| EtOH | Ethanol |
| IPA | Isopropyl alcohol |
| HATU | (1-[Bis(dimethylamino)methylene]-1H-1,2,3-triazolo[4,5-b]pyridinium 3-oxid hexafluorophosphate) |
| HOAc or AcOH | Acetic Acid |
| HOAT | 1-Hydroxy-7-azabenzotriazole |
| HOBt | 1-Hydroxybenzotriazole |
| HPLC | High-performance liquid chromatography |
| LAH | Lithium aluminum hydride |
| LiHMDS, LHMDS | Lithium bis(trimethylsilyl)amide |
| LDA | Lithium diisopropylamide |
| LCMS, LC/MS | Liquid chromatography-mass spectrometry |
| MeOH | Methanol |
| MsCl | Methanesulfonyl chloride |
| NBS | N-Bromosuccinimide |
| NMP | 1-Methyl-2-pyrrolidinone |
| OTs | p-Toluenesulfonic acid |
| Pd/C | Palladium on activated carbon |
| $Pd_2(dba)_3$ | Tris(dibenzylideneacetone)dipalladium (0) |
| $PdCl_2(dppf)-Cl_2$ adduct | [1'1'-Bis(diphenylphosphino)ferrocene]palladium(ll) dichloride dichloromethane adduct |
| $Pd(PPh_3)_4$ | Palladium-tetrakis(triphenylphosphine) |
| PE | Petroleum ether |
| PyBroP | Bromotripyrrolidinophosphonium hexafluorophosphate |
| Selectfluor ® | 1-Chloromethyl-4-fluoro-1,4-diazoniabicyclo[2.2.2]octane |
| S-Phos | 2-Dicyclohexylphosphino-2',6'-dimethoxybiphenyl |
| TEA, $Et_3N$ | Triethylamine |
| TFA | Trifluoroacetic acid |
| THF | Tetrahydrofuran |
| TMEDA | Tetramethylethylenediamine |
| Xantphos | 4,5-Bis(diphenylphosphino)-9,9-dimethylxanthene |
| XtalFluor ® | Diethylaminodifluorosulfinium tetrafluoroborate |

Terms and Definitions

The use of subheadings such as "General," "Chemistry," "Compositions," "Formulations," etc., in this section, as well as in other sections of this application, are solely for convenience of reference and not intended to be limiting.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated To provide a more concise description, some of the quantitative expressions given herein are not qualified with the term "about." It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

Although items, elements or components of the invention may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof; adjectives such as "conventional," "traditional," "normal," "criterion," "known," and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to," or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemistry

The term "alkyl" refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, "▬"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups may be optionally substituted with one or more substituents including, but not limited to, hydroxyl, alkoxy, thioalkoxy, amino, and aminoalkyl.

The term "alkenyl" refers to optionally substituted unsaturated aliphatic moieties having at least one carbon-carbon double bond and including E and Z isomers of said alkenyl moiety. Examples of alkenyl radicals include ethenyl, propenyl, butenyl, 1,4-butadienyl, cyclopentenyl, cyclohexenyl and the like.

The term "alkynyl" refers to an optionally substituted unsaturated aliphatic moieties having at least one carbon-carbon triple bond and includes straight and branched chain alkynyl groups. Examples of alkynyl radicals include ethynyl, propynyl, butynyl and the like.

The term "haloalkyl" refers to a straight- or branched-chain alkyl group having from 1 to 12 carbon atoms in the chain optionally substituting hydrogens with halogens. Examples of haloalkyl groups include, but are not limited to, $-CF_3$, $-CHF_2$, $-CH_2F$, $-CH_2CF_3$, $-CH_2CHF_2$, $-CH_2CH_2F$, $-CH_2CH_2C_1$, $-CH_2CF_2CF_3$ and other groups that in light of the ordinary skill in the art and the teachings provided herein, would be considered equivalent to any one of the foregoing examples.

The term "alkoxy" includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. "Aminoalkyl," "thioalkyl," and "sulfonylalkyl" are analogous to alkoxy, replacing the terminal oxygen atom of alkoxy with, respectively, NH (or NR), S, and $SO_2$.

The term "haloalkoxy" refer to alkoxy groups optionally substituting hydrogens with halogens. Examples of haloalkoxy groups include, but are not limited to, $-OCF_3$, $-OCH_2CF_3$, $-OCH_2CHF_2$, $-OCH_2CH_2Cl$, $-OCH_2CF_2CF_3$, $-OCH(CH_3)CHF_2$ and other groups that in light of the ordinary skill in the art and the teachings provided herein, would be considered equivalent to any one of the foregoing examples.

The term "amino" refers to the $-NH_2$ group.

The term "alkylamino" refers to the —NRR' group, where R and R' are independently selected from hydrogen (however, R and R' cannot both be hydrogen), alkyl, and aryl groups; or R and R', taken together, can form a cyclic ring system. Examples of amino groups include, but are not limited to, $-NH(CH_3)$, $-N(CH_3)_2$, $-NPhenyl(CH_3)$, —NHPhenyl, $-N(CH_2CH_3)(CH_3)$, and the like.

The term "cyano" refers to the group —CN.

The term "aryl" refers to a monocyclic, or fused or spiro polycyclic, aromatic carbocycle (ring structure having ring atoms that are all carbon), having from 3 to 12 ring atoms per ring (carbon atoms in aryl groups are sp2 hybridized). Illustrative examples of aryl groups include the following moieties:

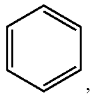,
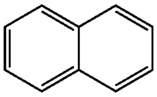,
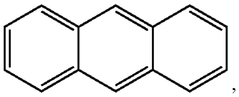,
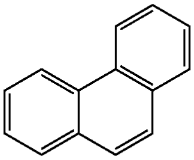, and the like.

The term "aryloxy" refers to a group having the formula, —O—R, wherein R is an aryl group.

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

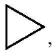,
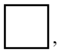,
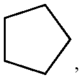,
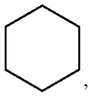,
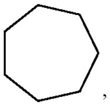,
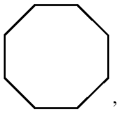,
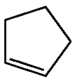,
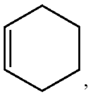,
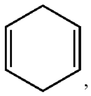,
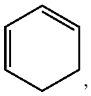,
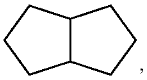,
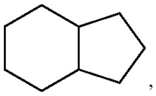,
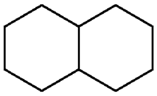,
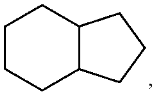,
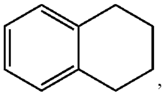,
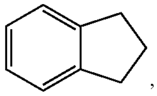,
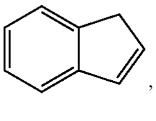,
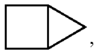,
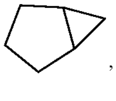,
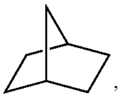, -continued

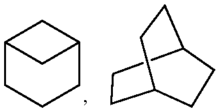

and

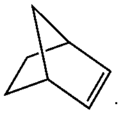

A “heterocycloalkyl” refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

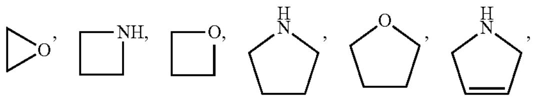

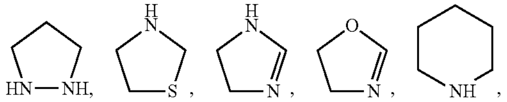

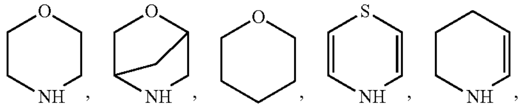

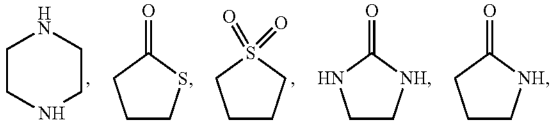

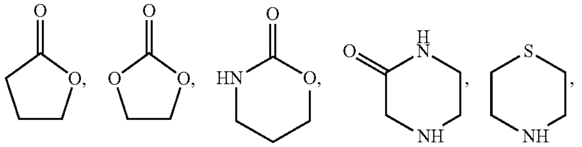

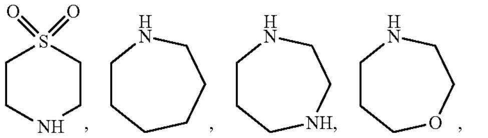

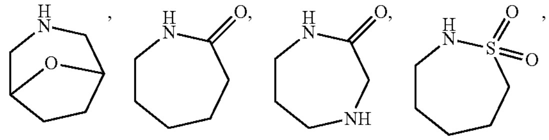

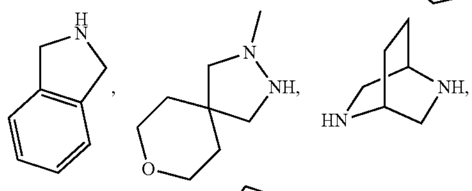

and

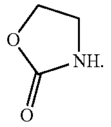

The term “heteroaryl” refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

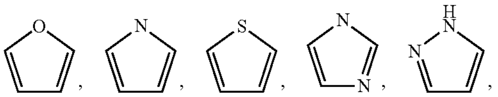

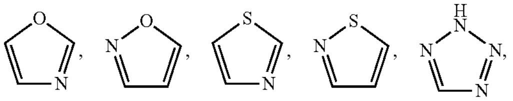

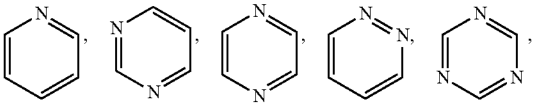

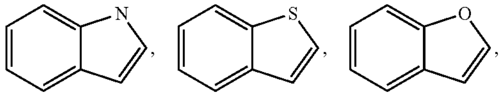

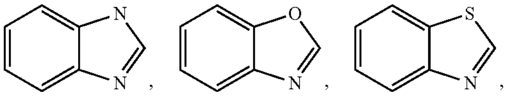

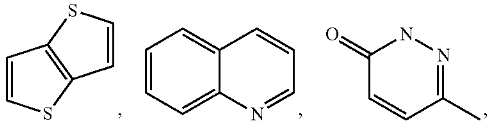

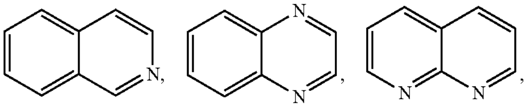

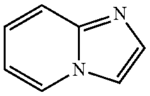

and

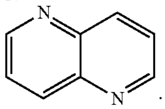

Those skilled in the art will recognize that the species of cycloalkyl, heterocycloalkyl, and heteroaryl groups listed or illustrated above are not exhaustive, and that additional species within the scope of these defined terms may also be selected.

The term “halogen” represents chlorine, fluorine, bromine or iodine. The term “halo” represents chloro, fluoro, bromo or iodo.

The term “heteroatom” used herein refers to, for example, O (oxygen), S (sulfur), or N (nitrogen).

The term “substituted” means that the specified group or moiety bears one or more substituents. Where the term “substituted” is used to describe a structural system, unless specified otherwise, the substitution is meant to occur at any valency-allowed position on the system. The term “unsubstituted” means that the specified group bears no substituents.

Formulas

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols and are used as meaning the same spacial arrangement in chemical structures shown herein. Analogously, the symbols and are used as meaning the same spacial arrangement in chemical structures shown herein.

Compounds

As used herein, a "compound" refers to any one of: (a) the actually recited form of such compound; and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

As used herein, the term "chemical entity" collectively refers to a compound, along with the derivatives of the compound, including salts, chelates, solvates, conformers, non-covalent complexes, metabolites, and prodrugs.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I).

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $+H_3NCH_2COO—$. Zwitterions, zwitterionic compounds, inner salts, and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Isotopes may be present in the compounds described. Each chemical element present in a compound either specifically or generically described herein may include any isotope of said element. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}p$, $^{35}S$, $^{18}F$, $^{36}Cl$, and $^{125}I$, respectively.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$ and "$S^2_{example}$ is one of $S_3$ and $S_4$ is accordingly used herein for the sake of brevity but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^a$, $R^b$, $R^c$, $R^d$, X, Y, and Z and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$ and $S_3$, the listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$ and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^a$, $R^b$, $R^c$, $R^d$, X, Y, and Z and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with the total number N of carbon members in the chain that satisfies $n \leq N \leq m$, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)).

A "pharmaceutically acceptable prodrug" is a prodrug that is preferably non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

A "metabolite" means a pharmacologically active product of metabolism in the body of a compound of Formula (I) or salt thereof. Preferably, the metabolite is in an isolated form outside the body.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I) and a pharmaceutically acceptable excipient.

The term "pharmaceutically acceptable," as used in connection with compositions of the invention, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in *Remington: The Science and Practice of Pharmacy,* 21st Ed., Lippincott Williams & Wilkins (2005).

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, 21st Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

Methods and Uses

As used herein, the term "disorder" is used interchangeably with "disease" or "condition." For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound according to the invention is administered to a subject (e.g., a mammal). An "effective amount" also means an amount or dose of a compound or composition effective to modulate activity of PDE2 or an associated signaling pathway.

The "effective amount" will vary, depending on the compound, the disease, the type of treatment desired, and its severity, and age, weight, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing," or "enhancement" is meant the ability to potentiate, increase, improve, or make greater or better, relative to normal, a biochemical or physiological action or effect. For example, enhancing long term memory formation refers to the ability to potentiate or increase long term memory formation in an animal relative to (or "compared to") the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to the embodiments of the present invention, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Compounds

The present invention provides certain substituted [1,2,4]triazolo[1,5-a]pyrimidin-7-yl derivatives, which are useful, for example, as inhibitors of PDE2 enzymatic activity. They are distinct from triazolo[1,5-a]pyrimidines (Vernalis Cambridge Limited, Int. Pat. App. WO2004/108136, Dec. 16, 2004), and methylsulfonyl compounds: Chemical Abstracts Service Registry Number 1381754-80-8, 1381750-79-3, 1381747-28-9, 1381743-97-0, 1240215-31-9, 1240208-98-3, 1240201-99-3, 1240195-90-7, 1240195-65-6, 1240181-24-1, 1240169-61-2, 1240166-99-7, 1240166-22-6, 1240153-22-3, 1240128-18-0, 1240115-42-7, 1240102-95-7, 1240093-87-1, 1240091-60-4, 1214610-92-0, 1214601-85-0, 1214591-56-6, 1214486-88-0, 1214427-36-7, 958707-04-5, 958706-09-7, 958706-04-2, 958618-14-9, 958596-27-5, 958586-25-9, 958585-88-1, 958583-82-9, 958583-78-3.

In certain embodiments, of Formula (I), where X is $—O—$, and Y is $—CH_2—$.

In some embodiments, where X is $—CH_2—$, Y is $—CF_2—$.

In some embodiments, where X is $—CH_2—$, Y is $—CH_2—$.

In some embodiments Z is $—CH_2—$.

In some embodiments Z is $—C(=O)—$.

In some embodiments $R^2$ is $—CH_3$.

In some embodiments $R^1$ is phenyl unsubstituted or substituted with one, two, three, four, or five $R^a$ members.

In some embodiments $R^a$ is a member independently selected from the group consisting of: H, halo, $—C_{1-6}$alkyl, $—C_{1-6}$haloalkyl, $—C_{1-6}$alkoxy, $—C_{1-6}$haloalkoxy, —CN, $—N(C_{1-6}alkyl)_2$, and $—C_{3-6}$cycloalkyl.

In some embodiments $R^a$ is a member independently selected from: —H, —Cl, —Br, —F, —I, —$C_{1-4}$alkyl, —$C_{1-4}$haloalkyl, —$C_{1-4}$alkoxy, —$C_{1-4}$haloalkoxy, —CN, —$N(CH_3)_2$, or -cyclopropyl.

In some embodiments $R^a$ is a member independently selected from: -pyrrolidine, -morpholine, -piperidine, -pyrazole, -furan, -imidazole, -thiophene, -thiazole, -pyridine, or phenyl substituted with one or more —H, —Cl or —F.

In some embodiments two adjacent $R^a$ members optionally come together to form a cyclopentyl, cyclohexyl, phenyl, pyridine, furan, tetrahydrofuran, tetrahydropyran, thiazole, thiophene, pyrrole, indole, 1,4-dioane, or 1,3-dioxolane ring, each optionally unsubstituted or substituted with one or more members independently selected from —H, -halo, —$C_{1-6}$alkyl or —$C_{1-6}$alkoxy.

In certain embodiments of Formula (I), $R^1$ is naphthalen-1-yl, naphthalen-2-yl, 6-methoxynaphthalen-2-yl, 1-methoxynaphthalen-2-yl, 3-methoxynaphthalen-2-yl, 3-methoxynaphthalene-2-yl, 6-fluoronaphthalen-2-yl, 5,6,7,8-tetrahydronaphthalen-2-yl, 5,6,7,8-tetrahydronaphthalene-2-yl, 2,3-dihydro-1H-inden-5-yl, 2,3-dihydro-1H-inden-5-yl, 2H-1,3-benzodioxol-4-yl, 2H-1,3-benzodioxol-5-yl, 2,3-dihydro-1,4-benzodioxin-6-yl, 2,2-difluoro-2H-1,3-benzodioxol-5-yl, 1-ethyl-1H-indole, indole, isoquinoline, 2,3-dihydro-1-benzofuran-5-yl, 2,3-dihydro-1-benzofuran-6-yl, 3,4-dihydro-2H-1-benzopyran-6-yl, 1-benzofuran, 1-benzofuran-5-yl, 1,3-benzothiazol-6-yl, or 1-benzothiophen-5-yl.

In certain embodiments of Formula (I), $R^1$ is 1-(1,3-thiazol-2-yl)-1H-pyrrol-2-yl, 1-(2-chlorophenyl)-1H-pyrazol-3-yl, 1-(2-fluorophenyl)-1H-pyrazol-3-yl, 1-(3-bromophenyl)-1H-pyrazol-3-yl, 1-(3-fluorophenyl)-1H-pyrazol-3-yl, 1-(4-chlorophenyl)-5-methyl-1H-pyrazol-3-yl, 1-(4-fluorophenyl)-5-methyl-1H-pyrazol-3-yl, 1-(4-isopropylphenyl)-5-methyl-1H-pyrazol-3-yl, 1,3-benzothiazole, 1,3-dimethyl-1H-pyrazol-5-yl, 1,5-dimethyl-1H-pyrazol-3-yl, 1,5-dimethyl-1H-pyrazol-4-yl, 1,6-naphthyridin-2-yl, 1-benzofuran-2-yl, 1-benzofuran-3-yl, 1-benzothiophen-2-yl, 1-benzothiophen-3-yl, 1-ethyl-1H-pyrazol-5-yl, 1H-indol-3-yl, 1-isopropyl-1H-pyrazol-4-yl, 1-methyl-1H-benzo[d]imidazol-2-yl, 1-methyl-1H-indazol-3-yl, 1-methyl-1H-indol-2-yl, 1-methyl-1H-indol-3-yl, 1-methyl-3-(propan-2-yl)-1H-pyrazole, 1-methyl-3-phenyl-1H-pyrazol-5-yl, 1-methyl-5-phenyl-1H-pyrazol-3-yl, 1-phenyl-1H-pyrazol-4-yl, 1-phenyl-1H-pyrazol-4-yl, 2-(3-fluorophenyl)-1,3-thiazol-5-yl]methyl, 2-(3-methoxyphenyl)-1,3-thiazol-5-yl, 2-(4-chlorophenoxy)pyridin-3-yl, 2-(4-fluorophenyl)-1,3-thiazol-5-yl, 2-(pyrrolidin-1-yl)-1,3-thiazol-5-yl, 2,4-dimethylthiazol-5-yl, 2,6-dimethylpyridin-3-yl, 2-bromo-1,3-thiazol-4-yl, 2-bromo-1,3-thiazol-5-yl, 2-methoxypyridin-4-yl, 2-methyl-1,3-thiazol-5-yl, 2-methyl-2H-indazol-3-yl, 2-methyl-6-(trifluoromethyl)pyridin-3-yl, 2-methylimidazo[1,2-a]pyridin-3-yl, 2-methylpyridin-3-yl, 2-morpholinothiazol-5-yl, 2-phenyl-1,3-thiazol-5-yl, 3,5-difluoropyridin-2-yl, 3,5-dimethyl-1-(propan-2-yl)-1H-pyrazol-4-yl, 3,6-dimethylimidazo[2,1-b][1,3]thiazol-5-yl, 3-bromo-1,2-oxazol-5-yl, 3-chloropyridin-4-yl, 3-cyclopropylisoxazol-5-yl, 3-fluoropyridin-4-yl, 3-isopropyl-1-methyl-1H-pyrazol-5-yl, 3-methylpyridin-2-yl, 3-methylpyridin-4-yl, 4-chloropyridin-2-yl, 4-methylpyridin-2-yl, 5-bromo-4-methyl-1,3-thiazol-2-yl, 5-bromo-4-methylpyridin-2-yl, 5-bromo-6-methylpyridin-2-yl, 5-bromopyridin-2-yl, 5-bromopyrimidin-2-yl, 5-chloropyridin-2-yl, 5-chloropyridin-3-yl, 5-cyclopropylisoxazol-3-yl, 5-cyclopropylisoxazol-4-yl, 5-fluoro-1H-indol-3-yl, 5-fluoropyridin-3-yl, 5-methylpyridin-3-yl, 6-methoxypyridin-3-yl, 6-methylpyridin-2-yl, 6-methylpyridin-3-yl, benzo[d]thiazol-2-yl, imidazo[1,2-a]pyridin-2-yl, imidazo[1,2-a]pyridin-6-yl, isoquinolin-1-yl, isoquinolin-3-yl, N,N,4-trimethylthiazol-2-amine, N,N-dimethylthiazol-2-amine, pyridin-2-yl, pyridin-3-yl, pyridin-4-yl, quinolin-2-yl, quinolin-3-yl, quinolin-4-yl, or quinoxalin-2-yl.

Some embodiments are given by compounds of Formula (I) where $R^1$ is indole, -benzothiophene, -pyrazole, -benzothiazole, -benzofuran, -oxazole, -indazole, -benzimidazole, -thiazole, -imidazo[2,1-b][1,3]thiazole, -imidazo[1,2-a]pyridine, -pyridine, -quinoxaline, -quinoline, -isoquinoline, -naphthyridine, or pyrimidine, each unsubstituted or substituted with one, two, three or four $R^c$ members.

In certain embodiments of Formula (I), $R^1$ is -3,4-dihydro-2H-benzopyran, -2,3-dihydro-1,4-benzodioxine, -2,3-dihydro-1-benzofuran, or -1,2,3,4-tetrahydroisoquinoline, each optionally unsubstituted or substituted with one or more —H, —F, or —$OCH_3$.

In certain embodiments of Formula (I), $R^1$ is chroman-2-yl, 6-fluorochroman-2-yl, chroman-3-yl, 7-methoxychroman-3-yl, 2,3-dihydrobenzofuran-2-yl, (2,3-dihydrobenzo[b][1,4]dioxin-2-yl, or 2-methyl-1,2,3,4-tetrahydroisoquinolin-3-yl.

Some embodiments are given by compounds of Formula (I) where $R^1$ is phenyl substituted with two or three $R^a$ members independently selected from the group consisting of: —H, -halo, and —$C_{1-6}$haloalkyl.

Some embodiments are given by compounds of Formula (I) where Z is —C═O, —$R^1$ is 2,3-dihydro-1-benzofuran, 3,4-dihydro-2H-1-benzopyran, benzofuran, benzothiophene, naphthalene, quinoline, or phenyl, wherein phenyl is unsubstituted or substituted with two, three, or four $R^a$ members, where $R^a$ is a member independently selected from: —H, —Cl, —Br, —F, —I, —$C_{1-4}$alkyl, —$C_{1-4}$haloalkyl, —$C_{1-4}$alkoxy, —$C_{1-4}$haloalkoxy, —CN, —$N(CH_3)_2$, or -cyclopropyl.

Some embodiments are given by compounds of Formula (I) where Z is —$CH_2$, —$R^1$ is phenyl unsubstituted or substituted with two, three, or four $R^a$ members, where $R^a$ is a member independently selected from: —H, —Cl, —Br, —F, —I, —$C_{1-4}$alkyl, —$C_{1-4}$haloalkyl, —$C_{1-4}$alkoxy, CN, —$N(CH_3)_2$, or -cyclopropyl.

In certain embodiments, a compound, or pharmaceutically acceptable salt thereof, of Formula (I) is selected from the group consisting of Examples 1-566, as disclosed herein.

Further embodiments are provided by pharmaceutically acceptable salts of compounds of Formula (I), pharmaceutically acceptable prodrugs of compounds of Formula (I), and pharmaceutically active metabolites of compounds of Formula (I).

Isotopically-Labeled Compounds

The invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$ $^{15}N$, $^{15}O$, $^{17}O$, $^{18}O$, $^{31}P$, $^{32}P$, $^{35}S$, and $^{99m}Tc$.

Compounds of the present invention (and derivatives of such compounds, such as pharmaceutically acceptable salts and prodrugs) that contain the aforementioned isotopes or other isotopes of other atoms are within the scope of the invention. Isotopically-labeled compounds of the present invention are useful in drug and substrate tissue distribution and target occupancy assays. For example, isotopically labeled compounds are particularly useful in SPECT (single photon emission computed tomography) and in PET (positron emission tomography), as discussed further herein.

Derivatives

The present invention also provides derivatives of a chemical entity of Formula (I), which include, but are not limited to, any salt, solvate, conformer, or crystalline form/polymorph.

Salts

Accordingly, in one embodiment the invention includes pharmaceutically acceptable salts of the compounds represented by Formula (I), and methods using such salts.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids (such as N-methyl-O-glucamine, lysine, choline, glycine, and arginine), ammonia, carbonates, bicarbonates, primary, secondary, and tertiary amines, cyclic amines (such as tromethamine, benzylamines, pyrrolidines, piperidine, morpholine, and piperazine), and inorganic salts derived from sodium, calcium, potassium, magnesium, manganese, iron, copper, zinc, aluminum, and lithium.

Solvates

In other embodiments, the invention provides a solvate of a compound of Formula (I), and the use of such solvates in methods of present invention. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the invention with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. Hydrates include compounds formed by an incorporation of one or more water molecules.

Conformers and Crystalline Forms/Polymorphs

In other embodiments, the invention provides conformer and crystalline form of a compound of Formula (I), and the use of these derivatives in methods of present invention. A conformer is a structure that is a conformational isomer. Conformational isomerism is the phenomenon of molecules with the same structural formula but different conformations (conformers) of atoms about a rotating bond.

A polymorph is a composition having the same chemical formula, but a different solid state or crystal structure. In certain embodiments of the invention, compounds of Formula (I) were obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

Prodrugs

The invention also relates to prodrugs of the compounds of Formula (I), and the use of such pharmaceutically acceptable prodrugs in methods of the present invention, particularly therapeutic methods. Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-6}$alkyl, $C_{1-6}$cycloalkyl, phenyl, and phenyl($C_{1-}$ 6alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy) methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers).

Metabolites

The present invention also relates to a metabolite of a compound of Formula (I), as defined herein, and salts thereof. The present invention further relates to the use of such metabolites, and salts thereof, in methods of present invention, including therapeutic methods.

Metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767; Bagshawe, Drug Dev. Res. 1995, 34, 220-230; and Bodor, *Adv Drug Res.* 1984, 13, 224-231).

Compositions

In some embodiments compounds of Formula (I) and pharmaceutically acceptable salts thereof are used, alone or in combination with one or more additional active ingredients, to formulate pharmaceutical compositions. A pharmaceutical composition of the invention comprises: (a) an effective amount of at least one active agent in accordance with the invention; and (b) a pharmaceutically acceptable excipient.

Formulations and Administration

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present invention is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose, aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar, and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949).

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 100 mg/kg, more specifically from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

Preferably, the active ingredient should be administered to achieve peak plasma concentrations of the active compound of from about 0.5 to about 75 μM, preferably, about 1 to 50 μM, and more preferably, about 2 to about 30 μM. This may be achieved, for example, by the intravenous injection of a 0.05 to 5% solution of the active ingredient, optionally in saline, or orally administered as a bolus containing about 1 to 100 mg of the active ingredient. Desirable blood levels may be maintained by continuous infusion to provide about 0.01 to 5.0 mg/kg/hr or by intermittent infusions containing about 0.4 to 15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of temporally-distinct administrations used according to the compositions and methods of the present invention.

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Methods and Uses

Uses of Isotopically-Labeled Compounds

In one aspect, the present invention provides a method of using isotopically labeled compounds and prodrugs of the present invention in: (i) metabolic studies (preferably with $^{14}C$), reaction kinetic studies (with, for example $^2H$ or $^3H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and prodrugs of the invention thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^2H$) may afford certain therapeutic advantages resulting from greater metabolic stability, for example increased in vivo half-life or reduced dosage requirements.

Therapeutic Methods

Generally

Chemical entities of the present invention are useful in methods (or in the manufacture of a medicament for use in such methods) of treating a disorder mediated by PDE2a by administering to a subject in need thereof an effective amount of a chemical entity of the present invention. They are also useful in methods (or in the manufacture of a medicament for use in such methods) of enhancing cognitive or motor function mediated by PDE2 by administering to a subject in need an effective amount of a chemical entity of the present invention.

In one embodiment the present invention provides a method of treating a subject suffering from or diagnosed with a disorder mediated by PDE2 activity, comprising administering to a subject in need of such treatment an effective amount of at least one chemical entity of the present invention. In a further embodiment, the subject is diagnosed with a disorder mediated by PDE2 activity.

Chemical entities of the present invention are also useful in enhancing neuronal plasticity—an essential property of the brain that can be augmented in healthy animals and impaired in numerous CNS disorders. Without being limited by mechanism, such chemical entities can enhance cyclic adenosine monophosphate (cAMP) response element binding protein (CREB) pathway function in cells, modulating transcription of multiple genes involved in synaptic plasticity. See, e.g., Tully et al., *Nat. Rev. Drug Discov.* 2003, 2, 267-277; Alberini, *Physiol. Rev.* 2009, 89, 121-145. Accordingly, the present invention provides a method of enhancing neuronal plasticity, comprising administering to a subject in need thereof an effective amount of a chemical entity of the present invention.

Chemical entities of the present invention are also useful as "agents" (also referred to as "augmenting agents") to augment the efficiency of training protocols, which facilitate functional reorganization in targeted "domains" (or "functions") in the brain. Training protocols can be directed to rehabilitating or enhancing a cognitive or motor function. The training protocol (cognitive or motor training) induces neuronal activity in specific brain regions and produces improved performance of a specific brain (cognitive or motor) function. Chemical entities of the present invention agents act as "augmenting agents," which shorten the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc., and a general administration of CREB pathway-enhancing drugs.

Neurological Disorders

Chemical entities of the present invention are useful in methods of treating a neurological disorder, comprising administering to a subject in need thereof an effective amount of a chemical entity of Formula (I). In a specific aspect, the methods are directed to a cognitive deficit ("cognitive impairment") or motor deficit ("motor impairment") associated with (or "due to") the neurological disorder.

A neurological disorder (or condition or disease) is any disorder of the body's nervous system. Neurological disorders can be categorized according to the primary location affected, the primary type of dysfunction involved, or the primary type of cause. The broadest division is between peripheral nervous system (PNS) disorders and central nervous system (CNS) disorders (such as mental and psychiatric disorders). Neurological disorders are well-known in the art, and they include, but are not limited to, the following mental and psychiatric disorders:

- Neurodevelopmental (or "developmental" disorders), such as intellectual disability disorders (e.g., Rubinstein-Taybi syndrome, Down syndrome); communication disorders; autism-spectrum disorder; attention-deficit/hyperactivity disorder; specific learning, language, or reading (e.g., dyslexia) disorders; motor disorders; fetal alcohol spectrum disorders (FASD); and other neurodevelopmental disorders;
- Schizophrenia spectrum and other psychotic disorders, such as schizophrenia, schizotypal (personality) disorder, delusional disorder, and schizophreniform disorder, and other schizophrenia spectrum and psychotic disorders;

- Bipolar and related disorders, such as Bipolar I and II disorders, cyclothymic disorder, and other bipolar and related disorders;
- Depressive disorders, such as major depressive disorder, persistent depressive disorder (dysthymia), and other depressive disorders;
- Anxiety disorders, such as specific phobias, social anxiety disorder (social phobia), panic disorder, generalized anxiety disorder (GAD), posttraumatic stress disorder (PTSD), and other anxiety disorders;
- Obsessive-compulsive and related disorders, such as obsessive-compulsive disorder, body dysmorphic disorder, and other obsessive-compulsive and related disorders;
- Dissociative disorders, such as dissociative identity disorder, dissociative amnesia, and other dissociative disorders;
- Disruptive, impulse-control, and conduct disorders, such as conduct disorders, antisocial personality disorder, and other disruptive, impulse-control, and conduct disorders;
- Trauma- and stressor-related disorders, such as posttraumatic stress disorder, adjustment disorders, and other trauma- and stressor-related disorders;
- Feeding and eating disorders, such as anorexia, bulimia, binge-eating disorder, and other feeding and eating disorders;
- Sleep-wake disorders, such as insomnia, narcolepsy, parasomnias, and other sleep-wake disorders;
- Sexual disorders, such as arousal disorders, desire disorders, substance and medication-induced dysfunctions, and other sexual disorders;
- Substance-related and addictive disorders, such as those involving alcohol, drugs, stimulants, opioids, tobacco, and non-substance-related disorders; and other substance-related and addictive disorders; and
- Personality disorders, such as paranoid personality disorder, antisocial personality disorder, borderline personality disorder, avoidance personality disorder, and other personality disorders; and In particular embodiments, the disorder is schizophrenia, an attention deficit disorder, or an anxiety disorder.

In other embodiments, the neurological disorder is an acquired disorder, in which the primary clinical feature is impaired cognition. In other words, it is a disorder in which the primary cognitive deficit has not been present since birth or very early life and therefore represents a decline from a previously attained level of functioning. Such disorders, which may be referred to herein as "cognitive disorders" or "neurocognitive disorders" include one or more of the following:

- Delirium, such as substance-intoxication (or withdrawal) delirium, medication-induced delirium, and other forms of delirium;
- Dementias and other cognitive impairments due to HIV infection or due to neurodegenerative diseases, such as Alzheimer's disease, Parkinson's disease, Huntington's disease, Lewy body disease, Pick's disease, a prion disease (e.g., Creutzfeldt-Jakob disease), Amyotrophic lateral sclerosis (ALS), multiple sclerosis, frontotemporal lobar degeneration, and corticobasal degeneration; dementia due to a vascular disease ("vascular disease"); and other dementias and neurodegenerative diseases;
- Age-associated cognitive deficits, including age-associated memory impairment (AAMI), also referred to as age-related memory impairment (AMI) (See, e.g., Crook et al., *Devel. Neuropsychol.* 1986, 2, 261-276); and deficits affecting patients in early stages of cognitive decline, as in Mild Cognitive Impairment (MCI) (See, e.g., Arnáiz and Almkvist, *Acta Neurol. Scand.* Suppl. 2003, 179, 34-41), and;
- Trauma-dependent losses of cognitive function, such as vascular diseases due to stroke (e.g., ischemic or hemorrhagic stroke) or ischemia; microvascular disease arising from diabetes or arthrosclerosis; traumatic brain injury (TBI), such as brain trauma, including subdural hematoma and brain tumor; head trauma (closed and penetrating); head injury; tumors, such as nervous system cancers, including cerebral tumors affecting the thalamic or temporal lobe; hypoxia; and viral infection (e.g., encephalitis); excitotoxicity; and seizures; and
- Cognitive impairments due to chemotherapy, such as post-chemotherapy cognitive impairments (PCCI); chemotherapy-induced cognitive dysfunction or impairments; chemo brain; or chemo fog.

Such acquired disorders are not necessarily limited to cognitive impairments. For example, trauma related disorders, such as stroke, traumatic brain injury, head trauma, and head injury, may also include impairments in other neurological functions, such as impairments in motor functions.

As used herein, the terms "Neurodevelopment disorders," "Schizophrenia spectrum and other psychotic disorders," Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep-wake disorders," "Sexual disorders," "Substance-related and addictive disorders," "Personality disorders," "Delirium," "Neurocognitive disorders," "Delirium," "Dementias," and "Trauma" include treatment of those mental disorders as described in the Diagnostic and Statistical Manual of Mental Disorders (DSM-5; $5^{th}$ ed., 2013, American Psychiatric Association). The skilled artisan will recognize that there are alternative nomenclatures and classification systems for mental disorders, and that these systems evolve with medical and scientific progress. Thus the terms described in this paragraph are intended to include like disorders that are described in other diagnostic sources.

In other embodiments, the neurological disorder is a movement or motor disorder, a group that includes, but is not limited to: kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor); chorea, such as that in Huntington's disease; myoclonus (including generalized myoclonus and focal myoclonus); tics (including simple tics, complex tics and symptomatic tics); dystonia; restless leg syndromes; Wilson's Disease; Hallerworden-Spatz disease; basal ganglia disorders; hyperkinetic, hypokinetic, and dyskinetic disorders; movement disorders induced by drugs; and other movement and motor disorders.

Augmented Training

In certain embodiments, chemical entities of the present invention provide augmenting agents to enhance the efficiency of training protocols, including cognitive training and motor training protocols. Such methods are known as "augmented training," and, more particularly, "augmented cognitive training" or "augmented motor training."

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol. (See, e.g., U.S. Pat. Nos. 7,868,015; 7,947,731; US 2008-0188525). When administered in combination with training protocols (or "training"), augmenting agents enhance functional reorganization in targeted domains (or "functions") in the brain.

Cognitive domains (or functions) that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (declarative memory) memory, such as episodic, semantic, and autobiographical memory, and into implicit memory (procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols

Training protocols (or "modules") are well known in the art and typically comprise a set of distinct exercises that can be process-specific or skill-based: See, e.g., Kim et al., *J. Phys. Ther. Sci.* 2014, 26, 1-6; Allen et al., *Parkinsons Dis.* 2012, 2012, 1-15; Jaeggi et al., *Proc. Natl. Acad. Sci. USA* 2011, 108, 10081-10086; Chein et al., *Psychon. Bull. Rev.* 2010, 17, 193-199; Klingberg, *Trends Cogn. Sci.* 2010, 14, 317-324; Owen et al., Nature 2010, 465, 775-778; Tsao et al., *J. Pain* 2010, 11, 1120-1128; Lustig et al., *Neuropsychol. Rev.* 2009, 19, 504-522; Park and Reuter-Lorenz, *Ann. Rev. Psych.* 2009, 60, 173-196; Oujamaa et al., *Ann. Phys. Rehabil. Med.* 2009, 52, 269-293; Frazzitta et al., *Movement Disorders* 2009, 8, 1139-1143; Jaeggi et al., *Proc. Natl. Acad. Sci. USA* 2008, 105, 6829-6833; Volpe et al., *Neurorehabil. Neural Repair* 2008, 22, 305-310; Fischer et al., *Top. Stroke Rehab.* 2007, 14, 1-12; Jonsdottir et al., *Neurorehabil. Neural Repair* 2007, 21, 191-194; Stewart et al., *J. Neurol. Sci.* 2006, 244, 89-95; Krakauer, *Curr. Opin. Neurol.* 2006, 19, 84-90; Belleville et al., *Dement. Geriatr. Cogn. Disord.* 2006, 22, 486-499; Klingberg et al., *J. Am. Acad. Child. Adolesc. Psychiatry* 2005, 44, 177-186; Dean et al., *Arch. Phys. Med. Rehabil.* 2000, 81, 409-417; Whitall et al., *Stroke* 2000, 31, 2390-2395; Hummelsheim and Eickhof, *Scand. J. Rehabil. Med.* 1999, 31, 250-256; Merzenich et al., *Science* 1996, 271, 77-81; Merzenich et al., *Cold Spring Harb. Symp. Quant. Biol.* 1996, 61, 1-8; Rider and Abdulahad, *Percept. Mot. Skills* 1991, 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of fact, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a PDE2 inhibitor, and more particularly, is a chemical entity of the present invention, and is administered in conjunction with training. By "in conjunction" is meant that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine.

In one aspect, a compound or composition of the present invention can be used as an augmenting agent in conjunction with any psychotherapeutic approach intended to modulate cognitive function in the brain, thereby enhancing the efficacy of such therapy by reducing the number of sessions necessary to attain benefits.

Stroke

In some embodiments, chemical entities and compositions of the present invention are useful in treating stroke, and in more specific embodiments, treating motor or cognitive impairments during post-stroke rehabilitation. Stroke care is a temporal continuum that includes immediate (acute) treatments and subsequent rehabilitative therapy.

Acute treatments directly target the initial damage, such as that triggered by ischemic or hemorrhagic stroke; they usually involve using agents to dissolve clots and restore blood flow to reduce tissue damage and stabilize the patient. The efficacy of acute treatments is typically limited to a short time window extending only a few hours from stroke onset.

The focus of stroke treatment shifts to rehabilitation after the patient has been medically stabilized. Rehabilitation (also referred to as "stroke rehabilitation" or "post-stroke rehabilitation") is directed to cognitive and motor deficits that persist after the initial stroke injury, the goal being to restore and recover neurological function as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; by problems with balance or coordination; deficits in gross motor skills such as gait and walking speed; deficits in fine motor skills or manual dexterity; and deficits in upper and lower extremity function.

Accordingly, the present invention provides the use of a PDE2 inhibitor in the treatment of stroke, including post stroke rehabilitation. In certain embodiments, chemical entities of the present invention are useful during stroke rehabilitation to treat stroke deficits (or "post-stroke deficits") resulting from impaired neurological functions. In some embodiments, the present invention provides methods of treating a neurological deficit during post-stroke rehabilitation comprising: (a) administering to a subject in need thereof a PDE2 inhibitor during recovery of the subject from stroke; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE2 inhibitor is a chemical entity of the present invention. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, said administering step (a) is in conjunction with said training step (b). In one aspect, the subject is a human. In another aspect, the subject has undergone neuronal stem cell manipulation. In other aspects, the compound is administered before and during each training session.

Traumatic Brain Injury

In some embodiments, chemical entities and compositions of the present invention are useful in treating traumatic brain injury, and in more specific embodiments, treating motor or cognitive impairments during rehabilitation after the initial trauma. Like stroke care, TBI case is a temporal continuum that includes immediate (acute) treatments and subsequent rehabilitative therapy.

Accordingly, the present invention provides the use of a PDE2 inhibitor in the treatment of TBI, including during TBI rehabilitation to treat TBI deficits (or "post-TBI deficits") resulting from impaired neurological functions. In some embodiments, the present invention provides methods of treating a neurological deficit during post-TBI rehabilitation comprising: (a) administering to a subject in need thereof a PDE2 inhibitor during recovery of the subject from TBI; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE2 inhibitor is a chemical entity of the present invention. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, said administering step (a) is in conjunction with said training step (b). In one aspect, the subject is a human. In another aspect, the subject has undergone neuronal stem cell manipulation. In other aspects, the compound is administered before and during each training session.

Peripheral Disorders

Chemical entities of the present invention are useful in methods of treating peripheral disorders, that is, disorders other than a primary neurological disorder. These uses are supported by PDE2A expression studies and other observations. See, e.g., Bayer Healthcare AG, Intl. Pat. Appl. Publ. WO/2004/044234, May 27, 2004; Donzeau-Gouge et al., 2001, J. Physiol. 533, 329-340; Herring et al., 2001, Card. Res. 52: 446-453; Keravis et al., 2000, J Vasc. Res. 37, 235-249; Wolda et al., 1999, J. Histochem. Cytochem. 47, 895-906; Dickinson et al., 1997, Biochem. J. 323: 371-377; Fischmeister et al., 1997, J Clin. Invest. 99, 2710-2718; Houslay et al., 1996, Cell. Signal. 8, 97-110; and Haynes et al., 1996, J. Pharm. Exp. Ther., 276, 752-757.

Accordingly, the present invention provides methods of treating a peripheral disorder, comprising administering to a subject in need thereof an effective amount of a chemical entity of Formula (I). Peripheral disorders include, but are not limited to, infectious diseases, such as bacterial, fungal, protozoan, and viral infections; hematological diseases, such as anemias, myeloproliferative disorders, hemorrhagic disorders, leukopenias, eosinophilic disorders, leukemias, lymphomas, and plasma cell dyscrasias; cardiovascular diseases such as congestive heart failure, myocardial infarction, ischemic diseases, atrial and ventricular anhythmias, hypertensive vascular diseases, and atherosclerosis; gastroenterological disorders, such as diseases of the esophagus, stomach, duodenum, pancreas, bowel, and liver; dermatological disorders, such as psoriasis, dermatitis, impetigo, folliculitis, melanoma; and other peripheral disorders, including renal diseases, in particular kidney failure, and inflammatory diseases.

Animal Skill Training Protocols

In some embodiments, chemical entities of the present invention are used to enhance the efficiency of training protocols directed to cognitive and motor skills in an animal. Such augmented training reduces the time necessary to acquire or enhance a cognitive or motor skill in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a single drug in a service animal. In other embodiments, the training protocol may be directed to a complex set of skills, such as those underlying search and rescue training of a service animal; for a complex set of skills, training will therefore comprise more than one task.

Accordingly, in some embodiments, the present invention provides a method of teaching a non-human animal one or more skills, comprising (a) administering to a non-human animal in need thereof a PDE2 inhibitor; (b) providing training to the animal under conditions sufficient to improve performance of said one or more skills; and (c) repeating steps (a) and (b) one or more times, whereby the amount of training sufficient to improve the performance is reduced compared to that produced by training alone.

PREPARATIVE EXAMPLES

Exemplary compounds useful in methods of the invention will now be described by reference to the illustrative synthetic schemes for their general preparation below and the specific examples to follow.

Synthetic Schemes

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

SCHEME A

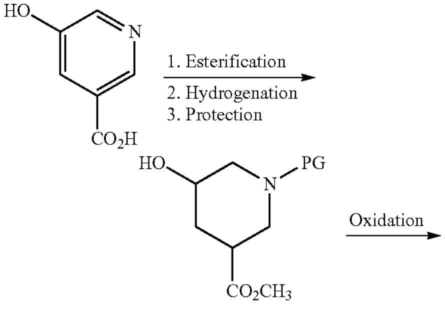

(II)

-continued

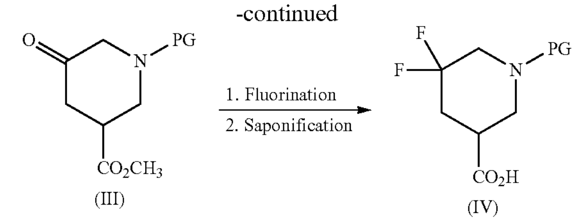

(III) (IV)

According to Scheme A, commercially available or synthetically accessible 5-hydroxynicotinic acid is reacted under esterification conditions, for example by treating an alcohol solution of 5-hydroxynicotinic acid with an acid, at elevated temperatures, for a period of 24 h to 7 days. In a preferred method 5-hydroxynicotinic acid is dissolved in MeOH, treated with $H_2SO_4$, and heated at reflux for a period of 7 days, to afford methyl 5-hydroxynicotinate. Hydrogenation of methyl 5-hydroxynicotinate, in the presence of a palladium catalyst such as Pd/C, $H_2$ under pressure, in a solvent such as AcOH, at temperatures ranging from rt to 60° C., affords methyl 5-hydroxypiperidine-3-carboxylate. Methyl 5-hydroxypiperidine-3-carboxylate is protected with a suitable protecting group such as BOC. In a preferred method, treating an alcohol solution of methyl 5-hydroxypiperidine-3-carboxylate with a base such as TEA, and the like, di-tert-butyl dicarbonate ($BOC_2O$), a room temperature, for a period of 8 to 24 h, provides a compound of formula (II). Oxidation of a compound of formula (II), under conditions known to one skilled in the art, such as Swern oxidation conditions, provides a compound of formula (III). A compound of formula (III) is treated under fluorination conditions known to one skilled in the art, for example, reaction with a fluorinating agent such as DAST®, Deoxo-Fluor®, and the like, in a solvent such as DCM. Subsequent saponification of fluoropiperidine under conditions known to one skilled in the art, provides a piperidine acid compound of formula (IV).

SCHEME B

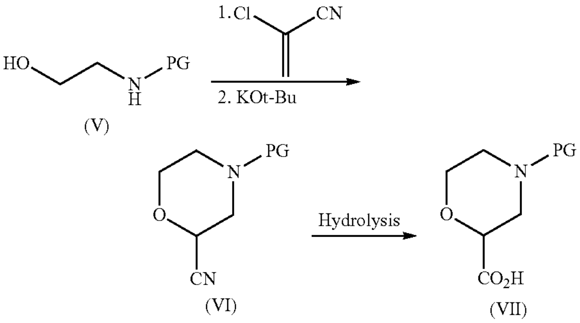

(V) (VI) (VII)

According to Scheme B, a cyanomorpholine compound of formula (VI) is commercially available or are prepared in two steps, using conventional synthetic methods as previously described in *OPRD,* 2004, 13(2), 209-224. For example, commercially available or synthetically accessible 2-aminoethanol compounds of formula (V), where PG is benzyl, is reacted in a Michael addition with 2-chloroacrylonitrile, in a solvent such as toluene, $Et_2O$, and the like, at temperatures ranging from −5° C. to 40° C., for a period of 1 to 24 h. Subsequent cyclization is achieved by reaction with a base such as t-BuOK, and the like, in a solvent such as THF, toluene, or a mixture thereof, at temperatures ranging from −5° C. to 15° C., for a period of 1 to 3 h. A cyanomorpholine compound of formula (VI) is hydrolyzed to a morpholine carboxylic acid compound of formula (VII), under acidic conditions, for example, in the presence of an acid such as HCl, $H_2SO_4$, and the like, in a solvent such as toluene, $H_2O$, or a mixture thereof, at temperatures ranging from rt to 95° C., for a period of 1 to 5 h, to provide a compound a formula (VII).

SCHEME C

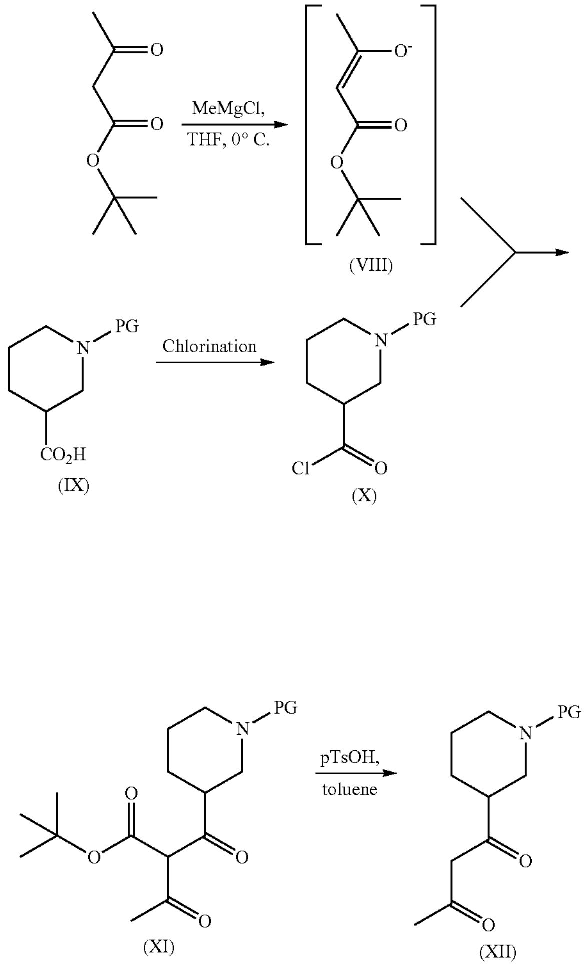

(VIII) (IX) (X) (XI) (XII)

According to Scheme C, a compound of formula (XI), where PG is Cbz, BOC, and the like, is prepared from an enolate compound of formula (VIII) and an acid chloride compound of formula (X). Reaction of commercially available or synthetically accessible tert-butyl 3-oxobutanoate with methylmagnesium chloride, and the like, in a solvent such as THF, at a temperature of 0° C., followed by addition of an acid chloride compound of formula (X), which is prepared using methods known to one skilled in the art, at temperatures ranging from 0° C. to room temperature, for a period of 1 to 24 h provides a compound of formula (XI). Acid catalyzed ester hydrolysis/decarboxylation of a compound of formula (XI) with an acid such as p-toluenesulfonic acid, and the like, in a solvent such as toluene, at temperatures ranging from 70° C. to 100° C., for a period of 6 to 16 h, provides a compound of formula (XII).

SCHEME D

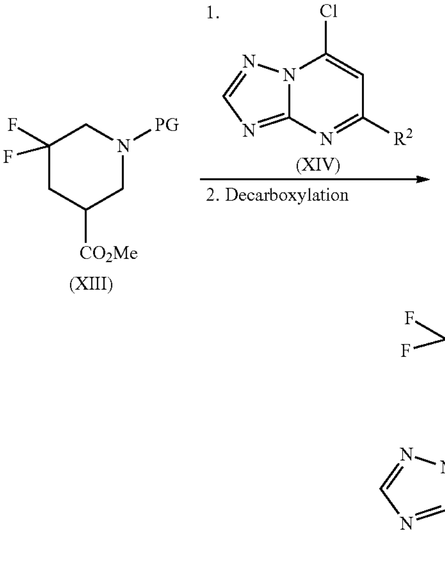

(XIII) (XIV) (XV)

According to Scheme D, a compound of formula (XV), where PG is BOC, is obtained in two steps by first reaction of fluoropiperidine of formula (XIII) with a suitable heteroaryl of formula (XIV), where $R^2$ is $C_{1-6}$alkyl, a base such as LiHMDS, NaHMDS, LDA, NaH, and the like, in a solvent such as THF, DCM, DME and the like, at temperatures of about −78 to 0° C., for a period of about 30 min to 2 h. In a preferred method, a compound of formula (XIII) is reacted with a compound of formula (XIV), LiHMDS, in THF, at −78° C., for a period of 45 minutes. Subsequent decarboxylation, under conditions known to one skilled in the art, for example, employing a base such as LiOH, in a solvent such as MeOH, $H_2O$ or a mixture thereof, at temperatures ranging from 0-25° C., for a period of 16 to 24 h, provides a compound of formula (XV).

SCHEME E

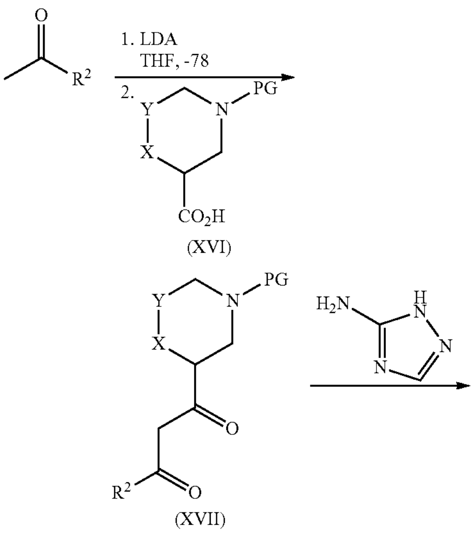

(XVI) (XVII)

-continued

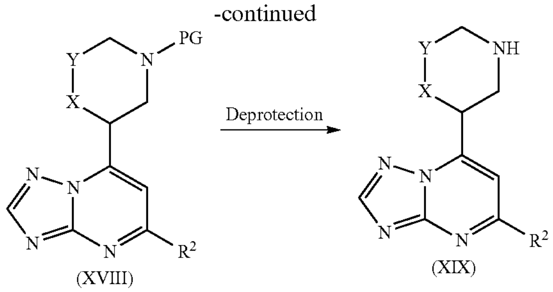

(XVIII) (XIX)

According to Scheme E, activation of a commercially available or synthetically accessible compound of formula (XVI), where Y is —$CH_2$— or —$CF_2$—; X is —$CH_2$— or —O—; and PG is a suitable protecting group such as Bn, CBz or BOC, with a reagent such as CDI, followed by reaction with the enolate of a compound of formula $R^2$—C(═O)$CH_3$, where $R^2$ is —$C_{1-6}$alkyl, and the like, (prepared by the reaction of LDA which is prepared insitu by reaction of diisopropylamine with n-BuLi, in a solvent such as THF, at temperatures of about −70° C., for a period of 1 hr), at temperatures of about −60° C., for a period of 1 h, provides a diketo compound of formula (XVII). In a similar fashion, a compound of formula $R^2$—C(═O)$CH_3$, where $R^2$ is —$C_{1-6}$alkyl substituted with on or more —F members may be employed. Condensation of 1H-1,2,4-triazol-5-amine with a diketo compound of formula (XVII) in a solvent such as AcOH, at temperatures ranging from 80° C. to 100° C., for a period of 8 to 24 h, provides a compound of formula (XVIII). Removal of the protecting group (PG), is accomplished by using methods known to one skilled in the art. For example, removal of the tert-butylcarbamate (BOC) protecting group (PG) in a compound of formula (XVIII) is accomplished by using HCl, TFA, or p-toluenesulfonic acid, in a solvent such as MeOH, dioxane, or $CH_2Cl_2$. In a preferred embodiment, a compound of formula (XVIII) is treated with TFA or HCl in DCM, to provide a compound of formula (XIX).

SCHEME F

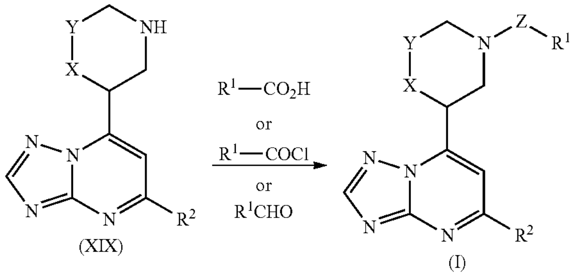

(XIX) (I)

A compound of Formula (I), where Z is —C(═O)—, is obtained by subsequent reaction of an amine of formula (XIX) with a suitable acid of formula $R^1$—$CO_2H$ under amide forming conditions. A compound of formula $R^1$—$CO_2H$, where $R^1$ is as defined in Formula (I), is commercially available, as described, or a synthetically accessible appropriately substituted aryl, cycloalkyl or heteroaryl carboxylic acid. In a preferred embodiment a compound of formula (XIX), where $R^2$ is —$CH_3$, either as a free base or as an acid salt, is reacted with a compound of formula $R^1$—$CO_2H$, in the presence of a dehydrating agent such as HOBt/EDAC, HATU, HOAT; a suitably selected base such as DIPEA, TEA, and the like; in an organic solvent or mixture thereof, such as toluene, acetonitrile, ethyl acetate, DMF, THF, methylene chloride, and the like; to afford a compound of Formula (I). In a particularly preferred embodiment the dehydrating agent is HATU, and the base is DIPEA.

In an alternative embodiment, a compound of formula $R^1$—$CO_2H$ (as described above) may be first converted to a compound of formula $R^1$—COCl, or compound of formula $R^1$—COCl is a commercially available substituted aryl chloride. A compound of formula $R^1$—$CO_2H$ may be treated with thionyl chloride in a solvent such as toluene to afford a compound of formula $R^1$—COCl. A compound of Formula (I) is obtained by treating a compound of formula $R^1$—COCl with a compound of formula (XIX), a suitably selected tertiary organic base such as TEA, and the like, in a solvent such as DCM, THF, and the like, at a temperature between room temperature and the reflux temperature of the solvent, to afford a compound of Formula (I)

A compound of Formula (I), where Z is —$CH_2$—, is obtained by subsequent reaction of the amines of formula (XIX) with a suitable aldehyde of formula $R^1$—CHO under reductive amination conditions. Compounds of formula $R^1$—CHO, where $R^1$ is as defined in Formula (I), are commercially available, as described, or synthetically accessible appropriately substituted aryl, cycloalkyl or heteroaryl aldehydes. In a preferred embodiment a compound of formula (XIX), either as a free base or as an acid salt, is reacted with a compound of formula $R^1$—CHO, in the presence of a reducing agent, such as sodium triacetoxyborohydride, sodium cyanoborohydride and the like, in a solvent such as THF, DCM, MeOH and the like, at temperatures ranging from 0 to 50° C., for a period of 1 to 4 h, to provide a compound of Formula (I).

A compound of Formula (I), is deuterated by treating a non-deuterated compound of Formula (I), with deuterated solvent, such as $CD_3OD$, in the presence of a base, such as DIEA, at temperatures ranging from room temperature to 50° C., for a period of 18 to 100 h. Exemplary preparations are given in the Examples. The level of deuteration can be determined by NMR analysis and by mass spectrometry.

Compounds prepared according to the schemes described above may be obtained as single enantiomers, diastereomers, or regioisomers, by enantio-, diastero-, or regiospecific synthesis, or by resolution. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry:

In obtaining the compounds described in the examples below, and the corresponding analytical data, the following experimental and analytical protocols were followed unless otherwise indicated.

Unless otherwise stated, reaction mixtures were magnetically stirred at room temperature (rt) under nitrogen atmosphere. Where solutions were "dried," they were generally dried over a drying agent such as $Na_2SO_4$ or $MgSO_4$. Where mixtures, solutions, and extracts were "concentrated," they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on Silica ($SiO_2$) using packed or prepackaged cartridges, eluting with the indicated solvents.

LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors.

Preparative HPLC was performed on a Shimadzu SIL-10AP system using a Waters SunFire™ OBD 30 mm×100 mm×2.5 μm (particle size) $C^{18}$ column with a 15 minute gradient of 10-100% acetonitrile in water and 0.05% trifluoroacetic acid added as a modifier to both phases. Elution profiles were monitored by UV at 254 and 220 nm.

Nuclear magnetic resonance (NMR) spectra were obtained in a Varian 400 MHz or Bruker 400 MHz NMR. Samples were analyzed in either deuterated acetone ($(CD_3)_2CO$)), chloroform ($CDCl_3$), methanol-$d_4$ ($CD_3OD$), or dimethyl sulfoxide-$d_6$ (DMSO-$d_6$). For $CDCl_3$ samples, the residual central resonance peak at 7.26 for $^1H$ was used for chemical shift assignment for $^1H$ NMR spectra. For $CD_3OD$ the residual central resonance peak at 3.31 for $^1H$ was used for chemical shift assignment and for DMSO-$d_6$ the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration).

Chemical names were generated using ChemDraw Ultra 12.0 (CambridgeSoft Corp., Cambridge, MA) or ChemAxon.

Intermediate 1. 2-(5-Methyl-[1,2,4]triazolo[1,5-a]pyrimidin-7-yl)morpholine

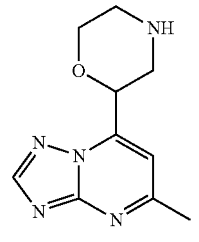 [SMILES: Cc1cc(C2CNCCO2)n2ncnc2n1]

Step A. 4-Benzylmorpholine-2-carbonitrile. 2-(Benzylamino)ethanol (46 g, 304 mmol) and 2-chloroacrylonitrile (26.5 g, 304 mmol) were stirred at rt for 18 h. THF (300 mL) was added followed by t-BuOK (38.9 g, 330 mmol) portionwise over 1 h, keeping the reaction temperature at <2° C. After 1 h post-stirring at 0° C., the mixture was quenched with sat. aq. $NaHCO_3$. The aqueous layer was extracted with EtOAc. The organic layer was dried ($Na_2SO_4$), filtered, and concentrated under reduced pressure. Purification (FCC, $SiO_2$, (PE/EtOAc=5/1) provided the title compound (45 g, 73%) as an oil. $^1H$ NMR ($CDCl_3$, 400 MHz) δ 7.36-7.27 (m, 5H), 4.63-4.60 (m, 1H), 4.15-4.00 (m, 1H), 3.82-3.75 (m, 1H), 3.64-3.53 (m, 2H), 2.80-2.75 (m, 1H), 2.67-2.54 (m, 2H), 2.46-2.39 (m, 1H).

Step B. 4-Benzylmorpholine-2-carboxylic acid. To a solution of 4-benzylmorpholine-2-carbonitrile (20.2 g, 100 mmol) in toluene (60 mL) was added 6M HCl (100 mL, 600 mmol). The reaction mixture was refluxed at 110° C. for 1.5 h and then cooled to rt and stirred for 18 h. The solid was filtered to give the title compound (22 g, 99%) as a white solid.

Step C. 1-(4-Benzylmorpholin-2-yl)butane-1,3-dione. To a solution of i-$Pr_2NH$ (7 mL, 50 mmol) in THF (40 mL) was added n-BuLi (20 mL, 50 mmol) at 0° C. and stirred for 0.5 h. The solution was cooled to −78° C., acetone (2.9 g, 50 mmol) was added drop wise mixture was allowed to stir at −78° C. for 1 h. A solution of 4-benzylmorpholine-2-carboxylic acid (5.52 g, 25 mmol) in THF (40 mL) with CDI (4.48 g, 27.5 mmol) stirred for 3 h, was added drop wise at −78° C. The mixture was stirred for 1 h, and allowed to warm to rt, then neutralized with 10% critic acid. The organic mixture was extracted with EtOAc and the organic phase was washed with and aq. $NaHCO_3$, dried ($Na_2SO_4$), filtered, and concentrated under reduced pressure. Purification (FCC, $SiO_2$, PE/EtOAc, 5/1) afforded the title compound (3.5 g, 53%) as a colorless oil. $^1H$ NMR ($CDCl_3$, 400 MHz) δ 7.25-7.19 (m, 5H), 5.77 (s, 1H), 4.06-4.03 (d, 1H), 3.88-3.84 (d, 1H), 3.66-3.60 (m, 1H), 3.50-3.41 (m, 2H), 3.01-2.97 (d, 1H), 2.61-2.58 (d, 1H), 2.16-2.10 (m, 2H), 2.02-1.97 (m, 4H).

Step D. 4-Benzyl-2-(5-methyl-[1,2,4]triazolo[1,5-a]pyrimidin-7-yl)morpholine. To a solution of 1-(4-benzylmorpholin-2-yl)butane-1,3-dione (3.4 g, 13 mmol) in HOAc (10 mL) was added 4H-1,2,4-triazol-3-amine (1.1 g, 13 mmol). The reaction mixture was refluxed at 125° C. for 1 h and then cooled to rt. Water was added and the mixture was extracted with EtOAc. The organic layer was dried ($Na_2SO_4$), filtered, and concentrated under reduced pressure. Purification (FCC, $SiO_2$, PE/EtOAc, 2/1) provided the title compound (3.5 g, 87%) as a white solid upon concentrating to a small volume. $^1H$ NMR ($CDCl_3$, 400 MHz): δ 8.33 (s, 1H), 7.29-7.18 (m, 5H), 7.07 (s, 1H), 5.29-5.26 (d, 1H), 4.00-3.96 (m, 1H), 3.87-3.81 (m, 1H), 3.65-3.62 (d, 1H), 3.52-3.48 (d, 1H), 3.42-3.38 (d, 1H), 2.72-2.68 (d, 1H), 2.64 (s, 3H), 2.25-2.19 (m, 1H), 2.04-1.98 (m, 1H).

Step E. 2-(5-Methyl-[1,2,4]triazolo[1,5-a]pyrimidin-7-yl)morpholine. To a solution of 4-benzyl-2-(5-methyl-[1,2,4]triazolo[1,5-a]pyrimidin-7-yl)morpholine (309 mg, 1.0 mmol) in $CH_2ClCH_2Cl$ (3.5 mL) was added 1-chloroethyl carbonochloridate (286 mg, 2 mmol). After refluxing the mixture for 2 h, the solvent was evaporated under reduced pressure and the residue was dissolved in MeOH. The mixture was stirred at rt for 2 h. The solvent was evaporated, the residue was dissolved in MeOH, and the mixture was treated with Amberlyst-26® (hydroxide) and stirred for 18 h. The reaction mixture was filtered and the filtrate was evaporated under reduced pressure to give the title compound (170 mg, 77%). $^1H$ NMR (DMSO-$d_6$, 400 MHz) δ 8.60 (s, 1H), 7.20 (s, 1H), 5.11-5.08 (d, 1H), 4.00-3.97 (d, 1H), 3.76-3.70

(m, 1H), 3.47-3.44 (m, 1H), 2.83-2.75 (m, 3H), 2.64 (s, 3H), 2.51-2.49 (m, 1H); [M+H]=220.

Chiral Separation:

The racemic Intermediate 1, (5 g, 22.8 mmol) was resolved to give the pure enantiomers using a preparative SFC instrument with a Chiralpak® OZ-H (2×25 cm) column and eluting with 30% 1:1 methanol:ACN (0.1% $NH_4OH$)/$CO_2$, 100 bar. Obtained were the two pure enantiomers: The first eluted compound (0.87 mg, >99% purity, 97% ee) was determined to be the (R)-stereoconfiguration. The second eluted compound (1.1 g, >99% purity, >99% ee) was determined to be the (S)-stereoconfiguration. The purified enantiomers were analyzed using a Chiralpak® OZ-H (25×0.46 cm) column and eluting with 20% methanol(DEA)/$CO_2$, 100 bar.

Intermediate 2. 5-Methyl-7-(piperidin-3-yl)-[1,2,4]triazolo[1,5-a]pyrimidine

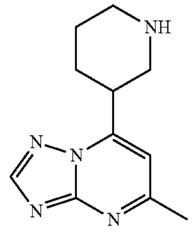 [SMILES: Cc1cc(C2CCCNC2)n2ncnc2n1]

Step A. tert-Butyl 3-(3-oxobutanoyl)piperidine-1-carboxylate. To a solution of i-$Pr_2NH$ (372 mL, 2.6 mol) in THF (850 mL) at −78° C. was added n-Buli (1040 mL, 2.6 mol). After stirring the reaction mixture for 1.5 h, acetone (209 mL, 2.6 mol) was added dropwise at −78° C. and the mixture was stirred for an additional 1 h. At the same time, a solution of 1-(tert-butoxycarbonyl)piperidine-3-carboxylic acid (300 g, 1.3 mol) in THF (1 L) was added CDI (233.4 g, 1.44 mol) at 0° C. and stirred at room temperature for 2 h. This solution was added drop wise at −78° C. and the resultant mixture stirred at −78° C. for 1 h and then allowed to warm to rt. The mixture was poured onto ice/water and extracted with EtOAc (2×2 L), the EtOAc layer was washed with 10% critic acid, aqueous $NaHCO_3$ and brine. The organic layer was dried ($Na_2SO_4$), concentrated under reduced pressure and purified (FCC, $SiO_2$, PE) to afford the title compound (300 g, 43%) as a yellow oil. $^1H$ NMR ($CDCl_3$, 400 MHz) δ 5.48 (s, 1H), 3.85-4.00 (m, 2H), 2.65-2.81 (m, 2H), 2.20-2.30 (m, 1H), 1.96 (s, 3H), 1.82-1.87 (m, 1H), 1.49-1.62 (m, 3H), 1.36 (s, 9H).

Step B. tert-Butyl 3-(5-methyl-[1,2,4]triazolo[1,5-a]pyrimidin-7-yl)piperidine-1-carboxylate. To a solution of tert-butyl 3-(3-oxobutanoyl)piperidine-1-carboxylate (150 g, 0.56 mol) in HOAc (300 mL) was added 4H-1,2,4-triazol-3-amine (47 g, 0.56 mol). The reaction mixture was refluxed at 125° C. for 2 h and then cooled to rt. Water was added and the mixture was extracted with EtOAc (3×1 L). The organic layer was dried ($Na_2SO_4$), filtered and evaporated under reduced pressure. The residue was purified by crystallization (PE/EtOAc; 50/1 to 15/1) to afford the title compound (160 g, 90%) as a white solid. $^1H$ NMR ($CDCl_3$, 400 MHz) δ 8.42 (s, 1H), 6.81 (s, 1H), 4.27-4.30 (m, 1H), 3.94-3.96 (m, 1H), 3.56-3.61 (m, 1H), 3.28-3.31 (m, 1H), 3.04-3.09 (m, 1H), 2.68 (s, 3H), 2.24-2.26 (m, 1H), 1.70-1.89 (m, 3H), 1.45 (s, 9H).

Step C. 5-Methyl-7-(piperidin-3-yl)-[1,2,4]triazolo[1,5-a]pyrimidine. To a solution of tert-butyl 3-(5-methyl-[1,2,4]triazolo[1,5-a]pyrimidin-7-yl)piperidine-1-carboxylate (160 g, 0.504 mol) in DCM (800 mL) was added HCl/MeOH (800 mL). After stirring at 30° C. for 3 h, the reaction mixture was filtered and the solid collected and dried. The collected solid was dissolved in MeOH (1 L), treated with Amberlyst-26® (hydroxide), then filtered and concentrated. The residue was dissolved in MeOH (1 L), basified with excessive solid $Na_2CO_3$, then filtered and concentrated under reduced pressure. The residue was dissolved in DCM (600 mL) and filtered to afford the title compound (50.52 g, 46.2%) as a yellow solid. $^1H$ NMR ($CDCl_3$, 400 MHz) δ 8.53 (s, 1H), 7.16 (s, 1H), 3.48-3.54 (m, 1H), 3.27-3.29 (m, 1H), 2.96-2.99 (m, 1H), 2.69-2.75 (m, 1H), 2.58 (s, 3H), 2.48-2.53 (m, 1H), 2.06-2.09 (m, 1H). 1.53-1.74 (m, 3H).

Chiral Separation:

The racemic Intermediate 2, (8 g, 36.8 mmol) was resolved to give the pure enantiomers using a Shimadzu LC-20AP preparative HPLC with a Chiralcel® OD 250×50 mm I.D. column and eluting with 80/20 mixture of n-hexane and ethanol (0.05% IPAm). Obtained were the two pure enantiomers: The first eluted compound (3.2 g, 97.3% purity, 97.6% ee) was determined to be the (R)-stereoconfiguration. The second eluted compound (3.1 g, 97.7% purity, 96.5% ee) was determined to be the (S)-stereoconfiguration. The purified enantiomers were analyzed using a Shimadzu LC-20AB analytical HPLC instrument with a Chiralcel® OD-H, 250×4.6 mm I.D column and eluting with 80/20 mixture of n-hexane and ethanol (0.05% IPAm).

Intermediate 3. 7-(5,5-Difluoropiperidin-3-yl)-5-methyl-[1,2,4]triazolo[1,5-a]pyrimidine

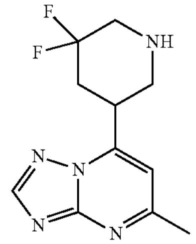 [SMILES: Cc1cc(C2CNCC(F)(F)C2)n2ncnc2n1]

Method A.

Step A. Methyl 5-hydroxynicotinate. To a solution of 5-hydroxynicotinic acid (833 g, 5.99 mol) in methanol (6.7 L) was added $H_2SO_4$ (292 mL) dropwise at a rate to keep the temperature of the mixture under 30° C. After addition, the reaction mixture was stirred at reflux for 7 days. The reaction mixture was cooled to rt and concentrated under reduce pressure. Water (4 L) was added and the mixture adjusted to pH 8 with $NaHCO_3$ which induced precipitation of a white solid. After stirring the reaction mixture for 1 h at rt, the solid was filtered and dried under vacuum at 60° C. for 3 days to afford the title compound (783 g, 85%) as a white solid. $^1H$ NMR (DMSO-$d_6$, 400 MHz) δ 10.46 (s, 1H), 8.54 (s, 1H), 8.34-8.35 (d, J=2.8 Hz, 1H), 7.59 (s, 1H), 3.85 (s, 3H).

Step B. Methyl 5-hydroxypiperidine-3-carboxylate. To a solution of methyl 5-hydroxynicotinate (100 g, 0.65 mol) in AcOH (1000 mL) was added Pd/C (20 g) at rt. The mixture was stirred under a hydrogen atmosphere (50 psi) at 60° C. overnight. The reaction mixture was cooled to rt and filtered. The filtrate was concentrated under reduce pressure to afford the title compound as a brown oil, which was used in the next step without further purification. $^1$H NMR (DMSO-$d_6$, 400 MHz) δ 3.62 (s, 3H), 2.68-2.99 (m, 4H), 2.33-2.45 (m, 1H), 2.03-2.14 (m, 2H), 1.37-1.82 (m, 3H).

Step C. 1-tert-Butyl 3-methyl 5-hydroxypiperidine-1,3-dicarboxylate. To a stirred solution of methyl 5-hydroxypiperidine-3-carboxylate (300 g, 1.89 mol) in MeOH (3 L) was added TEA (382.5 g, 3.78 mol) and $Boc_2O$ (412 g, 1.89 mol) at 0° C. The reaction mixture was stirred overnight at rt. The reaction mixture was concentrated under reduce pressure, and diluted with DCM (3 L). The mixture was washed with aq. sat. critic acid (2 L). The organic layer was separated, and the aqueous layer was extracted with DCM (3×500 mL). The combined organic layers were washed with water (1 L) and brine (500 mL), dried ($Na_2SO_4$), filtered, and concentrated under reduce pressure. Purification (FCC, $SiO_2$, PE/EtOAc, 30:1 to 5:1) afforded the title compound (170 g, 35%) as a brown solid. $^1$H NMR ($CDCl_3$, 400 MHz) δ 3.95-4.04 (m, 1H), 3.71 (s, 3H), 2.93-3.11 (m 2H), 2.89-2.92 (m, 1H), 2.57 (bs, 1H), 2.21-2.34 (m, 1H), 2.00-2.12 (m, 1H), 1.75-1.87 (m, 1H), 1.58-1.71 (m, 1H), 1.46 (s, 9H).

Step D. 1-tert-Butyl 3-methyl 5-oxopiperidine-1,3-dicarboxylate. To a solution of oxalyl chloride (98 g, 772 mmol) in anhydrous DCM (400 mL) was added a solution of DMSO (60.2 g, 772 mmol) in DCM (400 mL) dropwise at a rate so as to keep the temperature of the mixture below −60° C. under nitrogen. After stirring for 30 min, 1-tert-butyl 3-methyl 5-hydroxypiperidine-1,3-dicarboxylate (100 g, 386 mmol) was added. The mixture was stirred for 1 h at −60° C. before TEA (195.3 g, 1.93 mol) was added. The solution was further stirred for 1 h then allowed to warm to rt prior to adding ice-water (1 L). The pH of the mixture was adjusted to 6 by adding aqueous critic acid. The organic layer was separated and the aqueous layer extracted with DCM (3×300 mL). The combined organic layer was washed with water (1 L), brine (1 L), dried ($Na_2SO_4$), filtered and concentrated under reduce pressure to give the crude product as a brown oil, which was used in the next step without further purification. $^1$H NMR ($CDCl_3$, 400 MHz) δ 4.03 (s, 2H), 3.79-3.91 (m, 2H), 3.75 (s, 3H), 3.05-3.13 (m, 1H), 2.72-2.80 (m, 1H), 2.60-2.67 (m, 1H), 1.47 (s, 9H).

Step E. 1-tert-Butyl 3-methyl 5,5-difluoropiperidine-1,3-dicarboxylate. To a solution of 1-tert-butyl 3-methyl 5-oxopiperidine-1,3-dicarboxylate (102 g, 396.8 mmol) in anhydrous DCM (600 mL) was added a solution of DAST (95.8 g, 595.2 mmol) in DCM (200 mL) dropwise at −20° C. TLC (PE/EtOAc, 2:1) showed the starting material was consumed completely. The mixture was quenched with a sat. aq. $NH_4Cl$ (1 L). The organic layer was separated and the aqueous layer was extracted with DCM (2×300 mL). The combined organic layers were washed with water (500 mL), brine (500 mL), dried ($Na_2SO_4$), filtered, and concentrated under reduce pressure. Purification (FCC, $SiO_2$, PE/EtOAc, 30:1 to 5:1) afforded the title compound (87 g, 78%) as a brown oil. $^1$H NMR ($CDCl_3$, 400 MHz) δ 4.22-4.38 (m, 2H), 3.66 (s, 3H), 2.76-2.96 (m, 3H), 2.41 (bs, 1H), 1.85-2.00 (m, 1H), 1.40 (s, 9H).

Step F. 1-(tert-Butoxycarbonyl)-5,5-difluoropiperidine-3-carboxylic acid. To a solution of 1-tert-butyl 3-methyl 5,5-difluoropiperidine-1,3-dicarboxylate (220 g, 0.79 mmol) in MeOH (1425 mL) and water (75 mL) was added NaOH (48 g, 1.2 mol) in portions at 0° C. Then the reaction mixture was stirred at rt overnight. The mixture was concentrated under reduce pressure and water (1 L) was added. The pH value of the mixture was adjusted to 6 by critic acid. The resulting white solid was filtered. The filter cake was collected and dried in a vacuum drying oven to afford the title compound (173 g, 83%) as a white solid. $^1$H NMR ($CDCl_3$, 400 MHz) δ 4.17-4.32 (m, 2H), 2.76-2.92 (m, 3H), 2.40-2.42 (m, 1H), 1.89-2.03 (m, 1H), 1.40 (s, 9H).

Step G. tert-Butyl 3,3-difluoro-5-(3-oxobutanoyl)piperidine-1-carboxylate. To a solution of diisopropylamine (76 g, 754 mmol) in THF (400 mL) was added n-butyllithium (301.6 mL, 754 mmol) dropwise at −70° C. The mixture was stirred for 1 h at −70° C. Acetone (43.7 g, 754 mmol) was added dropwise at −70° C. and the mixture was stirred for 1 h at −70° C. In a separate flask, to a solution of 1-(tert-butoxycarbonyl)-5,5-difluoropiperidine-3-carboxylic acid (100 g, 377 mmol) in THF (800 mL) was added CDI (61.13 g, 377 mmol) in portions at 0° C. The mixture was stirred for 5 h at rt and then added dropwise to the enolate solution at −60° C. under a nitrogen atmosphere. The reaction mixture was stirred for 1 h at −60° C., and TLC (PE/EtOAc, 3:1) showed the starting material was consumed completely. The mixture was warmed to room temperature and EtOAc (1 L) was added. The pH value of the mixture was adjusted to 6 by with sat. aq. critic acid. The organic layer was separated, and the aqueous layer was extracted with EtOAc (2×500 mL). The combined organic layer was washed with water (500 mL) and brine (500 mL), dried ($Na_2SO_4$), filtered, and concentrated under reduce pressure. Purification (FCC, $SiO_2$, PE/EtOAc, 50:1 to 3:1) afforded the title compound (60 g, 52%) as a yellow oil. $^1$H NMR ($CDCl_3$, 400 MHz) δ 15.22 (br s, 1H), 5.52 (s, 1H), 4.17-4.32 (m, 2H), 2.76-2.92 (m, 3H), 2.40-2.42 (m, 1H), 1.97 (s, 3H), 1.40 (s, 9H).

Step H. tert-Butyl 3,3-difluoro-5-(5-methyl-[1,2,4]triazolo[1,5-a]pyrimidin-7-yl)piperidine-1-carboxylate. To a solution of tert-butyl 3,3-difluoro-5-(3-oxobutanoyl)piperidine-1-carboxylate (80 g, 262 mmol) in AcOH (400 mL) was added 4H-1,2,4-triazol-3-amine (22 g, 262 mmol) at rt. Then the reaction mixture was heated to 125° C. for 2 h. The mixture was cooled to room temperature and poured into water (1 L), and was extracted with EtOAc (3×500 mL). The combined organic layer was washed with sat. aq. $NaHCO_3$ (1 L) and brine (500 mL), dried ($Na_2SO_4$), filtered, and concentrated under reduce pressure to give the crude product (80 g) as brown oil, which was used in the next step without further purification. $^1$H NMR ($CDCl_3$, 400 MHz) δ 8.44 (s, 1H), 6.85 (s, 1H), 4.26-4.44 (m, 3H), 3.81 (bs, 1H), 3.32-3.39 (m, 2H), 2.70 (s, 3H), 1.49 (s, 9H).

Step I. 7-(5,5-Difluoropiperidin-3-yl)-5-methyl-[1,2,4]triazolo[1,5-a]pyrimidine HCl salt. To a solution of tert-butyl 3,3-difluoro-5-(5-methyl-[1,2,4]triazolo[1,5-a]pyrimidin-7-yl)piperidine-1-carboxylate (115 g, 325.8 mmol) in EtOAc (200 mL) was added a solution of 4N hydrochloric acid in EtOAc (600 mL) at 0° C. Then the reaction mixture was stirred for 3 h at rt. The resulting white precipitate was filtered, and the filter cake was collected, and used crude in the next step.

Step J. 7-(5,5-Difluoropiperidin-3-yl)-5-methyl-[1,2,4]triazolo[1,5-a]pyrimidine. 7-(5,5-Difluoropiperidin-3-yl)-5-methyl-[1,2,4]triazolo[1,5-a]pyrimidine HCl salt was mixed with DCM (500 mL) and TEA (200 mL) at 0° C. After stirring for 3 h the reaction mixture became homogeneous. Water (300 mL) was added and the organic layer separated. The aqueous layer was extracted with DCM (3×100 mL). The combined organic layer was washed with brine (300 mL), dried ($Na_2SO_4$), filtered, and concentrated under reduce pressure to afford the title compound (92 g) as a white solid. $^1$H NMR (DMSO-$d_6$, 400 MHz) δ 8.58 (s, 1H), 7.25 (s, 1H), 3.77 (t, J=11.2 Hz, 1H), 3.15-3.23 (m, 1H), 3.09-3.15 (m, 1H), 2.84-2.92 (m, 2H), 2.66-2.72 (m, 1H), 2.59 (s, 3H), 2.32-2.36 (m, 2H); [M+H]=254.1.

Method B.

Step A. tert-Butyl 3,3-difluoro-5-(5-methyl-[1,2,4]triazolo[1,5-a]pyrimidin-7-yl)piperidine-1-carboxylate. To a solution of 1-tert-butyl 3-methyl 5,5-difluoropiperidine-1,3-dicarboxylate (58.0 g, 207.6 mmol) in THF (1038 mL, 0.2M) cooled to −78° C. was added LiHMDS (207.6 mL, 207.6 mmol, 1M in THF) dropwise over 16 min. The reaction mixture was stirred at −78° C. for 45 min. before 7-chloro-5-methyl-[1,2,4]triazolo[1,5-a]pyrimidine (35.0 g, 207.61 mmol) was added. The reaction mixture temperature was raised to 0° C. and stirred for 25 min. Water (32 mL), MeOH (67 mL) and LiOH (4260 mg, 1245.7 mmol) were added and the reaction mixture was stirred at 0-25° C. for 18 h. The reaction mixture was diluted with DCM (500 mL) and quenched with $H_2O$ (500 mL). The aqueous layer was extracted with dichloromethane (2×500 mL) and the combined organic layers were dried ($Na_2SO_4$), filtered, and concentrated under reduced pressure. Purification (LC, EtOAc/MeOH/Hexane 45:5:50) afforded the title compound (62.8 g, 86%) as a yellow foam. $^1$H NMR (400 MHz, DMSO-$d_6$) δ 8.60 (s, 1H), 7.27 (s, 1H), 4.37 (d, J=13.3 Hz, 1H), 4.18 (br s, 1H), 3.69-3.80 (m, 1H), 3.37 (d, J=19.6 Hz, 1H), 3.20 (br s, 1H), 2.50-2.66 (m, 5H); [M+H]=354.4.

Step B. 7-(5,5-Difluoropiperidin-3-yl)-5-methyl-[1,2,4]triazolo[1,5-a]pyrimidine. To a solution of tert-butyl 3,3-difluoro-5-(5-methyl-[1,2,4]triazolo[1,5-a]pyrimidin-7-yl)piperidine-1-carboxylate (62.8 g, 177.7 mmol) in MeOH (444 mL, 0.4 M) cooled to 0° C. was slowly added 4N HCl in dioxane (600 mL). The mixture was stirred at 0-25° C. for 4 h and concentrated under reduced pressure to afford the title compound (58.1 g, 100%) as a beige solid (bis HCl salt). $^1$H NMR (400 MHz, DMSO-$d_6$) δ ppm 11.12 (br s, 1H), 9.87 (br s, 1H), 8.65 (s, 1H), 7.31 (s, 1H), 4.08 (tt, J=12.4, 3.6 Hz, 1H), 3.76-3.87 (m, 1H), 3.46-3.66 (m, 2H), 3.31-3.42 (m, 1H), 2.54-2.76 (m, 5H); [M+H]=254.4.

Chiral Separation:

The racemic Intermediate 3, (3.97 g, 15.3 mmol) was resolved to give the pure enantiomers using a preparative SFC instrument with a Chiralpak® OZ-H (2×25 cm) column and eluting with 25% 1:1 MeOH:ACN (0.1% $NH_4OH$)/$CO_2$, 100 bar. Obtained were the two pure enantiomers: The first eluted compound (0.51 mg, >99% purity, >99% ee) was determined to be the (R)-stereoconfiguration. The second eluted compound (0.5 g, >99% purity, >99% ee) was determined to be the (S)-stereoconfiguration. The purified enantiomers were analyzed using a Chiralpak® OZ-H (25×0.46 cm) column and eluting with 30% methanol/$CO_2$, 100 bar.

Example 1. 3-{5-Methyl-[1,2,4]triazolo[1,5-a]pyrimidin-7-yl}-1-(naphthalen-2-ylmethyl)piperidine

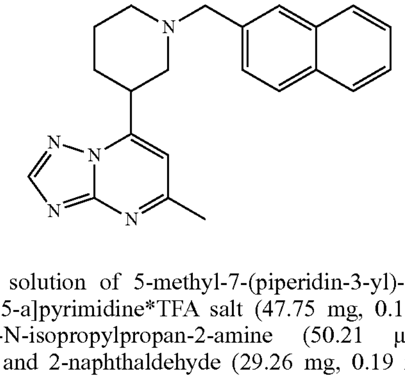

To a solution of 5-methyl-7-(piperidin-3-yl)-[1,2,4]triazolo[1,5-a]pyrimidine*TFA salt (47.75 mg, 0.14 mmol), N-ethyl-N-isopropylpropan-2-amine (50.21 μL, 0.29 mmol), and 2-naphthaldehyde (29.26 mg, 0.19 mmol) in 1,2-dichloroethane (0.50 mL) was added $NaBH(OAc)_3$ (40.00 mg, 0.19 mmol). The mixture was stirred at 50° C. for 21 h. The reaction mixture was diluted with DCM (5 mL) and water (5 mL) and the aqueous layers were extracted into DCM (3×5 mL). The combined organic extracts were dried ($MgSO_4$), filtered, and concentrated under reduced pressure. Purification (FCC, $SiO_2$, 0-10% MeOH/DCM) afforded the title compound (44.1 mg, 86%). $^1$H NMR (400 MHz, DMSO-$d_6$) δ=8.54 (s, 1H), 7.89 (d, J=8.03 Hz, 3H), 7.83 (s, 1H), 7.54 (d, J=8.41 Hz, 1H), 7.45-7.51 (m, 2H), 7.27 (s, 1H), 3.61-3.81 (m, 3H), 3.09 (d, J=10.16 Hz, 1H), 2.82 (d, J=10.54 Hz, 1H), 2.60 (s, 3H), 2.44 (t, J=9.79 Hz, 1H), 2.20-2.34 (m, 1H), 2.05 (br s, 1H), 1.63-1.81 (m, 3H); [M+H]=358.2.

Example 2. (3R)-3-{5-Methyl-[1,2,4]triazolo[1,5-a]pyrimidin-7-yl}-1-(naphthalen-2-ylmethyl)piperidine

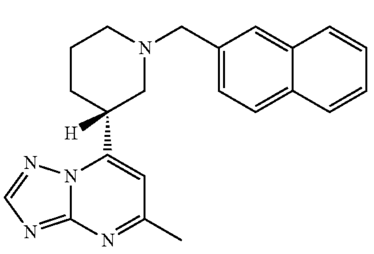 [SMILES: Cc1cc([C@@H]2CCCN(Cc3ccc4ccccc4c3)C2)n2ncnc2n1]

The racemic Example 1 (112 mg, 0.31 mmol) was resolved to give the pure enantiomers using a Thar 80 preparative SFC instrument with a Chiralpak® AD-H, 250×30 mm I.D. 5 μm column and eluting with 30% MeOH in supercritical $CO_2$. Obtained were the two pure enantiomers: The first eluted compound (title compound, 36.5 mg, 65%, 99.2% ee) was arbitrarily assigned the (R)-stereoconfiguration. The second eluted compound (40.7 mg, 72%, 95.2% ee) was assigned the (S)-stereoconfiguration, Example 3. The purified enantiomers were analyzed using a Shimadzu LC-20AB instrument with a Chiralpak® AS-H, 150×4.6 mm I.D. 5 μm column and eluting with 10% 2-propanol in hexanes. $^1$H NMR (400 MHz, $CD_3OD$) δ=8.38 (s, 1H), 7.77-7.82 (m, 4H), 7.50-7.53 (m, 1H), 7.41-7.44 (m, 2H), 7.20 (s, 1H), 3.65-3.85 (m, 3H), 3.15-3.25 (m, 1H), 2.84-2.96 (m, 1H), 2.63 (s, 3H), 2.40-2.50 (m, 1H), 2.30-2.39 (m, 1H), 2.04-2.18 (m, 1H), 1.70-1.86 (m, 3H); [M+H]=358.2.

Example 3. (3S)-3-{5-Methyl-[1,2,4]triazolo[1,5-a]pyrimidin-7-yl}-1-(naphthalen-2-ylmethyl)piperidine

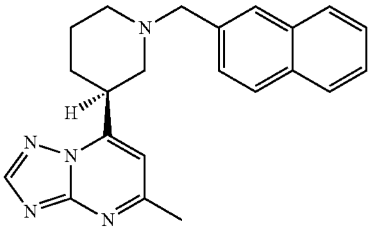 [SMILES: Cc1cc([C@H]2CCCN(Cc3ccc4ccccc4c3)C2)n2ncnc2n1]

The title compound was prepared in a manner analogous to Example 2. $^1$H NMR (400 MHz, $CD_3OD$) δ=8.38 (s, 1H), 7.77-7.82 (m, 4H), 7.50-7.53 (m, 1H), 7.41-7.44 (m, 2H), 7.20 (s, 1H), 3.65-3.85 (m, 3H), 3.15-3.25 (m, 1H), 2.84-2.96 (m, 1H), 2.63 (s, 3H), 2.40-2.50 (m, 1H), 2.30-2.39 (m, 1H), 2.04-2.18 (m, 1H), 1.70-1.86 (m, 3H); [M+H]=358.2.

Example 4. (3-(5-Methyl-[1,2,4]triazolo[1,5-a]pyrimidin-7-yl)piperidin-1-yl)(naphthalen-2-yl)methanone

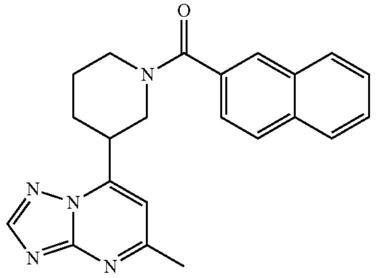 [SMILES: Cc1cc(C2CCCN(C(=O)c3ccc4ccccc4c3)C2)n2ncnc2n1]

To a solution of 5-methyl-7-(piperidin-3-yl)-[1,2,4]triazolo[1,5-a]pyrimidine (21.7 mg, 0.10 mmol), DIPEA (80 μL, 0.50 mmol) in DCM (1 mL), was added a solution of 2-naphthoyl chloride (28.6 mg, 0.15 mmol) in DCM (1 mL). The mixture was stirred overnight at rt. The reaction was washed with a 10% aq NaOH, dried ($K_2CO_3$), filtered and concentrated under reduced pressure. Purification (reverse-phase prep-LCMS with a solvent gradient of 5-95% ACN in water with 0.1% added TFA) afforded the title compound. The combined pure fractions were concentrated under reduced pressure and neutralized with sat. aq. $NaHCO_3$, extracted into DCM, dried ($Na_2SO_4$), filtered, and concentrated under reduced pressure to afford the title compound (23 mg, 62%). $^1H$ NMR (400 MHz, $CDCl_3$) δ=8.00 (s, 1H), 7.84-7.96 (m, 3H), 7.58 (dd, J=6.15, 3.14 Hz, 2H), 7.51 (d, J=8.41 Hz, 1H), 3.78 (br s, 1H), 3.00-3.69 (m, 2H), 2.73 (br s, 3H), 2.39 (br s, 1H), 1.94-2.14 (m, 1H); [M+H]=372.2.

Example 5. (2,3-Dihydro-1H-inden-5-yl)(3-(5-methyl-[1,2,4]triazolo[1,5-a]pyrimidin-7-yl)piperidin-1-yl)methanone

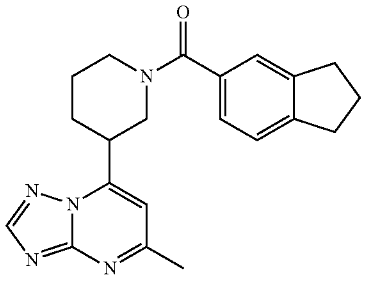 [SMILES: Cc1cc(C2CCCN(C(=O)c3ccc4c(c3)CCC4)C2)n2ncnc2n1]

To a solution of 2,3-dihydro-1H-indene-5-carboxylic acid (42.93 mg, 0.26 mmol) in DMF (0.5 mL), was added DIPEA (0.10 mL, 0.57 mmol) and 2-(3H-[1,2,3]triazolo[4,5-b]pyridin-3-yl)-1,1,3,3-tetramethylisouronium hexafluorophosphate(V) (104.52 mg, 0.27 mmol). The mixture was stirred in a sealed vial at rt. After 30 min, 5-methyl-7-(piperidin-3-yl)-[1,2,4]triazolo[1,5-a]pyrimidine (55.30 mg, 0.25 mmol) in DMF (0.5 mL) was added and the mixture stirred at rt for an additional 16 h. The mixture was diluted with DMF, filtered and purified (reverse-phase prep-HPLC, 15-60% ACN/$H_2O$/0.1% TFA) to obtain the title compound as the TFA salt (56 mg, 40%). $^1H$ NMR (400 MHz, DMSO-$d_6$) δ=8.56 (br s, 1H) 6.96-7.53 (m, 4H) 3.91-4.95 (m, 1H) 3.53-3.85 (m, 1H) 3.21-3.47 (m, 1H) 2.97-3.20 (m, 1H) 2.88 (br s, 4H) 2.63 (s, 3H) 2.13-2.28 (m, 1H) 1.78-2.10 (m, 4H) 1.48-1.75 (m, 2H); [M+H]=362.2.

Example 6. (S)-(3-(5-Methyl-[1,2,4]triazolo[1,5-a]pyrimidin-7-yl)piperidin-1-yl)(naphthalen-2-yl)methanone

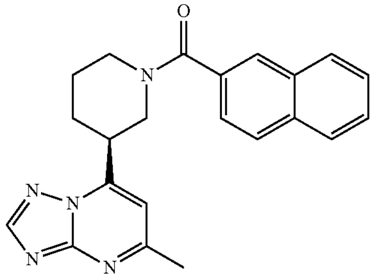 [SMILES: Cc1cc([C@H]2CCCN(C(=O)c3ccc4ccccc4c3)C2)n2ncnc2n1]

The racemic Example 4, (101 mg, 0.27 mmol) was resolved to give the pure enantiomers using a Thar 80 preparative SFC instrument with a Chiralpak® AS-H, 250×30 mm I.D. 5 μm column and eluting with 30% MeOH in supercritical $CO_2$. Obtained were the two pure enantiomers: The first eluted compound (title compound, 35.5 mg, 70%, >99% ee) was arbitrarily assigned the (S)-stereoconfiguration. The second eluted compound (36.1 mg, 71%, 97.7% ee) was assigned the (R)-stereoconfiguration. The purified enantiomers were analyzed using a Shimadzu LC-20AB instrument with a Chiralpak® AS-H, 150×4.6 mm I.D. 5 μm column and eluting with 40% ethanol in hexanes. $^1H$ NMR (400 MHz, $CD_3OD$) δ=8.40-8.60 (m, 1H), 7.80-8.10 (m, 4H), 7.40-7.60 (m, 3H), 7.05-7.25 (m, 1H), 4.60-5.00 (m, 1H), 4.20-4.35 (m, 1H), 3.70-3.90 (m, 1H), 3.30-3.50 (m, 1H), 3.10-3.25 (m, 1H), 2.55-2.70 (m, 3H), 2.25-2.40 (m, 1H), 1.70-2.20 (m, 3H); [M+H]=372.1.

Example 7. (3-(5-Methyl-[1,2,4]triazolo[1,5-a]pyrimidin-7-yl)piperidin-1-yl)(quinolin-4-yl)methanone

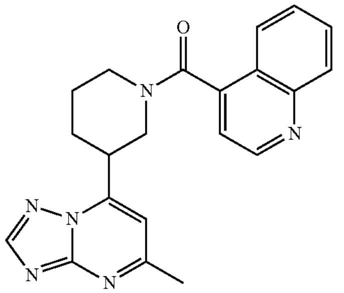 [SMILES: Cc1cc(C2CCCN(C(=O)c3ccnc4ccccc34)C2)n2ncnc2n1]

To a 1 dram screw cap vial was added quinoline-4-carboxylic acid (0.11 mmol), HATU (0.2 mL of a 0.55 M solution in DMF, 0.11 mmol) and DIPEA (20 μL, 0.11 mmol). The mixture was stirred at rt for 30 min then 5-methyl-7-(piperidin-3-yl)-[1,2,4]triazolo[1,5-a]pyrimidine (0.109 mmol, 0.6 mL of a 0.1817 M solution in DIPEA and DMF) was added. The vial was sealed and shaken at rt overnight. The mixture was filtered, a 5 μL aliquot taken and diluted with 200 μL DMF and an analytical reverse-phase-UPLC was taken. The desired product mass was observed. Subsequently, based on the retention time of the desired product from the analytical UPLC, a corresponding PREP-HPLC gradient was recommended and the compound was purified. Obtained was the title compound (15 mg, 29%) as the TFA salt. [M+H]=373.2.

Example 8. (2-(5-Methyl-[1,2,4]triazolo[1,5-a]pyrimidin-7-yl)morpholino)(quinolin-2-yl)methanone

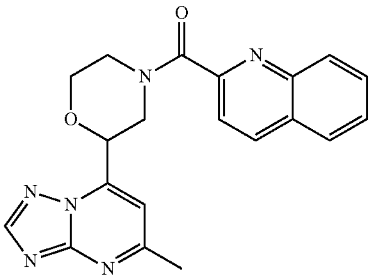 [SMILES: Cc1cc(C2CN(C(=O)c3ccc4ccccc4n3)CCO2)n2ncnc2n1]

2-(5-Methyl-[1,2,4]triazolo[1,5-a]pyrimidin-7-yl)morpholine (50.00 mg, 0.23 mmol) was dissolved in DCM (1.14 mL). DIPEA (79.45 μL, 0.46 mmol) and O-(benzotriazol-1-yl)-N,N,N',N'-tetramethyluronium hexafluorophosphate (121.04 mg, 0.27 mmol) was added, followed by quinoline-2-carboxylic acid (47.39 mg, 0.27 mmol). The reaction was stirred at room temperature overnight and then concentrated under reduced pressure. Purification (FCC, $SiO_2$, 0-5% MeOH/DCM) then purification by reverse phase HPLC afforded the title compound as an off white solid (41.00 mg, 37%). $^1$H NMR (400 MHz, DMSO-$d_6$) δ=8.69-8.25 (m, 2H), 8.15-7.99 (m, 2H), 7.88-7.81 (m, 1H), 7.80-7.74 (m, 1H), 7.72-7.66 (m, 1H), 7.35-7.23 (m, 1H), 5.45-5.24 (m, 1H), 4.79-4.38 (m, 1H), 4.29-4.00 (m, 1H), 3.89 (d, J=11.0 Hz, 1H), 3.50-3.39 (m, 1H), 3.31-3.19 (m, 1H), 3.03-2.93 (m, 1H), 2.69-2.57 (m, 3H); [M+H]=375.

Example 9. (3,3-Difluoro-5-(5-methyl-[1,2,4]triazolo[1,5-a]pyrimidin-7-yl)piperidin-1-yl)(3-iodo-4-methoxyphenyl)methanone

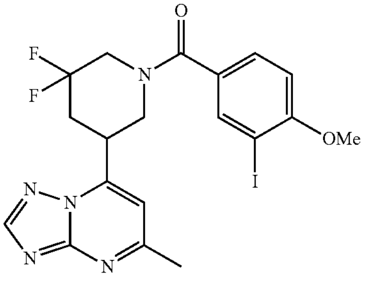 [SMILES: COc1ccc(C(=O)N2CC(c3cc(C)nc4ncnn34)CC(F)(F)C2)cc1I]

To a solution of 7-(5,5-difluoropiperidin-3-yl)-5-methyl-[1,2,4]triazolo[1,5-a]pyrimidine (35 mg, 0.10 mmol) in DCM (0.32 mL) was added TEA (15.94 μl, 0.11 mmol), 3-iodo-4-methoxybenzoic acid (26.50 mg, 0.10 mmol), HOBt (17.51 mg, 0.11 mmol) and EDCI (21.92 mg, 0.11 mmol). The reaction was stirred at rt for 16 h. The crude reaction was filtered and the residue was purified by preparative reverse phase HPLC to afford the title compound (14 mg, 29%). $^1$H NMR (400 MHz, $CDCl_3$) δ=8.58 (s, 1H), 7.95 (d, J=1.96 Hz, 1H), 7.50 (dd, J=8.41, 2.15 Hz, 1H), 6.94 (br s, 1H), 6.86 (d, J=8.61 Hz, 1H), 4.52-4.85 (m, 1H), 4.03 (br s, 2H), 3.88-3.99 (m, 3H), 3.23-3.58 (m, 2H), 2.65-2.76 (m, 5H), [M+H]=514.1.

Example 10. (3R)-1-[(3R)-3,4-Dihydro-2H-1-benzopyran-3-carbonyl]-3-{5-methyl-[1,2,4]triazolo[1,5-a]pyrimidin-7-yl}piperidine

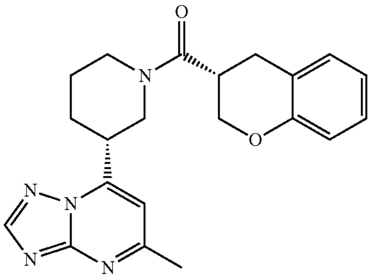 [SMILES: Cc1cc([C@@H]2CCCN(C(=O)[C@H]3COc4ccccc4C3)C2)n2ncnc2n1]

Preparative supercritical fluid chromatography (SFC) was performed using a 2.1 cm×25 cm (S,S) WhelkO®-1 column from Regis Technologies under isocratic condition using $CO_2$ with 45% of MeOH as the co-solvent at 70 mL per minutes, 100 bar, and 25° C. Elution profiles were monitored at UV. $^1$H NMR (400 MHz, $CDCl_3$) δ=8.50-8.35 (m, 1H), 7.20-6.77 (m, 5H), 4.92-4.74 (m, 1H), 4.71-4.55 (m, 1H), 4.44-3.97 (m, 2H), 3.60 (d, J=3.5 Hz, 1H), 3.42-2.62 (m, 8H), 2.47-2.24 (m, 1H), 2.10-1.91 (m, 2H), 1.78 (d, J=10.2 Hz, 1H); [M+H]=377.7.

Example 11. 7-(1-(3-Bromobenzyl)piperidin-3-yl)-5-methyl-[1,2,4]triazolo[1,5-a]pyrimidine

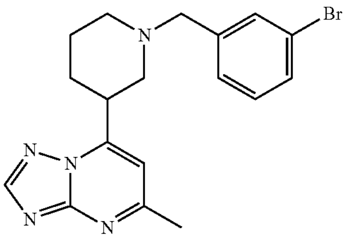 [SMILES: Cc1cc(C2CCCN(Cc3cccc(Br)c3)C2)n2ncnc2n1]

To 5-methyl-7-(piperidin-3-yl)-[1,2,4]triazolo[1,5-a]pyrimidine hydrochloride (136 mg, 0.53 mmol) suspended in a mixture of DCE (1 mL) and MeOH (1 mL) was added DIPEA (280 μL, 1.60 mmol). The suspension was sonicated until the mixture became completely homogeneous. To this solution was added 3-bromobenzaldehyde (75 μL, 0.64 mmol) followed by $NaBH_3CN$ (321 μL, 1.00 mol/L, 0.32 mmol) in THF. The resulting milky mixture was stirred at rt overnight. After diluting with DCM, the reaction mixture was washed with sat. $NaHCO_3$ and concentrated. Purification (FCC, $SiO_2$, 0-5% MeOH/DCM) afforded the title compound as a yellow oil (75.3 mg, 37%). $^1$H NMR (400

MHz, DMSO-$d_6$) δ=8.62 (s, 2H), 7.82 (br s, 1H), 7.70 (d, J=8.16 Hz, 1H), 7.55 (d, J=7.28 Hz, 1H), 7.41-7.48 (m, 1H), 7.24 (s, 1H), 4.33-4.47 (m, 2H), 3.94 (br s, 1H), 3.79 (d, J=11.67 Hz, 1H), 3.53 (d, J=11.67 Hz, 1H), 3.32 (t, J=11.11 Hz, 1H), 3.06 (br s, 1H), 2.65 (s, 3H), 1.78-2.25 (m, 4H); [M+H]=386.1, 388.1.

Example 12. 7-(1-((4'-Chloro-3,5-difluoro-[1,1'-biphenyl]-4-yl)methyl)piperidin-3-yl)-5-methyl-[1,2,4]triazolo[1,5-a]pyrimidine

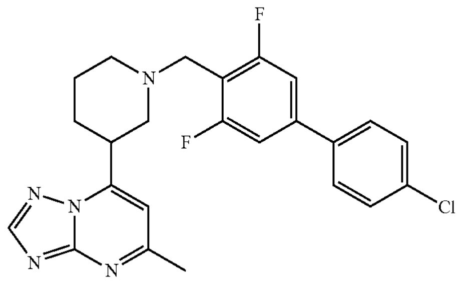 [SMILES: Cc1cc(C2CCCN(Cc3c(F)cc(-c4ccc(Cl)cc4)cc3F)C2)n2ncnc2n1]

A mixture consisting of 7-(1-(4-Bromo-2,6-difluorobenzyl)piperidin-3-yl)-5-methyl-[1,2,4]triazolo[1,5-a]pyrimidine (65 mg, 0.15 mmol), $Pd(PPh_3)_4$ (18 mg, 0.02 mmol), 4-chloro-phenyl-boronic acid (48 mg, 0.31 mmol) and $K_2CO_3$ (54 mg, 0.39 mmol) in ethyleneglycol dimethyl ether (1.50 mL), EtOH (0.50 mL) and water (0.50 mL) was heated employing microwave irradiation at 140° C. for 20 min. The reaction mixture was diluted with EtOAc, washed with water and concentrated to afford crude material that was purified (reverse-phase prep-HPLC, 20-80% ACN/$H_2O$/0.1% TFA) to obtain the title compound as the trifluoroacetate salt (36 mg, 41%). $^1H$ NMR (400 MHz, DMSO-$d_6$) δ=8.61 (s, 1H), 7.84 (d, J=8.53 Hz, 2H), 7.68 (d, J=9.16 Hz, 2H), 7.57 (d, J=8.41 Hz, 2H), 7.22 (s, 1H), 4.41 (br s, 2H), 3.50-3.86 (m, 3H), 2.86-3.26 (m, 2H), 2.63 (s, 3H), 1.72-2.18 (m, 4H); [M+H]=454.2, 456.2.

Example 13. 7-(1-([1,1'-Biphenyl]-4-ylmethyl)piperidin-3-yl)-5-methyl-[1,2,4]triazolo[1,5-a]pyrimidine

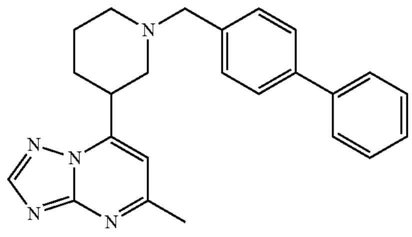 [SMILES: Cc1cc(C2CCCN(Cc3ccc(-c4ccccc4)cc3)C2)n2ncnc2n1]

To 5-methyl-7-(piperidin-3-yl)-[1,2,4]triazolo[1,5-a]pyrimidine hydrochloride (308.00 mg, 1.21 mmol) suspended in 1,2-dichloroethane (1.20 mL) and MeOH (1.20 mL) was added DIPEA (212 μL, 1.21 mmol) and sonicated until fully dissolved. The solution was diluted to a final volume of 3 mL with DCE/MeOH (1:1) to reach a final concentration of 0.40 M. To 1 dram screw cap vials containing triazolo[1,5-a]pyrimidine solution (250 μL, 0.1 mmol) and [1,1'-biphenyl]-4-carbaldehyde (20 mg, 0.11 mmol) dissolved in DCE/MeOH (110 μL) were added, AcOH (58 μL, 0.1 mmol) and $NaBH_3CN$ (100 μL, 1.00 mol/L) dissolved in THF. The vial containing the resultant milky mixture was sealed and shaken at rt overnight. After the required time, the reaction vial was diluted with 200 μL of DCE/MeOH (1:1), filtered through a 100 mg $SiO_2$ filter plate wetted with 200 μL of DCE/MeOH (1:1) and eluted with an additional 200 μL of DCE/MeOH (1:1). The solutions were quality controlled after filtration to ensure product elution and the reaction vials containing material concentrated under reduced pressure. Based on the retention time of the desired product from the analytical UPLC, a corresponding PREP-HPLC gradient was recommended and the compound purified.

Examples 14-39 were prepared in a manner analogous to Example 12, with the appropriate starting material and reagent substitutions.

Example 14. 1-{[4-(3-Chlorophenyl)-2,6-difluorophenyl]methyl}-3-{5-methyl-[1,2,4]triazolo[1,5-a]pyrimidin-7-yl}piperidine

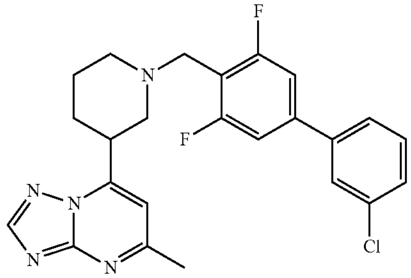 [SMILES: Cc1cc(C2CCCN(Cc3c(F)cc(-c4cccc(Cl)c4)cc3F)C2)n2ncnc2n1]

$^1H$ NMR (400 MHz, DMSO-$d_6$) δ=8.62 (s, 1H), 7.90 (s, 1H), 7.69-7.81 (m, 3H), 7.51-7.58 (m, 2H), 7.21 (s, 1H), 4.41 (br s, 2H), 3.72-4.05 (m, 2H), 3.32-3.65 (m, 2H), 3.12 (br s, 1H), 2.64 (s, 3H), 1.77-2.18 (m, 4H); [M+H]=454.2.

Example 15. 1-{[4-(2-Chlorophenyl)-2,6-difluorophenyl]methyl}-3-{5-methyl-[1,2,4]triazolo[1,5-a]pyrimidin-7-yl}piperidine

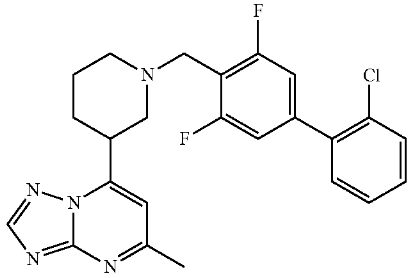 [SMILES: Cc1cc(C2CCCN(Cc3c(F)cc(-c4ccccc4Cl)cc3F)C2)n2ncnc2n1]

$^1H$ NMR (400 MHz, DMSO-$d_6$) δ=8.61 (s, 1H), 7.60-7.65 (m, 1H), 7.45-7.52 (m, 3H), 7.40 (d, J=8.41 Hz, 2H), 7.23 (s, 1H), 3.72-4.66 (m, 4H), 3.51 (br s, 2H), 3.15 (br s, 1H), 2.64 (s, 3H), 1.78-2.19 (m, 4H); [M+H]=454.2.

Example 16. 1-{[4-(4-Chlorophenyl)phenyl]methyl}-3-{5-methyl-[1,2,4]triazolo[1,5-a]pyrimidin-7-yl}piperidine

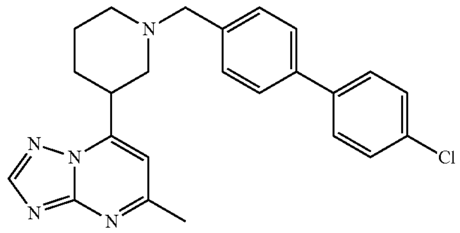 [SMILES: Cc1cc(C2CCCN(Cc3ccc(-c4ccc(Cl)cc4)cc3)C2)n2ncnc2n1]

$^1$H NMR (400 MHz, DMSO-$d_6$) δ=8.60 (s, 1H), 7.70-7.85 (m, 4H), 7.62 (d, J=8.03 Hz, 2H), 7.55 (d, J=8.41 Hz, 2H), 7.23 (s, 1H), 4.42 (br s, 2H), 3.94 (br s, 1H), 3.50-3.86 (m, 2H), 3.32 (br s, 1H), 3.05 (br s, 1H), 2.63 (s, 3H), 2.01-2.20 (m, 2H), 1.87 (br s, 2H); [M+H]=418.2.

Example 17. 1-{[4-(3-Chlorophenyl)phenyl]methyl}-3-{5-methyl-[1,2,4]triazolo[1,5-a]pyrimidin-7-yl}piperidine

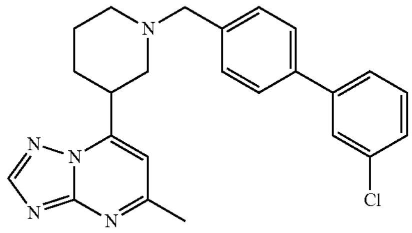 [SMILES: Cc1cc(C2CCCN(Cc3ccc(-c4cccc(Cl)c4)cc3)C2)n2ncnc2n1]

$^1$H NMR (400 MHz, DMSO-$d_6$) δ=10.02 (br s, 1H), 8.62 (s, 1H), 7.85 (d, J=7.91 Hz, 2H), 7.79 (s, 1H), 7.70 (d, J=7.65 Hz, 1H), 7.65 (d, J=8.03 Hz, 2H), 7.46-7.57 (m, 2H), 7.25 (s, 1H), 4.44 (br s, 2H), 3.71-4.09 (m, 2H), 3.57 (d, J=9.79 Hz, 1H), 3.35 (d, J=11.17 Hz, 1H), 3.07 (br s, 1H), 2.65 (s, 3H), 1.79-2.22 (m, 4H); [M+H]=418.2.

Example 18. 1-{[4-(2-Chlorophenyl)phenyl]methyl}-3-{5-methyl-[1,2,4]triazolo[1,5-a]pyrimidin-7-yl}piperidine

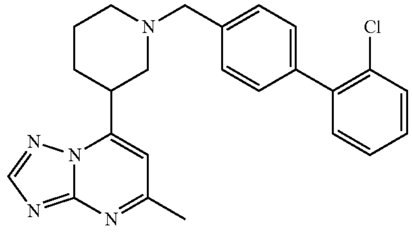 [SMILES: Cc1cc(C2CCCN(Cc3ccc(-c4ccccc4Cl)cc3)C2)n2ncnc2n1]

$^1$H NMR (400 MHz, DMSO-$d_6$) δ=10.04 (br s, 1H), 8.61 (s, 1H), 7.53-7.69 (m, 5H), 7.40-7.50 (m, 3H), 7.26 (s, 1H), 4.46 (br s, 2H), 3.96 (br s, 1H), 3.85 (d, J=11.80 Hz, 1H), 3.58 (d, J=11.42 Hz, 1H), 3.36 (br s, 1H), 3.10 (br s, 1H), 2.66 (s, 3H), 1.78-2.25 (m, 4H); [M+H]=418.2.

Example 19. 1-{[4-(2-Chloro-4-fluorophenyl)phenyl]methyl}-3-{5-methyl-[1,2,4]triazolo[1,5-a]pyrimidin-7-yl}piperidine

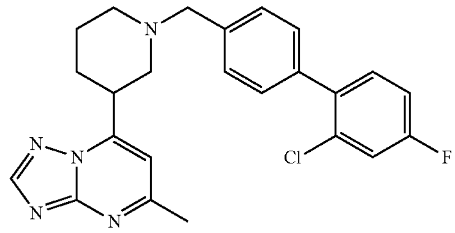 [SMILES: Cc1cc(C2CCCN(Cc3ccc(-c4ccc(F)cc4Cl)cc3)C2)n2ncnc2n1]

$^1$H NMR (400 MHz, DMSO-$d_6$) δ=10.00 (br s, 1H), 8.57-8.70 (m, 1H), 7.59-7.67 (m, 3H), 7.53-7.59 (m, 2H), 7.48 (dd, J=6.34, 8.47 Hz, 1H), 7.36 (dt, J=2.51, 8.47 Hz, 1H), 7.26 (s, 1H), 4.45 (br s, 2H), 3.94 (d, J=11.17 Hz, 2H), 3.58 (d, J=12.05 Hz, 1H), 3.36 (d, J=9.41 Hz, 1H), 3.09 (br s, 1H), 2.62-2.70 (m, 3H), 1.81-2.24 (m, 4H); [M+H]=436.2.

Example 20. 1-{[4-(4-Chlorophenyl)-2-fluorophenyl]methyl}-3-{5-methyl-[1,2,4]triazolo[1,5-a]pyrimidin-7-yl}piperidine

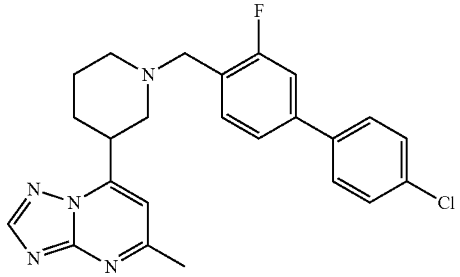 [SMILES: Cc1cc(C2CCCN(Cc3ccc(-c4ccc(Cl)cc4)cc3F)C2)n2ncnc2n1]

$^1$H NMR (400 MHz, DMSO-$d_6$) δ=10.16 (br s, 1H), 8.62 (s, 1H), 7.81 (d, J=8.41 Hz, 2H), 7.67-7.77 (m, 3H), 7.58 (d, J=8.41 Hz, 2H), 7.23 (s, 1H), 4.47 (br s, 2H), 3.75-4.14 (m, 2H), 3.58 (br s, 1H), 3.41 (br s, 1H), 3.12 (br s, 1H), 2.65 (s, 3H), 1.76-2.23 (m, 4H); [M+H]=436.2.

Example 21. 1-{[4-(3-Chlorophenyl)-2-fluorophenyl]methyl}-3-{5-methyl-[1,2,4]triazolo[1,5-a]pyrimidin-7-yl}piperidine

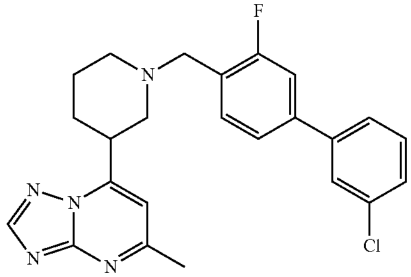 [SMILES: Cc1cc(C2CCCN(Cc3ccc(-c4cccc(Cl)c4)cc3F)C2)n2ncnc2n1]

$^1$H NMR (400 MHz, DMSO-$d_6$) δ=10.17 (br s, 1H), 8.63 (s, 1H), 7.86 (s, 1H), 7.69-7.82 (m, 4H), 7.49-7.58 (m, 2H), 7.24 (s, 1H), 4.47 (br s, 2H), 3.98 (br s, 1H), 3.84 (br s, 1H), 3.57 (br s, 1H), 3.42 (br s, 1H), 3.13 (br s, 1H), 2.65 (s, 3H), 1.78-2.22 (m, 4H); [M+H]=436.2.

Example 22. 1-{[4-(2-Chlorophenyl)-2-fluorophenyl]methyl}-3-{5-methyl-[1,2,4]triazolo[1,5-a]pyrimidin-7-yl}piperidine

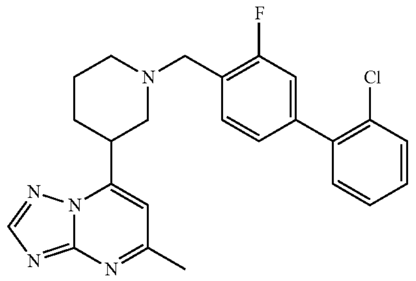 [SMILES: Cc1cc(C2CCCN(Cc3ccc(-c4ccccc4Cl)cc3F)C2)n2ncnc2n1]

$^1$H NMR (400 MHz, DMSO-$d_6$) δ=10.22 (br s, 1H), 8.62 (s, 1H), 7.74 (t, J=7.65 Hz, 1H), 7.59-7.66 (m, 1H), 7.40-7.53 (m, 5H), 7.25 (s, 1H), 4.49 (br s, 2H), 3.77-4.09 (m, 2H), 3.33-3.71 (m, 2H), 3.17 (br s, 1H), 2.66 (s, 3H), 1.84-2.21 (m, 4H); [M+H]=436.2.

Example 23. 4-{3-Fluoro-4-[(3-{5-methyl-[1,2,4]triazolo[1,5-a]pyrimidin-7-yl}piperidin-1-yl)methyl]phenyl}pyridine

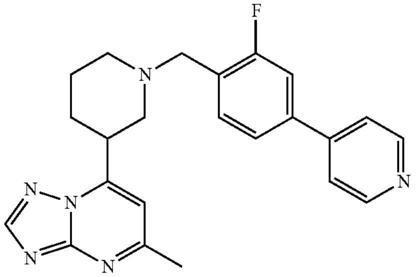 [SMILES: Cc1cc(C2CCCN(Cc3ccc(-c4ccncc4)cc3F)C2)n2ncnc2n1]

$^1$H NMR (400 MHz, DMSO-$d_6$) δ=10.10 (br s, 1H), 8.61 (s, 1H), 7.98 (d, J=5.14 Hz, 1H), 7.87 (br s, 1H), 7.73 (d, J=8.41 Hz, 2H), 7.59 (d, J=8.41 Hz, 2H), 7.46 (t, J=8.97 Hz, 1H), 7.24 (s, 1H), 4.49 (br s, 2H), 3.71-4.09 (m, 2H), 3.58 (br s, 1H), 3.44 (br s, 1H), 3.16 (br s, 1H), 2.65 (s, 3H), 1.78-2.23 (m, 4H); [M+H]=403.2.

Example 24. 1-{[5-(2-Chlorophenyl)-2-fluorophenyl]methyl}-3-{5-methyl-[1,2,4]triazolo[1,5-a]pyrimidin-7-yl}piperidine

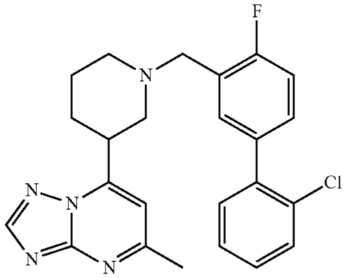 [SMILES: Cc1cc(C2CCCN(Cc3cc(-c4ccccc4Cl)ccc3F)C2)n2ncnc2n1]

$^1$H NMR (400 MHz, DMSO-$d_6$) δ=10.19 (br s, 1H), 8.59 (s, 1H), 7.72 (d, J=6.27 Hz, 1H), 7.55-7.68 (m, 2H), 7.40-7.52 (m, 4H), 7.22 (s, 1H), 4.47 (br s, 2H), 3.95 (br s, 1H), 3.84 (br s, 1H), 3.57 (br s, 1H), 3.38 (br s, 1H), 3.13 (br s, 1H), 2.64 (s, 3H), 1.79-2.19 (m, 4H); [M+H]=436.2.

Example 25. 1-{[5-(2-Chloro-4-fluorophenyl)-2-fluorophenyl]methyl}-3-{5-methyl-[1,2,4]triazolo[1,5-a]pyrimidin-7-yl}piperidine

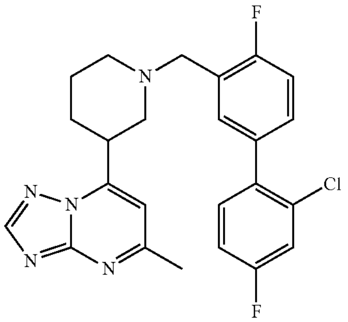 [SMILES: Cc1cc(C2CCCN(Cc3cc(-c4ccc(F)cc4Cl)ccc3F)C2)n2ncnc2n1]

$^1$H NMR (400 MHz, DMSO-$d_6$) δ=9.96-10.24 (br s, 1H), 8.59 (s, 1H), 7.70 (d, J=7.03 Hz, 1H), 7.61 (dd, J=2.45, 8.85 Hz, 2H), 7.42-7.54 (m, 2H), 7.37 (dt, J=2.38, 8.47 Hz, 1H), 7.22 (s, 1H), 4.47 (br s, 2H), 3.71-4.09 (m, 2H), 3.58 (br s, 1H), 3.38 (br s, 1H), 3.12 (br s, 1H), 2.64 (s, 3H), 1.77-2.20 (m, 4H); [M+H]=454.2.

Example 26. 3-{4-Fluoro-3-[(3-{5-methyl-[1,2,4]triazolo[1,5-a]pyrimidin-7-yl}piperidin-1-yl)methyl]phenyl}pyridine

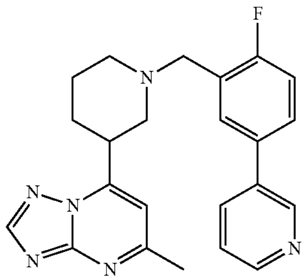 [SMILES: Cc1cc(C2CCCN(Cc3cc(-c4cccnc4)ccc3F)C2)n2ncnc2n1]

$^1$H NMR (400 MHz, DMSO-$d_6$) δ=8.98 (d, J=1.76 Hz, 1H), 8.51-8.76 (m, 2H), 8.20 (d, J=7.91 Hz, 1H), 8.06 (d, J=6.02 Hz, 1H), 7.92-8.00 (m, 1H), 7.63 (dd, J=4.89, 7.91 Hz, 1H), 7.52 (t, J=9.10 Hz, 1H), 7.24 (s, 1H), 4.51 (br s, 2H), 3.82-4.06 (m, 2H), 3.58 (br s, 1H), 3.46 (br s, 1H), 3.17 (br s, 1H), 2.62-2.70 (m, 3H), 1.81-2.23 (m, 4H); [M+H]=403.2.

Example 27. 4-{4-Fluoro-3-[(3-{5-methyl-[1,2,4]triazolo[1,5-a]pyrimidin-7-yl}piperidin-1-yl)methyl]phenyl}pyridine

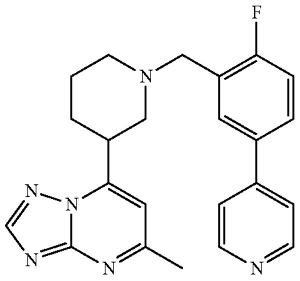 [SMILES: Cc1cc(C2CCCN(Cc3cc(-c4ccncc4)ccc3F)C2)n2ncnc2n1]

$^1$H NMR (400 MHz, DMSO-$d_6$) δ=8.85 (d, J=5.90 Hz, 2H), 8.59 (s, 1H), 8.22 (d, J=5.27 Hz, 1H), 8.08-8.15 (m, 1H), 8.00 (d, J=5.77 Hz, 2H), 7.57 (t, J=9.10 Hz, 1H), 7.24 (s, 1H), 4.52 (br s, 2H), 3.99 (br s, 1H), 3.86 (br s, 1H), 3.38-3.66 (m, 2H), 3.17 (br s, 1H), 2.65 (s, 3H), 1.80-2.22 (m, 4H); [M+H]=403.2.

Example 28. 1-{[3-(4-Chlorophenyl)phenyl]methyl}-3-{5-methyl-[1,2,4]triazolo[1,5-a]pyrimidin-7-yl}piperidine

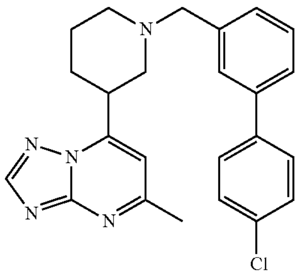 [SMILES: Cc1cc(C2CCCN(Cc3cccc(-c4ccc(Cl)cc4)c3)C2)n2ncnc2n1]

$^1$H NMR (400 MHz, DMSO-$d_6$) δ=10.06 (br s, 1H), 8.58 (s, 1H), 7.87 (s, 1H), 7.78 (d, J=7.53 Hz, 1H), 7.73 (d, J=8.53 Hz, 2H), 7.49-7.62 (m, 4H), 7.23 (s, 1H), 4.44 (br s, 2H), 3.94 (br s, 1H), 3.84 (d, J=11.29 Hz, 1H), 3.55 (d, J=11.04 Hz, 1H), 3.32 (br s, 1H), 3.07 (br s, 1H), 2.63 (s, 3H), 1.79-2.23 (m, 4H); [M+H]=418.2.

Example 29. 1-{[3-(3-Chlorophenyl)phenyl]methyl}-3-{5-methyl-[1,2,4]triazolo[1,5-a]pyrimidin-7-yl}piperidine

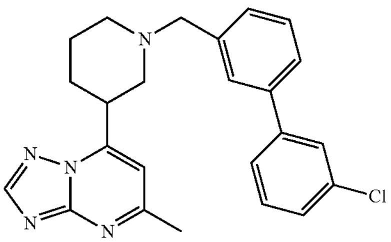 [SMILES: Cc1cc(C2CCCN(Cc3cccc(-c4cccc(Cl)c4)c3)C2)n2ncnc2n1]

$^1$H NMR (400 MHz, DMSO-$d_6$) δ=10.03 (br s, 1H), 8.58 (s, 1H), 7.90 (s, 1H), 7.82 (d, J=7.15 Hz, 1H), 7.77 (s, 1H), 7.68 (d, J=7.53 Hz, 1H), 7.44-7.63 (m, 4H), 7.24 (s, 1H), 4.45 (br s, 2H), 3.94 (br s, 1H), 3.84 (d, J=11.04 Hz, 1H), 3.55 (d, J=11.17 Hz, 1H), 3.34 (d, J=7.15 Hz, 1H), 3.07 (br s, 1H), 2.63 (s, 3H), 1.78-2.25 (m, 4H); [M+H]=418.2.

Example 30. 1-{[3-(2-Chlorophenyl)phenyl]methyl}-3-{5-methyl-[1,2,4]triazolo[1,5-a]pyrimidin-7-yl}piperidine

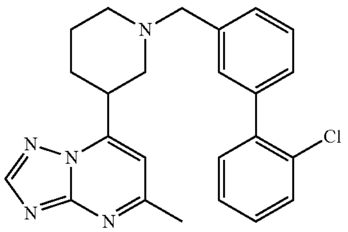 [SMILES: Cc1cc(C2CCCN(Cc3cccc(-c4ccccc4Cl)c3)C2)n2ncnc2n1]

$^1$H NMR (400 MHz, DMSO-$d_6$) δ=10.02 (br s, 1H), 8.58 (s, 1H), 7.52-7.64 (m, 5H), 7.40-7.47 (m, 3H), 7.23 (s, 1H), 4.44 (d, J=10.79 Hz, 2H), 3.93 (br s, 1H), 3.82 (d, J=11.29 Hz, 1H), 3.57 (d, J=10.92 Hz, 1H), 3.31 (d, J=8.91 Hz, 1H), 3.06 (br s, 1H), 2.64 (s, 3H), 1.79-2.21 (m, 4H); [M+H]=418.2.

Example 31. 4-{4-[(3-{5-Methyl-[1,2,4]triazolo[1,5-a]pyrimidin-7-yl}piperidin-1-yl)methyl]phenyl}pyridine

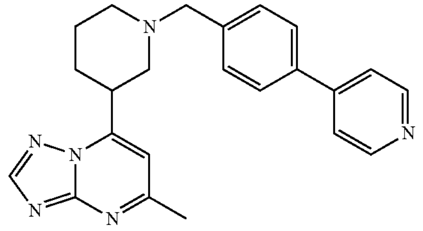 [SMILES: Cc1cc(C2CCCN(Cc3ccc(-c4ccncc4)cc3)C2)n2ncnc2n1]

$^1$H NMR (400 MHz, DMSO-$d_6$) δ=8.83 (d, J=6.02 Hz, 2H), 8.62 (s, 1H), 7.97-8.13 (m, 4H), 7.75 (d, J=7.28 Hz, 2H), 7.25 (s, 1H), 4.49 (br s, 2H), 3.97 (br s, 1H), 3.81 (d, J=9.91 Hz, 1H), 3.56 (d, J=9.79 Hz, 1H), 3.36 (t, J=11.80 Hz, 1H), 3.09 (br s, 1H), 2.65 (s, 3H), 1.80-2.24 (m, 4H); [M+H]=385.3.

Example 32. 1-{[4-(2-Chloro-4-fluorophenyl)-2-fluorophenyl]methyl}-3-{5-methyl-[1,2,4]triazolo[1,5-a]pyrimidin-7-yl}piperidine

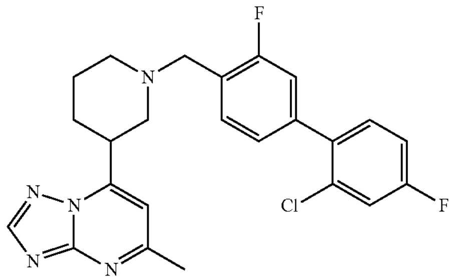 [SMILES: Cc1cc(C2CCCN(Cc3ccc(-c4ccc(F)cc4Cl)cc3F)C2)n2ncnc2n1]

$^1$H NMR (400 MHz, DMSO-$d_6$) δ=10.20 (br s, 1H), 8.60 (s, 1H), 7.72 (t, J=7.53 Hz, 1H), 7.62 (dd, J=2.51, 8.78 Hz, 1H), 7.32-7.54 (m, 4H), 7.23 (s, 1H), 4.47 (br s, 2H), 3.96 (br s, 1H), 3.84 (br s, 1H), 3.55 (br s, 1H), 3.43 (br s, 1H), 3.14 (br s, 1H), 2.64 (s, 3H), 1.78-2.21 (m, 4H); [M+H]=454.2.

Example 33. 1-{[5-(4-Chlorophenyl)-2-fluorophenyl]methyl}-3-{5-methyl-[1,2,4]triazolo[1,5-a]pyrimidin-7-yl}piperidine

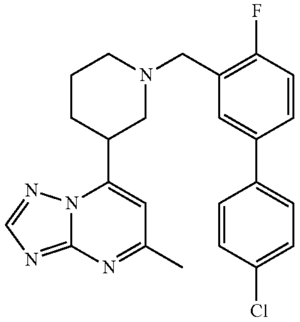 [SMILES: Cc1cc(C2CCCN(Cc3cc(-c4ccc(Cl)cc4)ccc3F)C2)n2ncnc2n1]

$^1$H NMR (400 MHz, DMSO-$d_6$) δ=10.10 (br s, 1H), 8.59 (s, 1H), 7.96 (d, J=5.90 Hz, 1H), 7.85 (br s, 1H), 7.71 (d, J=8.53 Hz, 2H), 7.57 (d, J=8.41 Hz, 2H), 7.45 (t, J=8.97 Hz, 1H), 7.22 (s, 1H), 4.47 (br s, 2H), 3.71-4.05 (m, 2H), 3.55 (br s, 1H), 3.42 (br s, 1H), 3.15 (br s, 1H), 2.63 (s, 3H), 1.76-2.20 (m, 4H); [M+H]=436.2.

Example 34. 1-{[5-(3-Chlorophenyl)-2-fluorophenyl]methyl}-3-{5-methyl-[1,2,4]triazolo[1,5-a]pyrimidin-7-yl}piperidine

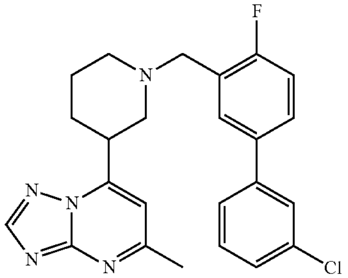 [SMILES: Cc1cc(C2CCCN(Cc3cc(-c4cccc(Cl)c4)ccc3F)C2)n2ncnc2n1]

$^1$H NMR (400 MHz, DMSO-$d_6$) δ=10.14 (br s, 1H), 8.59 (s, 1H), 8.01 (d, J=5.65 Hz, 1H), 7.89 (br s, 1H), 7.76 (s, 1H), 7.67 (d, J=7.53 Hz, 1H), 7.40-7.58 (m, 3H), 7.23 (s, 1H), 4.47 (br s, 2H), 3.71-4.2 (m, 2H), 3.55 (br s, 1H), 3.43 (br s, 1H), 3.14 (br s, 1H), 2.63 (s, 3H), 1.79-2.23 (m, 4H); [M+H]=436.2.

Example 35. 1-{[3-(2-Chloro-4-fluorophenyl)phenyl]methyl}-3-{5-methyl-[1,2,4]triazolo[1,5-a]pyrimidin-7-yl}piperidine

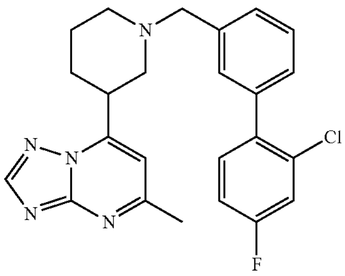 [SMILES: Cc1cc(C2CCCN(Cc3cccc(-c4ccc(F)cc4Cl)c3)C2)n2ncnc2n1]

$^1$H NMR (400 MHz, DMSO-$d_6$) δ=10.01 (br s, 1H), 8.59 (s, 1H), 7.46-7.63 (m, 6H), 7.36 (dt, J=2.32, 8.38 Hz, 1H), 7.23 (s, 1H), 4.44 (d, J=9.16 Hz, 2H), 3.93 (br s, 2H), 3.56 (d, J=11.42 Hz, 1H), 3.30 (d, J=9.41 Hz, 1H), 3.06 (br s, 1H), 2.63 (s, 3H), 1.79-2.22 (m, 4H); [M+H]=436.2.

Example 36. 3-{3-Fluoro-4-[(3-{5-methyl-[1,2,4]triazolo[1,5-a]pyrimidin-7-yl}piperidin-1-yl)methyl]phenyl}pyridine

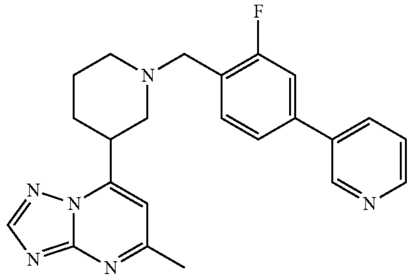 [SMILES: Cc1cc(C2CCCN(Cc3ccc(-c4cccnc4)cc3F)C2)n2ncnc2n1]

$^1$H NMR (400 MHz, DMSO-$d_6$) δ=9.04 (s, 1H), 8.69 (d, J=4.77 Hz, 1H), 8.63 (s, 1H), 8.28 (d, J=8.28 Hz, 1H), 7.85 (d, J=11.04 Hz, 1H), 7.78 (br s, 2H), 7.62 (dd, J=4.83, 7.84 Hz, 1H), 7.24 (s, 1H), 4.49 (br s, 2H), 3.99 (br s, 1H), 3.85 (d, J=10.54 Hz, 1H), 3.59 (d, J=10.79 Hz, 1H), 3.43 (br s, 1H), 3.15 (br s, 1H), 2.65 (s, 3H), 1.82-2.22 (m, 4H); [M+H]=403.2.

Example 37. 7-(1-(2,6-Difluoro-4-(pyridin-3-yl)benzyl)piperidin-3-yl)-5-methyl-[1,2,4]triazolo[1,5-a]pyrimidine

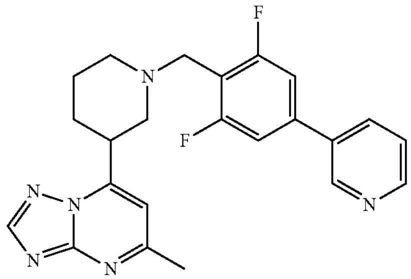 [SMILES: Cc1cc(C2CCCN(Cc3c(F)cc(-c4cccnc4)cc3F)C2)n2ncnc2n1]

$^1$H NMR (400 MHz, DMSO-$d_6$) δ=9.07 (d, J=1.88 Hz, 1H), 8.70 (d, J=4.77 Hz, 1H), 8.63 (s, 1H), 8.29 (d, J=8.03 Hz, 1H), 7.80 (d, J=9.03 Hz, 2H), 7.61 (dd, J=4.89, 7.91 Hz, 1H), 7.23 (s, 1H), 4.46 (br s, 2H), 4.00 (br s, 1H), 3.84 (br s, 1H), 3.40-3.66 (m, 2H), 3.09-3.22 (m, 1H), 2.65 (s, 3H), 1.78-2.18 (m, 4H); [M+H]=421.2.

Example 38. 3-{3-[(3-{5-Methyl-[1,2,4]triazolo[1,5-a]pyrimidin-7-yl}piperidin-1-yl)methyl] phenyl}pyridine

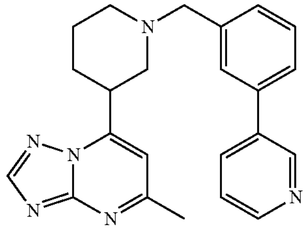 [SMILES: Cc1cc(C2CCCN(Cc3cccc(-c4cccnc4)c3)C2)n2ncnc2n1]

$^1$H NMR (400 MHz, DMSO-$d_6$) δ=10.21 (br s, 1H), 9.02 (s, 1H), 8.71 (d, J=4.77 Hz, 1H), 8.60 (s, 1H), 8.28 (d, J=7.78 Hz, 1H), 7.96 (s, 1H), 7.89 (d, J=6.78 Hz, 1H), 7.58-7.74 (m, 3H), 7.26 (s, 1H), 4.48 (br s, 2H), 3.97 (br s, 1H), 3.87 (d, J=10.29 Hz, 1H), 3.58 (d, J=11.67 Hz, 1H), 3.37 (t, J=10.92 Hz, 1H), 3.10 (br s, 1H), 2.64 (s, 3H), 1.80-2.24 (m, 4H); [M+H]=385.2.

Example 39. 4-{3-[(3-{5-Methyl-[1,2,4]triazolo[1,5-a]pyrimidin-7-yl}piperidin-1-yl)methyl] phenyl}pyridine

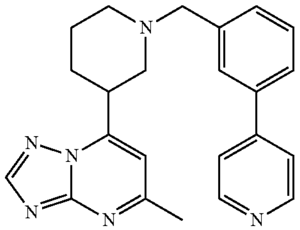 [SMILES: Cc1cc(C2CCCN(Cc3cccc(-c4ccncc4)c3)C2)n2ncnc2n1]

$^1$H NMR (400 MHz, DMSO-$d_6$) δ=10.30 (br s, 1H), 8.85 (d, J=5.77 Hz, 2H), 8.60 (s, 1H), 8.09 (br s, 1H), 8.02 (d, J=6.02 Hz, 3H), 7.60-7.82 (m, 2H), 7.25 (s, 1H), 4.50 (br s, 2H), 3.97 (br s, 1H), 3.86 (d, J=9.91 Hz, 1H), 3.57 (d, J=10.79 Hz, 1H), 3.36 (t, J=11.61 Hz, 1H), 3.10 (br s, 1H), 2.64 (s, 3H), 1.81-2.24 (m, 4H); [M+H]=385.3.

Examples 40-131 were prepared in a manner analogous to Example 13, with the appropriate starting material and reagent substitutions.

Example 40. 1-[(3,4-Dimethoxyphenyl)methyl]-3-{5-methyl-[1,2,4]triazolo[1,5-a]pyrimidin-7-yl}piperidine

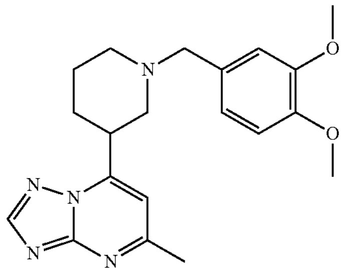 [SMILES: COc1ccc(CN2CCCC(c3cc(C)nc4ncnn34)C2)cc1OC]

[M+H]=368.2.

Example 41. 3-{5-Methyl-[1,2,4]triazolo[1,5-a]pyrimidin-7-yl}-1-(naphthalen-1-ylmethyl)piperidine

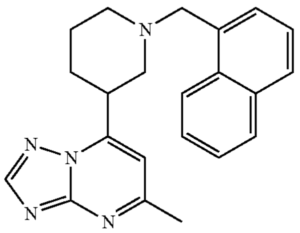 [SMILES: Cc1cc(C2CCCN(Cc3cccc4ccccc34)C2)n2ncnc2n1]

[M+H]=358.2.

Example 42. 1-[(4-Chloro-2-methylphenyl)methyl]-3-{5-methyl-[1,2,4]triazolo[1,5-a]pyrimidin-7-yl}piperidine

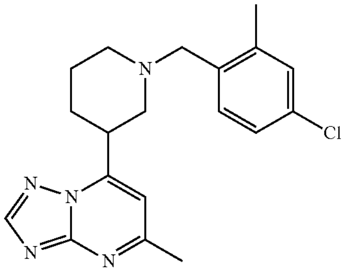 [SMILES: Cc1cc(C2CCCN(Cc3ccc(Cl)cc3C)C2)n2ncnc2n1]

[M+H]=356.1.

Example 43. 4-{4-[(3-{5-Methyl-[1,2,4]triazolo[1,5-a]pyrimidin-7-yl}piperidin-1-yl)methyl]phenyl}morpholine

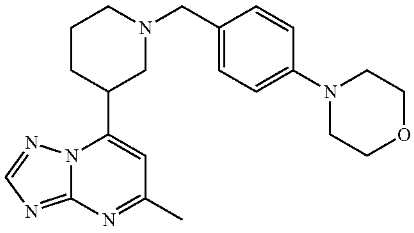 [SMILES: Cc1cc(C2CCCN(Cc3ccc(N4CCOCC4)cc3)C2)n2ncnc2n1]

[M+H]=393.2.

Example 44. 1-{[4-Fluoro-3-(trifluoromethyl)phenyl]methyl}-3-{5-methyl-[1,2,4]triazolo[1,5-a]pyrimidin-7-yl}piperidine

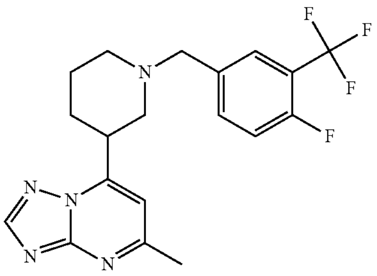 [SMILES: Cc1cc(C2CCCN(Cc3ccc(F)c(C(F)(F)F)c3)C2)n2ncnc2n1]

[M+H]=394.1.

Example 45. 1-{[3-(Furan-2-yl)phenyl]methyl}-3-{5-methyl-[1,2,4]triazolo[1,5-a]pyrimidin-7-yl}piperidine

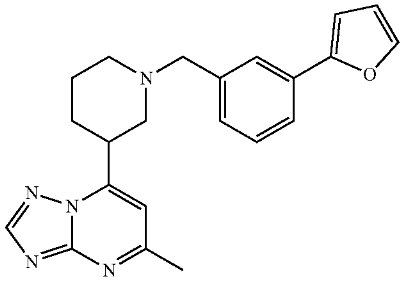 [SMILES: Cc1cc(C2CCCN(Cc3cccc(-c4ccco4)c3)C2)n2ncnc2n1]

[M+H]=374.2.

Example 46. 1-Methyl-3-[(3-{5-methyl-[1,2,4]triazolo[1,5-a]pyrimidin-7-yl}piperidin-1-yl)methyl]-1H-indole

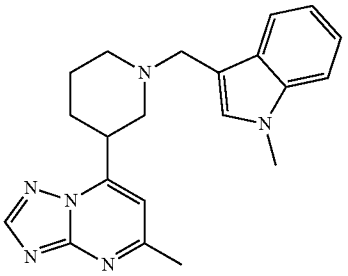 [SMILES: Cc1cc(C2CCCN(Cc3cn(C)c4ccccc34)C2)n2ncnc2n1]

[M+H]=361.2.

Example 47. 3-{5-Methyl-[1,2,4]triazolo[1,5-a]pyrimidin-7-yl}-1-{[4-(piperidin-1-yl)phenyl]methyl}piperidine

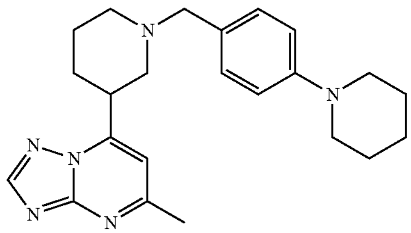 [SMILES: Cc1cc(C2CCCN(Cc3ccc(N4CCCCC4)cc3)C2)n2ncnc2n1]

[M+H]=391.1.

Example 48. 3-[(3-{5-Methyl-[1,2,4]triazolo[1,5-a]pyrimidin-7-yl}piperidin-1-yl)methyl]pyridine

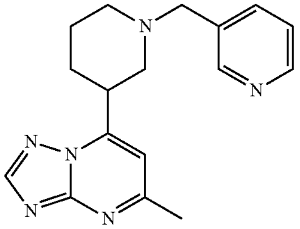 [SMILES: Cc1cc(C2CCCN(Cc3cccnc3)C2)n2ncnc2n1]

[M+H]=309.1.

Example 49. 2-{3-[(3-{5-Methyl-[1,2,4]triazolo[1,5-a]pyrimidin-7-yl}piperidin-1-yl)methyl]phenyl}pyridine

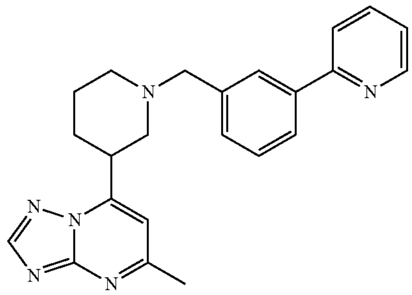 [SMILES: Cc1cc(C2CCCN(Cc3cccc(-c4ccccn4)c3)C2)n2ncnc2n1]

[M+H]=385.2.

Example 50. 4-{2-[(3-{5-Methyl-[1,2,4]triazolo[1,5-a]pyrimidin-7-yl}piperidin-1-yl)methyl]phenyl}morpholine

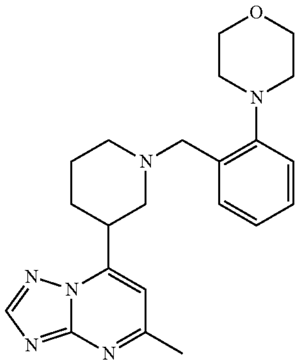 [SMILES: Cc1cc(C2CCCN(Cc3ccccc3N3CCOCC3)C2)n2ncnc2n1]

[M+H]=393.2.

Example 51. 3-Fluoro-4-[(3-{5-methyl-[1,2,4]triazolo[1,5-a]pyrimidin-7-yl}piperidin-1-yl)methyl]pyridine

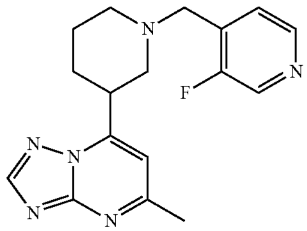 [SMILES: Cc1cc(C2CCCN(Cc3ccncc3F)C2)n2ncnc2n1]

[M+H]=327.2.

Example 52. 2,6-Dimethyl-3-[(3-{5-methyl-[1,2,4]triazolo[1,5-a]pyrimidin-7-yl}piperidin-1-yl)methyl]pyridine

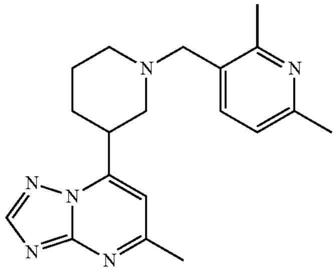 [SMILES: Cc1ccc(CN2CCCC(c3cc(C)nc4ncnn34)C2)c(C)n1]

[M+H]=337.2.

Example 53. 4-[(3-{5-Methyl-[1,2,4]triazolo[1,5-a]pyrimidin-7-yl}piperidin-1-yl)methyl]pyridine

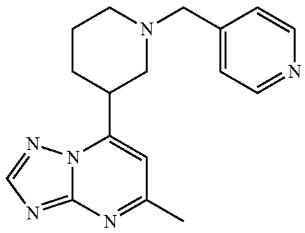 [SMILES: Cc1cc(C2CCCN(Cc3ccncc3)C2)n2ncnc2n1]

[M+H]=309.1.

Example 54. 2-[(3-{5-Methyl-[1,2,4]triazolo[1,5-a]pyrimidin-7-yl}piperidin-1-yl)methyl]pyridine

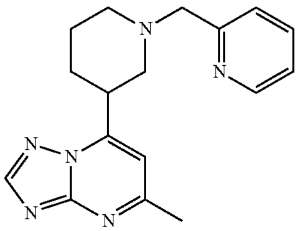 [SMILES: Cc1cc(C2CCCN(Cc3ccccn3)C2)n2ncnc2n1]

[M+H]=309.1.

Example 55. 1-[(2,4-Dichlorophenyl)methyl]-3-{5-methyl-[1,2,4]triazolo[1,5-a]pyrimidin-7-yl}piperidine

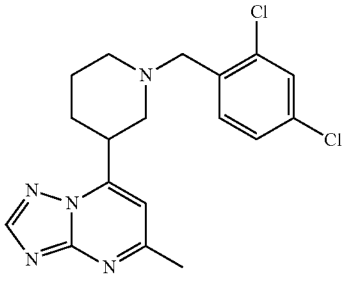 [SMILES: Cc1cc(C2CCCN(Cc3ccc(Cl)cc3Cl)C2)n2ncnc2n1]

[M+H]=376.1, 378.1.

Example 56. 3-{5-Methyl-[1,2,4]triazolo[1,5-a]pyrimidin-7-yl}-1-{[4-(1H-pyrrol-1-yl)phenyl]methyl}piperidine

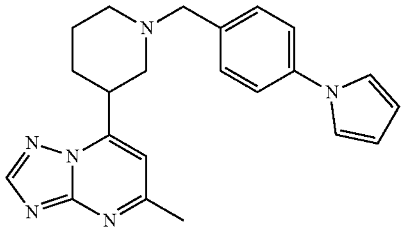 [SMILES: Cc1cc(C2CCCN(Cc3ccc(-n4cccc4)cc3)C2)n2ncnc2n1]

[M+H]=373.2.

Example 57. 1-(1-Benzothiophen-2-ylmethyl)-3-{5-methyl-[1,2,4]triazolo[1,5-a]pyrimidin-7-yl}piperidine

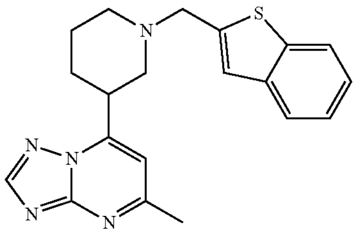 [SMILES: Cc1cc(C2CCCN(Cc3cc4ccccc4s3)C2)n2ncnc2n1]

[M+H]=364.1.

Example 58. 3-{5-Methyl-[1,2,4]triazolo[1,5-a]pyrimidin-7-yl}-1-[(1-phenyl-1H-pyrazol-4-yl)methyl]piperidine

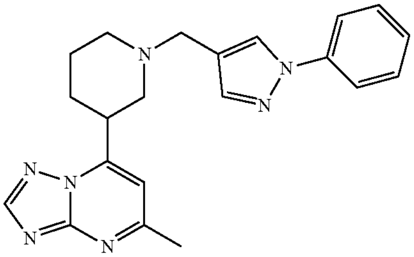 [SMILES: Cc1cc(C2CCCN(Cc3cnn(-c4ccccc4)c3)C2)n2ncnc2n1]

[M+H]=374.2.

Example 59. 3-{5-Methyl-[1,2,4]triazolo[1,5-a]pyrimidin-7-yl}-1-{[4-(pyrrolidin-1-yl)phenyl]methyl}piperidine

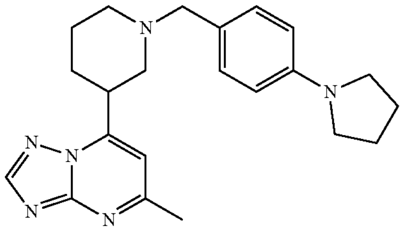 [SMILES: Cc1cc(C2CCCN(Cc3ccc(N4CCCC4)cc3)C2)n2ncnc2n1]

[M+H]=377.2.

Example 60. 1-[(2,5-Dichlorophenyl)methyl]-3-{5-methyl-[1,2,4]triazolo[1,5-a]pyrimidin-7-yl}piperidine

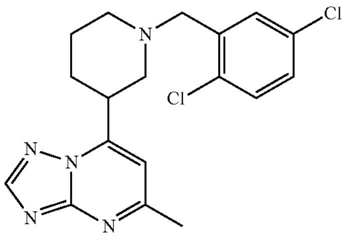 [SMILES: Cc1cc(C2CCCN(Cc3cc(Cl)ccc3Cl)C2)n2ncnc2n1]

[M+H]=376.1, 378.1.

Example 61. 3-{5-Methyl-[1,2,4]triazolo[1,5-a]pyrimidin-7-yl}-1-{[2-(1H-pyrazol-1-yl)phenyl]methyl}piperidine

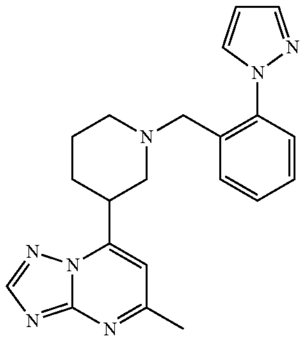 [SMILES: Cc1cc(C2CCCN(Cc3ccccc3-n3cccn3)C2)n2ncnc2n1]

[M+H]=374.2.

Example 62. 1-[(4-Chloro-2-methoxyphenyl)methyl]-3-{5-methyl-[1,2,4]triazolo[1,5-a]pyrimidin-7-yl}piperidine

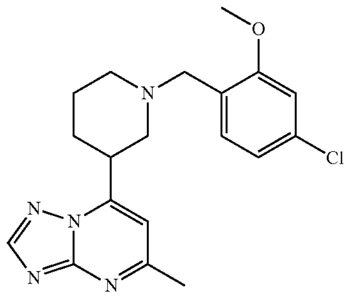 [SMILES: COc1cc(Cl)ccc1CN1CCCC(c2cc(C)nc3ncnn23)C1]

[M+H]=372.1.

Example 63. 1-[(3-Methoxy-4-methylphenyl)methyl]-3-{5-methyl-[1,2,4]triazolo[1,5-a]pyrimidin-7-yl}piperidine

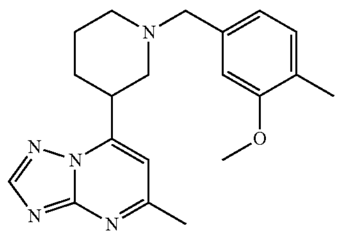 [SMILES: COc1cc(CN2CCCC(c3cc(C)nc4ncnn34)C2)ccc1C]

[M+H]=352.2.

Example 64. 1-[(2,4-Dimethoxyphenyl)methyl]-3-{5-methyl-[1,2,4]triazolo[1,5-a]pyrimidin-7-yl}piperidine

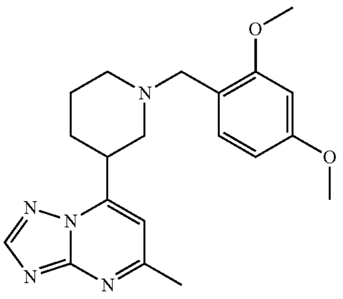 [SMILES: COc1ccc(CN2CCCC(c3cc(C)nc4ncnn34)C2)c(OC)c1]

[M+H]=368.2.

Example 65. 1-(2H-1,3-Benzodioxol-4-ylmethyl)-3-{5-methyl-[1,2,4]triazolo[1,5-a]pyrimidin-7-yl}piperidine

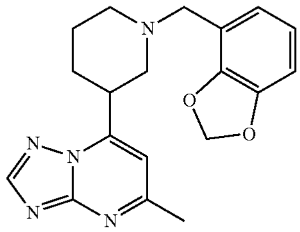 [SMILES: Cc1cc(C2CCCN(Cc3cccc4c3OCO4)C2)n2ncnc2n1]

[M+H]=352.2.

Example 66. 1-[(2,6-Dichlorophenyl)methyl]-3-{5-methyl-[1,2,4]triazolo[1,5-a]pyrimidin-7-yl}piperidine

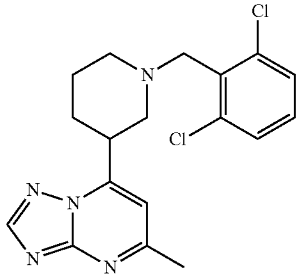 [SMILES: Cc1cc(C2CCCN(Cc3c(Cl)cccc3Cl)C2)n2ncnc2n1]

[M+H]=376.1, 378.1.

Example 67. 1-{[2-(1H-Imidazol-1-yl)phenyl]methyl}-3-{5-methyl-[1,2,4]triazolo[1,5-a]pyrimidin-7-yl}piperidine

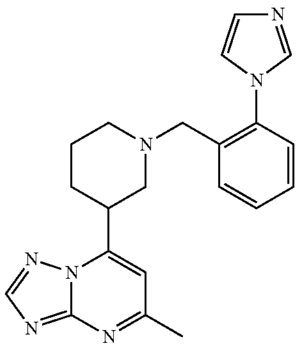 [SMILES: Cc1cc(C2CCCN(Cc3ccccc3-n3ccnc3)C2)n2ncnc2n1]

[M+H]=374.2.

Example 68. 1-[(4-Chlorophenyl)methyl]-3-{5-methyl-[1,2,4]triazolo[1,5-a]pyrimidin-7-yl}piperidine

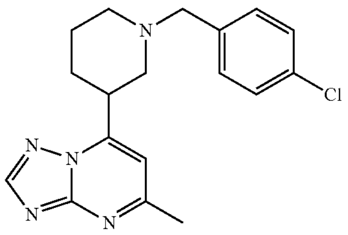 [SMILES: Cc1cc(C2CCCN(Cc3ccc(Cl)cc3)C2)n2ncnc2n1]

[M+H]=342.1.

Example 69. 2-[(3-{5-Methyl-[1,2,4]triazolo[1,5-a]pyrimidin-7-yl}piperidin-1-yl)methyl]quinoline

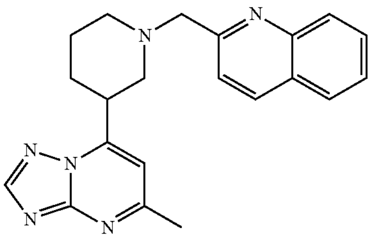 [SMILES: Cc1cc(C2CCCN(Cc3ccc4ccccc4n3)C2)n2ncnc2n1]

[M+H]=359.2.

Example 70. 1-[(2-Methoxyphenyl)methyl]-3-{5-methyl-[1,2,4]triazolo[1,5-a]pyrimidin-7-yl}piperidine

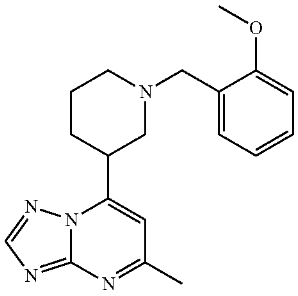 [SMILES: COc1ccccc1CN1CCCC(c2cc(C)nc3ncnn23)C1]

[M+H]=338.2.

Example 71. 1-[(4-Chloro-2,6-difluorophenyl)methyl]-3-{5-methyl-[1,2,4]triazolo[1,5-a]pyrimidin-7-yl}piperidine

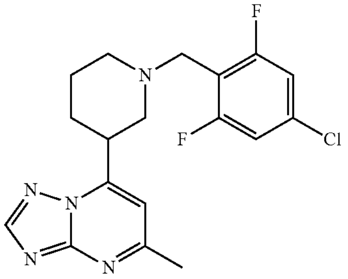 [SMILES: Cc1cc(C2CCCN(Cc3c(F)cc(Cl)cc3F)C2)n2ncnc2n1]

[M+H]=378.1.

Example 72. 1-[(2,5-Dimethoxyphenyl)methyl]-3-{5-methyl-[1,2,4]triazolo[1,5-a]pyrimidin-7-yl}piperidine

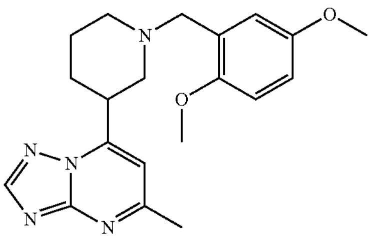 [SMILES: COc1ccc(OC)c(CN2CCCC(c3cc(C)nc4ncnn34)C2)c1]

[M+H]=368.2.

Example 73. 1-(2,3-Dihydro-1,4-benzodioxin-6-ylmethyl)-3-{5-methyl-[1,2,4]triazolo[1,5-a]pyrimidin-7-yl}piperidine

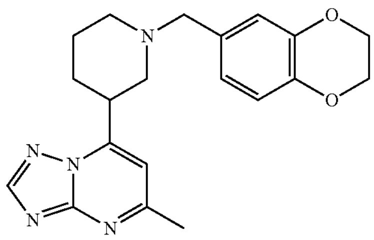 [SMILES: Cc1cc(C2CCCN(Cc3ccc4c(c3)OCCO4)C2)n2ncnc2n1]

[M+H]=366.2.

Example 74. 1-[(2-Chloro-6-methylphenyl)methyl]-3-{5-methyl-[1,2,4]triazolo[1,5-a]pyrimidin-7-yl}piperidine

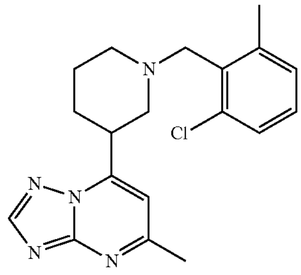 [SMILES: Cc1cc(C2CCCN(Cc3c(C)cccc3Cl)C2)n2ncnc2n1]

[M+H]=356.1.

Example 75. 1-[(2-Chlorophenyl)methyl]-3-{5-methyl-[1,2,4]triazolo[1,5-a]pyrimidin-7-yl}piperidine

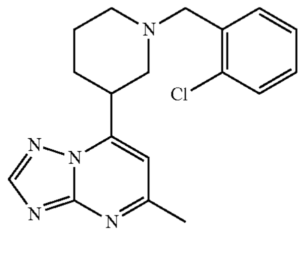 [SMILES: Cc1cc(C2CCCN(Cc3ccccc3Cl)C2)n2ncnc2n1]

[M+H]=342.1.

Example 76. 3-{5-Methyl-[1,2,4]triazolo[1,5-a]pyrimidin-7-yl}-1-[(4-methylphenyl)methyl]piperidine

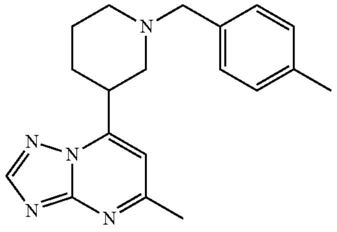 [SMILES: Cc1ccc(CN2CCCC(c3cc(C)nc4ncnn34)C2)cc1]

[M+H]=322.2.

Example 77. 3-{5-Methyl-[1,2,4]triazolo[1,5-a]pyrimidin-7-yl}-1-{[3-(1H-pyrazol-1-yl)phenyl]methyl}piperidine

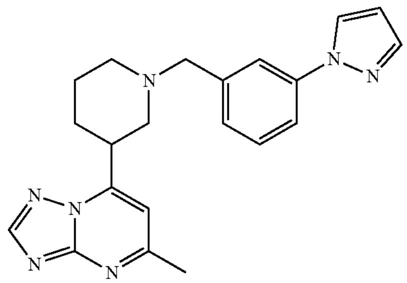 [SMILES: Cc1cc(C2CCCN(Cc3cccc(-n4cccn4)c3)C2)n2ncnc2n1]

[M+H]=374.2.

Example 78. 1-Benzyl-3-{5-methyl-[1,2,4]triazolo[1,5-a]pyrimidin-7-yl}piperidine

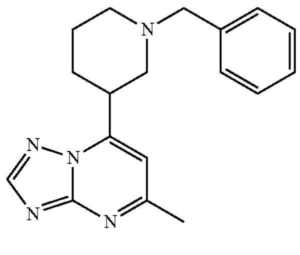 [SMILES: Cc1cc(C2CCCN(Cc3ccccc3)C2)n2ncnc2n1]

[M+H]=308.2.

Example 79. 1-[(3-Chloro-4-fluorophenyl)methyl]-3-{5-methyl-[1,2,4]triazolo[1,5-a]pyrimidin-7-yl}piperidine

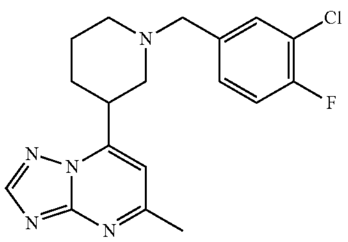 [SMILES: Cc1cc(C2CCCN(Cc3ccc(F)c(Cl)c3)C2)n2ncnc2n1]

[M+H]=360.1.

Example 80. 3-{5-Methyl-[1,2,4]triazolo[1,5-a]pyrimidin-7-yl}-1-{[4-(propan-2-yloxy)phenyl]methyl}piperidine

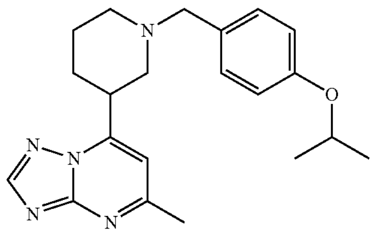 [SMILES: Cc1cc(C2CCCN(Cc3ccc(OC(C)C)cc3)C2)n2ncnc2n1]

[M+H]=366.2

Example 81. 1-[(2-Fluoro-3-methoxyphenyl)methyl]-3-{5-methyl-[1,2,4]triazolo[1,5-a]pyrimidin-7-yl}piperidine

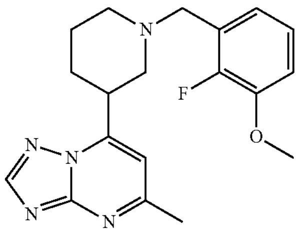 [SMILES: COc1cccc(CN2CCCC(c3cc(C)nc4ncnn34)C2)c1F]

[M+H]=356.2.

Example 82. 1-[(4-Fluorophenyl)methyl]-3-{5-methyl-[1,2,4]triazolo[1,5-a]pyrimidin-7-yl}piperidine

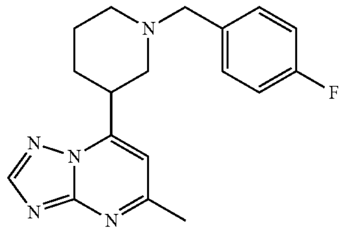 [SMILES: Cc1cc(C2CCCN(Cc3ccc(F)cc3)C2)n2ncnc2n1]

[M+H]=326.2.

Example 83. 1-[(4-Chloro-3-fluorophenyl)methyl]-3-{5-methyl-[1,2,4]triazolo[1,5-a]pyrimidin-7-yl}piperidine

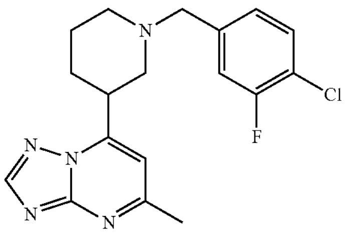 [SMILES: Cc1cc(C2CCCN(Cc3ccc(Cl)c(F)c3)C2)n2ncnc2n1]

[M+H]=360.1.

Example 84. 3-{5-Methyl-[1,2,4]triazolo[1,5-a]pyrimidin-7-yl}-1-{[4-(propan-2-yl)phenyl]methyl}piperidine

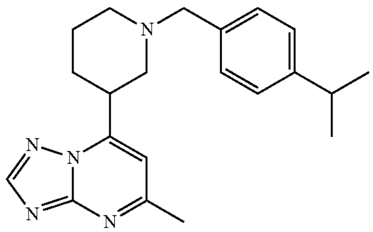 [SMILES: Cc1cc(C2CCCN(Cc3ccc(C(C)C)cc3)C2)n2ncnc2n1]

[M+H]=350.2.

Example 85. 1-[(4-Methoxy-2-methylphenyl)methyl]-3-{5-methyl-[1,2,4]triazolo[1,5-a]pyrimidin-7-yl}piperidine

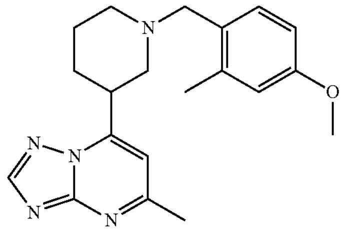

[M+H]=352.2.

Example 86. 1-[(3-Chloro-4-methoxyphenyl)methyl]-3-{5-methyl-[1,2,4]triazolo[1,5-a]pyrimidin-7-yl}piperidine

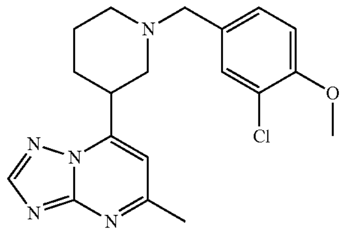 [SMILES: COc1ccc(CN2CCCC(c3cc(C)nc4ncnn34)C2)cc1Cl]

[M+H]=372.2.

Example 87. 4-[(3-{5-Methyl-[1,2,4]triazolo[1,5-a]pyrimidin-7-yl}piperidin-1-yl)methyl]-1H-indole

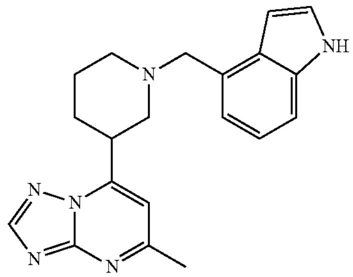 [SMILES: Cc1cc(C2CCCN(Cc3cccc4[nH]ccc34)C2)n2ncnc2n1]

[M+H]=347.2.

Example 88. 1-[(3-Methoxyphenyl)methyl]-3-{5-methyl-[1,2,4]triazolo[1,5-a]pyrimidin-7-yl}piperidine

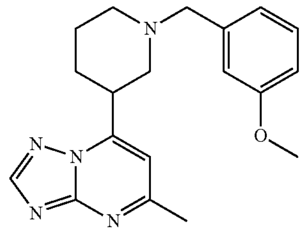 [SMILES: COc1cccc(CN2CCCC(c3cc(C)nc4ncnn34)C2)c1]

[M+H]=338.2.

Example 89. 3-{5-Methyl-[1,2,4]triazolo[1,5-a]pyrimidin-7-yl}-1-[(2-methylphenyl)methyl]piperidine

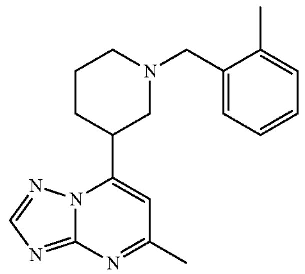 [SMILES: Cc1cc(C2CCCN(Cc3ccccc3C)C2)n2ncnc2n1]

[M+H]=322.2.

Example 90. N,N-Dimethyl-4-[(3-{5-methyl-[1,2,4]triazolo[1,5-a]pyrimidin-7-yl}piperidin-1-yl)methyl]aniline

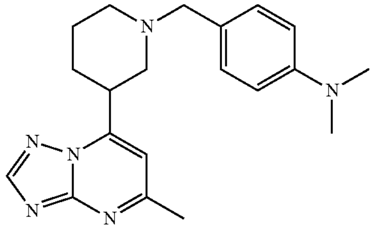 [SMILES: Cc1cc(C2CCCN(Cc3ccc(N(C)C)cc3)C2)n2ncnc2n1]

[M+H]=351.2.

Example 91. 1-[(3,4-Difluorophenyl)methyl]-3-{5-methyl-[1,2,4]triazolo[1,5-a]pyrimidin-7-yl}piperidine

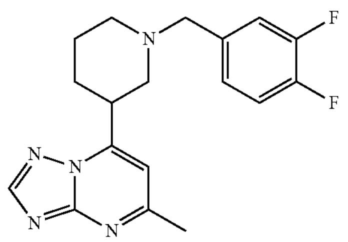 [SMILES: Cc1cc(C2CCCN(Cc3ccc(F)c(F)c3)C2)n2ncnc2n1]

[M+H]=344.2.

Example 92. 1-{[2-Fluoro-4-(trifluoromethyl)phenyl]methyl}-3-{5-methyl-[1,2,4]triazolo[1,5-a]pyrimidin-7-yl}piperidine

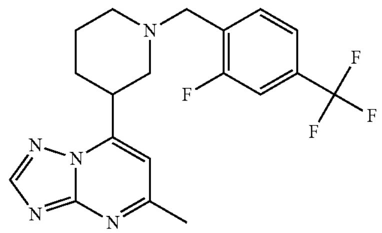 [SMILES: Cc1cc(C2CCCN(Cc3ccc(C(F)(F)F)cc3F)C2)n2ncnc2n1]

[M+H]=394.1.

Example 93. 1-[(3,4-Dimethylphenyl)methyl]-3-{5-methyl-[1,2,4]triazolo[1,5-a]pyrimidin-7-yl}piperidine

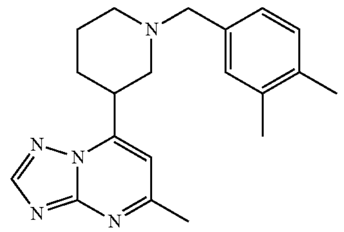 [SMILES: Cc1cc(C2CCCN(Cc3ccc(C)c(C)c3)C2)n2ncnc2n1]

[M+H]=336.2.

Example 94. 1-[(4-Methoxyphenyl)methyl]-3-{5-methyl-[1,2,4]triazolo[1,5-a]pyrimidin-7-yl}piperidine

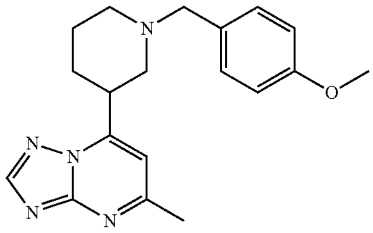 [SMILES: COc1ccc(CN2CCCC(c3cc(C)nc4ncnn34)C2)cc1]

[M+H]=338.2.

Example 95. 1-[(3-Fluoro-5-methylphenyl)methyl]-3-{5-methyl-[1,2,4]triazolo[1,5-a]pyrimidin-7-yl}piperidine

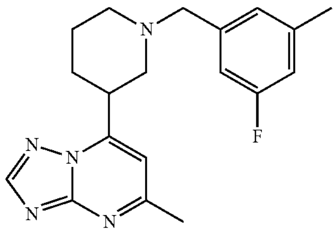 [SMILES: Cc1cc(F)cc(CN2CCCC(c3cc(C)nc4ncnn34)C2)c1]

[M+H]=340.2.

Example 96. 1-{[2-Methoxy-5-(propan-2-yl)phenyl]methyl}-3-{5-methyl-[1,2,4]triazolo[1,5-a]pyrimidin-7-yl}piperidine

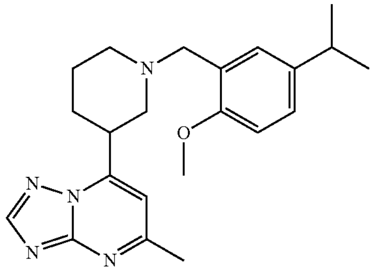 [SMILES: COc1ccc(C(C)C)cc1CN1CCCC(c2cc(C)nc3ncnn23)C1]

[M+H]=380.2.

Example 97. 1-(2H-1,3-Benzodioxol-5-ylmethyl)-3-{5-methyl-[1,2,4]triazolo[1,5-a]pyrimidin-7-yl}piperidine

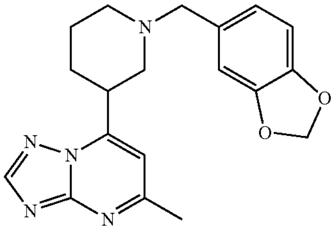 [SMILES: Cc1cc(C2CCCN(Cc3ccc4c(c3)OCO4)C2)n2ncnc2n1]

[M+H]=352.2.

Example 98. 3-{5-Methyl-[1,2,4]triazolo[1,5-a]pyrimidin-7-yl}-1-[(2-phenylphenyl)methyl]piperidine

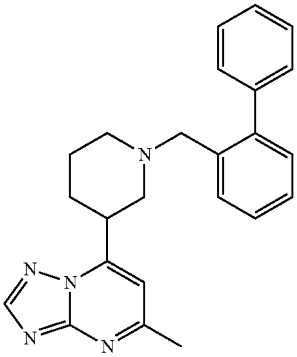 [SMILES: Cc1cc(C2CCCN(Cc3ccccc3-c3ccccc3)C2)n2ncnc2n1]

[M+H]=384.2.

Example 99. 3-[(3-{5-Methyl-[1,2,4]triazolo[1,5-a]pyrimidin-7-yl}piperidin-1-yl)methyl]-1H-indole

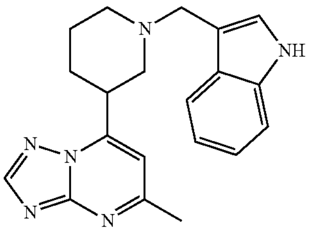 [SMILES: Cc1cc(C2CCCN(Cc3c[nH]c4ccccc34)C2)n2ncnc2n1]

[M+H]=347.2.

Example 100. 1-{[4-(Difluoromethoxy)phenyl]methyl}-3-{5-methyl-[1,2,4]triazolo[1,5-a]pyrimidin-7-yl}piperidine

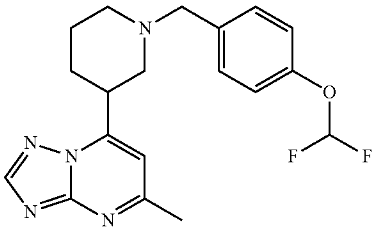 [SMILES: Cc1cc(C2CCCN(Cc3ccc(OC(F)F)cc3)C2)n2ncnc2n1]

[M+H]=374.2.

Example 101. 3-{5-Methyl-[1,2,4]triazolo[1,5-a]pyrimidin-7-yl}-1-[(3-methylphenyl)methyl]piperidine

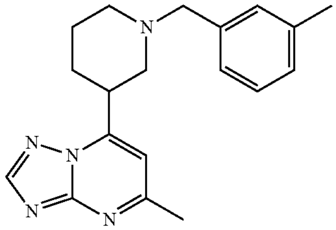 [SMILES: Cc1cccc(CN2CCCC(c3cc(C)nc4ncnn34)C2)c1]

[M+H]=322.2.

Example 102. 3-{5-Methyl-[1,2,4]triazolo[1,5-a]pyrimidin-7-yl}-1-{[2-(trifluoromethyl)phenyl]methyl}piperidine

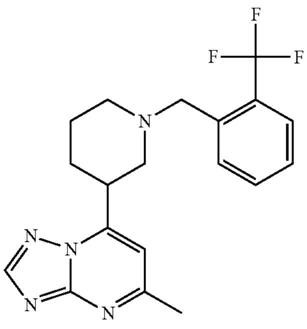 [SMILES: Cc1cc(C2CCCN(Cc3ccccc3C(F)(F)F)C2)n2ncnc2n1]

[M+H]=376.2.

Example 103. 1-[(2-Fluoro-4-methoxyphenyl) methyl]-3-{5-methyl-[1,2,4]triazolo[1,5-a]pyrimidin-7-yl}piperidine

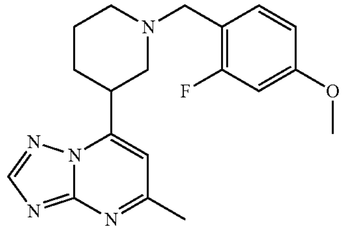 [SMILES: COc1ccc(CN2CCCC(c3cc(C)nc4ncnn34)C2)c(F)c1]

[M+H]=356.2.

Example 104. 1-(1-Benzofuran-2-ylmethyl)-3-{5-methyl-[1,2,4]triazolo[1,5-a]pyrimidin-7-yl}piperidine

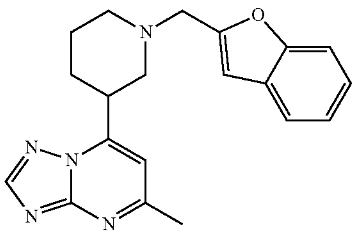 [SMILES: Cc1cc(C2CCCN(Cc3cc4ccccc4o3)C2)n2ncnc2n1]

[M+H]=348.2.

Example 105. 1-[(2,5-Difluorophenyl)methyl]-3-{5-methyl-[1,2,4]triazolo[1,5-a]pyrimidin-7-yl}piperidine

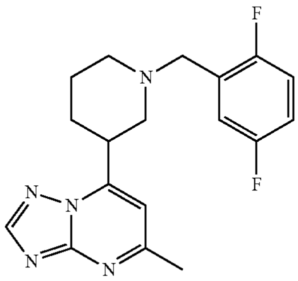 [SMILES: Cc1cc(C2CCCN(Cc3cc(F)ccc3F)C2)n2ncnc2n1]

[M+H]=344.2.

Example 106. 3-{5-Methyl-[1,2,4]triazolo[1,5-a]pyrimidin-7-yl}-1-{[4-(trifluoromethyl)phenyl]methyl}piperidine

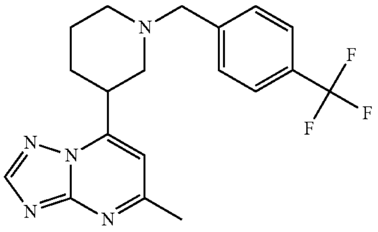 [SMILES: Cc1cc(C2CCCN(Cc3ccc(C(F)(F)F)cc3)C2)n2ncnc2n1]

[M+H]=376.2.

Example 107. 1-Methyl-2-[(3-{5-methyl-[1,2,4]triazolo[1,5-a]pyrimidin-7-yl}piperidin-1-yl)methyl]-1H-1,3-benzodiazole

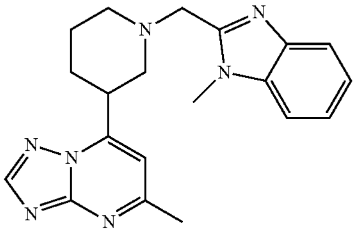 [SMILES: Cc1cc(C2CCCN(Cc3nc4ccccc4n3C)C2)n2ncnc2n1]

[M+H]=362.2.

Example 108. 5-Fluoro-3-[(3-{5-methyl-[1,2,4]triazolo[1,5-a]pyrimidin-7-yl}piperidin-1-yl)methyl]-1H-indole

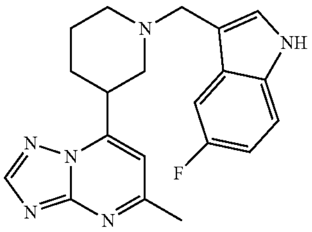 [SMILES: Cc1cc(C2CCCN(Cc3c[nH]c4ccc(F)cc34)C2)n2ncnc2n1]

[M+H]=365.2.

Example 109. 3-{5-Methyl-[1,2,4]triazolo[1,5-a]pyrimidin-7-yl}-1-[(2-phenyl-1,3-thiazol-5-yl)methyl]piperidine

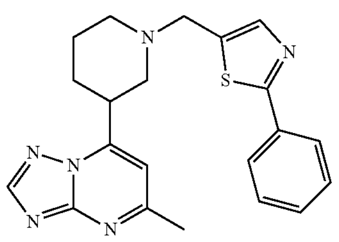 [SMILES: Cc1cc(C2CCCN(Cc3cnc(-c4ccccc4)s3)C2)n2ncnc2n1]

[M+H]=391.1.

Example 110. 1-[(3-Chloro-4-methylphenyl)methyl]-3-{5-methyl-[1,2,4]triazolo[1,5-a]pyrimidin-7-yl}piperidine

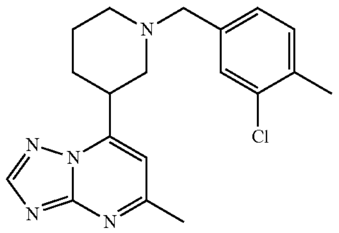 [SMILES: Cc1cc(C2CCCN(Cc3ccc(C)c(Cl)c3)C2)n2ncnc2n1]

[M+H]=356.1.

Example 111. 1-[(2-Fluorophenyl)methyl]-3-{5-methyl-[1,2,4]triazolo[1,5-a]pyrimidin-7-yl}piperidine

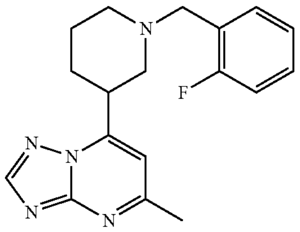 [SMILES: Cc1cc(C2CCCN(Cc3ccccc3F)C2)n2ncnc2n1]

[M+H]=326.2.

Example 112. 1-(1-Benzofuran-3-ylmethyl)-3-{5-methyl-[1,2,4]triazolo[1,5-a]pyrimidin-7-yl}piperidine

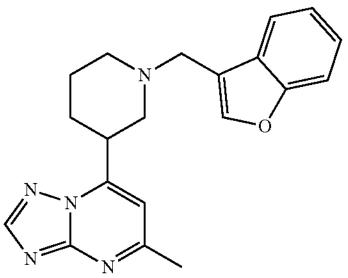 [SMILES: Cc1cc(C2CCCN(Cc3coc4ccccc34)C2)n2ncnc2n1]

[M+H]=348.2.

Example 113. 1-[(3-Chloro-2-fluorophenyl)methyl]-3-{5-methyl-[1,2,4]triazolo[1,5-a]pyrimidin-7-yl}piperidine

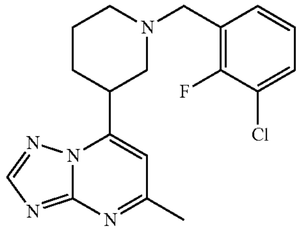 [SMILES: Cc1cc(C2CCCN(Cc3cccc(Cl)c3F)C2)n2ncnc2n1]

[M+H]=360.1.

Example 114. 1-[(3-Fluorophenyl)methyl]-3-{5-methyl-[1,2,4]triazolo[1,5-a]pyrimidin-7-yl}piperidine

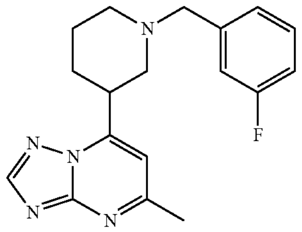 [SMILES: Cc1cc(C2CCCN(Cc3cccc(F)c3)C2)n2ncnc2n1]

[M+H]=326.2.

Example 115. 1-[(2,3-Dimethylphenyl)methyl]-3-{5-methyl-[1,2,4]triazolo[1,5-a]pyrimidin-7-yl}piperidine

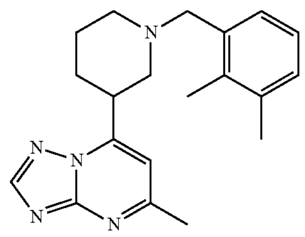 [SMILES: Cc1cc(C2CCCN(Cc3cccc(C)c3C)C2)n2ncnc2n1]

[M+H]=336.2.

Example 116. 1-(1-Benzothiophen-3-ylmethyl)-3-{5-methyl-[1,2,4]triazolo[1,5-a]pyrimidin-7-yl}piperidine

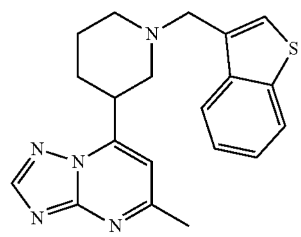 [SMILES: Cc1cc(C2CCCN(Cc3csc4ccccc34)C2)n2ncnc2n1]

[M+H]=364.1.

Example 117. 1-[(4-Fluoro-3-methoxyphenyl)methyl]-3-{5-methyl-[1,2,4]triazolo[1,5-a]pyrimidin-7-yl}piperidine

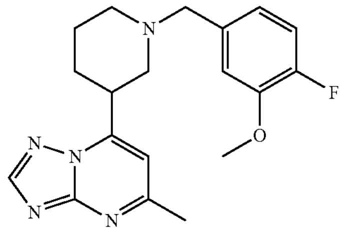 [SMILES: COc1cc(CN2CCCC(c3cc(C)nc4ncnn34)C2)ccc1F]

[M+H]=356.2.

Example 118. 1-[(4-Chloro-2-fluorophenyl)methyl]-3-{5-methyl-[1,2,4]triazolo[1,5-a]pyrimidin-7-yl}piperidine

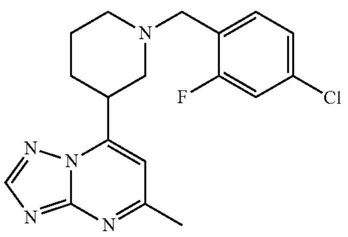 [SMILES: Cc1cc(C2CCCN(Cc3ccc(Cl)cc3F)C2)n2ncnc2n1]

[M+H]=360.1.

Example 119. 1-({3,6-Dimethylimidazo[2,1-b][1,3]thiazol-5-yl}methyl)-3-{5-methyl-[1,2,4]triazolo[1,5-a]pyrimidin-7-yl}piperidine

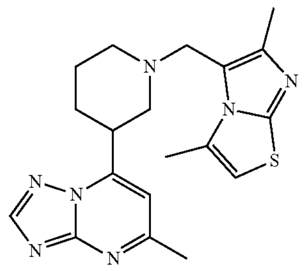 [SMILES: Cc1cc(C2CCCN(Cc3c(C)nc4scc(C)n34)C2)n2ncnc2n1]

[M+H]=382.2.

Example 120. 7-(1-((6-Methoxynaphthalen-2-yl)methyl)piperidin-3-yl)-5-methyl-[1,2,4]triazolo[1,5-a]pyrimidine

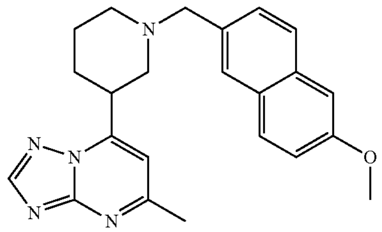 [SMILES: COc1ccc2cc(CN3CCCC(c4cc(C)nc5ncnn45)C3)ccc2c1]

[M+H]=388.2.

Example 121. 1-[(2,2-Difluoro-2H-1,3-benzodioxol-5-yl)methyl]-3-{5-methyl-[1,2,4]triazolo[1,5-a]pyrimidin-7-yl}piperidine

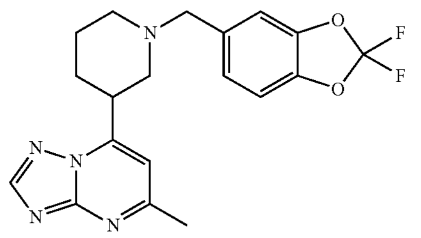 [SMILES: Cc1cc(C2CCCN(Cc3ccc4c(c3)OC(F)(F)O4)C2)n2ncnc2n1]

[M+H]=388.1.

Example 122. 1-{[3,5-Dimethyl-1-(propan-2-yl)-1H-pyrazol-4-yl]methyl}-3-{5-methyl-[1,2,4]triazolo[1,5-a]pyrimidin-7-yl}piperidine

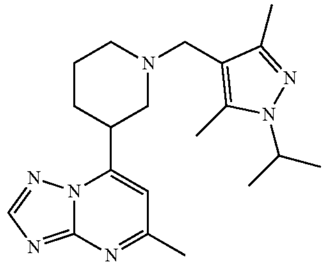 [SMILES: Cc1cc(C2CCCN(Cc3c(C)nn(C(C)C)c3C)C2)n2ncnc2n1]

[M+H]=368.2.

Example 123. 3-{5-Methyl-[1,2,4]triazolo[1,5-a]pyrimidin-7-yl}-1-{[1-(1,3-thiazol-2-yl)-1H-pyrrol-2-yl]methyl}piperidine

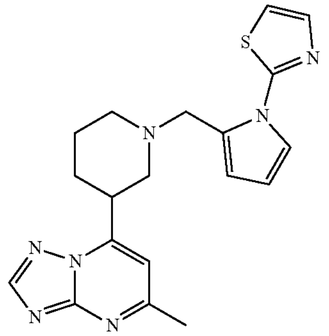 [SMILES: Cc1cc(C2CCCN(Cc3cccn3-c3nccs3)C2)n2ncnc2n1]

[M+H]=380.1.

Example 124. 2-Methyl-6-[(3-{5-methyl-[1,2,4]triazolo[1,5-a]pyrimidin-7-yl}piperidin-1-yl)methyl]pyridine

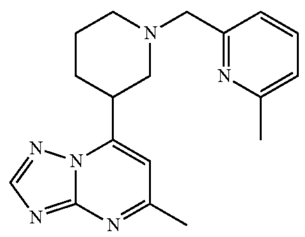 [SMILES: Cc1cccc(CN2CCCC(c3cc(C)nc4ncnn34)C2)n1]

[M+H]=323.2.

Example 125. 1-{[4-(Furan-2-yl)phenyl]methyl}-3-{5-methyl-[1,2,4]triazolo[1,5-a]pyrimidin-7-yl}piperidine

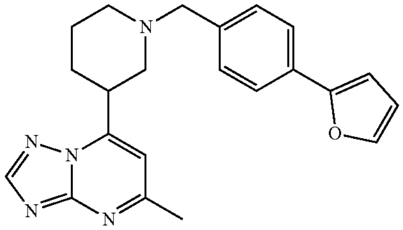

[M+H]=374.2.

Example 126. 3-{5-Methyl-[1,2,4]triazolo[1,5-a]pyrimidin-7-yl}-1-{[3-(propan-2-yloxy)phenyl]methyl}piperidine

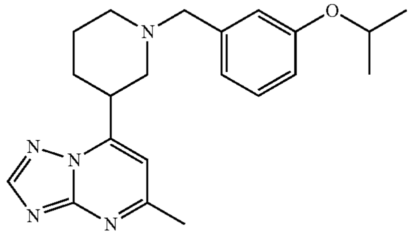 [SMILES: Cc1cc(C2CCCN(Cc3cccc(OC(C)C)c3)C2)n2ncnc2n1]

[M+H]=366.2.

Example 127. 4-[(3-{5-Methyl-[1,2,4]triazolo[1,5-a]pyrimidin-7-yl}piperidin-1-yl)methyl]quinoline

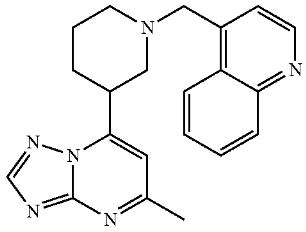 [SMILES: Cc1cc(C2CCCN(Cc3ccnc4ccccc34)C2)n2ncnc2n1]

[M+H]=359.2.

Example 128. 1-{[3-(Difluoromethoxy)phenyl]methyl}-3-{5-methyl-[1,2,4]triazolo[1,5-a]pyrimidin-7-yl}piperidine

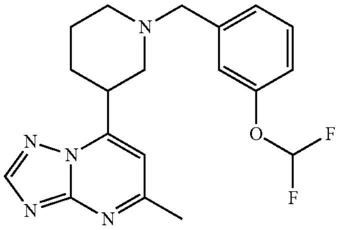 [SMILES: Cc1cc(C2CCCN(Cc3cccc(OC(F)F)c3)C2)n2ncnc2n1]

[M+H]=374.2.

Example 129. 1-{[4-(1H-Imidazol-1-yl)phenyl]methyl}-3-{5-methyl-[1,2,4]triazolo[1,5-a]pyrimidin-7-yl}piperidine

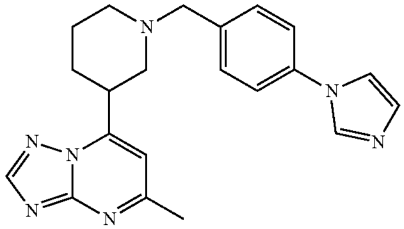 [SMILES: Cc1cc(C2CCCN(Cc3ccc(-n4ccnc4)cc3)C2)n2ncnc2n1]

[M+H]=374.2.

Example 130. 5-Chloro-2-[(3-{5-methyl-[1,2,4]triazolo[1,5-a]pyrimidin-7-yl}piperidin-1-yl)methyl]pyridine

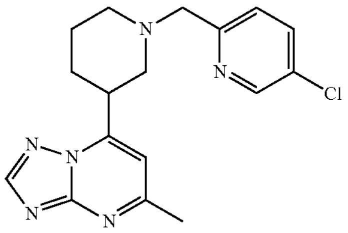 [SMILES: Cc1cc(C2CCCN(Cc3ccc(Cl)cn3)C2)n2ncnc2n1]

[M+H]=343.1.

Example 131. 3-Chloro-4-[(3-{5-methyl-[1,2,4]triazolo[1,5-a]pyrimidin-7-yl}piperidin-1-yl)methyl]pyridine

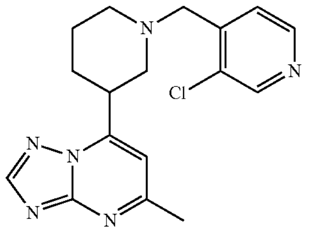 [SMILES: Cc1cc(C2CCCN(Cc3ccncc3Cl)C2)n2ncnc2n1]

[M+H]=343.1.

Examples 132-141 were prepared in a manner analogous to Example 11, with the appropriate starting material and reagent substitutions.

Example 132. 1-[(4-Bromo-2-fluorophenyl)methyl]-3-{5-methyl-[1,2,4]triazolo[1,5-a]pyrimidin-7-yl}piperidine

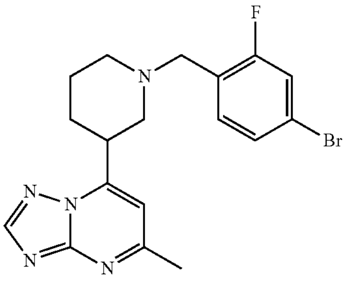

$^1$H NMR (400 MHz, $CDCl_3$) δ=8.52-8.39 (m, 1H), 7.55-7.46 (m, 1H), 7.46-7.38 (m, 1H), 7.38-7.28 (m, 1H), 6.96-6.86 (m, 1H), 4.37-4.23 (m, 2H), 4.08-3.93 (m, 2H), 3.80-3.66 (m, 2H), 3.02-2.83 (m, 1H), 2.70 (s, 3H), 2.52-2.35 (m, 1H), 2.33-2.20 (m, 1H), 2.18-2.03 (m, 2H); [M+H]=404.1.

Example 133. (3R)-1-[(4-Bromophenyl)methyl]-3-{5-methyl-[1,2,4]triazolo[1,5-a]pyrimidin-7-yl}piperidine

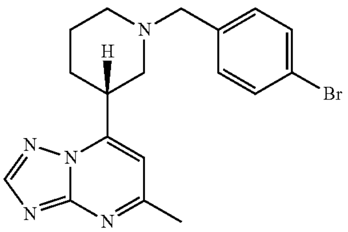

$^1$H NMR (400 MHz, $CDCl_3$) δ=8.54-8.38 (m, 1H), 7.65-7.50 (m, 2H), 7.37-7.27 (m, 2H), 6.93 (s, 1H), 4.37-4.14 (m,

2H), 4.07-3.88 (m, 1H), 3.69 (br s, 3H), 2.97-2.79 (m, 1H), 2.75-2.61 (m, 3H), 2.49-2.35 (m, 1H), 2.27-1.99 (m, 4H); [M+H]=388.1.

Example 134. (3S)-1-[(4-Bromophenyl)methyl]-3-{5-methyl-[1,2,4]triazolo[1,5-a]pyrimidin-7-yl}piperidine

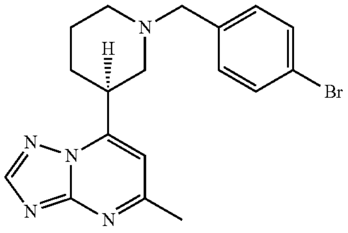

$^1$H NMR (400 MHz, $CDCl_3$) δ=8.51-8.37 (m, 1H), 7.63-7.47 (m, 2H), 7.36-7.27 (m, 2H), 6.93 (s, 1H), 4.37-4.16 (m, 2H), 4.06-3.90 (m, 1H), 3.69 (br s, 3H), 2.98-2.80 (m, 1H), 2.76-2.62 (m, 3H), 2.58-2.33 (m, 1H), 2.17 (s, 4H); [M+H]=388.1.

Example 135. 5-bromo-2-[(3-{5-Methyl-[1,2,4]triazolo[1,5-a]pyrimidin-7-yl}piperidin-1-yl)methyl]pyridine

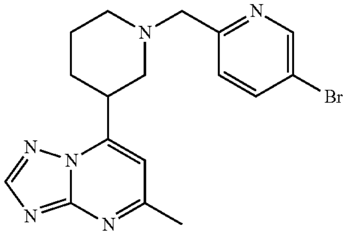 [SMILES: Cc1cc(C2CCCN(Cc3ccc(Br)cn3)C2)n2ncnc2n1]

$^1$H NMR (400 MHz, $CD_3OD$) δ=8.83-8.73 (m, 1H), 8.54-8.46 (m, 1H), 8.13-8.05 (m, 1H), 7.50-7.38 (m, 1H), 7.24-7.14 (m, 1H), 4.70-4.65 (m, 1H), 4.63-4.49 (m, 2H), 4.19-3.97 (m, 2H), 3.78-3.64 (m, 1H), 3.53-3.40 (m, 1H), 2.69 (s, 3H), 2.40-2.27 (m, 1H), 2.25-1.96 (m, 3H); [M+H]=388.1.

Example 136. 5-Bromo-4-methyl-2-[(3-{5-methyl-[1,2,4]triazolo[1,5-a]pyrimidin-7-yl}piperidin-1-yl)methyl]pyridine

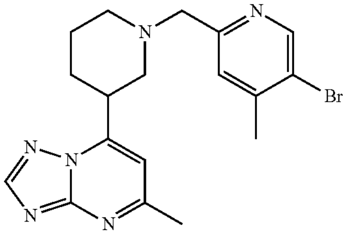 [SMILES: Cc1cc(C2CCCN(Cc3cc(C)c(Br)cn3)C2)n2ncnc2n1]

$^1$H NMR (400 MHz, $CD_3OD$) δ=8.79-8.67 (m, 1H), 8.53-8.45 (m, 1H), 7.50-7.40 (m, 1H), 7.26-7.12 (m, 1H), 4.60-4.45 (m, 2H), 4.19-3.95 (m, 3H), 3.76-3.63 (m, 1H), 3.52-3.40 (m, 1H), 2.69 (s, 3H), 2.45 (s, 3H), 2.38-2.28 (m, 1H), 2.21-1.98 (m, 3H); [M+H]=401.1.

Example 137. 3-Bromo-2-methyl-6-[(3-{5-methyl-[1,2,4]triazolo[1,5-a]pyrimidin-7-yl}piperidin-1-yl)methyl]pyridine

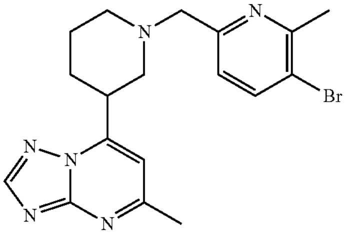 [SMILES: Cc1cc(C2CCCN(Cc3ccc(Br)c(C)n3)C2)n2ncnc2n1]

$^1$H NMR (400 MHz, $CD_3OD$) δ=8.52-8.47 (m, 1H), 8.07-7.98 (m, 1H), 7.30-7.15 (m, 2H), 4.62-4.44 (m, 2H), 4.20-4.05 (m, 2H), 3.79-3.65 (m, 2H), 3.48-3.35 (m, 1H), 2.70 (d, J=8.2 Hz, 6H), 2.41-2.25 (m, 1H), 2.24-1.97 (m, 3H); [M+H]=401.1.

Example 138. 5-Bromo-2-[(3-{5-methyl-[1,2,4]triazolo[1,5-a]pyrimidin-7-yl}piperidin-1-yl)methyl]pyrimidine

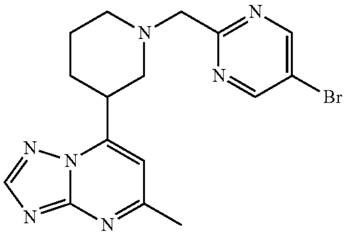 [SMILES: Cc1cc(C2CCCN(Cc3ncc(Br)cn3)C2)n2ncnc2n1]

$^1$H NMR (400 MHz, $CDCl_3$) δ=8.88-8.76 (m, 2H), 8.46-8.37 (m, 1H), 7.00-6.90 (m, 1H), 4.59-4.42 (m, 2H), 4.01-3.83 (m, 2H), 3.77-3.58 (m, 1H), 3.21-3.06 (m, 1H), 2.69 (s, 3H), 2.48-2.30 (m, 2H), 2.23-2.03 (m, 2H), 1.33-1.17 (m, 2H); [M+H]=388.1.

Example 139. 1-[(4-Bromo-3-fluorophenyl)methyl]-3-{5-methyl-[1,2,4]triazolo[1,5-a]pyrimidin-7-yl}piperidine

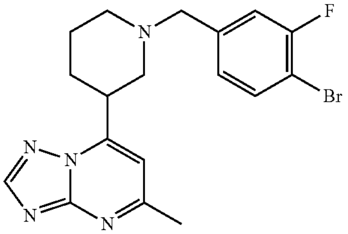

$^1$H NMR (400 MHz, $CDCl_3$) δ=8.52-8.41 (m, 1H), 7.68-7.56 (m, 1H), 7.23-7.12 (m, 1H), 6.99-6.87 (m, 1H), 4.32-

4.13 (m, 2H), 4.10-3.94 (m, 1H), 3.78-3.57 (m, 4H), 2.96-2.78 (m, 2H), 2.69 (s, 3H), 2.59-2.38 (m, 1H), 2.37-2.20 (m, 1H), 2.17-2.00 (m, 2H); [M+H]=406.1.

Example 140. (3R)-1-[(4-Chloro-3-fluorophenyl)methyl]-3-{5-methyl-[1,2,4]triazolo[1,5-a]pyrimidin-7-yl}piperidine

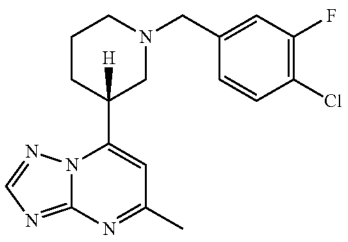

$^1$H NMR (400 MHz, $CDCl_3$) δ=8.50-8.42 (m, 1H), 7.53-7.42 (m, 1H), 7.26 (s, 2H), 7.00-6.90 (m, 1H), 4.35-4.15 (m, 2H), 4.09-3.94 (m, 1H), 3.79-3.62 (m, 4H), 2.95-2.85 (m, 1H), 2.69 (s, 3H), 2.55-2.38 (m, 1H), 2.34-2.19 (m, 1H), 2.17-1.99 (m, 1H); [M+H]=360.1.

Example 141. (3S)-1-[(4-Chloro-3-fluorophenyl)methyl]-3-{5-methyl-[1,2,4]triazolo[1,5-a]pyrimidin-7-yl}piperidine

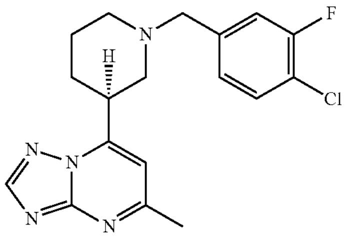

$^1$H NMR (400 MHz, $CDCl_3$) δ=8.50-8.42 (m, 1H), 7.53-7.42 (m, 1H), 7.26 (s, 2H), 7.00-6.90 (m, 1H), 4.35-4.15 (m, 2H), 4.09-3.94 (m, 1H), 3.79-3.62 (m, 4H), 2.95-2.85 (m, 1H), 2.69 (s, 3H), 2.55-2.38 (m, 1H), 2.34-2.19 (m, 1H), 2.17-1.99 (m, 1H); [M+H]=360.1.

Examples 142-206 were prepared in a manner analogous to Example 1, with the appropriate starting material and reagent substitutions.

Example 142. 1-(2,3-Dihydro-1H-inden-5-ylmethyl)-3-{5-methyl-[1,2,4]triazolo[1,5-a]pyrimidin-7-yl}piperidine

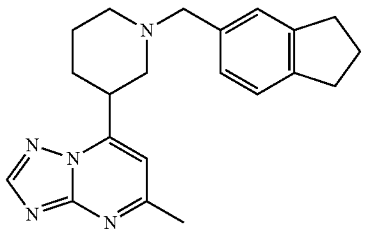 [SMILES: Cc1cc(C2CCCN(Cc3ccc4c(c3)CCC4)C2)n2ncnc2n1]

$^1$H NMR (400 MHz, DMSO-$d_6$) δ=1.58-1.75 (m, 3H), 1.95-2.08 (m, 3H), 2.21 (br s, 1H), 2.38 (t, J=10.16 Hz, 1H), 2.61 (s, 3H), 2.70-2.78 (m, 1H), 2.83 (q, J=7.32 Hz, 4H), 3.02 (d, J=9.91 Hz, 1H), 3.43-3.57 (m, 2H), 3.60-3.70 (m, 1H), 7.07 (d, J=7.53 Hz, 1H), 7.14-7.20 (m, 2H), 7.28 (s, 1H), 8.55 (s, 1H); [M+H]=348.3.

Example 143. 1-[(4-Bromophenyl)methyl]-3-{5-methyl-[1,2,4]triazolo[1,5-a]pyrimidin-7-yl}piperidine

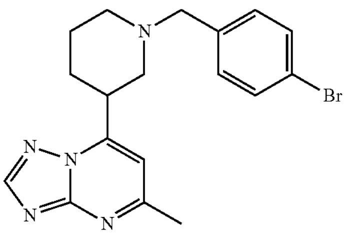 [SMILES: Cc1cc(C2CCCN(Cc3ccc(Br)cc3)C2)n2ncnc2n1]

$^1$H NMR (400 MHz, $CDCl_3$) δ=8.40 (s, 1H), 7.46 (d, J=8.28 Hz, 2H), 7.25 (d, J=8.03 Hz, 2H), 6.96 (s, 1H), 3.79 (br s, 1H), 3.45-3.63 (m, 2H), 3.07 (d, J=10.42 Hz, 1H), 2.77 (br s, 1H), 2.68 (s, 4H), 2.44 (br s, 1H), 2.31 (br s, 1H), 2.15 (dd, J=4.08, 12.11 Hz, 1H), 1.68-1.82 (m, 3H); [M+H]=386.1, 388.1.

Example 144. 1-[(4-Bromo-2,6-difluorophenyl)methyl]-3-{5-methyl-[1,2,4]triazolo[1,5-a]pyrimidin-7-yl}piperidine

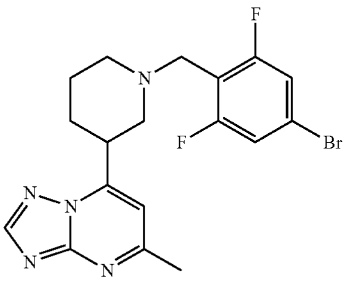 [SMILES: Cc1cc(C2CCCN(Cc3c(F)cc(Br)cc3F)C2)n2ncnc2n1]

$^1$H NMR (400 MHz, $CDCl_3$) δ=8.40 (s, 1H), 7.18 (br s, 1H), 7.10-7.16 (m, 3H), 3.79 (br s, 1H), 3.70 (s, 2H), 3.01 (d, J=10.54 Hz, 1H), 2.68 (s, 5H), 2.51 (d, J=5.02 Hz, 1H), 1.95-2.14 (m, 1H), 1.66-1.84 (m, 3H); [M+H]=422.1, 424.1.

Example 145. 1-[(5-Bromo-2-fluorophenyl)methyl]-3-{5-methyl-[1,2,4]triazolo[1,5-a]pyrimidin-7-yl}piperidine

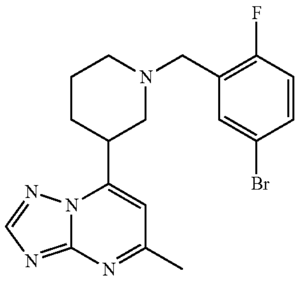 [SMILES: Cc1cc(C2CCCN(Cc3cc(Br)ccc3F)C2)n2ncnc2n1]

$^{1}$H NMR (400 MHz, $CDCl_3$) δ=8.41 (s, 1H), 7.60 (d, J=5.14 Hz, 1H), 7.34-7.40 (m, 1H), 7.09 (br s, 1H), 6.95 (t, J=9.10 Hz, 1H), 3.82 (br s, 1H), 3.62 (s, 2H), 3.00-3.13 (m, 1H), 2.70 (m, 4H), 2.52-2.64 (m, 1H), 2.47 (br s, 1H), 2.10 (d, J=6.90 Hz, 1H), 1.77 (br s, 3H);

[M+H]=404.1, 406.1.

Example 146. 1-Ethyl-6-[(3-{5-methyl-[1,2,4]triazolo[1,5-a]pyrimidin-7-yl}piperidin-1-yl)methyl]-1H-indole

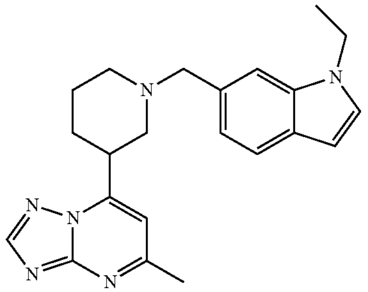 [SMILES: CCn1ccc2ccc(CN3CCCC(c4cc(C)nc5ncnn45)C3)cc21]

$^{1}$H NMR (400 MHz, DMSO-$d_6$) δ=10.17 (br s, 1H), 8.54-8.65 (m, 1H), 7.69 (s, 1H), 7.63 (d, J=8.03 Hz, 1H), 7.52 (d, J=2.89 Hz, 1H), 7.24 (s, 1H), 7.16 (d, J=8.03 Hz, 1H), 6.49 (d, J=2.89 Hz, 1H), 4.48 (br s, 2H), 4.23 (q, J=7.15 Hz, 2H), 3.97 (t, J=11.86 Hz, 1H), 3.83 (d, J=11.04 Hz, 1H), 3.56 (d, J=11.80 Hz, 1H), 3.25-3.43 (m, 1H), 3.06 (d, J=10.29 Hz, 1H), 2.64 (s, 3H), 2.02-2.21 (m, 2H), 1.79-1.99 (m, 2H), 1.39 (t, J=7.15 Hz, 3H); [M+H]=375.2.

Example 147. 3-{5-Methyl-[1,2,4]triazolo[1,5-a]pyrimidin-7-yl}-1-{[4-(1,3-thiazol-2-yl)phenyl]methyl}piperidine

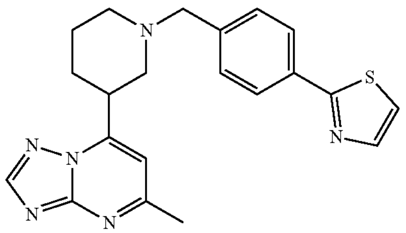 [SMILES: Cc1cc(C2CCCN(Cc3ccc(-c4nccs4)cc3)C2)n2ncnc2n1]

$^{1}$H NMR (400 MHz, DMSO-$d_6$) δ=10.30 (br s, 1H), 8.61 (s, 1H), 8.06 (d, J=7.91 Hz, 2H), 7.98 (d, J=3.14 Hz, 1H), 7.86 (d, J=3.14 Hz, 1H), 7.68 (d, J=7.91 Hz, 2H), 7.23 (s, 1H), 4.39-4.54 (m, 2H), 3.90-4.02 (m, 1H), 3.79 (d, J=10.42 Hz, 1H), 3.57 (d, J=11.54 Hz, 1H), 3.35 (t, J=11.36 Hz, 1H), 3.07 (br s, 1H), 2.64 (s, 3H), 1.79-2.23 (m, 4H); [M+H]=391.2.

Example 148. 3-{5-Methyl-[1,2,4]triazolo[1,5-a]pyrimidin-7-yl}-1-{[4-(1H-pyrazol-1-yl)phenyl]methyl}piperidine

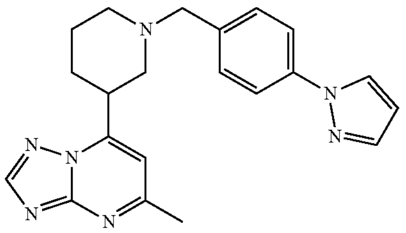

$^{1}$H NMR (400 MHz, DMSO-$d_6$) δ=10.39 (br s, 1H), 8.52-8.69 (m, 2H), 7.96 (d, J=8.16 Hz, 2H), 7.79 (s, 1H), 7.67 (d, J=8.16 Hz, 2H), 7.24 (s, 1H), 6.59 (s, 1H), 4.37-4.52 (m, 2H), 3.90-4.03 (m, 1H), 3.80 (d, J=10.92 Hz, 1H), 3.57 (d, J=11.54 Hz, 1H), 3.34 (t, J=11.48 Hz, 1H), 3.08 (d, J=10.16 Hz, 1H), 2.64 (s, 3H), 1.79-2.22 (m, 4H); [M+H]=374.2.

Example 149. 3-{5-Methyl-[1,2,4]triazolo[1,5-a]pyrimidin-7-yl}-1-{[4-(2-methylpropyl)phenyl]methyl}piperidine

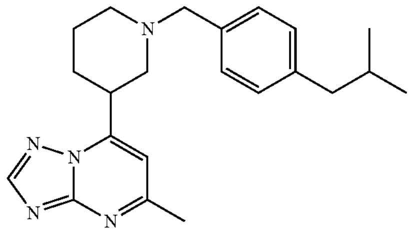 [SMILES: Cc1cc(C2CCCN(Cc3ccc(CC(C)C)cc3)C2)n2ncnc2n1]

$^{1}$H NMR (400 MHz, DMSO-$d_6$) δ=10.07 (br s, 1H), 8.56 (s, 1H), 7.43 (d, J=7.78 Hz, 2H), 7.20-7.29 (m, 3H), 4.25-4.41 (m, 2H), 3.92 (t, J=11.36 Hz, 1H), 3.75 (d, J=10.79 Hz, 1H), 3.50 (d, J=11.92 Hz, 1H), 3.28 (d, J=6.90 Hz, 1H), 3.02 (br s, 1H), 2.63 (s, 3H), 2.47 (d, J=7.15 Hz, 2H), 1.75-2.19 (m, 5H), 0.85 (d, J=6.53 Hz, 6H); [M+H]=364.2.

Example 150. 1-[(4-Bromo-3-chlorophenyl)methyl]-3-{5-methyl-[1,2,4]triazolo[1,5-a]pyrimidin-7-yl}piperidine

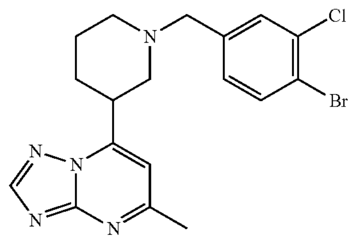

$^1$H NMR (400 MHz, DMSO-$d_6$) δ=10.16 (br s, 1H), 8.61 (s, 1H), 7.78-7.95 (m, 2H), 7.43 (d, J=8.16 Hz, 1H), 7.21 (s, 1H), 4.37 (br s, 2H), 3.91 (br s, 1H), 3.75 (d, J=9.66 Hz, 1H), 3.51 (d, J=9.41 Hz, 1H), 3.29 (br s, 1H), 3.02 (br s, 1H), 2.63 (s, 3H), 1.77-2.19 (m, 4H); [M+H]=420.1, 422.1.

Example 151. 1-[(4-Cyclopropylphenyl)methyl]-3-{5-methyl-[1,2,4]triazolo[1,5-a]pyrimidin-7-yl}piperidine

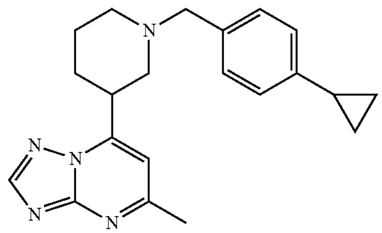 [SMILES: Cc1cc(C2CCCN(Cc3ccc(C4CC4)cc3)C2)n2ncnc2n1]

$^1$H NMR (400 MHz, DMSO-$d_6$) δ=10.04 (br s, 1H), 8.60 (s, 1H), 7.38 (d, J=7.91 Hz, 2H), 7.21 (s, 1H), 7.15 (d, J=7.91 Hz, 2H), 4.23-4.39 (m, 2H), 3.92 (t, J=11.48 Hz, 1H), 3.73 (d, J=11.29 Hz, 1H), 3.49 (d, J=11.67 Hz, 1H), 3.19-3.34 (m, 1H), 2.99 (br s, 1H), 2.63 (s, 3H), 1.75-2.20 (m, 5H), 0.93-1.03 (m, 2H), 0.69 (q, J=4.89 Hz, 2H); [M+H]=348.2.

Example 152. 1-[(4-Bromo-2-chlorophenyl)methyl]-3-{5-methyl-[1,2,4]triazolo[1,5-a]pyrimidin-7-yl}piperidine

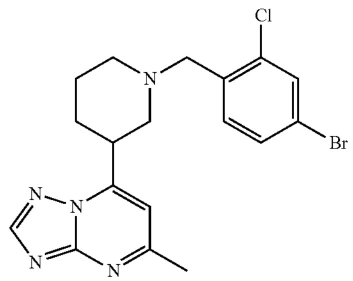

$^1$H NMR (400 MHz, DMSO-$d_6$) δ=8.61 (s, 1H), 7.90 (s, 1H), 7.60-7.81 (m, 2H), 7.20 (s, 1H), 4.46 (br s, 2H), 3.96 (br s, 1H), 3.76 (br s, 1H), 3.48 (br s, 2H), 3.14 (br s, 1H), 2.63 (s, 3H), 1.76-2.19 (m, 4H); [M+H]=420.1, 422.1.

Example 153. 1-[(4-tert-Butylphenyl)methyl]-3-{5-methyl-[1,2,4]triazolo[1,5-a]pyrimidin-7-yl}piperidine

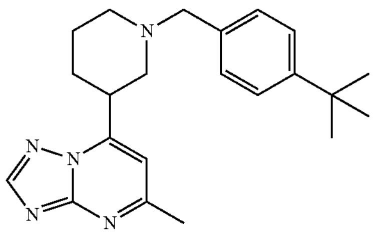 [SMILES: Cc1cc(C2CCCN(Cc3ccc(C(C)(C)C)cc3)C2)n2ncnc2n1]

$^1$H NMR (400 MHz, DMSO-$d_6$) δ=10.00 (br s, 1H), 8.60 (s, 1H), 7.48 (q, J=8.28 Hz, 4H), 7.24 (s, 1H), 4.35 (br s, 2H), 3.94 (t, J=11.36 Hz, 1H), 3.78 (d, J=11.54 Hz, 1H), 3.52 (d, J=12.17 Hz, 1H), 3.25-3.40 (m, 1H), 3.03 (br s, 1H), 2.65 (s, 3H), 1.79-2.21 (m, 4H), 1.30 (s, 9H); [M+H]=364.3.

Example 154. 7-[(3-{5-Methyl-[1,2,4]triazolo[1,5-a]pyrimidin-7-yl}piperidin-1-yl)methyl]isoquinoline

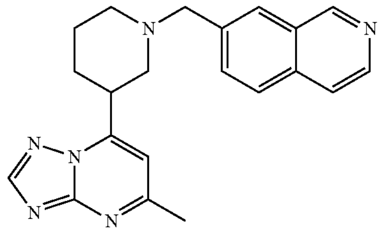 [SMILES: Cc1cc(C2CCCN(Cc3ccc4ccncc4c3)C2)n2ncnc2n1]

$^1$H NMR (400 MHz, DMSO-$d_6$) δ=9.49 (br s, 1H), 8.54-8.69 (m, 2H), 8.30 (br s, 1H), 8.17 (br s, 1H), 7.82-8.06 (m, 2H), 7.23 (s, 1H), 4.61 (br s, 2H), 3.77-4.01 (m, 2H), 3.57 (br s, 1H), 3.38 (br s, 1H), 3.11 (br s, 2H), 2.61-2.70 (m, 3H), 1.81-2.24 (m, 3H); [M+H]=359.2.

Example 155. 1-[(2,3-Difluoro-4-methylphenyl)methyl]-3-{5-methyl-[1,2,4]triazolo[1,5-a]pyrimidin-7-yl}piperidine

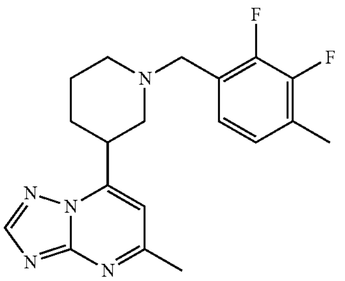 [SMILES: Cc1cc(C2CCCN(Cc3ccc(C)c(F)c3F)C2)n2ncnc2n1]

$^1$H NMR (400 MHz, DMSO-$d_6$) δ=8.62 (s, 1H), 7.30-7.38 (m, 1H), 7.19-7.28 (m, 2H), 4.44 (br s, 2H), 3.96 (br s, 1H), 3.79 (d, J=9.41 Hz, 1H), 3.55 (d, J=10.29 Hz, 1H), 3.39 (d, J=10.92 Hz, 1H), 3.09 (br s, 1H), 2.65 (s, 3H), 2.33 (s, 3H), 1.78-2.20 (m, 4H);

[M+H]=358.2.

Example 156. 3-{5-Methyl-[1,2,4]triazolo[1,5-a]pyrimidin-7-yl}-1-{[4-(trifluoromethoxy)phenyl]methyl}piperidine

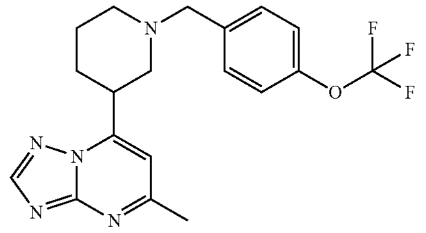 [SMILES: Cc1cc(C2CCCN(Cc3ccc(OC(F)(F)F)cc3)C2)n2ncnc2n1]

$^1$H NMR (400 MHz, DMSO-$d_6$) δ=10.09 (br s, 1H), 8.60 (s, 1H), 7.69 (d, J=8.28 Hz, 2H), 7.50 (d, J=8.16 Hz, 2H), 7.23 (s, 1H), 4.33-4.54 (m, 2H), 3.93 (br s, 1H), 3.78 (d, J=11.17 Hz, 1H), 3.54 (d, J=11.92 Hz, 1H), 3.32 (br s, 1H), 3.05 (br s, 1H), 2.65 (s, 3H), 1.78-2.22 (m, 4H); [M+H]=392.2.

Example 157. 3-{5-Methyl-[1,2,4]triazolo[1,5-a]pyrimidin-7-yl}-1-{[2-(trifluoromethoxy)phenyl]methyl}piperidine

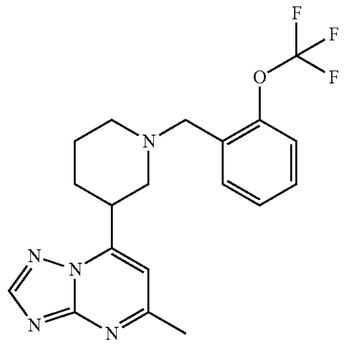 [SMILES: Cc1cc(C2CCCN(Cc3ccccc3OC(F)(F)F)C2)n2ncnc2n1]

$^1$H NMR (400 MHz, DMSO-$d_6$) δ=8.62 (s, 1H), 7.80 (d, J=7.53 Hz, 1H), 7.61-7.69 (m, 1H), 7.47-7.58 (m, 2H), 7.21 (s, 1H), 4.47 (br s, 2H), 3.99 (br s, 1H), 3.79 (d, J=9.54 Hz, 1H), 3.46 (d, J=10.79 Hz, 2H), 3.14 (br s, 1H), 2.65 (s, 3H), 1.81-2.24 (m, 4H); [M+H]=392.2.

Example 158. 1-{[2-Methoxy-4-(trifluoromethyl)phenyl]methyl}-3-{5-methyl-[1,2,4]triazolo[1,5-a]pyrimidin-7-yl}piperidine

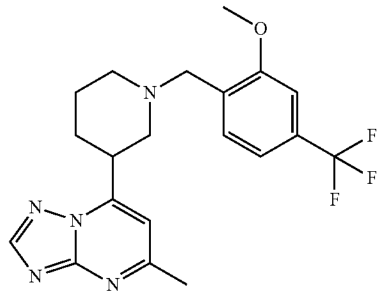 [SMILES: COc1cc(C(F)(F)F)ccc1CN1CCCC(c2cc(C)nc3ncnn23)C1]

$^1$H NMR (400 MHz, DMSO-$d_6$) δ=10.00 (br s, 1H), 8.61 (s, 1H), 7.72 (d, J=8.16 Hz, 1H), 7.42 (br s, 2H), 7.20 (s, 1H), 4.40 (br s, 2H), 3.95 (s, 4H), 3.80 (d, J=10.29 Hz, 1H), 3.36-3.57 (m, 2H), 3.09 (br s, 1H), 2.63 (s, 3H), 1.74-2.20 (m, 4H); [M+H]=406.2.

Example 159. 7-[(3-{5-Methyl-[1,2,4]triazolo[1,5-a]pyrimidin-7-yl}piperidin-1-yl)methyl]quinoline

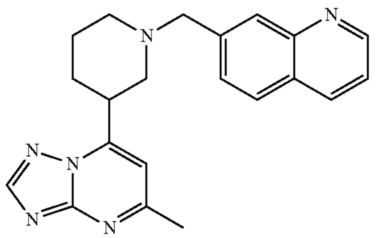 [SMILES: Cc1cc(C2CCCN(Cc3ccc4cccnc4c3)C2)n2ncnc2n1]

$^1$H NMR (400 MHz, DMSO-$d_6$) δ=10.26 (br s, 1H), 9.01 (d, J=4.02 Hz, 1H), 8.58 (s, 1H), 8.48 (d, J=8.16 Hz, 1H), 8.27 (s, 1H), 8.12 (d, J=8.41 Hz, 1H), 7.77 (d, J=8.16 Hz, 1H), 7.65 (dd, J=4.20, 8.22 Hz, 1H), 7.23 (s, 1H), 4.57-4.72 (m, 2H), 3.96 (br s, 1H), 3.83 (d, J=11.17 Hz, 1H), 3.61 (d, J=11.92 Hz, 1H), 3.40 (br s, 1H), 3.13 (br s, 1H), 2.64 (s, 3H), 1.80-2.20 (m, 4H); [M+H]=359.2.

Example 160. 3-{5-Methyl-[1,2,4]triazolo[1,5-a]pyrimidin-7-yl}-1-{[4-(thiophen-2-yl)phenyl]methyl}piperidine

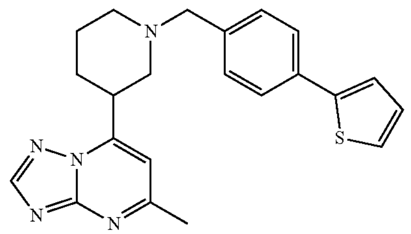 [SMILES: Cc1cc(C2CCCN(Cc3ccc(-c4cccs4)cc3)C2)n2ncnc2n1]

$^1$H NMR (400 MHz, DMSO-$d_6$) δ=10.21 (br s, 1H), 8.60 (s, 1H), 7.76 (d, J=7.91 Hz, 2H), 7.53-7.62 (m, 4H), 7.22 (s, 1H), 7.16 (t, J=4.33 Hz, 1H), 4.33-4.47 (m, 2H), 3.94 (t, J=11.42 Hz, 1H), 3.78 (d, J=11.04 Hz, 1H), 3.55 (d, J=11.92 Hz, 1H), 3.32 (t, J=10.73 Hz, 1H), 3.04 (br s, 1H), 2.63 (s, 3H), 1.77-2.21 (m, 4H); [M+H]=390.2.

Example 161. 1-[(3-Fluoro-4-methylphenyl)methyl]-3-{5-methyl-[1,2,4]triazolo[1,5-a]pyrimidin-7-yl}piperidine

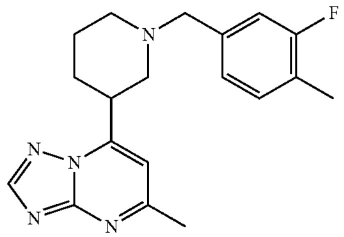 [SMILES: Cc1cc(C2CCCN(Cc3ccc(C)c(F)c3)C2)n2ncnc2n1]

$^1$H NMR (400 MHz, DMSO-$d_6$) δ=10.15 (br s, 1H), 8.62 (s, 1H), 7.33-7.43 (m, 2H), 7.27 (d, J=7.53 Hz, 1H), 7.23 (s, 1H), 4.27-4.46 (m, 2H), 3.94 (t, J=11.17 Hz, 1H), 3.76 (d, J=11.17 Hz, 1H), 3.52 (d, J=11.67 Hz, 1H), 3.29 (t, J=11.36 Hz, 1H), 3.03 (br s, 1H), 2.64 (s, 3H), 2.27 (s, 3H), 1.78-2.20 (m, 4H); [M+H]=340.2.

Example 162. 1-[(2-Chloro-4-fluorophenyl)methyl]-3-{5-methyl-[1,2,4]triazolo[1,5-a]pyrimidin-7-yl}piperidine

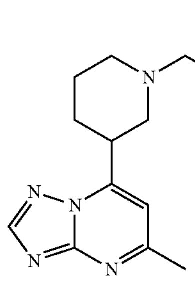

$^1$H NMR (400 MHz, DMSO-$d_6$) δ=10.28 (br s, 1H), 8.61 (s, 1H), 7.80 (t, J=7.15 Hz, 1H), 7.62 (dd, J=2.38, 8.78 Hz, 1H), 7.39 (dt, J=2.38, 8.41 Hz, 1H), 7.21 (s, 1H), 4.49 (br s, 2H), 3.97 (br s, 1H), 3.80 (d, J=9.29 Hz, 1H), 3.43-3.59 (m, 2H), 3.19 (d, J=10.54 Hz, 1H), 2.63 (s, 3H), 1.77-2.20 (m, 4H); [M+H]=360.1.

Example 163. 1-{[2-Methyl-4-(trifluoromethyl)phenyl]methyl}-3-{5-methyl-[1,2,4]triazolo[1,5-a]pyrimidin-7-yl}piperidine

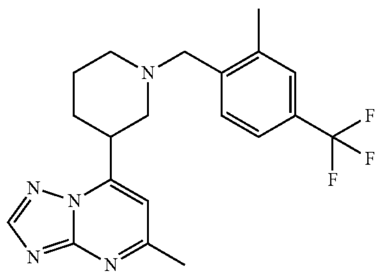 [SMILES: Cc1cc(C2CCCN(Cc3ccc(C(F)(F)F)cc3C)C2)n2ncnc2n1]

$^1$H NMR (400 MHz, DMSO-$d_6$) δ=10.01 (br s, 1H), 8.60 (s, 1H), 7.64-7.80 (m, 3H), 7.21 (s, 1H), 4.48 (br s, 2H), 3.91-4.03 (m, 1H), 3.78 (d, J=10.54 Hz, 1H), 3.53 (br s, 2H), 3.20 (br s, 1H), 2.64 (s, 3H), 1.77-2.21 (m, 4H); [M+H]=390.2.

Example 164. 1-{[4-Chloro-3-(trifluoromethyl)phenyl]methyl}-3-{5-methyl-[1,2,4]triazolo[1,5-a]pyrimidin-7-yl}piperidine

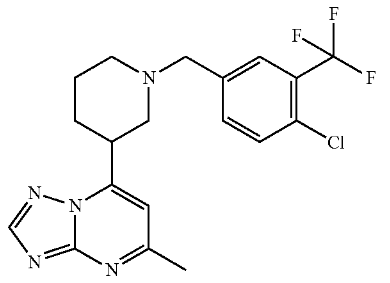 [SMILES: Cc1cc(C2CCCN(Cc3ccc(Cl)c(C(F)(F)F)c3)C2)n2ncnc2n1]

$^1$H NMR (400 MHz, DMSO-$d_6$) δ=8.61 (s, 1H), 8.11 (br s, 1H), 7.86 (s, 2H), 7.23 (s, 1H), 4.51 (br s, 2H), 3.94 (br s, 1H), 3.80 (d, J=8.53 Hz, 1H), 3.54 (d, J=10.42 Hz, 1H), 3.37 (t, J=11.73 Hz, 1H), 3.09 (br s, 1H), 2.64 (s, 3H), 1.78-2.24 (m, 4H); [M+H]=410.1.

Example 165. 1-[(4-Chloro-3-methylphenyl)methyl]-3-{5-methyl-[1,2,4]triazolo[1,5-a]pyrimidin-7-yl}piperidine

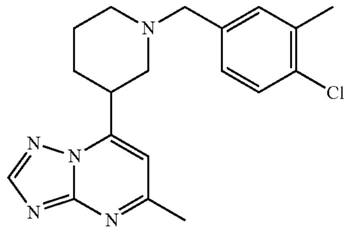 [SMILES: Cc1cc(C2CCCN(Cc3ccc(Cl)c(C)c3)C2)n2ncnc2n1]

$^1$H NMR (400 MHz, DMSO-$d_6$) δ=8.62 (s, 1H), 7.52 (d, J=8.03 Hz, 2H), 7.39 (d, J=7.91 Hz, 1H), 7.23 (s, 1H), 4.36 (br s, 2H), 3.95 (br s, 1H), 3.77 (d, J=10.92 Hz, 1H), 3.53 (d, J=11.67 Hz, 1H), 3.33 (t, J=11.61 Hz, 1H), 2.97-3.13 (m, 1H), 2.64 (s, 3H), 2.35 (s, 3H), 1.78-2.22 (m, 4H); [M+H]=356.1.

Example 166. 1-[(3,4-Dichlorophenyl)methyl]-3-{5-methyl-[1,2,4]triazolo[1,5-a]pyrimidin-7-yl}piperidine

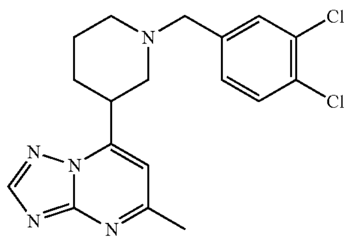

$^1$H NMR (400 MHz, DMSO-$d_6$) δ=8.63 (s, 1H), 7.87 (br s, 1H), 7.77 (d, J=8.16 Hz, 1H), 7.54 (d, J=8.03 Hz, 1H), 7.23 (s, 1H), 4.32-4.49 (m, 2H), 3.94 (br s, 1H), 3.78 (d,

J=10.92 Hz, 1H), 3.54 (d, J=11.17 Hz, 1H), 3.32 (t, J=11.29 Hz, 1H), 3.05 (br s, 1H), 2.64 (s, 3H), 1.78-2.24 (m, 4H); [M+H]=376.1, 378.1.

Example 167.1-[(4-Chloro-3-methoxyphenyl) methyl]-3-{5-methyl-[1,2,4]triazolo[1,5-a]pyrimidin-7-yl}piperidine

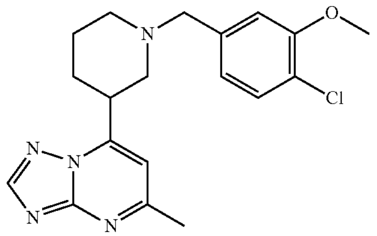 [SMILES: COc1cc(CN2CCCC(c3cc(C)nc4ncnn34)C2)ccc1Cl]

$^1$H NMR (400 MHz, DMSO-$d_6$) δ=8.62 (s, 1H), 7.53 (d, J=8.03 Hz, 1H), 7.36 (s, 1H), 7.23 (s, 1H), 7.12 (d, J=7.91 Hz, 1H), 4.39 (br s, 2H), 3.86-4.04 (m, 4H), 3.79 (d, J=11.17 Hz, 1H), 3.54 (d, J=11.67 Hz, 1H), 3.33 (t, J=11.67 Hz, 1H), 3.05 (br s, 1H), 2.64 (s, 3H), 1.77-2.23 (m, 4H); [M+H]=372.2.

Example 168. 1-[(3-Bromo-4-chlorophenyl)methyl]-3-{5-methyl-[1,2,4]triazolo[1,5-a]pyrimidin-7-yl}piperidine

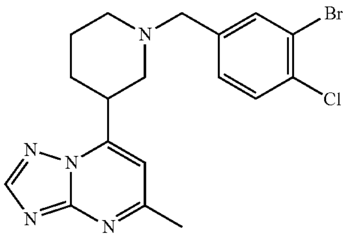 [SMILES: Cc1cc(C2CCCN(Cc3ccc(Cl)c(Br)c3)C2)n2ncnc2n1]

$^1$H NMR (400 MHz, DMSO-$d_6$) δ=10.19 (br s, 1H), 8.63 (s, 1H), 8.01 (br s, 1H), 7.76 (d, J=8.16 Hz, 1H), 7.57 (d, J=7.15 Hz, 1H), 7.23 (s, 1H), 4.40 (br s, 2H), 3.93 (br s, 1H), 3.78 (d, J=9.79 Hz, 1H), 3.54 (d, J=11.29 Hz, 1H), 3.31 (t, J=11.48 Hz, 1H), 3.04 (br s, 1H), 2.64 (s, 3H), 1.78-2.22 (m, 4H); [M+H]=420.1-424.1.

Example 169. 1-[(3-Bromo-4-methylphenyl) methyl]-3-{5-methyl-[1,2,4]triazolo[1,5-a]pyrimidin-7-yl}piperidine

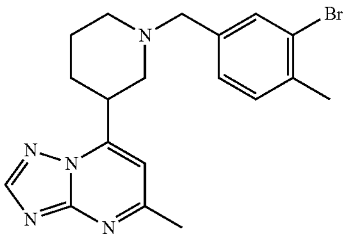 [SMILES: Cc1cc(C2CCCN(Cc3ccc(C)c(Br)c3)C2)n2ncnc2n1]

$^1$H NMR (400 MHz, DMSO-$d_6$) δ=10.17 (br s, 1H), 8.62 (s, 1H), 7.82 (s, 1H), 7.45 (s, 2H), 7.23 (s, 1H), 4.36 (br s, 2H), 3.94 (br s, 1H), 3.77 (d, J=10.67 Hz, 1H), 3.52 (d, J=11.92 Hz, 1H), 3.32 (t, J=11.36 Hz, 1H), 3.04 (br s, 1H), 2.64 (s, 3H), 2.38 (s, 3H), 1.78-2.23 (m, 4H); [M+H]=400.1, 402.1.

Example 170. 1-[(3-Bromo-4-methoxyphenyl) methyl]-3-{5-methyl-[1,2,4]triazolo[1,5-a]pyrimidin-7-yl}piperidine

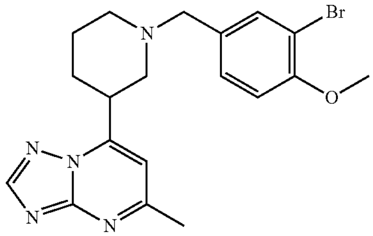 [SMILES: COc1ccc(CN2CCCC(c3cc(C)nc4ncnn34)C2)cc1Br]

$^1$H NMR (400 MHz, DMSO-$d_6$) δ=9.99 (br s, 1H), 8.62 (s, 1H), 7.81 (s, 1H), 7.52 (d, J=8.41 Hz, 1H), 7.05-7.31 (m, 2H), 4.33 (br s, 2H), 3.85-3.98 (m, 4H), 3.77 (d, J=11.80 Hz, 1H), 3.51 (d, J=11.67 Hz, 1H), 3.28 (d, J=7.15 Hz, 1H), 3.02 (br s, 1H), 2.65 (s, 3H), 1.76-2.22 (m, 4H); [M+H]=416.1, 418.1.

Example 171. 1-[(3-Bromo-4-fluorophenyl)methyl]-3-{5-methyl-[1,2,4]triazolo[1,5-a]pyrimidin-7-yl}piperidine

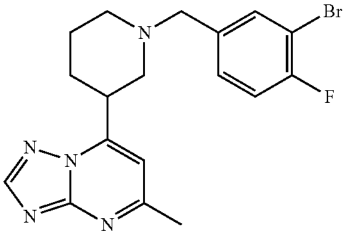 [SMILES: Cc1cc(C2CCCN(Cc3ccc(F)c(Br)c3)C2)n2ncnc2n1]

$^1$H NMR (400 MHz, DMSO-$d_6$) δ=8.62 (s, 1H), 7.96 (d, J=5.52 Hz, 1H), 7.60 (br s, 1H), 7.50 (t, J=8.60 Hz, 1H), 7.24 (s, 1H), 4.40 (br s, 2H), 3.93 (br s, 1H), 3.78 (d, J=10.42 Hz, 1H), 3.54 (d, J=11.67 Hz, 1H), 3.32 (t, J=11.54 Hz, 1H), 3.05 (br s, 1H), 2.64 (s, 3H), 1.76-2.23 (m, 4H); [M+H]=404.2, 406.2.

Example 172. 1-[(4-Bromo-3-methylphenyl) methyl]-3-{5-methyl-[1,2,4]triazolo[1,5-a]pyrimidin-7-yl}piperidine

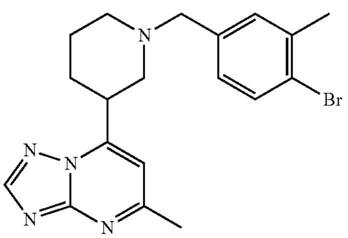 [SMILES: Cc1cc(C2CCCN(Cc3ccc(Br)c(C)c3)C2)n2ncnc2n1]

$^1H$ NMR (400 MHz, DMSO-$d_6$) δ=10.21 (br s, 1H), 8.62 (s, 1H), 7.70 (d, J=8.16 Hz, 1H), 7.52 (s, 1H), 7.30 (d, J=7.91 Hz, 1H), 7.23 (s, 1H), 4.35 (br s, 2H), 3.88-4.02 (m, 1H), 3.77 (d, J=11.17 Hz, 1H), 3.52 (d, J=12.05 Hz, 1H), 3.32 (t, J=11.80 Hz, 1H), 3.04 (br s, 1H), 2.64 (s, 3H), 2.38 (s, 3H), 1.72-2.21 (m, 4H); [M+H]=400.1, 402.1.

Example 173. 1-[(4-Iodophenyl)methyl]-3-{5-methyl-[1,2,4]triazolo[1,5-a]pyrimidin-7-yl}piperidine

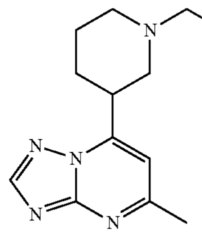

$^1H$ NMR (400 MHz, DMSO-$d_6$) δ=10.25 (br s, 1H), 8.62 (s, 1H), 7.86 (d, J=8.03 Hz, 2H), 7.34 (d, J=7.78 Hz, 2H), 7.22 (s, 1H), 4.28-4.45 (m, 2H), 3.88-4.00 (m, 1H), 3.75 (d, J=11.17 Hz, 1H), 3.53 (d, J=11.80 Hz, 1H), 3.31 (t, J=11.73 Hz, 1H), 2.96-3.11 (m, 1H), 2.64 (s, 3H), 1.75-2.21 (m, 4H); [M+H]=434.1.

Example 174. (3R)-1-[(4-Bromo-3-fluorophenyl)methyl]-3-{5-methyl-[1,2,4]triazolo[1,5-a]pyrimidin-7-yl}piperidine

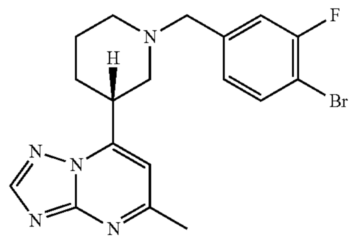

$^1H$ NMR (400 MHz, $CDCl_3$) δ=8.51-8.35 (m, 1H), 7.70-7.54 (m, 1H), 7.26 (s, 2H), 7.19-7.12 (m, 1H), 6.90 (s, 1H), 4.36-4.12 (m, 2H), 4.11-3.91 (m, 1H), 3.76-3.56 (m, 3H), 3.00-2.79 (m, 1H), 2.67 (s, 2H), 2.53-2.37 (m, 1H), 2.33-2.01 (m, 3H); [M+H]=405.1.

Example 175. 3-[(3-{5-Methyl-[1,2,4]triazolo[1,5-a]pyrimidin-7-yl}piperidin-1-yl)methyl]benzonitrile

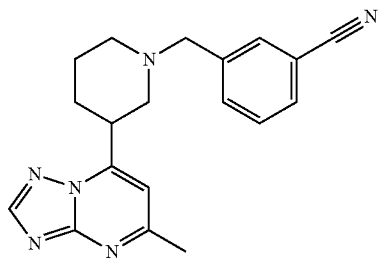 [SMILES: Cc1cc(C2CCCN(Cc3cccc(C#N)c3)C2)n2ncnc2n1]

$^1H$ NMR (400 MHz, $CDCl_3$) δ=8.52-8.40 (m, 1H), 7.86-7.68 (m, 3H), 7.65-7.53 (m, 1H), 6.98-6.85 (m, 1H), 4.42-4.24 (m, 2H), 4.10-3.91 (m, 1H), 3.78-3.61 (m, 3H), 3.05-2.86 (m, 1H), 2.68 (s, 3H), 2.54-2.36 (m, 1H), 2.33-2.01 (m, 3H); [M+H]=333.1.

Example 176. 2-Fluoro-5-[(3-{5-methyl-[1,2,4]triazolo[1,5-a]pyrimidin-7-yl}piperidin-1-yl)methyl]benzonitrile

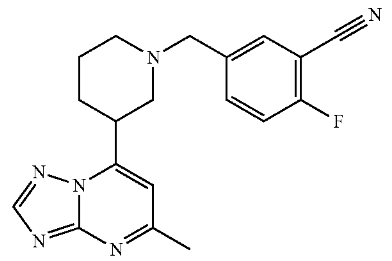 [SMILES: Cc1cc(C2CCCN(Cc3ccc(F)c(C#N)c3)C2)n2ncnc2n1]

$^1H$ NMR (400 MHz, $CDCl_3$) δ=8.52-8.36 (m, 1H), 7.93-7.81 (m, 1H), 7.79-7.67 (m, 1H), 7.37-7.29 (m, 1H), 6.93 (s, 1H), 4.41-4.18 (m, 2H), 4.08-3.90 (m, 1H), 3.77-3.62 (m, 3H), 3.02-2.85 (m, 1H), 2.69 (s, 3H), 2.57-2.38 (m, 1H), 2.30-2.02 (m, 3H); [M+H]=351.1.

Example 177. 4-[(3-{5-Methyl-[1,2,4]triazolo[1,5-a]pyrimidin-7-yl}piperidin-1-yl)methyl]benzonitrile

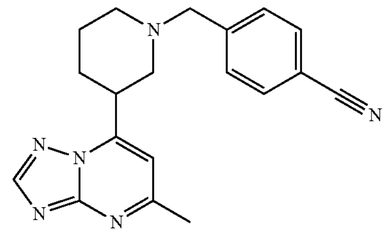 [SMILES: Cc1cc(C2CCCN(Cc3ccc(C#N)cc3)C2)n2ncnc2n1]

$^1H$ NMR (400 MHz, $CDCl_3$) δ=8.52-8.33 (m, 1H), 7.79-7.68 (m, 2H), 7.66-7.55 (m, 2H), 6.98-6.83 (m, 1H), 4.40-4.25 (m, 2H), 4.04-3.94 (m, 1H), 3.80-3.62 (m, 3H), 3.01-2.84 (m, 1H), 2.68 (s, 3H), 2.53-2.40 (m, 1H), 2.32-2.03 (m, 3H); [M+H]=333.1.

Example 178. 1-{[3-Fluoro-4-(trifluoromethyl)phenyl]methyl}-3-{5-methyl-[1,2,4]triazolo[1,5-a]pyrimidin-7-yl}piperidine

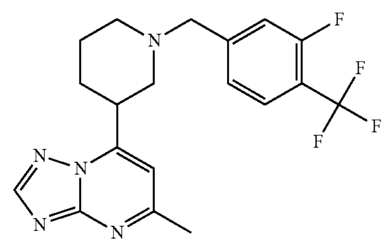 [SMILES: Cc1cc(C2CCCN(Cc3ccc(C(F)(F)F)c(F)c3)C2)n2ncnc2n1]

$^1$H NMR (400 MHz, $CDCl_3$) δ=8.50-8.38 (m, 1H), 7.74-7.61 (m, 1H), 7.45-7.34 (m, 2H), 6.96-6.86 (m, 1H), 4.37-4.24 (m, 2H), 4.05-3.94 (m, 1H), 3.77-3.62 (m, 3H), 2.99-2.83 (m, 1H), 2.69 (s, 3H), 2.56-2.39 (m, 1H), 2.32-2.03 (m, 3H); [M+H]=394.1.

Example 179. (3S)-1-{[3-Fluoro-4-(trifluoromethyl)phenyl]methyl}-3-{5-methyl-[1,2,4]triazolo[1,5-a]pyrimidin-7-yl}piperidine

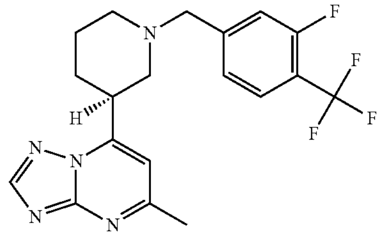 [SMILES: Cc1cc([C@H]2CCCN(Cc3ccc(C(F)(F)F)c(F)c3)C2)n2ncnc2n1]

$^1$H NMR (400 MHz, $CDCl_3$) δ=8.50-8.39 (m, 1H), 7.73-7.64 (m, 1H), 7.44-7.32 (m, 2H), 6.99-6.82 (m, 1H), 4.39-4.24 (m, 3H), 4.05-3.95 (m, 1H), 3.77-3.63 (m, 3H), 2.99-2.86 (m, 1H), 2.69 (s, 2H), 2.55-2.41 (m, 1H), 2.33-2.02 (m, 3H); [M+H]=394.3.

Example 180. 2-Methyl-5-[(3-{5-methyl-[1,2,4]triazolo[1,5-a]pyrimidin-7-yl}piperidin-1-yl)methyl]benzonitrile

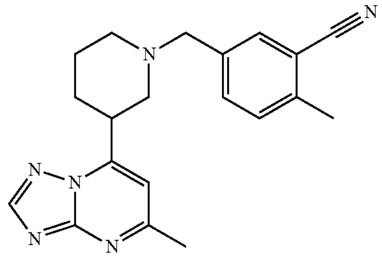 [SMILES: Cc1cc(C2CCCN(Cc3ccc(C)c(C#N)c3)C2)n2ncnc2n1]

$^1$H NMR (400 MHz, $CDCl_3$) δ=8.51-8.36 (m, 1H), 7.71-7.55 (m, 2H), 7.46-7.34 (m, 1H), 6.91 (s, 1H), 4.35-4.18 (m, 2H), 4.06-3.89 (m, 1H), 3.77-3.55 (m, 3H), 3.03-2.83 (m, 1H), 2.68 (s, 3H), 2.55 (s, 4H), 2.17 (s, 3H); [M+H]=347.2.

Example 181. 1-{[3-Fluoro-5-(trifluoromethyl)phenyl]methyl}-3-{5-methyl-[1,2,4]triazolo[1,5-a]pyrimidin-7-yl}piperidine

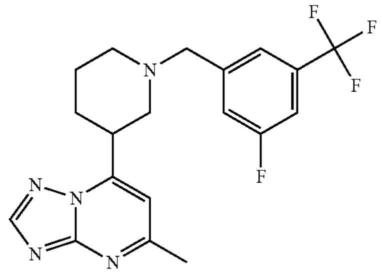 [SMILES: Cc1cc(C2CCCN(Cc3cc(F)cc(C(F)(F)F)c3)C2)n2ncnc2n1]

$^1$H NMR (400 MHz, $CDCl_3$) δ=8.48-8.37 (m, 1H), 7.61-7.52 (m, 1H), 7.49-7.39 (m, 2H), 6.98-6.87 (m, 1H), 4.38-4.27 (m, 2H), 4.04-3.91 (m, 1H), 3.80-3.59 (m, 3H), 2.99-2.85 (m, 1H), 2.69 (s, 3H), 2.54-2.38 (m, 1H), 2.31-2.04 (m, 3H); [M+H]=394.2.

Example 182. 1-[(4-Chloro-3,5-difluorophenyl)methyl]-3-{5-methyl-[1,2,4]triazolo[1,5-a]pyrimidin-7-yl}piperidine

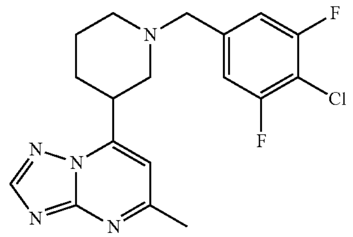 [SMILES: Cc1cc(C2CCCN(Cc3cc(F)c(Cl)c(F)c3)C2)n2ncnc2n1]

$^1$H NMR (400 MHz, $CDCl_3$) δ=8.48-8.37 (m, 1H), 7.30-7.21 (m, 1H), 7.19-7.09 (m, 2H), 6.99-6.87 (m, 1H), 4.33-4.16 (m, 2H), 4.04-3.92 (m, 1H), 3.75-3.61 (m, 3H), 3.00-2.84 (m, 1H), 2.68 (s, 3H), 2.52-2.34 (m, 1H), 2.28-2.05 (m, 3H); [M+H]=378.2.

Example 183. 2-Fluoro-4-[(3-{5-methyl-[1,2,4]triazolo[1,5-a]pyrimidin-7-yl}piperidin-1-yl)methyl]benzonitrile

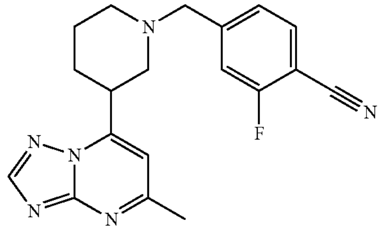 [SMILES: Cc1cc(C2CCCN(Cc3ccc(C#N)c(F)c3)C2)n2ncnc2n1]

$^1$H NMR (400 MHz, $CDCl_3$) δ=8.48-8.38 (m, 1H), 7.77-7.66 (m, 1H), 7.51-7.36 (m, 2H), 6.98-6.83 (m, 1H), 4.39-4.22 (m, 2H), 4.06-3.92 (m, 1H), 3.79-3.57 (m, 4H), 2.94-2.89 (m, 1H), 2.69 (s, 3H), 2.57-2.42 (m, 1H), 2.33-2.03 (m, 3H); [M+H]=351.2.

Example 184. (3R)-1-[(4-Chloro-3,5-difluorophenyl)methyl]-3-{5-methyl-[1,2,4]triazolo[1,5-a]pyrimidin-7-yl}piperidine

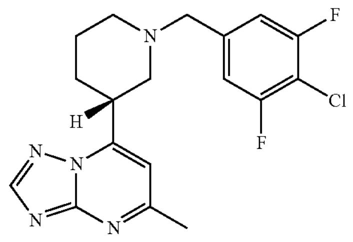 [SMILES: Cc1cc([C@@H]2CCCN(Cc3cc(F)c(Cl)c(F)c3)C2)n2ncnc2n1]

$^1$H NMR (400 MHz, $CDCl_3$) δ=8.32-8.49 (m, 1H), 7.12-7.22 (m, 2H), 6.91 (s, 1H), 4.16-4.34 (m, 2H), 3.90-4.06 (m, 1H), 3.52-3.76 (m, 3H), 2.85-3.01 (m, 1H), 2.66 (s, 3H), 2.32-2.48 (m, 1H), 2.00-2.32 (m, 3H); [M+H]=378.1.

Example 185. 1-[(3,5-Difluorophenyl)methyl]-3-{5-methyl-[1,2,4]triazolo[1,5-a]pyrimidin-7-yl}piperidine

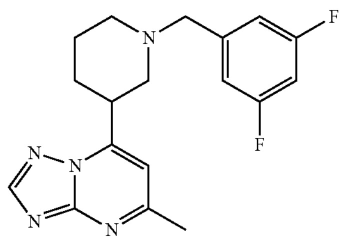 [SMILES: Cc1cc(C2CCCN(Cc3cc(F)cc(F)c3)C2)n2ncnc2n1]

$^1$H NMR (400 MHz, $CDCl_3$) δ=8.39-8.49 (m, 1H), 6.99-7.08 (m, 2H), 6.85-6.97 (m, 2H), 4.15-4.33 (m, 2H), 3.91-4.07 (m, 1H), 3.56-3.74 (m, 4H), 2.81-2.99 (m, 1H), 2.69 (s, 3H), 2.38-2.55 (m, 1H), 2.02-2.32 (m, 3H); [M+H]=344.2.

Example 186. (3R)-1-[(4-Bromo-3,5-difluorophenyl)methyl]-3-{5-methyl-[1,2,4]triazolo[1,5-a]pyrimidin-7-yl}piperidine

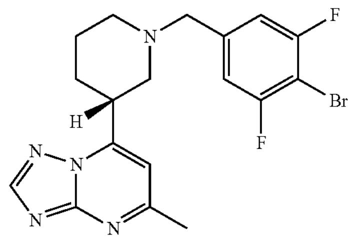 [SMILES: Cc1cc([C@@H]2CCCN(Cc3cc(F)c(Br)c(F)c3)C2)n2ncnc2n1]

$^1$H NMR (400 MHz, $CDCl_3$) δ=2.04-2.32 (m, 3H), 2.34-2.53 (m, 1H), 2.66 (s, 2H), 2.68 (s, 2H), 2.86-3.00 (m, 1H), 3.60-3.77 (m, 3H), 3.90-4.05 (m, 1H), 4.17-4.34 (m, 2H), 6.86-6.97 (m, 1H), 7.06-7.19 (m, 2H), 8.38-8.50 (m, 1H); [M+H]=423.1.

Example 187. 3-{5-Methyl-[1,2,4]triazolo[1,5-a]pyrimidin-7-yl}-1-[(3,4,5-trifluorophenyl)methyl]piperidine

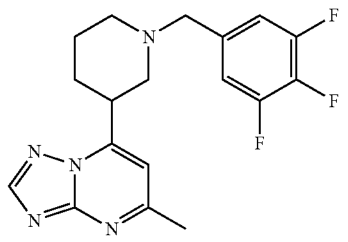 [SMILES: Cc1cc(C2CCCN(Cc3cc(F)c(F)c(F)c3)C2)n2ncnc2n1]

$^1$H NMR (400 MHz, DMSO-$d_6$) δ=8.61 (s, 1H), 7.46-7.64 (m, 2H), 7.22 (s, 1H), 4.33 (br s, 2H), 3.69-4.01 (m, 2H), 3.21-3.54 (m, 2H), 2.87-3.06 (m, 1H), 2.63 (s, 3H), 1.74-2.22 (m, 4H); [M+H]=362.2.

Example 188. 1-{[3-Fluoro-4-(trifluoromethoxy)phenyl]methyl}-3-{5-methyl-[1,2,4]triazolo[1,5-a]pyrimidin-7-yl}piperidine

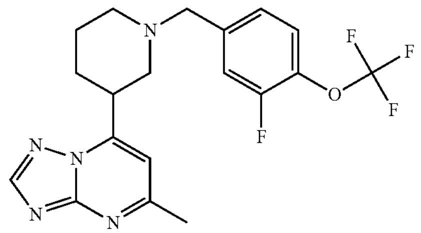 [SMILES: Cc1cc(C2CCCN(Cc3ccc(OC(F)(F)F)c(F)c3)C2)n2ncnc2n1]

$^1$H NMR (400 MHz, DMSO-$d_6$) δ=8.59 (s, 1H), 7.64-7.81 (m, 2H), 7.50 (d, J=7.4 Hz, 1H), 7.22 (s, 1H), 4.40 (br s, 2H), 3.63-4.02 (m, 4H), 3.02 (br s, 1H), 2.63 (s, 3H), 1.76-2.21 (m, 4H); [M+H]=410.3.

Example 189. 1-{[3-Fluoro-4-(1H-pyrazol-1-yl)phenyl]methyl}-3-{5-methyl-[1,2,4]triazolo[1,5-a]pyrimidin-7-yl}piperidine

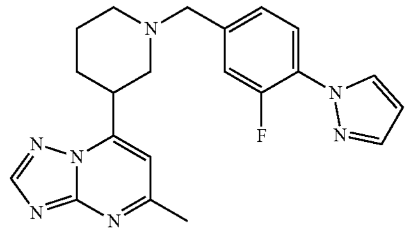 [SMILES: Cc1cc(C2CCCN(Cc3ccc(-n4cccn4)c(F)c3)C2)n2ncnc2n1]

$^1$H NMR (400 MHz, DMSO-$d_6$) δ=8.61 (s, 1H), 8.24 (t, J=2.5 Hz, 1H), 7.92 (t, J=8.2 Hz, 1H), 7.79-7.86 (m, 1H), 7.69 (d, J=12.2 Hz, 1H), 7.51 (d, J=7.7 Hz, 1H), 7.23 (s, 1H), 6.53-6.66 (m, 1H), 4.42 (br s, 2H), 3.69-4.04 (m, 4H), 3.23-3.43 (m, 1H), 2.63 (s, 3H), 1.76-2.22 (m, 4H); [M+H]=392.3.

Example 190. (3S)-1-{[3,5-Difluoro-4-(trifluoromethyl)phenyl]methyl}-3-{5-methyl-[1,2,4]triazolo[1,5-a]pyrimidin-7-yl}piperidine

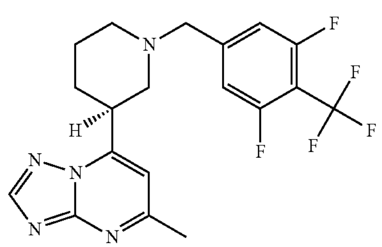 [SMILES: Cc1cc([C@H]2CCCN(Cc3cc(F)c(C(F)(F)F)c(F)c3)C2)n2ncnc2n1]

$^1$H NMR (400 MHz, $CDCl_3$) δ=9.22-9.22 (m, 1H), 8.44-8.57 (m, 1H), 7.40-7.52 (m, 2H), 7.16-7.24 (m, 1H), 4.43-4.54 (m, 2H), 3.98-4.11 (m, 1H), 3.87-3.98 (m, 1H), 3.57-3.68 (m, 1H), 3.33-3.43 (m, 1H), 3.07-3.24 (m, 1H), 2.71 (s, 2H), 2.26-2.36 (m, 1H), 2.16-2.25 (m, 1H), 1.98-2.14 (m, 2H); [M+H]=412.1.

Example 191. (3S)-3-{5-Methyl-[1,2,4]triazolo[1,5-a]pyrimidin-7-yl}-1-[(3,4,5-trifluorophenyl)methyl]piperidine

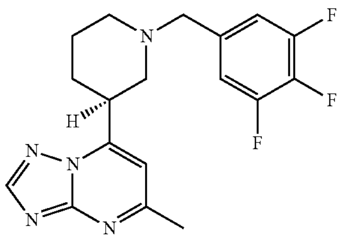 [SMILES: Cc1cc([C@H]2CCCN(Cc3cc(F)c(F)c(F)c3)C2)n2ncnc2n1]

$^{1}$H NMR (400 MHz, DMSO-$d_6$) δ=8.53 (s, 1H), 7.27 (dd, J=8.8, 6.8 Hz, 2H), 7.22 (s, 1H), 3.59-3.69 (m, 1H), 3.53 (s, 2H), 3.00-3.08 (m, 1H), 2.71-2.80 (m, 1H), 2.58 (s, 3H), 2.34 (t, J=10.4 Hz, 1H), 2.13-2.24 (m, 1H), 1.99-2.08 (m, 1H), 1.58-1.77 (m, 3H); [M+H]=362.3.

Example 192. 3-Fluoro-5-[(3-{5-methyl-[1,2,4]triazolo[1,5-a]pyrimidin-7-yl}piperidin-1-yl)methyl]pyridine

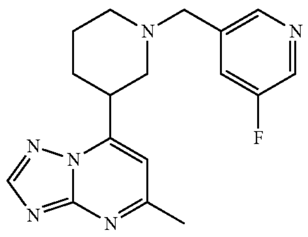 [SMILES: Cc1cc(C2CCCN(Cc3cncc(F)c3)C2)n2ncnc2n1]

$^{1}$H NMR (400 MHz, $CDCl_3$) δ=8.56-8.71 (m, 2H), 8.43-8.54 (m, 1H), 7.85-7.97 (m, 1H), 7.15-7.30 (m, 1H), 4.48-4.65 (m, 2H), 3.93-4.15 (m, 2H), 3.64-3.76 (m, 1H), 3.34-3.50 (m, 1H), 3.08-3.29 (m, 1H), 2.71 (s, 3H), 2.15-2.37 (m, 2H), 1.94-2.15 (m, 2H); [M+H]=327.1.

Example 193. 1-[(2-Bromo-1,3-thiazol-5-yl)methyl]-3-{5-methyl-[1,2,4]triazolo[1,5-a]pyrimidin-7-yl}piperidine

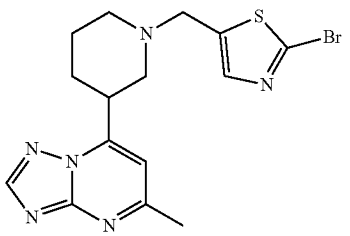 [SMILES: Cc1cc(C2CCCN(Cc3cnc(Br)s3)C2)n2ncnc2n1]

$^{1}$H NMR (400 MHz, $CD_3OD$) δ=8.41-8.53 (m, 1H), 7.72-7.84 (m, 1H), 7.11-7.22 (m, 1H), 4.58-4.70 (m, 2H), 3.81-4.07 (m, 2H), 3.54-3.67 (m, 1H), 3.32-3.37 (m, 1H), 3.02-3.16 (m, 1H), 2.69 (br s, 3H), 2.12-2.37 (m, 2H), 1.94-2.12 (m, 2H); [M+H]=393.1.

Example 194. 1-[(2-Methyl-1,3-thiazol-5-yl)methyl]-3-{5-methyl-[1,2,4]triazolo[1,5-a]pyrimidin-7-yl}piperidine

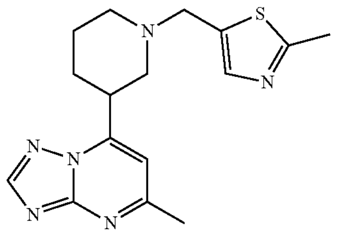 [SMILES: Cc1cc(C2CCCN(Cc3cnc(C)s3)C2)n2ncnc2n1]

$^{1}$H NMR (400 MHz, $CD_3OD$) δ=8.37-8.47 (m, 1H), 7.41-7.50 (m, 1H), 7.19-7.29 (m, 1H), 3.80 (s, 3H), 3.12-3.24 (m, 1H), 2.78-2.93 (m, 1H), 2.60-2.73 (m, 6H), 2.45-2.56 (m, 1H), 2.28-2.40 (m, 1H), 2.07-2.21 (m, 1H), 1.67-1.92 (m, 4H); [M+H]=329.2.

Example 195. 1-{[2-(4-Fluorophenyl)-1,3-thiazol-5-yl]methyl}-3-{5-methyl-[1,2,4]triazolo[1,5-a]pyrimidin-7-yl}piperidine

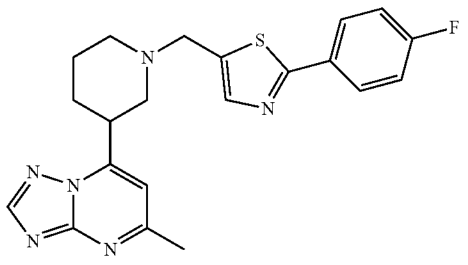 [SMILES: Cc1cc(C2CCCN(Cc3cnc(-c4ccc(F)cc4)s3)C2)n2ncnc2n1]

$^{1}$H NMR (400 MHz, $CD_3OD$) δ=8.45-8.56 (m, 1H), 7.94-8.07 (m, 3H), 7.18-7.32 (m, 3H), 4.71-4.81 (m, 2H), 3.98-4.12 (m, 2H), 3.66-3.80 (m, 1H), 3.34-3.46 (m, 1H), 3.11-3.26 (m, 1H), 2.70 (s, 3H), 2.17-2.39 (m, 2H), 2.03-2.15 (m, 2H); [M+H]=409.1.

Example 196. 1-{[2-(3-Fluorophenyl)-1,3-thiazol-5-yl]methyl}-3-{5-methyl-[1,2,4]triazolo[1,5-a]pyrimidin-7-yl}piperidine

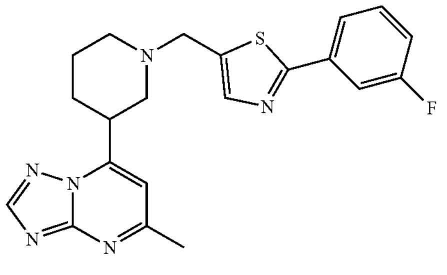 [SMILES: Cc1cc(C2CCCN(Cc3cnc(-c4cccc(F)c4)s3)C2)n2ncnc2n1]

$^{1}$H NMR (400 MHz, $CD_3OD$) δ=8.35-8.62 (m, 1H), 8.03-8.11 (m, 1H), 7.67-7.82 (m, 2H), 7.46-7.58 (m, 1H), 7.17-7.34 (m, 2H), 4.74-4.82 (m, 2H), 3.99-4.13 (m, 2H), 3.69-3.79 (m, 1H), 3.34-3.45 (m, 1H), 3.14-3.28 (m, 1H), 2.70 (s, 3H), 2.20-2.36 (m, 2H), 1.99-2.14 (m, 2H); [M+H]=409.2.

Example 197. 1-{[2-(3-Methoxyphenyl)-1,3-thiazol-5-yl]methyl}-3-{5-methyl-[1,2,4]triazolo[1,5-a]pyrimidin-7-yl}piperidine

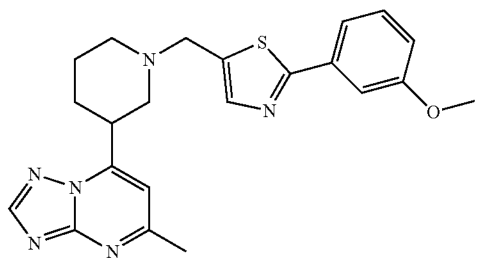 [SMILES: COc1cccc(-c2ncc(CN3CCCC(c4cc(C)nc5ncnn45)C3)s2)c1]

$^1$H NMR (400 MHz, $CD_3OD$) δ=8.39-8.56 (m, 1H), 7.98-8.07 (m, 1H), 7.47-7.54 (m, 2H), 7.33-7.45 (m, 1H), 7.14-7.23 (m, 1H), 7.00-7.12 (m, 1H), 4.72-4.83 (m, 2H), 3.97-4.13 (m, 2H), 3.86 (s, 3H), 3.66-3.82 (m, 1H), 3.34-3.47 (m, 1H), 3.10-3.27 (m, 1H), 2.70 (s, 3H), 2.19-2.38 (m, 2H), 2.00-2.14 (m, 2H); [M+H]=421.1.

Example 198. 4-{5-[(3-{5-Methyl-[1,2,4]triazolo[1,5-a]pyrimidin-7-yl}piperidin-1-yl)methyl]-1,3-thiazol-2-yl}morpholine

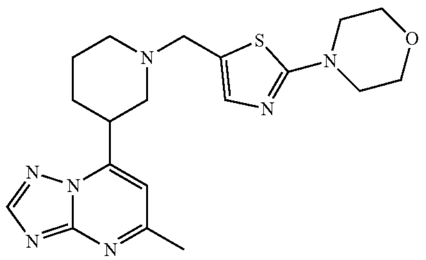 [SMILES: Cc1cc(C2CCCN(Cc3cnc(N4CCOCC4)s3)C2)n2ncnc2n1]

$^1$H NMR (400 MHz, $CD_3OD$) δ=8.44-8.57 (m, 1H), 7.33-7.45 (m, 1H), 7.09-7.28 (m, 1H), 4.46-4.61 (m, 2H), 3.91-4.10 (m, 2H), 3.72-3.82 (m, 4H), 3.63-3.72 (m, 1H), 3.45-3.53 (m, 4H), 3.34-3.39 (m, 1H), 3.07-3.17 (m, 1H), 2.70 (s, 3H), 2.16-2.35 (m, 2H), 2.02-2.11 (m, 2H); [M+H]=400.1.

Example 199. 1-[(2-Bromo-1,3-thiazol-4-yl)methyl]-3-{5-methyl-[1,2,4]triazolo[1,5-a]pyrimidin-7-yl}piperidine

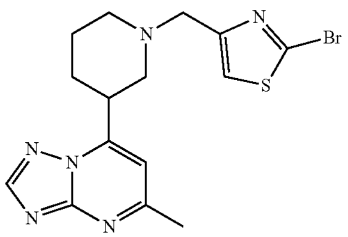 [SMILES: Cc1cc(C2CCCN(Cc3csc(Br)n3)C2)n2ncnc2n1]

$^1$H NMR (400 MHz, $CD_3OD$) δ=8.45-8.55 (m, 1H), 7.76-7.91 (m, 1H), 7.11-7.25 (m, 1H), 4.45-4.63 (m, 2H), 3.97-4.11 (m, 2H), 3.67-3.77 (m, 1H), 3.34-3.47 (m, 1H), 3.10-3.28 (m, 1H), 2.70 (s, 3H), 1.98-2.37 (m, 5H); [M+H]=393.1.

Example 200. 1-[(2-Bromo-1,3-thiazol-5-yl)methyl]-3-{5-methyl-[1,2,4]triazolo[1,5-a]pyrimidin-7-yl}piperidine

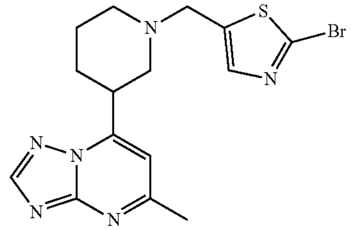 [SMILES: Cc1cc(C2CCCN(Cc3cnc(Br)s3)C2)n2ncnc2n1]

$^1$H NMR (400 MHz, $CD_3OD$) δ=8.41-8.61 (m, 1H), 7.67-7.92 (m, 1H), 7.10-7.29 (m, 1H), 4.66-4.80 (m, 2H), 3.92-4.11 (m, 2H), 3.61-3.75 (m, 1H), 3.33-3.43 (m, 1H), 3.08-3.21 (m, 1H), 2.70 (s, 3H), 2.15-2.38 (m, 2H), 1.91-2.14 (m, 2H); [M+H]=393.1.

Example 201. N,N-Dimethyl-5-[(3-{5-methyl-[1,2,4]triazolo[1,5-a]pyrimidin-7-yl}piperidin-1-yl)methyl]-1,3-thiazol-2-amine

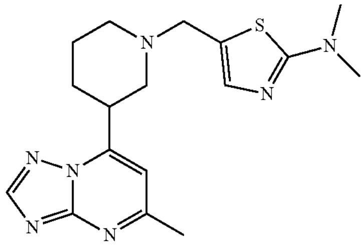 [SMILES: Cc1cc(C2CCCN(Cc3cnc(N(C)C)s3)C2)n2ncnc2n1]

$^1$H NMR (400 MHz, $CD_3OD$) δ=8.46-8.58 (m, 1H), 7.43-7.51 (m, 1H), 7.16-7.24 (m, 1H), 4.47-4.60 (m, 2H), 3.91-4.10 (m, 2H), 3.61-3.73 (m, 1H), 3.32-3.41 (m, 1H), 3.21 (s, 7H), 2.70 (s, 3H), 1.96-2.37 (m, 5H); [M+H]=358.2.

Example 202. 3-{5-Methyl-[1,2,4]triazolo[1,5-a]pyrimidin-7-yl}-1-{[2-(pyrrolidin-1-yl)-1,3-thiazol-5-yl]methyl}piperidine

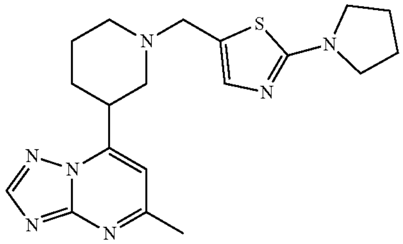 [SMILES: Cc1cc(C2CCCN(Cc3cnc(N4CCCC4)s3)C2)n2ncnc2n1]

$^1H$ NMR (400 MHz, $CD_3OD$) δ=8.44-8.60 (m, 1H), 7.54-7.65 (m, 1H), 7.15-7.23 (m, 1H), 4.48-4.62 (m, 2H), 3.90-4.13 (m, 2H), 3.63-3.72 (m, 1H), 3.52-3.62 (m, 4H), 3.34-3.45 (m, 1H), 3.07-3.19 (m, 1H), 2.70 (s, 3H), 2.25-2.34 (m, 1H), 2.17 (s, 7H); [M+H]=384.1.

Example 203. 1-[(3-Bromo-1,2-oxazol-5-yl)methyl]-3-{5-methyl-[1,2,4]triazolo[1,5-a]pyrimidin-7-yl}piperidine

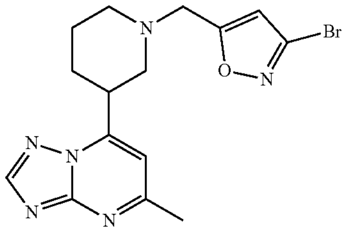 [SMILES: Cc1cc(C2CCCN(Cc3cc(Br)no3)C2)n2ncnc2n1]

$^1H$ NMR (400 MHz, $CD_3OD$) δ=8.40-8.56 (m, 1H), 7.15-7.26 (m, 1H), 6.87-7.00 (m, 1H), 4.65 (s, 2H), 3.87-4.09 (m, 2H), 3.58-3.67 (m, 1H), 3.32-3.42 (m, 1H), 3.09-3.24 (m, 1H), 2.70 (s, 3H), 1.95-2.34 (m, 4H); [M+H]=377.2.

Example 204. 1-[(3-Bromo-4,5-difluorophenyl)methyl]-3-{5-methyl-[1,2,4]triazolo[1,5-a]pyrimidin-7-yl}piperidine

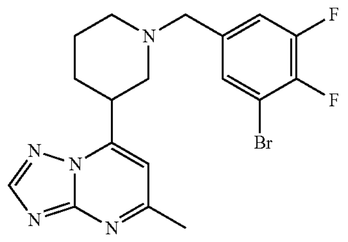 [SMILES: Cc1cc(C2CCCN(Cc3cc(F)c(F)c(Br)c3)C2)n2ncnc2n1]

$^1H$ NMR (400 MHz, DMSO-$d_6$) δ=8.52 (s, 1H), 7.82 (dd, J=10.2, 7.8 Hz, 1H), 7.56 (dd, J=11.7, 9.0 Hz, 2H), 7.26 (s, 1H), 3.61-3.71 (m, 1H), 3.55 (s, 2H), 3.00-3.08 (m, 1H), 2.70-2.80 (m, 1H), 2.58 (s, 3H), 2.49-2.54 (m, 1H), 2.28-2.38 (m, 1H), 1.99-2.10 (m, 1H), 1.59-1.76 (m, 3H); [M+H]= 422.2.

Example 205. 1-[(5-Bromo-4-methyl-1,3-thiazol-2-yl)methyl]-3-{5-methyl-[1,2,4]triazolo[1,5-a]pyrimidin-7-yl}piperidine

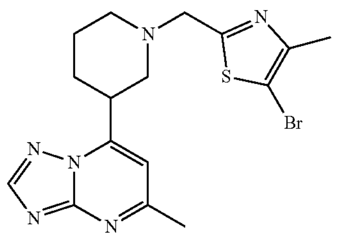 [SMILES: Cc1cc(C2CCCN(Cc3nc(C)c(Br)s3)C2)n2ncnc2n1]

$^1H$ NMR (400 MHz, $CD_3OD$) δ=8.46-8.57 (m, 1H), 7.16-7.25 (m, 1H), 4.61-4.76 (m, 2H), 4.00-4.16 (m, 2H), 3.69-3.80 (m, 1H), 3.38-3.49 (m, 1H), 3.15-3.28 (m, 1H), 2.70 (s, 3H), 2.41 (s, 3H), 2.26-2.35 (m, 1H), 1.95-2.23 (m, 3H); [M+H]=407.1.

Example 206. N,N,4-Trimethyl-5-[(3-{5-methyl-[1,2,4]triazolo[1,5-a]pyrimidin-7-yl}piperidin-1-yl)methyl]-1,3-thiazol-2-amine

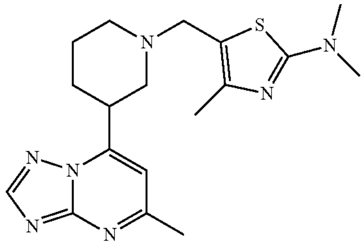 [SMILES: Cc1cc(C2CCCN(Cc3sc(N(C)C)nc3C)C2)n2ncnc2n1]

$^1H$ NMR (400 MHz, $CD_3OD$) δ=8.47-8.54 (m, 1H), 7.16-7.25 (m, 1H), 4.52 (s, 2H), 3.94-4.11 (m, 2H), 3.65-3.75 (m, 1H), 3.41-3.51 (m, 1H), 3.27 (s, 6H), 3.11-3.21 (m, 1H), 2.70 (s, 3H), 2.24-2.39 (m, 4H), 2.17-2.22 (m, 1H), 2.02-2.12 (m, 2H); [M+H]=372.1.

Examples 207-289 were prepared in a manner analogous to Example 4, with the appropriate starting material and reagent substitutions.

Example 207. 1-[(2,3-Dihydro-1-benzofuran-5-yl)carbonyl]-3-{5-methyl-[1,2,4]triazolo[1,5-a]pyrimidin-7-yl}piperidine

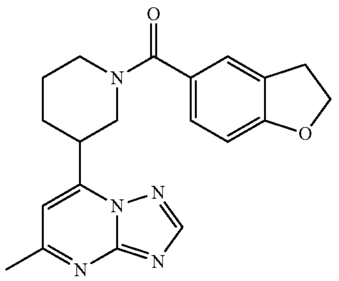 [SMILES: Cc1cc(C2CCCN(C(=O)c3ccc4c(c3)CCO4)C2)n2ncnc2n1]

$^1H$ NMR (400 MHz, $CDCl_3$) δ=1.85 (br s, 1H), 1.98-2.15 (m, 1H), 2.40 (d, J=10.54 Hz, 1H), 2.77 (s, 3H), 3.17-3.35 (m, 3H), 3.45 (t, J=11.29 Hz, 1H), 3.67-3.83 (m, 1H), 4.58-4.85 (m, 6H), 6.82 (d, J=8.28 Hz, 1H), 6.95 (br s, 1H), 7.27 (s, 1H), 7.34 (br s, 1H), 8.54 (br s, 1H); [M+H]=364.4.

Example 208. 1-[(3,4-Dihydro-2H-1-benzopyran-6-yl)carbonyl]-3-{5-methyl-[1,2,4]triazolo[1,5-a]pyrimidin-7-yl}piperidine

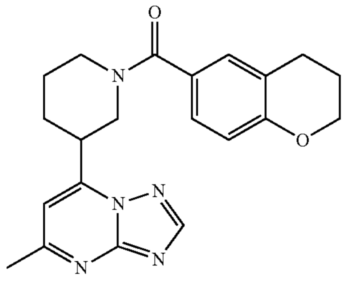 [SMILES: Cc1cc(C2CCCN(C(=O)c3ccc4c(c3)CCCO4)C2)n2ncnc2n1]

$^1$H NMR (400 MHz, $CDCl_3$) δ=1.95-2.13 (m, 4H), 2.40 (d, J=10.29 Hz, 1H), 2.76 (s, 4H), 2.82 (t, J=6.27 Hz, 3H), 3.44 (t, J=11.17 Hz, 1H), 3.67-3.82 (m, 1H), 4.13-4.31 (m, 4H), 6.82 (d, J=8.03 Hz, 1H), 6.93 (br s, 1H), 7.15-7.26 (m, 2H), 8.52 (br s, 1H); [M+H]=378.4.

Example 209. 4-[(3-Iodophenyl)carbonyl]-2-{5-methyl-[1,2,4]triazolo[1,5-a]pyrimidin-7-yl}morpholine

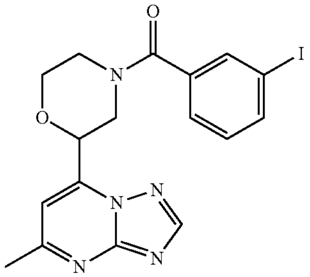 [SMILES: Cc1cc(C2CN(C(=O)c3cccc(I)c3)CCO2)n2ncnc2n1]

$^1$H NMR (400 MHz, DMSO-$d_6$) δ=8.68-8.42 (m, 1H), 7.84 (d, J=16.8 Hz, 2H), 7.55 (br s, 1H), 7.30-7.18 (m, 2H), 4.25-3.86 (m, 2H), 3.77-3.51 (m, 3H), 2.61 (d, J=11.0 Hz, 3H), 2.46-2.38 (m, 1H), 2.32-2.14 (m, 1H); [M+H]=450.1.

Example 210. 2-{5-Methyl-[1,2,4]triazolo[1,5-a]pyrimidin-7-yl}-4-[(naphthalen-2-yl)carbonyl]morpholine

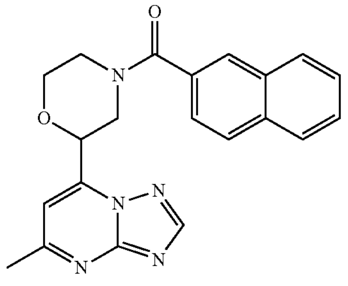 [SMILES: Cc1cc(C2CN(C(=O)c3ccc4ccccc4c3)CCO2)n2ncnc2n1]

$^1$H NMR (400 MHz, DMSO-$d_6$) δ=8.68-8.42 (m, 1H), 7.84 (d, J=16.8 Hz, 2H), 7.55 (br s, 1H), 7.30-7.18 (m, 2H), 4.25-3.86 (m, 2H), 3.77-3.51 (m, 3H), 2.61 (d, J=11.0 Hz, 3H), 2.46-2.38 (m, 1H), 2.32-2.14 (m, 1H); [M+H]=374.2.

Example 211. 3,3-Difluoro-1-[(3-iodophenyl)carbonyl]-5-{5-methyl-[1,2,4]triazolo[1,5-a]pyrimidin-7-yl}piperidine

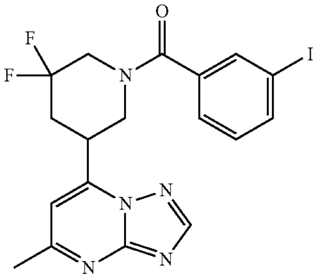 [SMILES: Cc1cc(C2CN(C(=O)c3cccc(I)c3)CC(F)(F)C2)n2ncnc2n1]

$^1$H NMR (400 MHz, DMSO-$d_6$) δ=8.77-8.35 (m, 1H), 7.78 (t, J=1.6 Hz, 2H), 7.46 (s, 1H), 7.28 (t, J=7.2 Hz, 3H), 4.92-3.31 (m, 5H), 2.59 (br s, 5H); [M+H]=484.2.

Example 212. 4-[(4-Fluorophenyl)carbonyl]-2-{5-methyl-[1,2,4]triazolo[1,5-a]pyrimidin-7-yl}morpholine

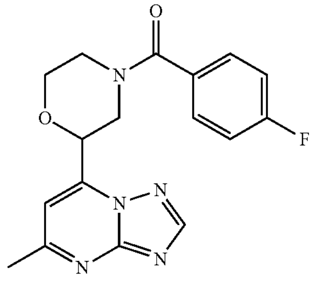 [SMILES: Cc1cc(C2CN(C(=O)c3ccc(F)cc3)CCO2)n2ncnc2n1]

$^1$H NMR (400 MHz, DMSO-$d_6$) δ=8.58 (br s, 1H), 7.70-7.47 (m, 2H), 7.35-7.12 (m, 3H), 5.33-3.67 (m, 5H), 3.23-2.78 (m, 2H), 2.70-2.54 (m, 3H); [M+H]=342.2.

Example 213. 4-Benzoyl-2-{5-methyl-[1,2,4]triazolo[1,5-a]pyrimidin-7-yl}morpholine

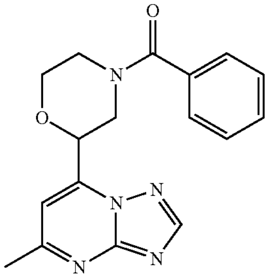 [SMILES: Cc1cc(C2CN(C(=O)c3ccccc3)CCO2)n2ncnc2n1]

$^1$H NMR (400 MHz, DMSO-$d_6$) δ=8.73-8.40 (m, 1H), 7.52-7.43 (m, 5H), 7.33-7.20 (m, 1H), 5.37-3.49 (m, 5H), 3.19-2.80 (m, 2H), 2.63 (s, 3H); [M+H]=324.2.

Example 214. 4-[(3-Chloro-4-fluorophenyl)carbonyl]-2-{5-methyl-[1,2,4]triazolo[1,5-a]pyrimidin-7-yl}morpholine

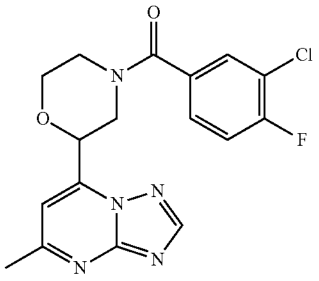 [SMILES: Cc1cc(C2CN(C(=O)c3ccc(F)c(Cl)c3)CCO2)n2ncnc2n1]

$^1$H NMR (400 MHz, DMSO-$d_6$) δ=8.75-8.40 (m, 1H), 7.89-7.65 (m, 1H), 7.63-7.36 (m, 2H), 7.31-7.11 (m, 1H), 5.49-3.75 (m, 5H), 3.27-2.70 (m, 2H), 2.69-2.56 (m, 3H); [M+H]=376.2.

Example 215. 4-[(3-Fluorophenyl)carbonyl]-2-{5-methyl-[1,2,4]triazolo[1,5-a]pyrimidin-7-yl}morpholine

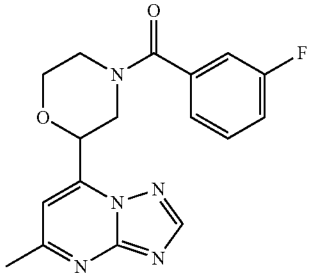 [SMILES: Cc1cc(C2CN(C(=O)c3cccc(F)c3)CCO2)n2ncnc2n1]

$^1$H NMR (400 MHz, DMSO-$d_6$) δ=8.78-8.34 (m, 1H), 7.33 (d, J=8.6 Hz, 5H), 5.40-4.87 (m, 2H), 4.52-3.73 (m, 3H), 3.21-2.78 (m, 2H), 2.63 (br s, 3H); [M+H]=342.2.

Example 216. 4-{[4-Fluoro-3-(trifluoromethyl)phenyl]carbonyl}-2-{5-methyl-[1,2,4]triazolo[1,5-a]pyrimidin-7-yl}morpholine

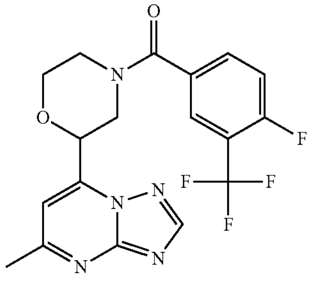 [SMILES: Cc1cc(C2CN(C(=O)c3ccc(F)c(C(F)(F)F)c3)CCO2)n2ncnc2n1]

$^1$H NMR (400 MHz, DMSO-$d_6$) δ=8.82-8.24 (m, 1H), 7.92 (br s, 2H), 7.64 (t, J=9.8 Hz, 1H), 7.44-7.12 (m, 1H), 5.42-5.08 (m, 1H), 4.61-3.36 (m, 4H), 3.23-2.74 (m, 2H), 2.63 (br s, 3H); [M+H]=410.2.

Example 217. 4-[(4-Methoxyphenyl)carbonyl]-2-{5-methyl-[1,2,4]triazolo[1,5-a]pyrimidin-7-yl}morpholine

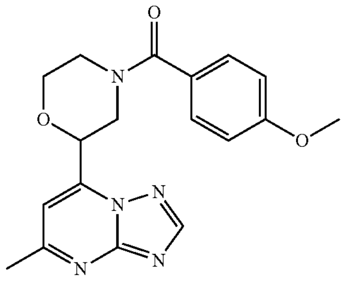

$^1$H NMR (400 MHz, DMSO-$d_6$) δ=8.60 (s, 1H), 7.48 (d, J=8.6 Hz, 2H), 7.26 (s, 1H), 7.07-6.94 (m, 2H), 5.27 (d, J=7.4 Hz, 1H), 5.02-3.80 (m, 4H), 3.79 (s, 3H), 3.27-2.82 (m, 2H), 2.63 (s, 3H); [M+H]=354.2.

Example 218. 2-{5-Methyl-[1,2,4]triazolo[1,5-a]pyrimidin-7-yl}-4-[(4-phenylphenyl)carbonyl]morpholine

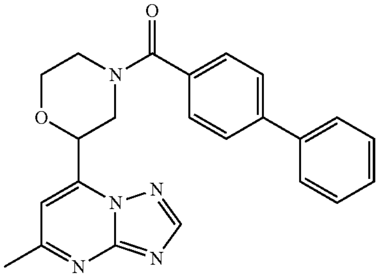 [SMILES: Cc1cc(C2CN(C(=O)c3ccc(-c4ccccc4)cc3)CCO2)n2ncnc2n1]

$^1$H NMR (400 MHz, DMSO-$d_6$) δ=8.74-8.51 (m, 1H), 7.86-7.19 (m, 10H), 5.51-3.40 (m, 5H), 3.14 (d, J=5.1 Hz, 2H), 2.74-2.56 (m, 3H); [M+H]=400.2.

Example 219. 4-[(4-Chlorophenyl)carbonyl]-2-{5-methyl-[1,2,4]triazolo[1,5-a]pyrimidin-7-yl}morpholine

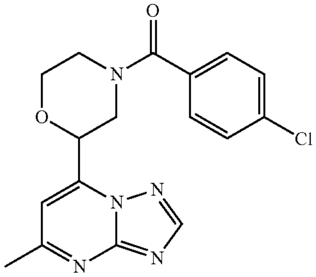 [SMILES: Cc1cc(C2CN(C(=O)c3ccc(Cl)cc3)CCO2)n2ncnc2n1]

$^1$H NMR (400 MHz, DMSO-$d_6$) δ=8.70-8.48 (m, 1H), 7.54 (s, 4H), 7.35-7.20 (m, 1H), 5.40-3.43 (m, 5H), 3.27-2.71 (m, 2H), 2.63 (s, 3H); [M+H]=358.2.

Example 220. 4-[(3-Chlorophenyl)carbonyl]-2-{5-methyl-[1,2,4]triazolo[1,5-a]pyrimidin-7-yl}morpholine

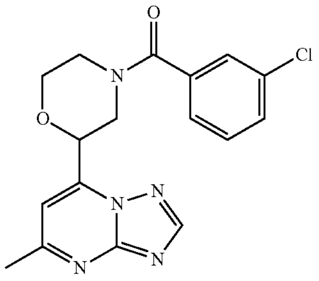 [SMILES: Cc1cc(C2CN(C(=O)c3cccc(Cl)c3)CCO2)n2ncnc2n1]

$^1$H NMR (400 MHz, $CDCl_3$) δ=8.49-7.51 (m, 1H), 7.46-7.35 (m, 2H), 7.25 (br s, 1H), 7.17-7.08 (m, 1H), 5.66-2.70 (m, 7H), 1.60 (br s, 3H); [M+H]=358.2.

Example 221. 2-{5-Methyl-[1,2,4]triazolo[1,5-a]pyrimidin-7-yl}-4-{[3-(trifluoromethoxy)phenyl]carbonyl}morpholine

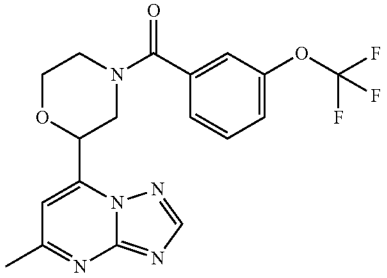 [SMILES: Cc1cc(C2CN(C(=O)c3cccc(OC(F)(F)F)c3)CCO2)n2ncnc2n1]

$^1$H NMR (400 MHz, DMSO-$d_6$) δ=8.75-8.27 (m, 1H), 7.65-7.59 (m, 1H), 7.59-7.45 (m, 3H), 7.27 (br s, 1H), 5.39-3.95 (m, 4H), 3.52-2.81 (m, 3H), 2.63 (br s, 3H); [M+H]=408.2.

Example 222. 4-[(3,5-Dichlorophenyl)carbonyl]-2-{5-methyl-[1,2,4]triazolo[1,5-a]pyrimidin-7-yl}morpholine

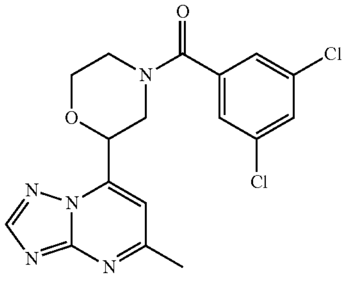 [SMILES: Cc1cc(C2CN(C(=O)c3cc(Cl)cc(Cl)c3)CCO2)n2ncnc2n1]

$^1$H NMR (400 MHz, DMSO-$d_6$) δ=8.74-8.38 (m, 1H), 7.74 (t, J=2.0 Hz, 1H), 7.66-7.50 (m, 2H), 7.36-7.13 (m, 1H), 5.52-4.92 (m, 1H), 4.54-3.33 (m, 4H), 3.20-2.76 (m, 2H), 2.62 (br s, 3H); [M+H]=392.2.

Example 223. 4-[(2-{5-Methyl-[1,2,4]triazolo[1,5-a]pyrimidin-7-yl}morpholin-4-yl)carbonyl]benzonitrile

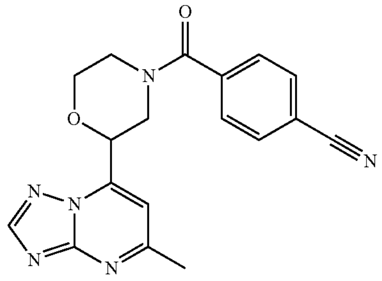 [SMILES: Cc1cc(C2CN(C(=O)c3ccc(C#N)cc3)CCO2)n2ncnc2n1]

$^1$H NMR (400 MHz, DMSO-$d_6$) δ=8.74-8.41 (m, 1H), 7.96 (d, J=7.8 Hz, 2H), 7.81-7.58 (m, 2H), 7.42-7.08 (m, 1H), 5.40-5.10 (m, 1H), 4.55-3.35 (m, 4H), 3.22-2.77 (m, 2H), 2.67-2.54 (m, 3H); [M+H]=349.2.

Example 224. 4-[(3,4-Difluorophenyl)carbonyl]-2-{5-methyl-[1,2,4]triazolo[1,5-a]pyrimidin-7-yl}morpholine

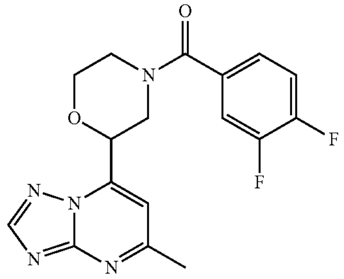 [SMILES: Cc1cc(C2CN(C(=O)c3ccc(F)c(F)c3)CCO2)n2ncnc2n1]

$^1$H NMR (400 MHz, DMSO-$d_6$) δ=8.84-8.33 (m, 1H), 7.87-7.06 (m, 4H), 5.43-5.04 (m, 1H), 4.59-3.44 (m, 3H), 3.22-2.78 (m, 2H), 2.63 (s, 3H); [M+H]=360.2.

Example 225. 3,3-Difluoro-5-{5-methyl-[1,2,4]triazolo[1,5-a]pyrimidin-7-yl}-1-[(naphthalen-2-yl)carbonyl]piperidine

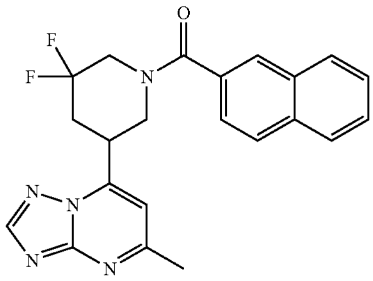 [SMILES: Cc1cc(C2CN(C(=O)c3ccc4ccccc4c3)CC(F)(F)C2)n2ncnc2n1]

$^1$H NMR (400 MHz, DMSO-$d_6$) δ=8.22-7.86 (m, 4H), 7.77-7.44 (m, 3H), 7.40-7.18 (m, 1H), 5.07-4.74 (m, 1H), 4.70-3.33 (m, 4H), 2.83-2.53 (m, 5H); [M+H]=408.3.

Example 226. 4-[(3-Bromophenyl)carbonyl]-2-{5-methyl-[1,2,4]triazolo[1,5-a]pyrimidin-7-yl}morpholine

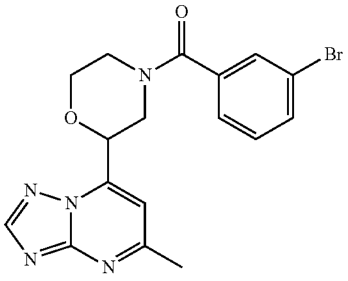

$^1H$ NMR (400 MHz, DMSO-$d_6$) δ=8.78-8.35 (m, 1H), 7.88-7.13 (m, 5H), 5.64-3.34 (m, 6H), 3.17-2.80 (m, 1H), 2.63 (br s, 3H); [M+H]=402.2.

Example 227. 3-[(2-{5-Methyl-[1,2,4]triazolo[1,5-a]pyrimidin-7-yl}morpholin-4-yl)carbonyl]benzonitrile

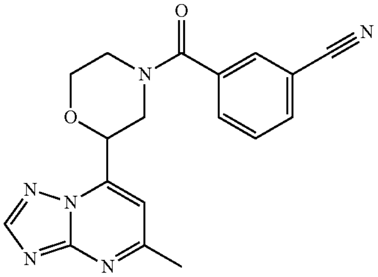 [SMILES: Cc1cc(C2CN(C(=O)c3cccc(C#N)c3)CCO2)n2ncnc2n1]

$^1H$ NMR (400 MHz, DMSO-$d_6$) δ=8.71-8.36 (m, 1H), 8.18-7.54 (m, 4H), 7.40-7.18 (m, 1H), 5.52-3.71 (m, 5H), 3.15 (d, J=5.1 Hz, 2H), 2.62 (br s, 3H); [M+H]=349.3.

Example 228. 2-{5-Methyl-[1,2,4]triazolo[1,5-a]pyrimidin-7-yl}-4-{[3-(trifluoromethyl)phenyl]carbonyl}morpholine

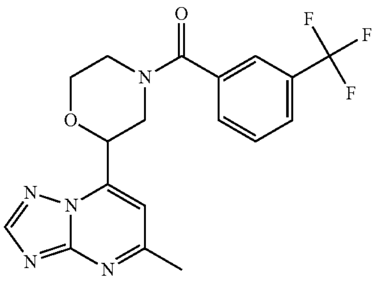 [SMILES: Cc1cc(C2CN(C(=O)c3cccc(C(F)(F)F)c3)CCO2)n2ncnc2n1]

$^1H$ NMR (400 MHz, DMSO-$d_6$) δ=8.79-8.26 (m, 1H), 8.04-7.66 (m, 4H), 7.36-7.14 (m, 1H), 5.50-3.39 (m, 5H), 3.25-2.80 (m, 2H), 2.63 (br s, 3H); [M+H]=392.2.

Example 229. 2-{5-Methyl-[1,2,4]triazolo[1,5-a]pyrimidin-7-yl}-4-{[4-(trifluoromethyl)phenyl]carbonyl}morpholine

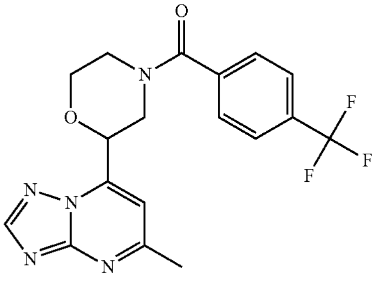 [SMILES: Cc1cc(C2CN(C(=O)c3ccc(C(F)(F)F)cc3)CCO2)n2ncnc2n1]

$^1H$ NMR (400 MHz, DMSO-$d_6$) δ=8.77-8.29 (m, 1H), 7.85 (d, J=8.2 Hz, 4H), 7.42-7.13 (m, 1H), 5.49-3.40 (m, 5H), 3.23-2.68 (m, 2H), 2.71-2.53 (m, 3H); [M+H]=392.2.

Example 230. 4-[(3-Ethoxyphenyl)carbonyl]-2-{5-methyl-[1,2,4]triazolo[1,5-a]pyrimidin-7-yl}morpholine

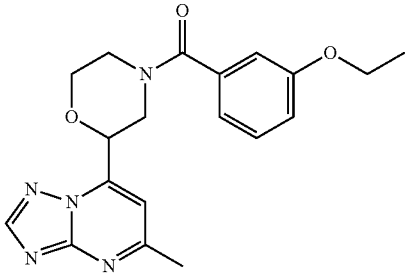 [SMILES: CCOc1cccc(C(=O)N2CCOC(c3cc(C)nc4ncnn34)C2)c1]

$^1H$ NMR (400 MHz, DMSO-$d_6$) δ=8.75-8.22 (m, 1H), 7.49-7.14 (m, 2H), 7.07-6.92 (m, 3H), 5.43-3.33 (m, 8H), 3.25-2.74 (m, 1H), 2.71-2.56 (m, 3H), 1.33 (t, J=7.0 Hz, 3H); [M+H]=368.3.

Example 231. 4-[(3-Bromo-4-fluorophenyl)carbonyl]-2-{5-methyl-[1,2,4]triazolo[1,5-a]pyrimidin-7-yl}morpholine

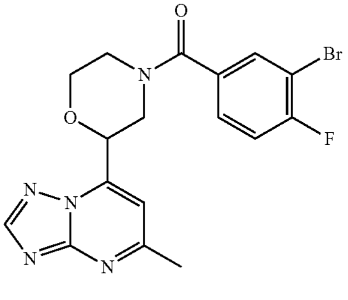

$^1H$ NMR (400 MHz, DMSO-$d_6$) δ=8.73-8.45 (m, 1H), 8.12-7.80 (m, 1H), 7.66-7.55 (m, 1H), 7.53-7.44 (m, 1H), 7.25 (br s, 1H), 5.46-4.96 (m, 1H), 4.01 (d, J=7.0 Hz, 3H), 3.60-3.38 (m, 1H), 3.24-2.75 (m, 2H), 2.63 (s, 3H); [M+H]=421.2.

Example 232. 1-[(3-Chlorophenyl)carbonyl]-3,3-difluoro-5-{5-methyl-[1,2,4]triazolo[1,5-a]pyrimidin-7-yl}piperidine

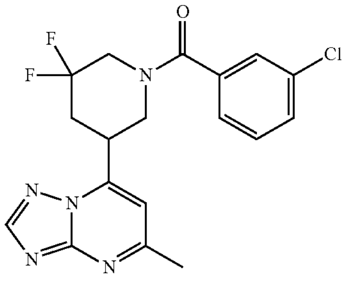 [SMILES: Cc1cc(C2CN(C(=O)c3cccc(Cl)c3)CC(F)(F)C2)n2ncnc2n1]

$^1$H NMR (400 MHz, DMSO-$d_6$) δ=8.75-8.34 (m, 1H), 7.52 (s, 5H), 5.00-4.55 (m, 1H), 4.49-3.31 (m, 4H), 2.59 (m, 5H); [M+H]=392.2.

Example 233. 1-[(3,5-Dichlorophenyl)carbonyl]-3,3-difluoro-5-{5-methyl-[1,2,4]triazolo[1,5-a]pyrimidin-7-yl}piperidine

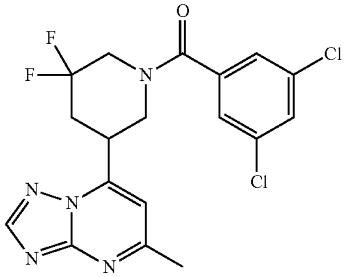 [SMILES: Cc1cc(C2CN(C(=O)c3cc(Cl)cc(Cl)c3)CC(F)(F)C2)n2ncnc2n1]

$^1$H NMR (400 MHz, DMSO-$d_6$) δ=8.75-8.36 (m, 1H), 7.91-7.71 (m, 1H), 7.51 (d, J=2.0 Hz, 2H), 7.35-7.20 (m, 1H), 4.93-4.66 (m, 1H), 4.14-3.65 (m, 2H), 3.51-3.33 (m, 1H), 2.81-2.51 (m, 6H); [M+H]=426.2.

Example 234. 1-[(3-Bromophenyl)carbonyl]-3,3-difluoro-5-{5-methyl-[1,2,4]triazolo[1,5-a]pyrimidin-7-yl}piperidine

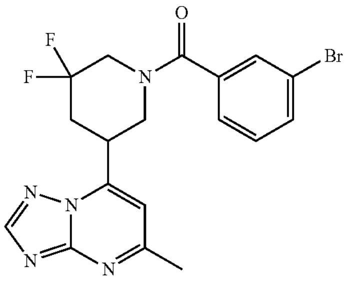 [SMILES: Cc1cc(C2CN(C(=O)c3cccc(Br)c3)CC(F)(F)C2)n2ncnc2n1]

$^1$H NMR (400 MHz, DMSO-$d_6$) δ=8.74-8.31 (m, 1H), 7.72-7.61 (m, 2H), 7.49-7.40 (m, 2H), 7.36-7.19 (m, 1H), 5.12-4.51 (m, 1H), 4.24-3.65 (m, 3H), 2.59 (br s, 6H); [M+H]=437.2.

Example 235. 1-[(3-Bromo-4-fluorophenyl)carbonyl]-3,3-difluoro-5-{5-methyl-[1,2,4]triazolo[1,5-a]pyrimidin-7-yl}piperidine

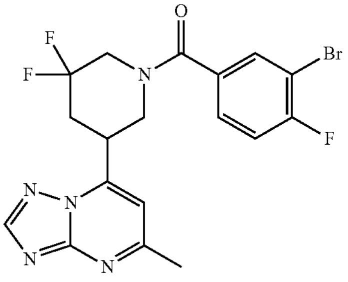 [SMILES: Cc1cc(C2CN(C(=O)c3ccc(F)c(Br)c3)CC(F)(F)C2)n2ncnc2n1]

$^1$H NMR (400 MHz, DMSO-$d_6$) δ=8.57 (br s, 1H), 7.82 (dd, J=6.7, 2.0 Hz, 1H), 7.43-7.61 (m, 2H), 7.27 (br s, 1H), 4.77 (br s, 1H), 4.02-4.26 (m, 1H), 3.59-3.97 (m, 2H), 3.32-3.52 (m, 1H), 2.53-2.81 (m, 5H); [M+H]=454.2.

Example 236. 3-[(3,3-Difluoro-5-{5-methyl-[1,2,4]triazolo[1,5-a]pyrimidin-7-yl}piperidin-1-yl)carbonyl]benzonitrile

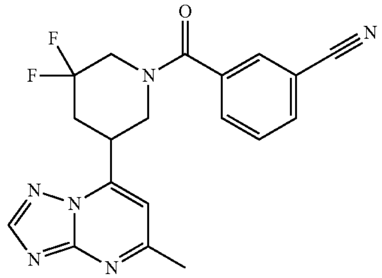 [SMILES: Cc1cc(C2CN(C(=O)c3cccc(C#N)c3)CC(F)(F)C2)n2ncnc2n1]

$^1$H NMR (400 MHz, DMSO-$d_6$) δ=8.75-8.36 (m, 1H), 8.06-7.93 (m, 2H), 7.83-7.65 (m, 2H), 7.42-7.07 (m, 1H), 4.94-4.61 (m, 1H), 4.18-3.74 (m, 3H), 2.59 (br s, 6H); [M+H]=383.2.

Example 237. 3,3-Difluoro-1-{[4-fluoro-3-(trifluoromethyl)phenyl]carbonyl}-5-{5-methyl-[1,2,4]triazolo[1,5-a]pyrimidin-7-yl}piperidine

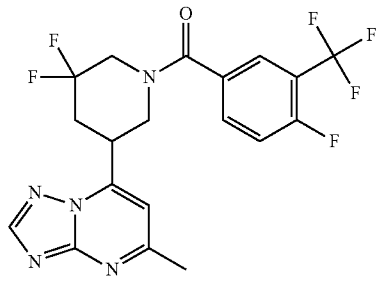

$^1$H NMR (400 MHz, DMSO-$d_6$) δ=8.68-8.35 (m, 1H), 7.86-7.81 (m, 2H), 7.68-7.62 (m, 1H), 7.35-7.21 (m, 1H), 4.96-4.61 (m, 1H), 4.17-3.77 (m, 3H), 2.70-2.58 (m, 6H); [M+H]=444.3.

Example 238. 3,3-Difluoro-5-{5-methyl-[1,2,4]triazolo[1,5-a]pyrimidin-7-yl}-1-{[3-(trifluoromethyl)phenyl]carbonyl}piperidine

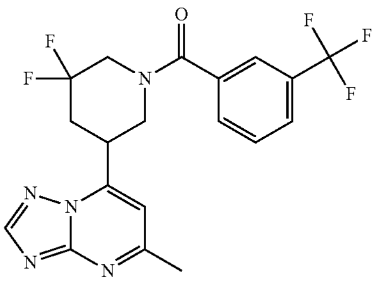 [SMILES: Cc1cc(C2CN(C(=O)c3cccc(C(F)(F)F)c3)CC(F)(F)C2)n2ncnc2n1]

$^1$H NMR (400 MHz, DMSO-$d_6$) δ=8.68-8.30 (m, 1H), 7.89-7.74 (m, 4H), 7.37-7.15 (m, 1H), 5.06-4.71 (m, 1H), 4.19-3.76 (m, 3H), 2.75-2.57 (m, 6H); [M+H]=426.2.

Example 239. 1-[(3-Chloro-4-fluorophenyl)carbonyl]-3,3-difluoro-5-{5-methyl-[1,2,4]triazolo[1,5-a]pyrimidin-7-yl}piperidine

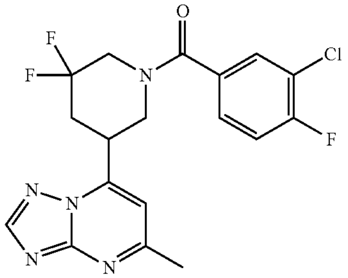 [SMILES: Cc1cc(C2CN(C(=O)c3ccc(F)c(Cl)c3)CC(F)(F)C2)n2ncnc2n1]

$^1$H NMR (400 MHz, DMSO-$d_6$) δ=8.67-8.47 (m, 1H), 7.74-7.71 (m, 1H), 7.55-7.50 (m, 2H), 7.36-7.15 (m, 1H), 4.93-4.65 (m, 1H), 4.23-3.68 (m, 3H), 2.75-2.53 (m, 6H); [M+H]=410.2.

Example 240. 3,3-Difluoro-5-{5-methyl-[1,2,4]triazolo[1,5-a]pyrimidin-7-yl}-1-{[4-(trifluoromethyl)phenyl]carbonyl}piperidine

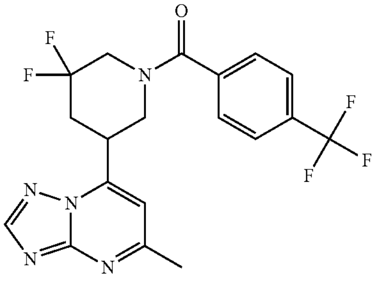 [SMILES: Cc1cc(C2CN(C(=O)c3ccc(C(F)(F)F)cc3)CC(F)(F)C2)n2ncnc2n1]

$^1$H NMR (400 MHz, DMSO-$d_6$) δ=8.75-8.44 (m, 1H), 7.89-7.82 (m, 2H), 7.70-7.66 (m, 2H), 7.41-7.13 (m, 1H), 5.01-4.75 (m, 1H), 4.17-3.71 (m, 3H), 2.78-2.57 (m, 6H); [M+H]=426.2.

Example 241. (2R)-2-{5-methyl-[1,2,4]triazolo[1,5-a]pyrimidin-7-yl}-4-[(naphthalen-2-yl)carbonyl]morpholine

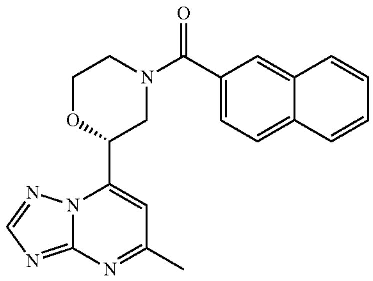 [SMILES: Cc1cc([C@H]2CN(C(=O)c3ccc4ccccc4c3)CCO2)n2ncnc2n1]

$^1$H NMR (400 MHz, DMSO-$d_6$) δ=8.78-8.24 (m, 1H), 8.21-7.85 (m, 4H), 7.68-7.47 (m, 3H), 7.28 (br s, 1H), 5.54-3.48 (m, 5H), 3.24-2.77 (m, 2H), 2.63 (br s, 3H); [M+H]=374.3.

Example 242. (2S)-2-{5-Methyl-[1,2,4]triazolo[1,5-a]pyrimidin-7-yl}-4-[(naphthalen-2-yl)carbonyl]morpholine

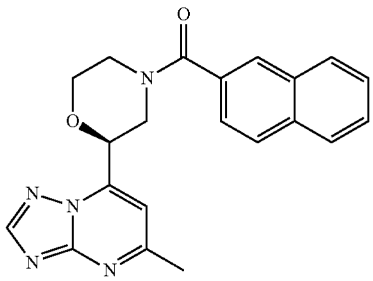 [SMILES: Cc1cc([C@@H]2CN(C(=O)c3ccc4ccccc4c3)CCO2)n2ncnc2n1]

$^1$H NMR (400 MHz, DMSO-$d_6$) δ=8.73-8.27 (m, 1H), 8.24-7.89 (m, 4H), 7.73-7.53 (m, 3H), 7.28 (br s, 1H), 5.64-3.51 (m, 5H), 3.21-2.71 (m, 2H), 2.63 (br s, 3H); [M+H]=374.3.

Example 243. 1-Benzoyl-3,3-difluoro-5-{5-methyl-[1,2,4]triazolo[1,5-a]pyrimidin-7-yl}piperidine

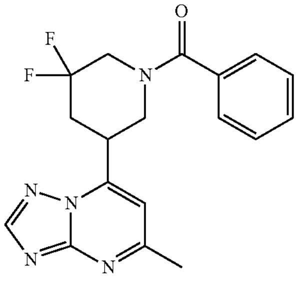 [SMILES: Cc1cc(C2CN(C(=O)c3ccccc3)CC(F)(F)C2)n2ncnc2n1]

$^1$H NMR (400 MHz, DMSO-$d_6$) δ=8.70-8.38 (m, 1H), 7.46 (br s, 5H), 7.39-7.19 (m, 1H), 4.87-4.46 (m, 1H), 3.99-3.35 (m, 3H), 2.87-2.55 (m, 6H); [M+H]=358.3.

Example 244. 1-[(3,4-Difluorophenyl)carbonyl]-3,3-difluoro-5-{5-methyl-[1,2,4]triazolo[1,5-a]pyrimidin-7-yl}piperidine

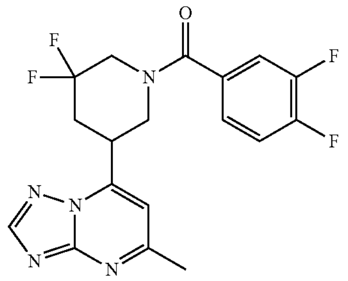 [SMILES: Cc1cc(C2CN(C(=O)c3ccc(F)c(F)c3)CC(F)(F)C2)n2ncnc2n1]

$^1$H NMR (400 MHz, DMSO-$d_6$) δ=8.71-8.26 (m, 1H), 7.67-7.55 (m, 2H), 7.39-7.33 (m, 1H), 7.31-7.16 (m, 1H), 4.94-4.58 (m, 1H), 3.98-3.73 (m, 2H), 3.39-3.32 (m, 1H), 2.75-2.56 (m, 6H); [M+H]=394.2.

Example 245. 3,3-Difluoro-1-[(3-fluorophenyl)carbonyl]-5-{5-methyl-[1,2,4]triazolo[1,5-a]pyrimidin-7-yl}piperidine

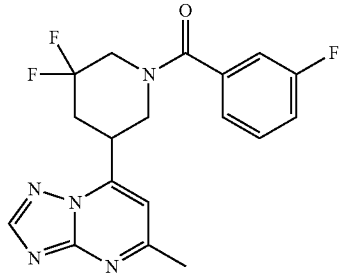 [SMILES: Cc1cc(C2CN(C(=O)c3cccc(F)c3)CC(F)(F)C2)n2ncnc2n1]

$^1$H NMR (400 MHz, DMSO-$d_6$) δ=8.71-8.39 (m, 1H), 7.58-7.46 (m, 1H), 7.34-7.28 (m, 4H), 4.91-4.67 (m, 1H), 3.95-3.79 (m, 2H), 3.44-3.35 (m, 1H), 2.80-2.59 (m, 6H); [M+H]=376.2.

Example 246. 3,3-Difluoro-1-[(4-fluorophenyl)carbonyl]-5-{5-methyl-[1,2,4]triazolo[1,5-a]pyrimidin-7-yl}piperidine

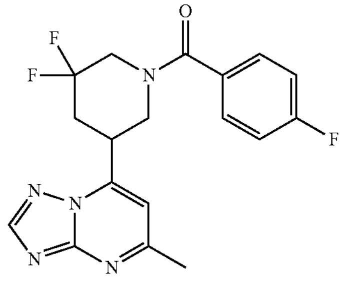 [SMILES: Cc1cc(C2CN(C(=O)c3ccc(F)cc3)CC(F)(F)C2)n2ncnc2n1]

$^1$H NMR (400 MHz, DMSO-$d_6$) δ=8.59 (br s, 1H), 7.67-7.42 (m, 2H), 7.31 (t, J=8.8 Hz, 3H), 5.02-4.51 (m, 1H), 3.93-3.78 (m, 2H), 3.40-3.32 (m, 1H), 2.60 (s, 6H); [M+H]=376.2.

Example 247. 4-[(3,3-Difluoro-5-{5-methyl-[1,2,4]triazolo[1,5-a]pyrimidin-7-yl}piperidin-1-yl)carbonyl]benzonitrile

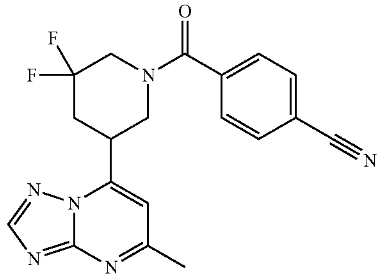 [SMILES: Cc1cc(C2CN(C(=O)c3ccc(C#N)cc3)CC(F)(F)C2)n2ncnc2n1]

$^1$H NMR (400 MHz, DMSO-$d_6$) δ=8.75-8.44 (m, 1H), 8.02-7.85 (m, 2H), 7.65 (br s, 2H), 7.45-7.15 (m, 1H), 4.92-4.69 (m, 1H), 4.06 (s, 3H), 2.57 (br s, 6H); [M+H]=383.3.

Example 248. 1-[(3-Ethoxyphenyl)carbonyl]-3,3-difluoro-5-{5-methyl-[1,2,4]triazolo[1,5-a]pyrimidin-7-yl}piperidine

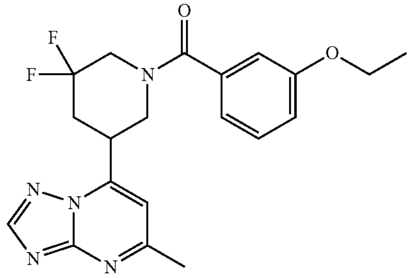 [SMILES: CCOc1cccc(C(=O)N2CC(c3cc(C)nc4ncnn34)CC(F)(F)C2)c1]

$^1$H NMR (400 MHz, DMSO-$d_6$) δ=8.70-8.35 (m, 1H), 7.45-7.16 (m, 2H), 7.10-6.78 (m, 3H), 4.96-4.53 (m, 1H), 4.14-3.96 (m, 2H), 4.34-3.95 (m, 3H), 3.94-3.61 (m, 2H), 3.52-3.31 (m, 1H), 2.60 (br s, 5H), 1.31 (t, J=6.8 Hz, 3H); [M+H]=402.3.

Example 249. 3,3-Difluoro-5-{5-methyl-[1,2,4]triazolo[1,5-a]pyrimidin-7-yl}-1-{[3-(trifluoromethoxy)phenyl]carbonyl}piperidine

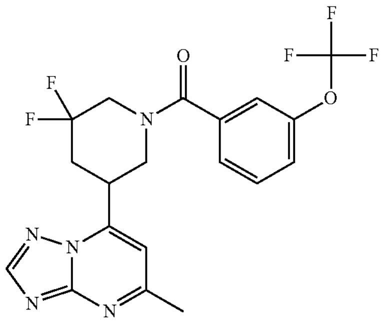 [SMILES: Cc1cc(C2CN(C(=O)c3cccc(OC(F)(F)F)c3)CC(F)(F)C2)n2ncnc2n1]

$^1$H NMR (400 MHz, DMSO-$d_6$) δ=8.71-8.32 (m, 1H), 7.68-7.58 (m, 1H), 7.55-7.47 (m, 2H), 7.45-7.41 (m, 1H), 7.35-7.13 (m, 1H), 4.93-4.70 (m, 1H), 4.27-3.35 (m, 4H), 2.78-2.59 (m, 5H); [M+H]=442.2

Example 250. (2R)-4-[(3-Bromophenyl)carbonyl]-2-{5-methyl-[1,2,4]triazolo[1,5-a]pyrimidin-7-yl}morpholine

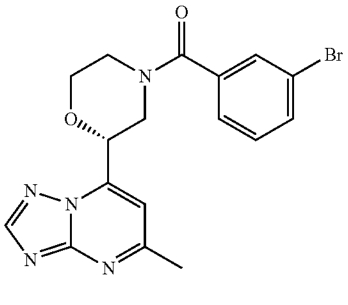 [SMILES: Cc1cc([C@H]2CN(C(=O)c3cccc(Br)c3)CCO2)n2ncnc2n1]

$^1H$ NMR (400 MHz, DMSO-$d_6$) δ=8.83-8.33 (m, 1H), 7.83-7.61 (m, 2H), 7.54-7.46 (m, 1H), 7.46-7.40 (m, 1H), 7.35-7.21 (m, 1H), 5.65-4.99 (m, 2H), 4.55-3.90 (m, 3H), 3.24-2.85 (m, 2H), 2.63 (br s, 3H); [M+H]=402.2.

Example 251. (2R)-4-[(3-Bromo-4-fluorophenyl)carbonyl]-2-{5-methyl-[1,2,4]triazolo[1,5-a]pyrimidin-7-yl}morpholine

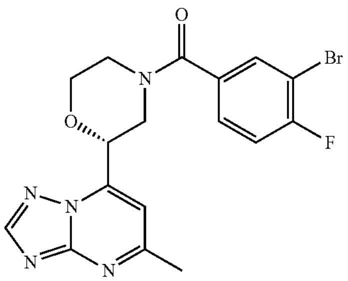 [SMILES: Cc1cc([C@H]2CN(C(=O)c3ccc(F)c(Br)c3)CCO2)n2ncnc2n1]

$^1H$ NMR (400 MHz, DMSO-$d_6$) d=8.70-8.44 (m, 1H), 8.02-7.85 (m, 1H), 7.62-7.54 (m, 1H), 7.53-7.43 (m, 1H), 7.33-7.16 (m, 1H), 5.47-5.02 (m, 2H), 4.55-3.92 (m, 3H), 3.19-2.91 (m, 2H), 2.63 (s, 3H); [M+H]=420.2.

Example 252. (2S)-4-[(3,5-Dichlorophenyl)carbonyl]-2-{5-methyl-[1,2,4]triazolo[1,5-a]pyrimidin-7-yl}morpholine

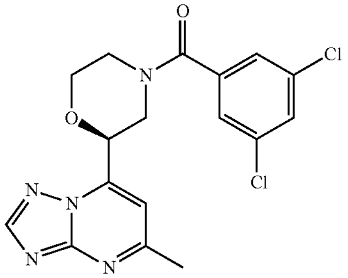

$^1H$ NMR (400 MHz, DMSO-$d_6$) δ=8.75-8.33 (m, 1H), 7.74 (t, J=1.8 Hz, 1H), 7.67-7.55 (m, 2H), 7.33-7.18 (m, 1H), 5.56-5.00 (m, 2H), 4.47-3.88 (m, 3H), 3.17-2.82 (m, 2H), 2.62 (br s, 3H); [M+H]=392.2.

Example 253. (2S)-4-[(3-Bromophenyl)carbonyl]-2-{5-methyl-[1,2,4]triazolo[1,5-a]pyrimidin-7-yl}morpholine

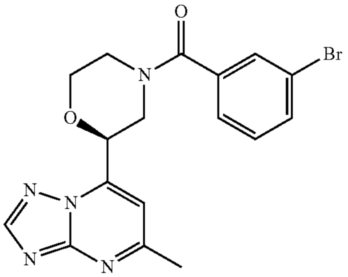 [SMILES: Cc1cc([C@@H]2CN(C(=O)c3cccc(Br)c3)CCO2)n2ncnc2n1]

$^1H$ NMR (400 MHz, DMSO-$d_6$) δ=8.71-8.43 (m, 1H), 7.79-7.64 (m, 2H), 7.49 (s, 1H), 7.46-7.40 (m, 1H), 7.33-7.20 (m, 1H), 5.49-4.96 (m, 2H), 4.51-3.92 (m, 3H), 3.14 (s, 2H), 2.63 (br s, 3H); [M+H]=402.2.

Example 254. (2S)-4-[(3-Bromo-4-fluorophenyl)carbonyl]-2-{5-methyl-[1,2,4]triazolo[1,5-a]pyrimidin-7-yl}morpholine

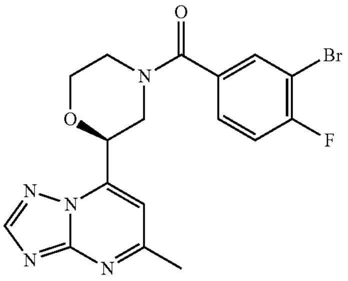 [SMILES: Cc1cc([C@@H]2CN(C(=O)c3ccc(F)c(Br)c3)CCO2)n2ncnc2n1]

$^1H$ NMR (400 MHz, DMSO-$d_6$) δ=8.73-8.45 (m, 1H), 8.03-7.82 (m, 1H), 7.65-7.56 (m, 1H), 7.53-7.43 (m, 1H), 7.25 (br s, 1H), 5.45-5.01 (m, 1H), 4.49-3.79 (m, 3H), 3.66-3.38 (m, 1H), 3.18-3.01 (m, 1H), 2.94-2.74 (m, 1H), 2.63 (s, 3H); [M+H]=420.3.

Example 255. (2R)-4-[(3,5-Dichlorophenyl)carbonyl]-2-{5-methyl-[1,2,4]triazolo[1,5-a]pyrimidin-7-yl}morpholine

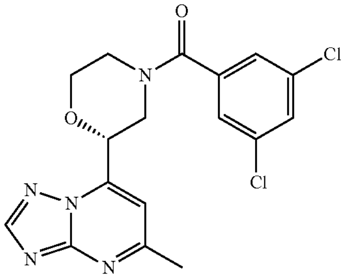 [SMILES: Cc1cc([C@H]2CN(C(=O)c3cc(Cl)cc(Cl)c3)CCO2)n2ncnc2n1]

$^1$H NMR (400 MHz, DMSO-$d_6$) δ=8.70-8.37 (m, 1H), 7.78-7.72 (m, 1H), 7.68-7.52 (m, 2H), 7.30-7.20 (m, 1H), 5.60-5.02 (m, 2H), 4.47-3.77 (m, 3H), 3.18-2.82 (m, 2H), 2.71-2.59 (m, 3H); [M+H]=392.2.

Example 256. 4-[(3-Bromo-5-fluorophenyl)carbonyl]-2-{5-methyl-[1,2,4]triazolo[1,5-a]pyrimidin-7-yl}morpholine

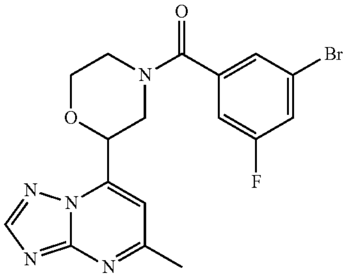 [SMILES: Cc1cc(C2CN(C(=O)c3cc(F)cc(Br)c3)CCO2)n2ncnc2n1]

$^1$H NMR (400 MHz, DMSO-$d_6$) δ=8.78-8.33 (m, 1H), 7.68 (s, 1H), 7.66-7.53 (m, 1H), 7.47-7.42 (m, 1H), 7.33-7.20 (m, 1H), 5.54-4.99 (m, 1H), 4.52-3.73 (m, 3H), 3.56-3.36 (m, 1H), 3.17-2.77 (m, 2H), 2.62 (br s, 3H); [M+H]=420.2.

Example 257. 4-[(3,5-Dibromophenyl)carbonyl]-2-{5-methyl-[1,2,4]triazolo[1,5-a]pyrimidin-7-yl}morpholine

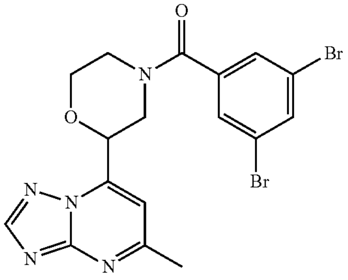 [SMILES: Cc1cc(C2CN(C(=O)c3cc(Br)cc(Br)c3)CCO2)n2ncnc2n1]

$^1$H NMR (400 MHz, DMSO-$d_6$) δ=8.75-8.43 (m, 1H), 7.97 (t, J=1.8 Hz, 1H), 7.82-7.71 (m, 2H), 7.39-7.18 (m, 1H), 5.50-5.04 (m, 1H), 4.50-3.77 (m, 3H), 3.56-3.36 (m, 1H), 3.22-2.73 (m, 2H), 2.62 (br s, 3H); [M+H]=482.1

Example 258. 1-[(3-Bromo-5-fluorophenyl)carbonyl]-3,3-difluoro-5-{5-methyl-[1,2,4]triazolo[1,5-a]pyrimidin-7-yl}piperidine

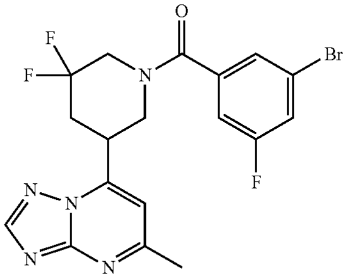 [SMILES: Cc1cc(C2CN(C(=O)c3cc(F)cc(Br)c3)CC(F)(F)C2)n2ncnc2n1]

$^1$H NMR (400 MHz, DMSO-$d_6$) δ=8.66-8.42 (m, 1H), 7.78-7.62 (m, 1H), 7.50 (t, J=1.4 Hz, 1H), 7.41-7.35 (m, 1H), 7.28-7.20 (m, 1H), 4.99-4.59 (m, 1H), 4.27-3.73 (m, 3H), 2.71-2.57 (m, 6H); [M+H]=454.2.

Example 259. 1-[(3,5-Dibromophenyl)carbonyl]-3,3-difluoro-5-{5-methyl-[1,2,4]triazolo[1,5-a]pyrimidin-7-yl}piperidine

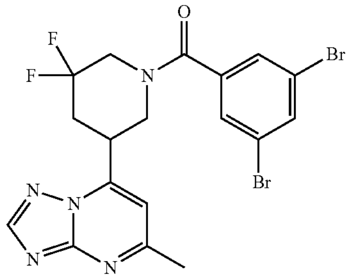 [SMILES: Cc1cc(C2CN(C(=O)c3cc(Br)cc(Br)c3)CC(F)(F)C2)n2ncnc2n1]

$^1$H NMR (400 MHz, DMSO-$d_6$) δ=8.70-8.42 (m, 1H), 8.06-7.91 (m, 1H), 7.66 (d, J=1.6 Hz, 2H), 7.36-7.21 (m, 1H), 4.94-4.69 (m, 1H), 4.18-3.71 (m, 3H), 2.59 (br s, 6H); [M+H]=516.1.

Example 260. 3,3-Difluoro-5-{5-methyl-[1,2,4]triazolo[1,5-a]pyrimidin-7-yl}-1-{[3-(pentafluorosulfanyl)phenyl]carbonyl}piperidine

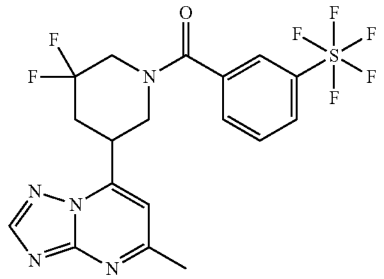 [SMILES: Cc1cc(C2CN(C(=O)c3cccc(S(F)(F)(F)(F)F)c3)CC(F)(F)C2)n2ncnc2n1]

$^1$H NMR (400 MHz, DMSO-$d_6$) δ=8.71-8.36 (m, 1H), 8.10-7.76 (m, 4H), 7.46-7.09 (m, 1H), 4.96-4.68 (m, 1H), 4.27-3.61 (m, 3H), 2.60 (br s, 6H); [M+H]=484.3.

Example 261. 2-{5-Methyl-[1,2,4]triazolo[1,5-a]pyrimidin-7-yl}-4-{[3-(pentafluorosulfanyl)phenyl]carbonyl}morpholine

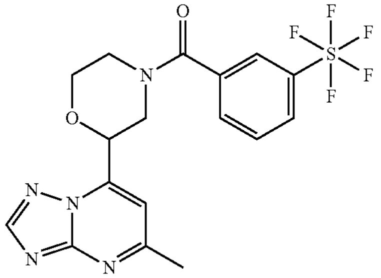 [SMILES: Cc1cc(C2CN(C(=O)c3cccc(S(F)(F)(F)(F)F)c3)CCO2)n2ncnc2n1]

$^{1}$H NMR (400 MHz, DMSO-$d_6$) δ=8.77-8.27 (m, 1H), 8.10-7.63 (m, 4H), 7.43-7.13 (m, 1H), 5.43-5.08 (m, 1H), 4.55-3.79 (m, 3H), 3.73-3.33 (m, 2H), 3.23-2.83 (m, 1H), 2.74-2.56 (m, 3H); [M+H]=450.3.

Example 262. 1-[(3-Bromo-4-methylphenyl)carbonyl]-3,3-difluoro-5-{5-methyl-[1,2,4]triazolo[1,5-a]pyrimidin-7-yl}piperidine

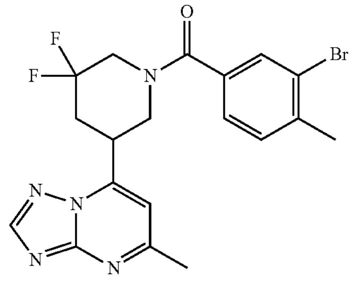 [SMILES: Cc1cc(C2CN(C(=O)c3ccc(C)c(Br)c3)CC(F)(F)C2)n2ncnc2n1]

$^{1}$H NMR (400 MHz, DMSO-$d_6$) δ=8.71-8.39 (m, 1H), 7.75-7.60 (m, 1H), 7.52-7.36 (m, 2H), 7.32-7.19 (m, 1H), 4.91-4.51 (m, 1H), 4.33-3.34 (m, 3H), 2.60 (br s, 6H), 2.37 (s, 3H); [M+H]=450.2.

Example 263. 4-[(3-Bromo-4-methylphenyl)carbonyl]-2-{5-methyl-[1,2,4]triazolo[1,5-a]pyrimidin-7-yl}morpholine

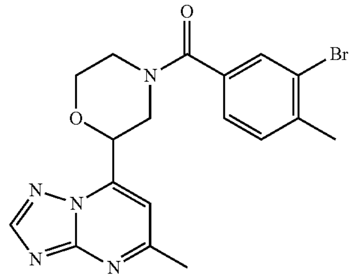 [SMILES: Cc1cc(C2CN(C(=O)c3ccc(C)c(Br)c3)CCO2)n2ncnc2n1]

$^{1}$H NMR (400 MHz, DMSO-$d_6$) δ=8.69-8.34 (m, 1H), 7.89-7.66 (m, 1H), 7.56-7.35 (m, 2H), 7.25 (br s, 1H), 5.47-4.99 (m, 1H), 4.52-3.45 (m, 4H), 3.22-2.76 (m, 1H), 2.63 (s, 3H), 2.38 (s, 3H); [M+H]=416.2.

Example 264. 4-[(4-Chloropyridin-2-yl)carbonyl]-2-{5-methyl-[1,2,4]triazolo[1,5-a]pyrimidin-7-yl}morpholine

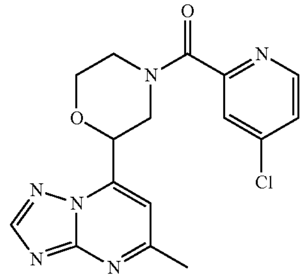 [SMILES: Cc1cc(C2CN(C(=O)c3cc(Cl)ccn3)CCO2)n2ncnc2n1]

$^{1}$H NMR (400 MHz, $CDCl_3$) δ=8.54-8.12 (m, 1H), 8.05-7.45 (m, 2H), 7.21-7.05 (m, 1H), 5.56-5.21 (m, 1H), 5.14-4.73 (m, 2H), 4.37-3.70 (m, 3H), 3.48-2.82 (m, 3H), 2.76-2.47 (m, 4H); [M+H]=359.0.

Example 265. 4-Chloro-2-[(3,3-difluoro-5-{5-methyl-[1,2,4]triazolo[1,5-a]pyrimidin-7-yl}piperidin-1-yl)carbonyl]pyridine

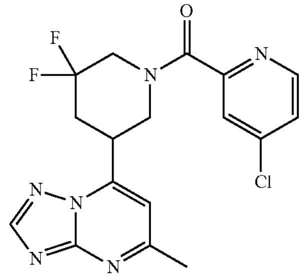

$^{1}$H NMR (400 MHz, $CDCl_3$) δ=8.58-8.28 (m, 2H), 7.90-7.75 (m, 1H), 7.47-7.32 (m, 1H), 6.94-6.80 (m, 1H), 4.97 (d, J=11.3 Hz, 1H), 4.72-4.52 (m, 1H), 4.10-3.32 (m, 4H), 2.71 (d, J=13.7 Hz, 4H); [M+H]=393.0.

Example 266. 2-(4-Chlorophenoxy)-3-[(3,3-difluoro-5-{5-methyl-[1,2,4]triazolo[1,5-a]pyrimidin-7-yl}piperidin-1-yl)carbonyl]pyridine

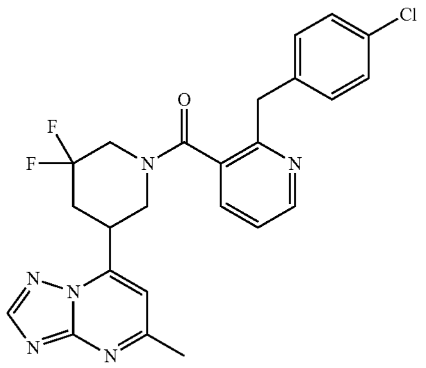 [SMILES: Cc1cc(C2CN(C(=O)c3cccnc3Cc3ccc(Cl)cc3)CC(F)(F)C2)n2ncnc2n1]

$^{1}$H NMR (400 MHz, $CDCl_3$) δ=8.60-8.19 (m, 2H), 7.83 (br s, 2H), 7.47-7.27 (m, 2H), 7.25-6.95 (m, 3H), 4.92-3.63 (m, 7H), 2.70 (br s, 3H); [M+H]=485.2.

Example 267. 4-{[2-Methyl-6-(trifluoromethyl)pyridin-3-yl]carbonyl}-2-{5-methyl-[1,2,4]triazolo[1,5-a]pyrimidin-7-yl}morpholine

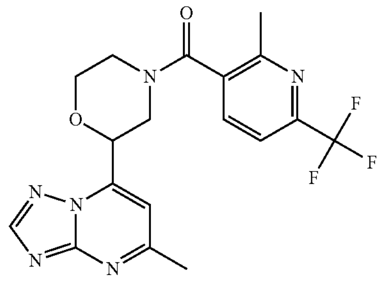 [SMILES: Cc1cc(C2CN(C(=O)c3ccc(C(F)(F)F)nc3C)CCO2)n2ncnc2n1]

$^1$H NMR (400 MHz, $CDCl_3$) δ=8.54-8.12 (m, 1H), 8.05-7.41 (m, 2H), 7.20-7.06 (m, 1H), 5.59-4.73 (m, 2H), 4.39-2.94 (m, 3H), 2.92-2.50 (m, 6H); [M+H]=407.1.

Example 268. (5R)-1-[(3-Bromo-4-fluorophenyl)carbonyl]-3,3-difluoro-5-{5-methyl-[1,2,4]triazolo[1,5-a]pyrimidin-7-yl}piperidine

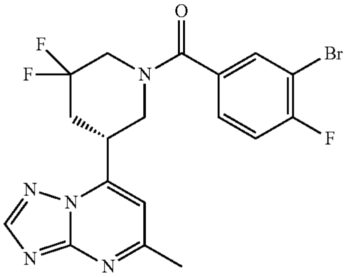 [SMILES: Cc1cc([C@H]2CN(C(=O)c3ccc(F)c(Br)c3)CC(F)(F)C2)n2ncnc2n1]

$^1$H NMR (400 MHz, DMSO-$d_6$) δ=8.75-8.44 (m, 1H), 7.92-7.71 (m, 1H), 7.63-7.46 (m, 2H), 7.36-7.05 (m, 1H), 5.04-3.74 (m, 4H), 2.79-2.58 (m, 6H); [M+H]=456.2.

Example 269. (5S)-1-[(3-Bromo-4-fluorophenyl)carbonyl]-3,3-difluoro-5-{5-methyl-[1,2,4]triazolo[1,5-a]pyrimidin-7-yl}piperidine

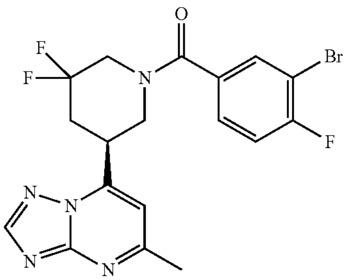 [SMILES: Cc1cc([C@@H]2CN(C(=O)c3ccc(F)c(Br)c3)CC(F)(F)C2)n2ncnc2n1]

$^1$H NMR (400 MHz, DMSO-$d_6$) δ=8.69-8.48 (m, 1H), 7.85-7.76 (m, 1H), 7.48 (s, 2H), 7.37-7.18 (m, 1H), 5.04-4.62 (m, 1H), 4.31-3.64 (m, 3H), 2.60 (br s, 6H); [M+H]=456.2.

Example 270. (5R)-1-(3-Bromo-5-fluorobenzoyl)-3,3-difluoro-5-{5-methyl-[1,2,4]triazolo[1,5-a]pyrimidin-7-yl}piperidine

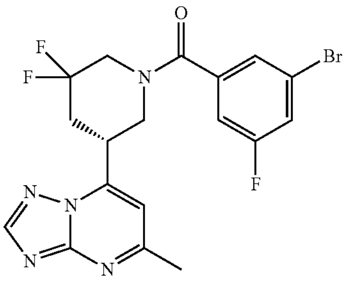 [SMILES: Cc1cc([C@H]2CN(C(=O)c3cc(F)cc(Br)c3)CC(F)(F)C2)n2ncnc2n1]

$^1$H NMR (400 MHz, DMSO-$d_6$) δ=8.75-8.35 (m, 1H), 7.76-7.64 (m, 1H), 7.50 (t, J=1.6 Hz, 1H), 7.42-7.35 (m, 1H), 7.30-7.17 (m, 1H), 4.93-4.67 (m, 1H), 4.17-3.74 (m, 3H), 2.77-2.56 (m, 6H); [M+H]=454.2.

Example 271. (5S)-1-(3-Bromo-5-fluorobenzoyl)-3,3-difluoro-5-{5-methyl-[1,2,4]triazolo[1,5-a]pyrimidin-7-yl}piperidine

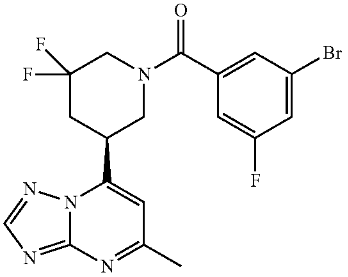 [SMILES: Cc1cc([C@@H]2CN(C(=O)c3cc(F)cc(Br)c3)CC(F)(F)C2)n2ncnc2n1]

$^1$H NMR (400 MHz, DMSO-$d_6$) δ=8.46 (br s, 1H), 7.70 (br s, 1H), 7.50 (t, J=1.4 Hz, 1H), 7.37 (qd, J=1.2, 8.6 Hz, 1H), 7.24 (br s, 1H), 4.90-4.67 (m, 1H), 4.18-3.98 (m, 1H), 3.92-3.67 (m, 2H), 2.59 (br s, 6H); [M+H]=454.2.

Example 272. 3-(3,3-Difluoro-5-{5-methyl-[1,2,4]triazolo[1,5-a]pyrimidin-7-yl}piperidine-1-carbonyl)-2-methyl-6-(trifluoromethyl)pyridine

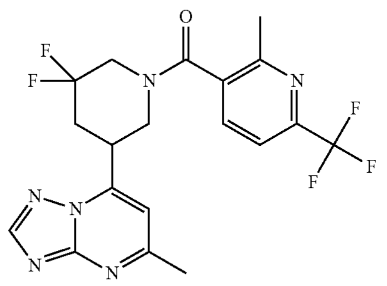 [SMILES: Cc1cc(C2CN(C(=O)c3ccc(C(F)(F)F)nc3C)CC(F)(F)C2)n2ncnc2n1]

$^1$H NMR (400 MHz, $CDCl_3$) δ=8.28-7.29 (m, 3H), 7.30-7.29 (m, 1H), 6.95-6.70 (m, 1H), 4.99-4.88 (m, 1H), 5.02-4.74 (m, 1H), 3.93-3.32 (m, 3H), 3.18-2.90 (m, 1H), 2.68-2.20 (m, 8H); M+H=441.0.

Example 273. (2S)-4-(3,5-Dibromobenzoyl)-2-{5-methyl-[1,2,4]triazolo[1,5-a]pyrimidin-7-yl}morpholine

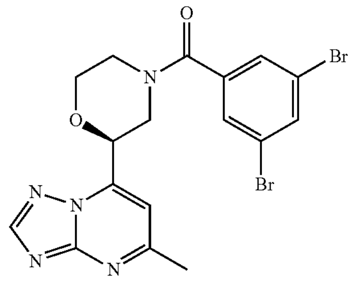 [SMILES: Cc1cc([C@@H]2CN(C(=O)c3cc(Br)cc(Br)c3)CCO2)n2ncnc2n1]

$^1$H NMR (400 MHz, DMSO-$d_6$) δ=8.78-8.44 (m, 1H), 7.98 (t, J=1.8 Hz, 1H), 7.79 (br s, 2H), 7.32-7.14 (m, 1H), 5.46-5.07 (m, 1H), 4.47-3.77 (m, 3H), 3.55-3.38 (m, 1H), 3.16-2.76 (m, 2H), 2.64 (br s, 3H); [M+H]=482.1.

Example 274. (5R)-1-(3,5-Dibromobenzoyl)-3,3-difluoro-5-{5-methyl-[1,2,4]triazolo[1,5-a]pyrimidin-7-yl}piperidine

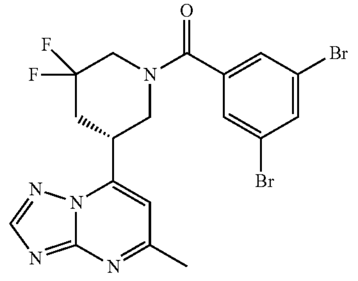 [SMILES: Cc1cc([C@H]2CN(C(=O)c3cc(Br)cc(Br)c3)CC(F)(F)C2)n2ncnc2n1]

$^1$H NMR (400 MHz, DMSO-$d_6$) δ=8.78-8.38 (m, 1H), 8.09-7.92 (m, 1H), 7.68 (d, J=2.0 Hz, 2H), 7.45-7.01 (m, 1H), 4.89-4.60 (m, 1H), 4.28-3.39 (m, 3H), 2.61 (br s, 6H); [M+H]=516.1.

Example 275. (5S)-1-(3,5-Dibromobenzoyl)-3,3-difluoro-5-{5-methyl-[1,2,4]triazolo[1,5-a]pyrimidin-7-yl}piperidine

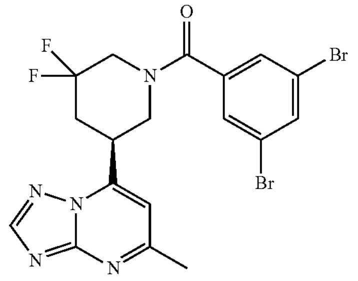 [SMILES: Cc1cc([C@@H]2CN(C(=O)c3cc(Br)cc(Br)c3)CC(F)(F)C2)n2ncnc2n1]

$^1$H NMR (400 MHz, DMSO-$d_6$) δ=8.73-8.44 (m, 1H), 8.09-7.92 (m, 1H), 7.68 (d, J=1.6 Hz, 2H), 7.45-7.18 (m, 1H), 4.89-4.67 (m, 1H), 4.19-3.40 (m, 3H), 2.62 (d, J=9.8 Hz, 6H); [M+H]=516.1.

Example 276. (5S)-1-[3,5-Bis(trifluoromethyl)benzoyl]-3,3-difluoro-5-{5-methyl-[1,2,4]triazolo[1,5-a]pyrimidin-7-yl}piperidine

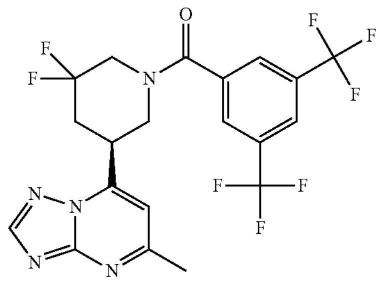 [SMILES: Cc1cc([C@@H]2CN(C(=O)c3cc(C(F)(F)F)cc(C(F)(F)F)c3)CC(F)(F)C2)n2ncnc2n1]

$^1$H NMR (400 MHz, DMSO-$d_6$) δ=8.68-8.19 (m, 2H), 8.14 (s, 2H), 7.40-7.13 (m, 1H), 5.04-4.69 (m, 1H), 4.15-3.35 (m, 3H), 2.57 (br s, 6H); [M+H]=494.2.

Example 277. (5S)-1-(3,5-Dimethylbenzoyl)-3,3-difluoro-5-{5-methyl-[1,2,4]triazolo[1,5-a]pyrimidin-7-yl}piperidine

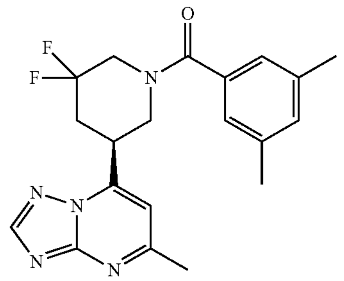 [SMILES: Cc1cc(C)cc(C(=O)N2C[C@@H](c3cc(C)nc4ncnn34)CC(F)(F)C2)c1]

$^1$H NMR (400 MHz, DMSO-$d_6$) δ=8.75-8.32 (m, 1H), 7.42-7.19 (m, 1H), 7.09 (br s, 1H), 7.03 (d, J=0.8 Hz, 2H), 5.36-3.30 (m, 5H), 2.59 (br s, 5H), 2.30 (s, 6H); [M+H]=386.3.

Example 278. (2S)-4-(3-Bromo-5-chlorobenzoyl)-2-{5-methyl-[1,2,4]triazolo[1,5-a]pyrimidin-7-yl}morpholine

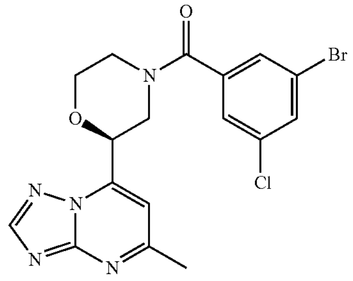 [SMILES: Cc1cc([C@@H]2CN(C(=O)c3cc(Cl)cc(Br)c3)CCO2)n2ncnc2n1]

$^1$H NMR (400 MHz, DMSO-$d_6$) δ=8.75-8.37 (m, 1H), 7.85 (s, 1H), 7.76-7.55 (m, 2H), 7.39-7.12 (m, 1H), 5.48-4.94 (m, 1H), 4.52-3.34 (m, 4H), 3.16-2.81 (m, 2H), 2.63 (d, J=10.2 Hz, 3H); [M+H]=438.1.

Example 279. (2S)-4-(3-Bromo-5-fluorobenzoyl)-2-{5-methyl-[1,2,4]triazolo[1,5-a]pyrimidin-7-yl}morpholine

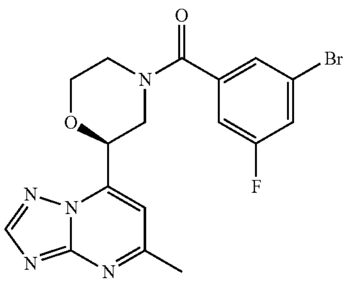 [SMILES: Cc1cc([C@@H]2CN(C(=O)c3cc(F)cc(Br)c3)CCO2)n2ncnc2n1]

$^1$H NMR (400 MHz, DMSO-$d_6$) δ=8.80-8.29 (m, 1H), 7.73-7.67 (m, 1H), 7.66-7.55 (m, 1H), 7.47-7.41 (m, 1H), 7.31-7.19 (m, 1H), 5.50-5.02 (m, 1H), 4.42-3.37 (m, 4H), 3.18-2.76 (m, 2H), 2.62 (br s, 3H); [M+H]=420.2.

Example 280. (5S)-1-(3,5-Dichlorobenzoyl)-3,3-difluoro-5-{5-methyl-[1,2,4]triazolo[1,5-a]pyrimidin-7-yl}piperidine

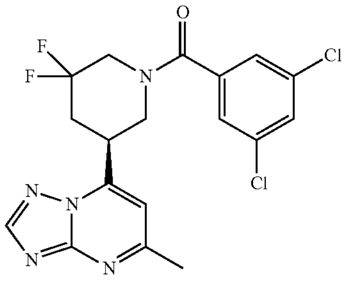 [SMILES: Cc1cc([C@@H]2CN(C(=O)c3cc(Cl)cc(Cl)c3)CC(F)(F)C2)n2ncnc2n1]

$^1$H NMR (400 MHz, DMSO-$d_6$) δ=8.71-8.42 (m, 1H), 7.75 (br s, 1H), 7.51 (d, J=2.0 Hz, 2H), 7.24 (br s, 1H), 5.09-3.30 (m, 5H), 2.59 (br s, 5H); [M+H]=436.3.

Example 281. (5S)-1-(4-Bromobenzoyl)-3,3-difluoro-5-{5-methyl-[1,2,4]triazolo[1,5-a]pyrimidin-7-yl}piperidine

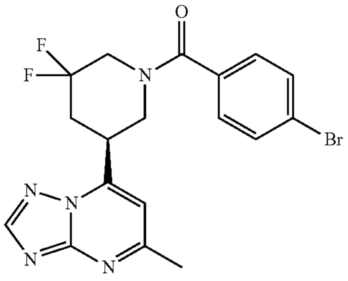 [SMILES: Cc1cc([C@@H]2CN(C(=O)c3ccc(Br)cc3)CC(F)(F)C2)n2ncnc2n1]

$^1$H NMR (400 MHz, DMSO-$d_6$) δ=8.61-8.47 (m, 1H), 7.68 (d, J=8.2 Hz, 2H), 7.44 (s, 2H), 7.33-7.20 (m, 1H), 4.92-3.32 (m, 5H), 2.79-2.54 (m, 5H); [M+H]=438.3.

Example 282. (5S)-1-(3-Bromo-2,4,5,6-tetrafluorobenzoyl)-3,3-difluoro-5-{5-methyl-[1,2,4]triazolo[1,5-a]pyrimidin-7-yl}piperidine

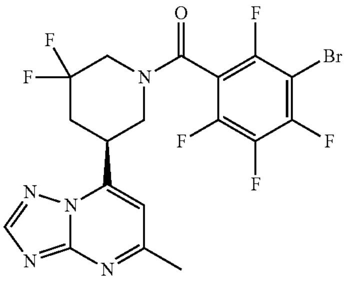 [SMILES: Cc1cc([C@@H]2CN(C(=O)c3c(F)c(F)c(F)c(Br)c3F)CC(F)(F)C2)n2ncnc2n1]

$^1$H NMR (400 MHz, DMSO-$d_6$) δ=8.69-8.27 (m, 1H), 7.23 (d, J=3.9 Hz, 1H), 4.93-3.35 (m, 5H), 2.76-2.56 (m, 5H); [M+H]=508.2.

Example 283. (S)-1-(3-Cyclopropyl-4,5-difluorobenzoyl)-3,3-difluoro-5-{5-methyl-[1,2,4]triazolo[1,5-a]pyrimidin-7-yl}piperidine

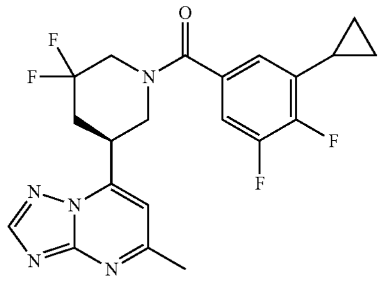 [SMILES: Cc1cc([C@@H]2CN(C(=O)c3cc(F)c(F)c(C4CC4)c3)CC(F)(F)C2)n2ncnc2n1]

$^1$H NMR (400 MHz, DMSO-$d_6$) δ=8.77-8.30 (m, 1H), 7.33 (br s, 2H), 6.87 (d, J=5.5 Hz, 1H), 4.94-4.63 (m, 1H), 3.92-3.77 (m, 2H), 3.47-3.07 (m, 2H), 2.81-2.53 (m, 5H), 2.18-2.03 (m, 1H), 1.11-0.94 (m, 2H), 0.89-0.69 (m, 2H); [M+H]=434.4.

Example 284. (2S)-4-[3-Methyl-4-(propan-2-yloxy)benzoyl]-2-{5-methyl-[1,2,4]triazolo[1,5-a]pyrimidin-7-yl}morpholine

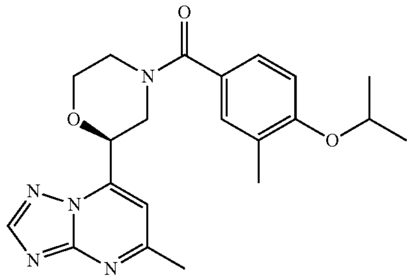 [SMILES: Cc1cc([C@@H]2CN(C(=O)c3ccc(OC(C)C)c(C)c3)CCO2)n2ncnc2n1]

$^1$H NMR (400 MHz, $CDCl_3$) δ=8.37 (s, 1H), 7.43-7.31 (m, 2H), 7.19-7.12 (m, 1H), 6.85 (d, J=8.6 Hz, 1H), 5.33-5.23 (m, 1H), 4.90 (br s, 1H), 4.58 (spt, J=6.1 Hz, 1H), 4.39 (d, J=6.3 Hz, 1H), 4.21 (d, J=10.6 Hz, 1H), 3.89 (t, J=11.0

Hz, 1H), 3.20 (br s, 1H), 2.90 (dd, J=10.0, 13.1 Hz, 1H), 2.71 (s, 3H), 2.26 (s, 3H), 1.35 (d, J=5.9 Hz, 6H); [M+H]=395.7.

Example 285. (2S)-4-(4-Ethoxy-3-methylbenzoyl)-2-{5-methyl-[1,2,4]triazolo[1,5-a]pyrimidin-7-yl}morpholine

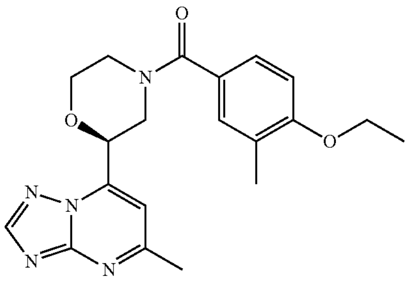 [SMILES: CCOc1ccc(C(=O)N2CCO[C@H](c3cc(C)nc4ncnn34)C2)cc1C]

$^1$H NMR (400 MHz, $CDCl_3$) δ=8.38 (s, 1H), 7.45-7.33 (m, 2H), 7.16 (d, J=0.8 Hz, 1H), 6.83 (d, J=8.2 Hz, 1H), 5.33-5.25 (m, 1H), 4.89 (br s, 1H), 4.42 (br s, 1H), 4.27-4.14 (m, 1H), 4.13-4.02 (m, 2H), 3.96-3.83 (m, 1H), 3.21 (br s, 1H), 2.97-2.82 (m, 1H), 2.72 (s, 3H), 2.29 (s, 3H), 1.50-1.40 (m, 3H); [M+H]=381.9.

Example 286. (2S)-4-(3-Bromo-5-methylbenzoyl)-2-{5-methyl-[1,2,4]triazolo[1,5-a]pyrimidin-7-yl}morpholine

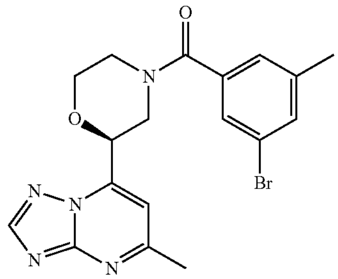 [SMILES: Cc1cc(Br)cc(C(=O)N2CCO[C@H](c3cc(C)nc4ncnn34)C2)c1]

$^1$H NMR (400 MHz, DMSO-$d_6$) δ=8.78-8.36 (m, 1H), 7.52 (s, 4H), 5.58-4.91 (m, 1H), 4.52-3.35 (m, 4H), 3.18-2.73 (m, 2H), 2.63 (br s, 3H), 2.36 (br s, 3H); [M+H]=416.4.

Example 287. (2S)-4-(3-Chloro-5-methylbenzoyl)-2-{5-methyl-[1,2,4]triazolo[1,5-a]pyrimidin-7-yl}morpholine

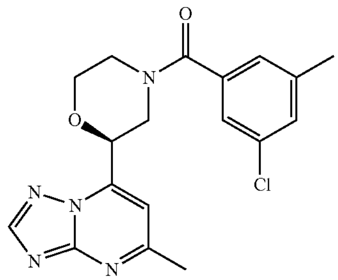 [SMILES: Cc1cc(Cl)cc(C(=O)N2CCO[C@H](c3cc(C)nc4ncnn34)C2)c1]

$^1$H NMR (400 MHz, DMSO-$d_6$) δ=8.71-8.40 (m, 1H), 7.46-7.20 (m, 4H), 5.58-3.78 (m, 4H), 3.64-3.47 (m, 1H), 3.16-2.81 (m, 2H), 2.63 (br s, 3H), 2.37 (br s, 3H); [M+H]=372.3.

Example 288. (2S)-4-[1-Methyl-3-(propan-2-yl)-1H-pyrazole-5-carbonyl]-2-{5-methyl-[1,2,4]triazolo[1,5-a]pyrimidin-7-yl}morpholine

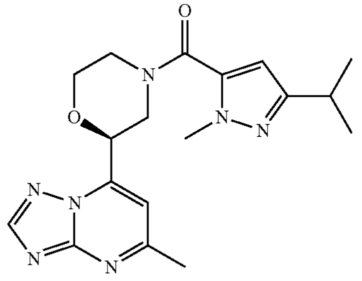 [SMILES: Cc1cc([C@@H]2CN(C(=O)c3cc(C(C)C)nn3C)CCO2)n2ncnc2n1]

$^1$H NMR (400 MHz, $CDCl_3$) δ=8.42 (s, 1H), 7.22-7.13 (m, 1H), 6.60 (br s, 1H), 5.25 (dd, J=2.2, 10.4 Hz, 1H), 5.10 (br s, 1H), 4.62 (br s, 1H), 4.26 (d, J=11.0 Hz, 1H), 3.97 (s, 3H), 3.88 (t, J=11.9 Hz, 1H), 3.67-3.08 (m, 1H), 3.06-2.87 (m, 2H), 2.79-2.67 (m, 4H), 1.31 (dd, J=4.9, 6.8 Hz, 7H); [M+H]=370.5.

Example 289. (2S)-4-[3,5-Dimethyl-4-(propan-2-yloxy)benzoyl]-2-{5-methyl-[1,2,4]triazolo[1,5-a]pyrimidin-7-yl}morpholine

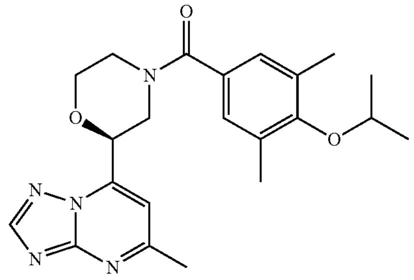 [SMILES: Cc1cc([C@@H]2CN(C(=O)c3cc(C)c(OC(C)C)c(C)c3)CCO2)n2ncnc2n1]

$^1$H NMR (400 MHz, $CDCl_3$) δ=8.34 (br s, 1H), 7.22 (br s, 2H), 7.16 (s, 1H), 5.27 (dd, J=1.6, 10.2 Hz, 1H), 4.22 (spt, J=6.1 Hz, 2H), 3.90 (t, J=10.6 Hz, 1H), 3.17 (br s, 1H), 2.90 (dd, J=10.4, 13.1 Hz, 1H), 2.72 (s, 3H), 2.32 (s, 6H), 1.30 (dd, J=0.8, 5.9 Hz, 6H); [M+H]=410.7.

Examples 290-333 were prepared in a manner analogous to Example 8, with the appropriate starting material and reagent substitutions.

Example 290. 2-[(3,3-Difluoro-5-{5-methyl-[1,2,4]triazolo[1,5-a]pyrimidin-7-yl}piperidin-1-yl)carbonyl]quinoline

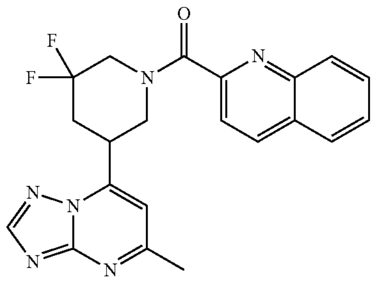 [SMILES: Cc1cc(C2CN(C(=O)c3ccc4ccccc4n3)CC(F)(F)C2)n2ncnc2n1]

$^1$H NMR (400 MHz, DMSO-$d_6$) δ=8.69-8.23 (m, 2H), 8.11-7.99 (m, 2H), 7.91-7.62 (m, 3H), 7.41-7.20 (m, 1H), 5.06-4.81 (m, 1H), 4.42-4.31 (m, 1H), 3.63-3.33 (m, 2H), 2.78-2.53 (m, 6H); [M+H]=409.3.

Example 291. 4-[(3-Bromo-5-chlorophenyl)carbonyl]-2-{5-methyl-[1,2,4]triazolo[1,5-a]pyrimidin-7-yl}morpholine

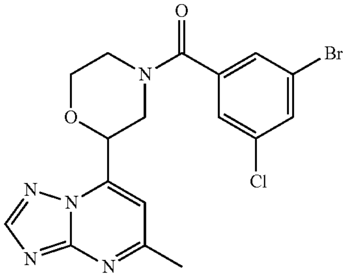

$^1$H NMR (400 MHz, DMSO-$d_6$) δ=8.73-8.36 (m, 1H), 7.85 (t, J=1.8 Hz, 1H), 7.77-7.58 (m, 2H), 7.36-7.07 (m, 1H), 5.45-5.11 (m, 1H), 4.51-4.13 (m, 2H), 4.06-3.75 (m, 2H), 3.13-2.74 (m, 2H), 2.62 (br s, 3H); [M+H]=438.1.

Example 292. 1-[(3-Bromo-5-chlorophenyl)carbonyl]-3,3-difluoro-5-{5-methyl-[1,2,4]triazolo[1,5-a]pyrimidin-7-yl}piperidine

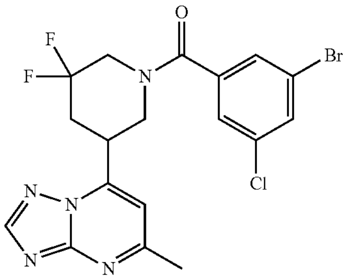

$^1$H NMR (400 MHz, DMSO-$d_6$) δ=8.69-8.43 (m, 1H), 7.91-7.81 (m, 1H), 7.66-7.59 (m, 1H), 7.55 (d, J=1.6 Hz, 1H), 7.38-7.16 (m, 1H), 4.93-4.67 (m, 1H), 4.15-3.73 (m, 3H), 2.59 (br s, 6H); [M+H]=472.1.

Example 293. 3-[(2-{5-Methyl-[1,2,4]triazolo[1,5-a]pyrimidin-7-yl}morpholin-4-yl)carbonyl]isoquinoline

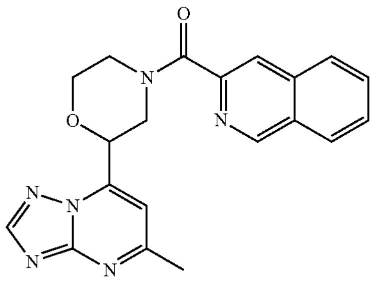 [SMILES: Cc1cc(C2CN(C(=O)c3cc4ccccc4cn3)CCO2)n2ncnc2n1]

$^1$H NMR (400 MHz, DMSO-$d_6$) δ=9.43-9.22 (m, 1H), 8.72-8.62 (m, 1H), 8.27-8.19 (m, 2H), 8.10 (d, J=8.2 Hz, 1H), 7.86 (ddd, J=1.2, 7.0, 8.2 Hz, 1H), 7.82-7.71 (m, 1H), 7.39-7.25 (m, 1H), 5.28 (dd, J=2.3, 10.2 Hz, 1H), 4.62-4.42 (m, 1H), 4.27-3.99 (m, 1H), 3.95-3.84 (m, 1H), 3.67-3.54 (m, 1H), 3.47-3.36 (m, 1H), 3.27-2.88 (m, 2H), 2.69-2.57 (m, 3H); [M+H]=375.3.

Example 294. 3-[(2-{5-Methyl-[1,2,4]triazolo[1,5-a]pyrimidin-7-yl}morpholin-4-yl)carbonyl]quinoline

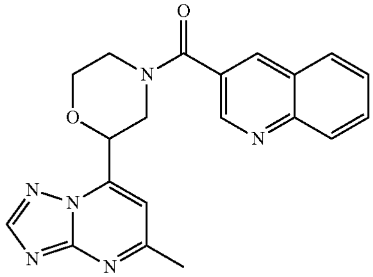 [SMILES: Cc1cc(C2CN(C(=O)c3cnc4ccccc4c3)CCO2)n2ncnc2n1]

$^1$H NMR (400 MHz, DMSO-$d_6$) δ=8.98 (d, J=1.6 Hz, 1H), 8.74-8.48 (m, 2H), 8.07 (d, J=8.6 Hz, 2H), 7.86 (ddd, J=1.6, 6.8, 8.4 Hz, 1H), 7.80-7.63 (m, 1H), 7.37-7.16 (m, 1H), 5.52-5.17 (m, 1H), 4.59-3.52 (m, 4H), 3.22-2.87 (m, 2H), 2.75-2.57 (m, 3H); [M+H]=375.3.

Example 295. 6-[(2-{5-Methyl-[1,2,4]triazolo[1,5-a]pyrimidin-7-yl}morpholin-4-yl)carbonyl]quinoline

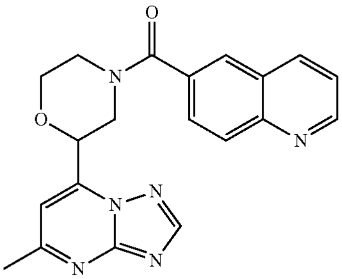

$^1$H NMR (400 MHz, DMSO-$d_6$) δ=8.97 (dd, J=2.0, 4.3 Hz, 1H), 8.47 (d, J=7.8 Hz, 1H), 8.41-8.11 (m, 2H), 8.09 (d,

J=8.6 Hz, 1H), 7.86 (dd, J=1.6, 8.6 Hz, 1H), 7.68-7.56 (m, 1H), 7.35-7.16 (m, 1H), 5.55-5.12 (m, 1H), 4.60-3.86 (m, 3H), 3.75-3.40 (m, 1H), 3.15 (d, J=5.1 Hz, 2H), 2.63 (br s, 3H); [M+H]=375.3.

Example 296. 6-[(2-{5-Methyl-[1,2,4]triazolo[1,5-a]pyrimidin-7-yl}morpholin-4-yl)carbonyl]isoquinoline

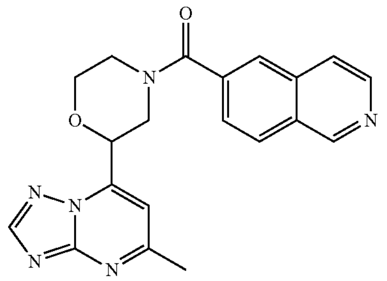 [SMILES: Cc1cc(C2CN(C(=O)c3ccc4cnccc4c3)CCO2)n2ncnc2n1]

$^1$H NMR (400 MHz, DMSO-$d_6$) δ=9.38 (s, 1H), 8.59 (br s, 2H), 8.23 (d, J=8.6 Hz, 2H), 7.92 (br s, 1H), 7.77 (dd, J=1.6, 8.2 Hz, 1H), 7.41-7.15 (m, 1H), 5.52-4.41 (m, 2H), 4.39-3.41 (m, 3H), 3.23-2.85 (m, 2H), 2.63 (d, J=18.0 Hz, 3H); [M+H]=375.3.

Example 297. 7-[(2-{5-Methyl-[1,2,4]triazolo[1,5-a]pyrimidin-7-yl}morpholin-4-yl)carbonyl]isoquinoline

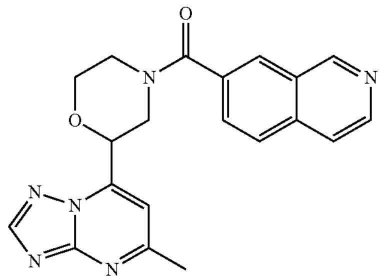 [SMILES: Cc1cc(C2CN(C(=O)c3ccc4ccncc4c3)CCO2)n2ncnc2n1]

$^1$H NMR (400 MHz, DMSO-$d_6$) δ=9.40 (s, 1H), 8.58 (d, J=5.5 Hz, 1H), 8.39-8.08 (m, 1H), 8.07 (d, J=8.6 Hz, 1H), 7.95-7.83 (m, 2H), 7.43-7.18 (m, 1H), 5.54-5.06 (m, 1H), 4.57-3.83 (m, 3H), 3.74-3.39 (m, 1H), 3.22-2.78 (m, 2H), 2.71-2.54 (m, 3H); [M+H]=375.3.

Example 298. 7-[(2-{5-Methyl-[1,2,4]triazolo[1,5-a]pyrimidin-7-yl}morpholin-4-yl)carbonyl]quinoline

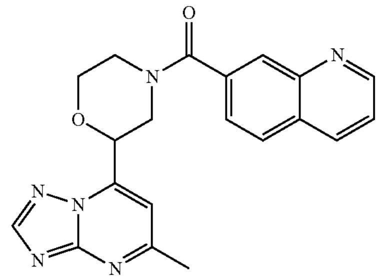 [SMILES: Cc1cc(C2CN(C(=O)c3ccc4cccnc4c3)CCO2)n2ncnc2n1]

$^1$H NMR (400 MHz, DMSO-$d_6$) δ=8.98 (dd, J=1.6, 4.3 Hz, 1H), 8.43 (d, J=7.4 Hz, 1H), 8.09 (d, J=8.2 Hz, 3H), 7.73-7.65 (m, 1H), 7.63-7.56 (m, 1H), 7.33-7.14 (m, 1H), 5.50-5.13 (m, 1H), 4.65-3.78 (m, 3H), 3.69-3.47 (m, 1H), 3.26-2.83 (m, 2H), 2.66 (d, J=11.3 Hz, 3H); [M+H]=375.3.

Example 299. 1-[(4-Cyclopropylphenyl)carbonyl]-3,3-difluoro-5-{5-methyl-[1,2,4]triazolo[1,5-a]pyrimidin-7-yl}piperidine

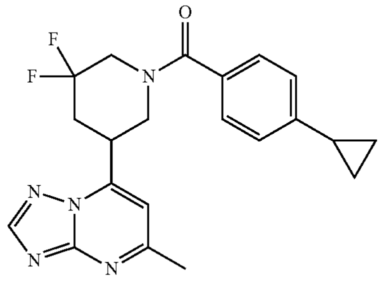 [SMILES: Cc1cc(C2CN(C(=O)c3ccc(C4CC4)cc3)CC(F)(F)C2)n2ncnc2n1]

$^1$H NMR (400 MHz, DMSO-$d_6$) δ=8.64-8.44 (m, 1H), 7.35 (d, J=8.2 Hz, 2H), 7.31-7.25 (m, 1H), 7.18-7.12 (m, 2H), 3.94-3.76 (m, 1H), 3.68-3.51 (m, 3H), 3.19-3.05 (m, 3H), 2.60 (s, 3H), 2.00-1.88 (m, 1H), 1.05-0.93 (m, 2H), 0.75-0.64 (m, 2H); [M+H]=398.0.

Example 300. 4-[(4-Cyclopropylphenyl)carbonyl]-2-{5-methyl-[1,2,4]triazolo[1,5-a]pyrimidin-7-yl}morpholine

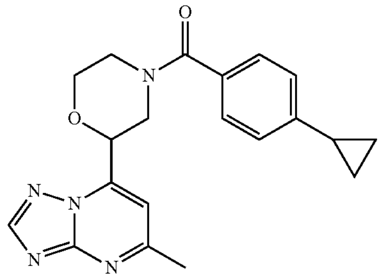 [SMILES: Cc1cc(C2CN(C(=O)c3ccc(C4CC4)cc3)CCO2)n2ncnc2n1]

$^1$H NMR (400 MHz, DMSO-$d_6$) δ=8.64-8.52 (m, 1H), 7.44-7.36 (m, 2H), 7.29-7.24 (m, 1H), 7.15 (d, J=8.2 Hz, 2H), 5.43-5.12 (m, 1H), 4.76-3.38 (m, 4H), 3.18-2.79 (m, 2H), 2.67-2.60 (m, 3H), 2.10-1.80 (m, 1H), 1.06-0.90 (m, 2H), 0.81-0.60 (m, 2H); [M+H]=364.3.

Example 301. (2S)-4-(4-Cyclopropylbenzoyl)-2-{5-methyl-[1,2,4]triazolo[1,5-a]pyrimidin-7-yl}morpholine

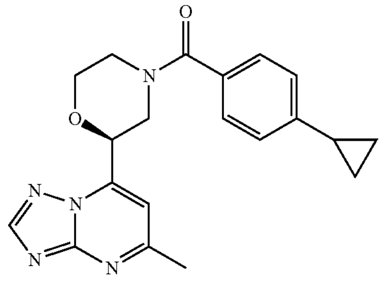 [SMILES: Cc1cc([C@@H]2CN(C(=O)c3ccc(C4CC4)cc3)CCO2)n2ncnc2n1]

$^1$H NMR (400 MHz, $CD_3OD$) δ=9.54-9.33 (m, 1H), 8.19 (d, J=7.8 Hz, 2H), 8.07 (s, 1H), 8.00-7.89 (m, 2H), 6.18-5.96 (m, 1H), 5.26-4.55 (m, 3H), 3.96 (s, 3H), 3.44 (s, 3H), 2.83-2.68 (m, 1H), 1.86-1.72 (m, 2H), 1.60-1.46 (m, 2H); [M+H]=364.4.

Example 302. (5S)-1-(4-Cyclopropylbenzoyl)-3,3-difluoro-5-{5-methyl-[1,2,4]triazolo[1,5-a]pyrimidin-7-yl}piperidine

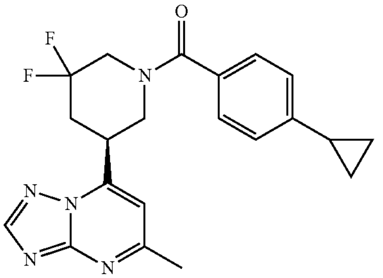 [SMILES: Cc1cc([C@@H]2CN(C(=O)c3ccc(C4CC4)cc3)CC(F)(F)C2)n2ncnc2n1]

$^1$H NMR (400 MHz, DMSO-$d_6$) δ=8.58 (s, 1H), 7.95-7.90 (m, 1H), 7.38-7.30 (m, 2H), 7.30-7.24 (m, 1H), 7.20-7.09 (m, 2H), 3.95-3.32 (m, 3H), 2.76-2.52 (m, 7H), 2.00-1.86 (m, 1H), 1.02-0.91 (m, 2H), 0.78-0.63 (m, 2H); [M+H]=398.3.

Example 303. 4-[3-Bromo-5-(trifluoromethyl)benzoyl]-2-{5-methyl-[1,2,4]triazolo[1,5-a]pyrimidin-7-yl}morpholine

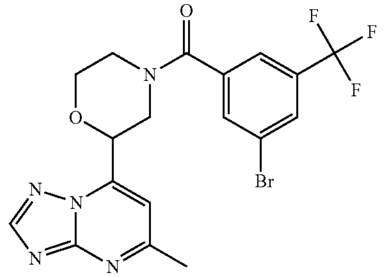 [SMILES: Cc1cc(C2CN(C(=O)c3cc(Br)cc(C(F)(F)F)c3)CCO2)n2ncnc2n1]

$^1$H NMR (400 MHz, DMSO-$d_6$) δ=8.75-8.32 (m, 1H), 8.19-7.82 (m, 3H), 7.32-7.13 (m, 1H), 5.47-3.40 (m, 5H), 3.19-2.94 (m, 2H), 2.68-2.56 (m, 3H); [M+H]=470.2.

Example 304. 1-[3-Bromo-5-(trifluoromethyl)benzoyl]-3,3-difluoro-5-{5-methyl-[1,2,4]triazolo[1,5-a]pyrimidin-7-yl}piperidine

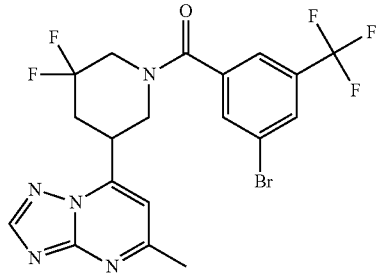 [SMILES: Cc1cc(C2CN(C(=O)c3cc(Br)cc(C(F)(F)F)c3)CC(F)(F)C2)n2ncnc2n1]

$^1$H NMR (400 MHz, DMSO-$d_6$) δ=8.71-6.93 (m, 5H), 5.01-3.44 (m, 3H), 2.88-2.53 (m, 7H); [M+H]=504.2.

Example 305. (5S)-1-[3-Bromo-4-(trifluoromethyl)benzoyl]-3,3-difluoro-5-{5-methyl-[1,2,4]triazolo[1,5-a]pyrimidin-7-yl}piperidine

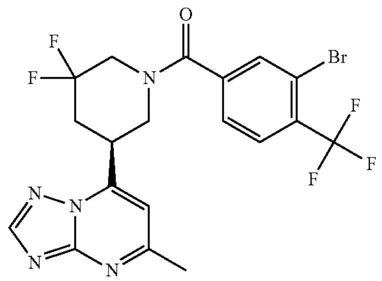 [SMILES: Cc1cc([C@@H]2CN(C(=O)c3ccc(C(F)(F)F)c(Br)c3)CC(F)(F)C2)n2ncnc2n1]

$^1$H NMR (400 MHz, DMSO-$d_6$) δ=8.21-8.10 (m, 2H), 7.94 (d, J=5.5 Hz, 2H), 7.69-7.60 (m, 1H), 3.85 (br s, 3H), 3.53-3.31 (m, 2H), 2.67-2.53 (m, 5H); [M+H]=505.1.

Example 306. (5S)-1-(3-Bromo-5-fluoro-4-methylbenzoyl)-3,3-difluoro-5-{5-methyl-[1,2,4]triazolo[1,5-a]pyrimidin-7-yl}piperidine

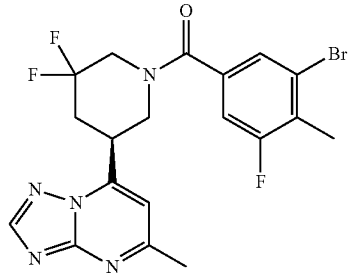 [SMILES: Cc1cc([C@@H]2CN(C(=O)c3cc(F)c(C)c(Br)c3)CC(F)(F)C2)n2ncnc2n1]

$^1$H NMR (400 MHz, DMSO-$d_6$) δ=8.70-8.19 (m, 1H), 7.73-7.52 (m, 1H), 7.39-7.09 (m, 2H), 4.94-4.69 (m, 1H), 3.91-3.34 (m, 3H), 2.76-2.53 (m, 6H), 2.36-2.18 (m, 3H); [M+H]=568.2.

Example 307. (5S)-3,3-Difluoro-1-(4-fluoro-3,5-dimethylbenzoyl)-5-{5-methyl-[1,2,4]triazolo[1,5-a]pyrimidin-7-yl}piperidine

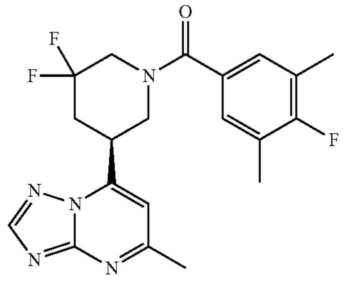 [SMILES: Cc1cc([C@@H]2CN(C(=O)c3cc(C)c(F)c(C)c3)CC(F)(F)C2)n2ncnc2n1]

$^1$H NMR (400 MHz, DMSO-$d_6$) δ=8.14 (br s, 2H), 7.38-7.14 (m, 2H), 3.89 (br s, 3H), 3.53-3.30 (m, 2H), 2.88-2.51 (m, 5H); [M+H]=404.2.

Example 308. (5S)-1-(3-Chloro-5-fluoro-4-methoxybenzoyl)-3,3-difluoro-5-{5-methyl-[1,2,4]triazolo[1,5-a]pyrimidin-7-yl}piperidine

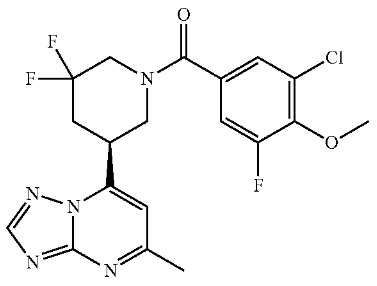 [SMILES: COc1c(F)cc(C(=O)N2C[C@@H](c3cc(C)nc4ncnn34)CC(F)(F)C2)cc1Cl]

$^1$H NMR (400 MHz, DMSO-$d_6$) δ=8.70-8.23 (m, 1H), 7.49-7.39 (m, 2H), 7.36-7.19 (m, 1H), 3.94 (s, 5H), 2.67-2.57 (m, 5H); [M+H]=440.1.

Example 309. (5S)-1-(3,4-Difluoro-5-methylbenzoyl)-3,3-difluoro-5-{5-methyl-[1,2,4]triazolo[1,5-a]pyrimidin-7-yl}piperidine

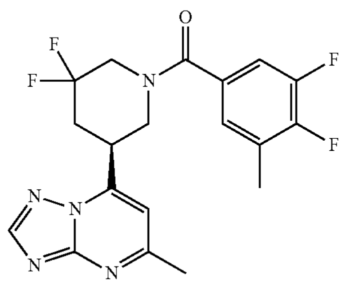

$^1$H NMR (400 MHz, DMSO-$d_6$) δ=8.66-8.40 (m, 1H), 8.30-8.00 (m, 1H), 7.38 (ddd, J=2.0, 7.5, 10.1 Hz, 1H), 7.24 (d, J=5.9 Hz, 2H), 3.88 (br s, 3H), 3.56-3.31 (m, 2H), 2.67-2.57 (m, 5H); [M+H]=408.2.

Example 310. (5S)-1-(3,5-Dibromo-4-methylbenzoyl)-3,3-difluoro-5-{5-methyl-[1,2,4]triazolo[1,5-a]pyrimidin-7-yl}piperidine

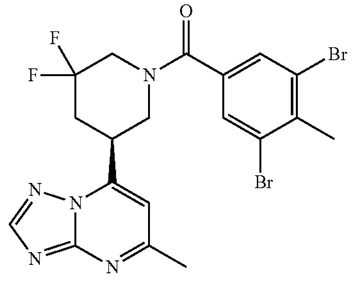 [SMILES: Cc1cc([C@@H]2CN(C(=O)c3cc(Br)c(C)c(Br)c3)CC(F)(F)C2)n2ncnc2n1]

$^1$H NMR (400 MHz, DMSO-$d_6$) δ=8.68-8.47 (m, 1H), 7.70 (s, 2H), 7.40-7.15 (m, 1H), 5.16-3.52 (m, 3H), 3.23-2.55 (m, 7H); [M+H]=528.0.

Example 311. (5S)-3,3-Difluoro-5-{5-methyl-[1,2,4]triazolo[1,5-a]pyrimidin-7-yl}-1-(3,4,5-trifluorobenzoyl)piperidine

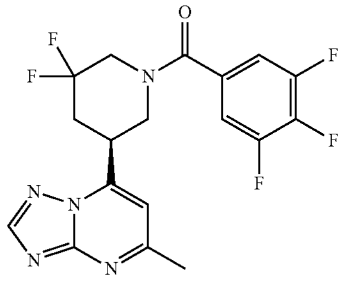 [SMILES: Cc1cc([C@@H]2CN(C(=O)c3cc(F)c(F)c(F)c3)CC(F)(F)C2)n2ncnc2n1]

$^1$H NMR (400 MHz, DMSO-$d_6$) δ=8.27-8.03 (m, 1H), 7.54-7.37 (m, 2H), 7.37-7.11 (m, 1H), 3.85 (d, J=3.9 Hz, 3H), 2.69-2.54 (m, 7H); [M+H]=412.1.

Example 312. (5S)-3,3-Difluoro-5-{5-methyl-[1,2,4]triazolo[1,5-a]pyrimidin-7-yl}-1-(3,4,5-trichlorobenzoyl)piperidine

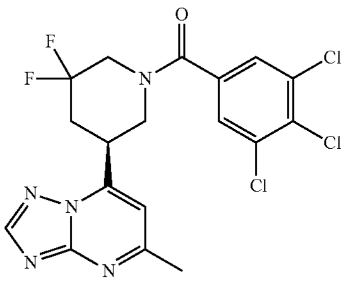 [SMILES: Cc1cc([C@@H]2CN(C(=O)c3cc(Cl)c(Cl)c(Cl)c3)CC(F)(F)C2)n2ncnc2n1]

$^1$H NMR (400 MHz, DMSO-$d_6$) δ=8.48 (br s, 1H), 7.74 (s, 2H), 7.23 (br s, 1H), 3.37 (s, 3H), 3.28-2.72 (m, 2H), 2.67-2.51 (m, 5H); [M+H]=460.1.

Example 313. (5S)-1-(3,5-Dichloro-4-fluorobenzoyl)-3,3-difluoro-5-{5-methyl-[1,2,4]triazolo[1,5-a]pyrimidin-7-yl}piperidine

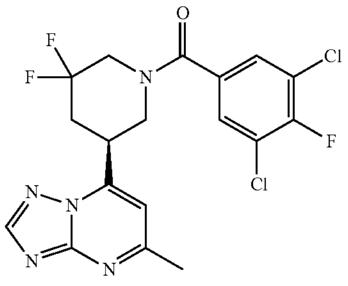 [SMILES: Cc1cc([C@@H]2CN(C(=O)c3cc(Cl)c(F)c(Cl)c3)CC(F)(F)C2)n2ncnc2n1]

$^1$H NMR (400 MHz, DMSO-$d_6$) δ=8.71-8.21 (m, 1H), 7.72 (d, J=6.3 Hz, 2H), 7.53-7.10 (m, 1H), 4.94-4.55 (m, 1H), 4.15-3.81 (m, 2H), 3.56-3.22 (m, 2H), 2.60 (br s, 5H); [M+H]=444.1.

Example 314. (5S)-1-(3-Chloro-4,5-difluorobenzoyl)-3,3-difluoro-5-{5-methyl-[1,2,4]triazolo[1,5-a]pyrimidin-7-yl}piperidine

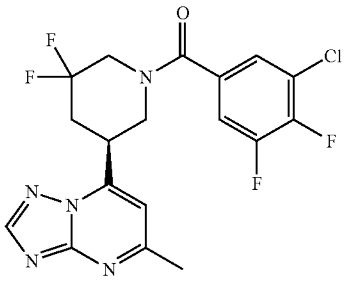 [SMILES: Cc1cc([C@@H]2CN(C(=O)c3cc(F)c(F)c(Cl)c3)CC(F)(F)C2)n2ncnc2n1]

$^1$H NMR (400 MHz, DMSO-$d_6$) δ=8.75-8.32 (m, 1H), 7.75-7.47 (m, 2H), 7.42-7.19 (m, 1H), 4.90-4.63 (m, 1H), 4.26-3.85 (m, 2H), 3.44-3.28 (m, 1H), 2.79-2.55 (m, 6H); [M+H]=428.4.

Example 315. (5S)-1-(3-Bromo-4,5-difluorobenzoyl)-3,3-difluoro-5-{5-methyl-[1,2,4]triazolo[1,5-a]pyrimidin-7-yl}piperidine

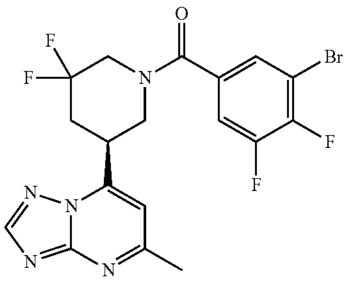 [SMILES: Cc1cc([C@@H]2CN(C(=O)c3cc(F)c(F)c(Br)c3)CC(F)(F)C2)n2ncnc2n1]

$^1$H NMR (400 MHz, DMSO-$d_6$) δ=8.72-8.40 (m, 1H), 7.65 (d, J=6.3 Hz, 2H), 7.40-7.09 (m, 1H), 5.04-4.58 (m, 1H), 4.21-3.80 (m, 2H), 3.50-3.29 (m, 1H), 2.60 (br s, 6H); [M+H]=472.3.

Example 316. (2S)-4-(3-Cyclopropylbenzoyl)-2-{5-methyl-[1,2,4]triazolo[1,5-a]pyrimidin-7-yl}morpholine

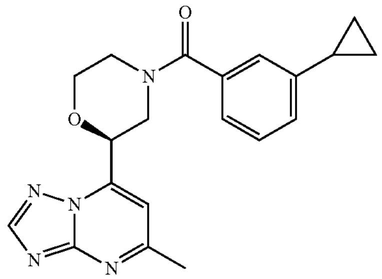 [SMILES: Cc1cc([C@@H]2CN(C(=O)c3cccc(C4CC4)c3)CCO2)n2ncnc2n1]

$^1$H NMR (400 MHz, DMSO-$d_6$) δ=8.78-8.31 (m, 1H), 7.31 (d, J=7.8 Hz, 5H), 5.43-4.92 (m, 1H), 4.40-3.69 (m, 3H), 3.48-3.32 (m, 1H), 3.14-2.72 (m, 2H), 2.63 (br s, 3H), 2.07-1.93 (m, 1H), 0.98 (d, J=8.2 Hz, 2H), 0.70 (td, J=2.1, 4.8 Hz, 2H); [M+H]=364.4.

Example 317. (5S)-1-(3-Cyclopropylbenzoyl)-3,3-difluoro-5-{5-methyl-[1,2,4]triazolo[1,5-a]pyrimidin-7-yl}piperidine

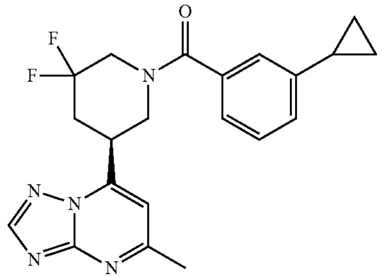 [SMILES: Cc1cc([C@@H]2CN(C(=O)c3cccc(C4CC4)c3)CC(F)(F)C2)n2ncnc2n1]

$^1$H NMR (400 MHz, DMSO-$d_6$) δ=8.71-8.43 (m, 1H), 7.36-7.28 (m, 2H), 7.23-7.09 (m, 3H), 5.04-4.44 (m, 1H), 3.91-3.69 (m, 2H), 2.79-2.53 (m, 7H), 2.02-1.92 (m, 1H), 0.97 (ddd, J=2.3, 3.9, 8.2 Hz, 2H), 0.74-0.66 (m, 2H); [M+H]=398.4.

Example 318. (2S)-4-(3-Cyclopropyl-4-fluorobenzoyl)-2-{5-methyl-[1,2,4]triazolo[1,5-a]pyrimidin-7-yl}morpholine

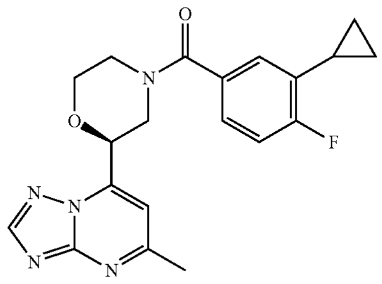 [SMILES: Cc1cc([C@@H]2CN(C(=O)c3ccc(F)c(C4CC4)c3)CCO2)n2ncnc2n1]

$^1$H NMR (400 MHz, DMSO-$d_6$) δ=8.64 (s, 1H), 7.36-7.08 (m, 4H), 5.45-3.97 (m, 3H), 3.95-2.65 (m, 4H), 2.63 (s, 3H), 2.16-1.96 (m, 1H), 1.05-0.92 (m, 2H), 0.76 (br s, 2H); [M+H]=382.4.

Example 319. (5S)-1-(3-Cyclopropyl-4-fluorobenzoyl)-3,3-difluoro-5-{5-methyl-[1,2,4]triazolo[1,5-a]pyrimidin-7-yl}piperidine

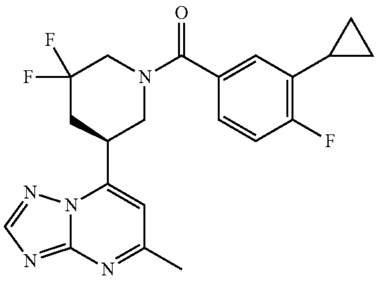 [SMILES: Cc1cc([C@@H]2CN(C(=O)c3ccc(F)c(C4CC4)c3)CC(F)(F)C2)n2ncnc2n1]

$^1$H NMR (400 MHz, DMSO-$d_6$) δ=8.57 (s, 1H), 7.40-6.85 (m, 4H), 4.82-3.83 (m, 5H), 2.60 (s, 5H), 2.09-2.00 (m, 1H), 0.98 (d, J=8.6 Hz, 2H), 0.76 (dd, J=5.3, 18.6 Hz, 2H); [M+H]=416.4.

Example 320. (2S)-4-(3-Cyclopropyl-4,5-difluorobenzoyl)-2-{5-methyl-[1,2,4]triazolo[1,5-a]pyrimidin-7-yl}morpholine

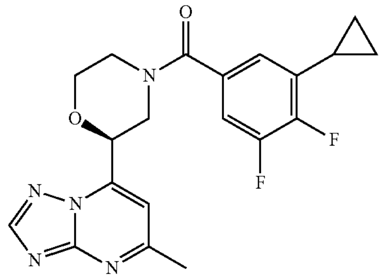 [SMILES: Cc1cc([C@@H]2CN(C(=O)c3cc(F)c(F)c(C4CC4)c3)CCO2)n2ncnc2n1]

$^1$H NMR (400 MHz, DMSO-$d_6$) δ=8.70-8.42 (m, 1H), 7.43-7.34 (m, 1H), 7.30-7.22 (m, 1H), 7.00-6.91 (m, 1H), 5.43-4.99 (m, 2H), 3.99-2.89 (m, 5H), 2.64 (d, J=4.3 Hz, 3H), 2.18-2.06 (m, 1H), 1.07-1.00 (m, 2H), 0.86-0.74 (m, 2H); [M+H]=400.4.

Example 321. (5S)-1-(4-Cyclopropyl-3-fluorobenzoyl)-3,3-difluoro-5-{5-methyl-[1,2,4]triazolo[1,5-a]pyrimidin-7-yl}piperidine

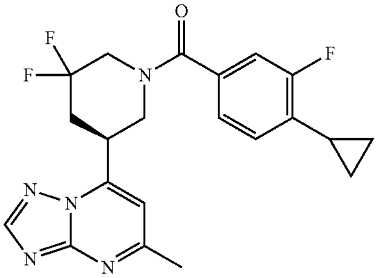 [SMILES: Cc1cc([C@@H]2CN(C(=O)c3ccc(C4CC4)c(F)c3)CC(F)(F)C2)n2ncnc2n1]

$^1$H NMR (400 MHz, DMSO-$d_6$) δ=8.83-8.34 (m, 1H), 7.35-7.03 (m, 4H), 5.06-3.85 (m, 4H), 3.39-3.28 (m, 1H), 2.60 (s, 5H), 2.20-1.74 (m, 1H), 1.05-0.96 (m, 2H), 0.77 (d, J=4.3 Hz, 2H); [M+H]=416.4.

Example 322. (S)-1-(4-Cyclopropyl-2,3-difluorobenzoyl)-3,3-difluoro-5-{5-methyl-[1,2,4]triazolo[1,5-a]pyrimidin-7-yl}piperidine

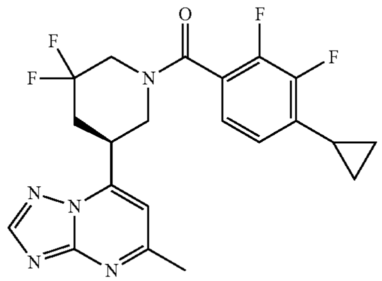 [SMILES: Cc1cc([C@@H]2CN(C(=O)c3ccc(C4CC4)c(F)c3F)CC(F)(F)C2)n2ncnc2n1]

$^1$H NMR (400 MHz, DMSO-$d_6$) δ=8.68-8.26 (m, 1H), 7.37-7.16 (m, 1H), 7.14-6.72 (m, 2H), 5.06-4.45 (m, 1H), 4.04-3.75 (m, 4H), 2.77-2.54 (m, 5H), 2.17-2.01 (m, 1H), 1.04 (d, J=5.9 Hz, 2H), 0.91-0.73 (m, 2H); [M+H]=434.4.

Example 323. (2S)-4-(4-Cyclopropyl-3-fluorobenzoyl)-2-{5-methyl-[1,2,4]triazolo[1,5-a]pyrimidin-7-yl}morpholine

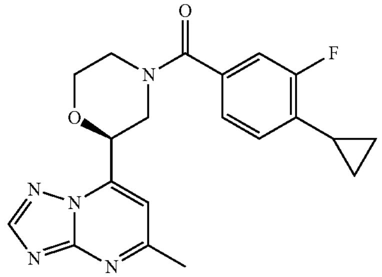 [SMILES: Cc1cc([C@@H]2CN(C(=O)c3ccc(C4CC4)c(F)c3)CCO2)n2ncnc2n1]

$^1$H NMR (400 MHz, DMSO-$d_6$) δ=8.83-8.27 (m, 1H), 7.43-7.15 (m, 3H), 7.07 (t, J=7.8 Hz, 1H), 5.40-4.24 (m, 2H), 3.79-2.72 (m, 5H), 2.63 (s, 3H), 2.12-2.01 (m, 1H), 1.05-0.98 (m, 2H), 0.86-0.67 (m, 2H); [M+H]=382.4.

Example 324. (2R)-4-(4-Cyclopropyl-3-fluorobenzoyl)-2-{5-methyl-[1,2,4]triazolo[1,5-a]pyrimidin-7-yl}morpholine

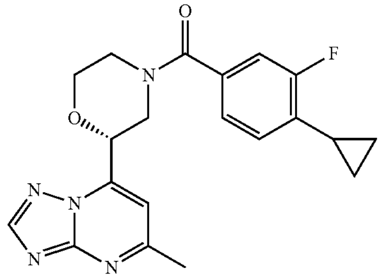 [SMILES: Cc1cc([C@H]2CN(C(=O)c3ccc(C4CC4)c(F)c3)CCO2)n2ncnc2n1]

$^1$H NMR (400 MHz, DMSO-$d_6$) δ=8.78-8.25 (m, 1H), 7.39-7.19 (m, 3H), 7.07 (t, J=7.8 Hz, 1H), 5.35-4.43 (m, 2H), 3.85-2.81 (m, 5H), 2.63 (s, 3H), 2.15-1.95 (m, 1H), 1.06-0.92 (m, 2H), 0.85-0.68 (m, 2H); [M+H]=382.4.

Example 325. (2S)-4-(4-Cyclopropyl-2,3-difluorobenzoyl)-2-{5-methyl-[1,2,4]triazolo[1,5-a]pyrimidin-7-yl}morpholine

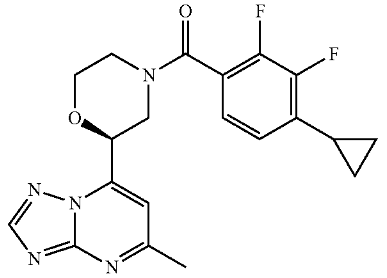 [SMILES: Cc1cc([C@@H]2CN(C(=O)c3ccc(C4CC4)c(F)c3F)CCO2)n2ncnc2n1]

$^1$H NMR (400 MHz, DMSO-$d_6$) δ=8.70-8.23 (m, 1H), 7.35-7.10 (m, 2H), 6.99-6.83 (m, 1H), 5.16 (br s, 1H), 4.00 (br s, 3H), 3.48-2.84 (m, 3H), 2.63 (d, J=18.8 Hz, 3H), 2.19-2.00 (m, 1H), 1.09-0.99 (m, 2H), 0.81 (d, J=5.1 Hz, 2H); [M+H]=400.4.

Example 326. (2R)-4-(4-Cyclopropyl-2,3-difluorobenzoyl)-2-{5-methyl-[1,2,4]triazolo[1,5-a]pyrimidin-7-yl}morpholine

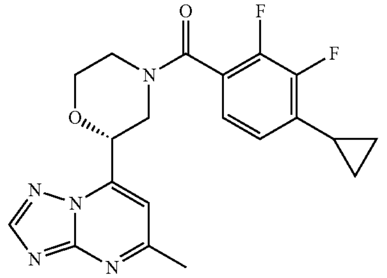 [SMILES: Cc1cc([C@H]2CN(C(=O)c3ccc(C4CC4)c(F)c3F)CCO2)n2ncnc2n1]

$^1$H NMR (400 MHz, DMSO-$d_6$) δ=8.69-8.29 (m, 1H), 7.35-7.10 (m, 2H), 6.97-6.83 (m, 1H), 5.26-5.10 (m, 1H), 4.50-3.93 (m, 3H), 3.50-2.77 (m, 3H), 2.63 (d, J=18.8 Hz, 3H), 2.20-1.97 (m, 1H), 1.10-0.98 (m, 2H), 0.81 (d, J=5.1 Hz, 2H); [M+H]=400.4.

Example 327. (5S)-1-(4-Bromo-3-chlorobenzoyl)-3,3-difluoro-5-{5-methyl-[1,2,4]triazolo[1,5-a]pyrimidin-7-yl}piperidine

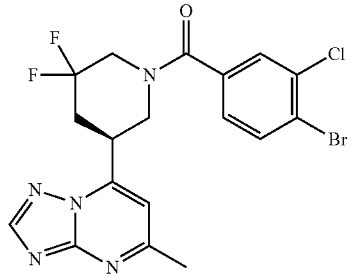 [SMILES: Cc1cc([C@@H]2CN(C(=O)c3ccc(Br)c(Cl)c3)CC(F)(F)C2)n2ncnc2n1]

$^1$H NMR (400 MHz, DMSO-$d_6$) δ=8.81-8.36 (m, 1H), 7.73 (s, 2H), 7.51-7.09 (m, 2H), 4.89-4.71 (m, 1H), 4.35-4.10 (m, 2H), 3.57-3.29 (m, 1H), 2.61 (br s, 5H); [M+H]=472.3.

Example 328. (2R)-4-(4-Bromo-3-chlorobenzoyl)-2-{5-methyl-[1,2,4]triazolo[1,5-a]pyrimidin-7-yl}morpholine

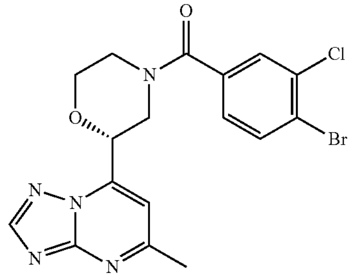 [SMILES: Cc1cc([C@H]2CN(C(=O)c3ccc(Br)c(Cl)c3)CCO2)n2ncnc2n1]

$^1$H NMR (400 MHz, DMSO-$d_6$) δ=8.71-8.45 (m, 1H), 7.89 (d, J=8.2 Hz, 2H), 7.47-7.36 (m, 1H), 7.34-7.15 (m, 1H), 5.46-4.89 (m, 1H), 4.42-3.99 (m, 4H), 3.57-3.28 (m, 1H), 3.12-2.79 (m, 1H), 2.65 (br s, 3H); [M+H]=436.3.

Example 329. (2S)-4-(4-Bromo-3-chlorobenzoyl)-2-{5-methyl-[1,2,4]triazolo[1,5-a]pyrimidin-7-yl}morpholine

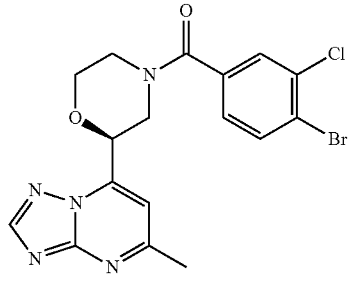 [SMILES: Cc1cc([C@@H]2CN(C(=O)c3ccc(Br)c(Cl)c3)CCO2)n2ncnc2n1]

$^1$H NMR (400 MHz, DMSO-$d_6$) δ=8.79-8.40 (m, 1H), 7.90 (d, J=8.2 Hz, 2H), 7.50-7.36 (m, 1H), 7.25 (br s, 1H), 5.54-5.00 (m, 1H), 4.52-3.65 (m, 4H), 3.13-2.72 (m, 2H), 2.65 (br s, 3H); [M+H]=436.3.

Example 330. (2S)-4-(3-Chloro-4-cyclopropylbenzoyl)-2-{5-methyl-[1,2,4]triazolo[1,5-a]pyrimidin-7-yl}morpholine

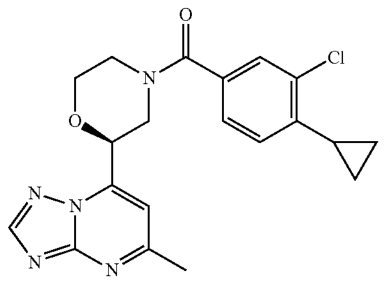

$^1$H NMR (400 MHz, DMSO-$d_6$) δ=8.63-7.52 (m, 1H), 7.37-6.96 (m, 4H), 5.39-4.95 (m, 2H), 4.45-2.85 (m, 5H), 2.63 (s, 3H), 2.26-2.10 (m, 1H), 1.12-0.98 (m, 2H), 0.80-0.69 (m, 2H); [M+H]=398.4.

Example 331. (5S)-1-(3-Chloro-4-cyclopropylbenzoyl)-3,3-difluoro-5-{5-methyl-[1,2,4]triazolo[1,5-a]pyrimidin-7-yl}piperidine

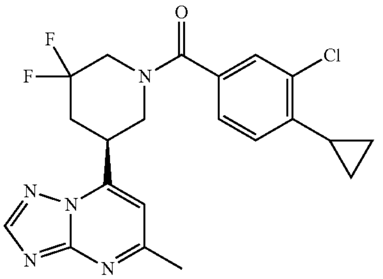 [SMILES: Cc1cc([C@@H]2CN(C(=O)c3ccc(C4CC4)c(Cl)c3)CC(F)(F)C2)n2ncnc2n1]

$^1$H NMR (400 MHz, DMSO-$d_6$) δ=8.71-8.40 (m, 1H), 7.50 (d, J=1.6 Hz, 1H), 7.31 (d, J=1.6 Hz, 1H), 7.23-6.93 (m, 2H), 4.90-4.58 (m, 1H), 3.99-2.66 (m, 6H), 2.60 (s, 3H), 2.24-2.09 (m, 1H), 1.14-0.94 (m, 2H), 0.75 (d, J=3.1 Hz, 2H); [M+H]=432.4.

Example 332. (2S)-4-(3-Fluoro-5-methylbenzoyl)-2-{5-methyl-[1,2,4]triazolo[1,5-a]pyrimidin-7-yl}morpholine

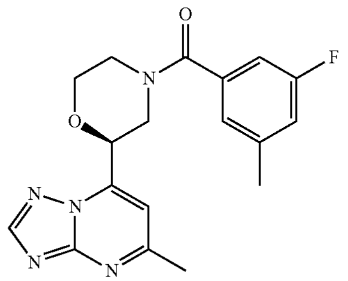 [SMILES: Cc1cc(F)cc(C(=O)N2CCO[C@H](c3cc(C)nc4ncnn34)C2)c1]

$^1$H NMR (400 MHz, DMSO-$d_6$) δ=8.74-8.34 (m, 1H), 7.35-7.21 (m, 1H), 7.15 (dd, J=2.3, 9.0 Hz, 3H), 5.56-4.94 (m, 1H), 4.57-3.71 (m, 3H), 3.65-2.75 (m, 3H), 2.71-2.56 (m, 3H), 2.45-2.29 (m, 3H); [M+H]=356.4.

Example 333. (2S)-4-(4-Fluoro-3-methylbenzoyl)-2-{5-methyl-[1,2,4]triazolo[1,5-a]pyrimidin-7-yl}morpholine

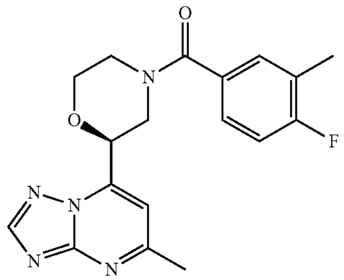 [SMILES: Cc1cc([C@@H]2CN(C(=O)c3ccc(F)c(C)c3)CCO2)n2ncnc2n1]

$^1$H NMR (400 MHz, DMSO-$d_6$) δ=8.58 (br s, 1H), 7.48 (br s, 1H), 7.38 (br s, 1H), 7.27-7.19 (m, 2H), 5.56-5.11 (m, 1H), 4.44-3.97 (m, 6H), 2.69-2.62 (m, 3H), 2.35-2.26 (m, 3H); [M+H]=356.4.

Examples 334-338 were prepared in a manner analogous to Example 6, with the appropriate starting material and reagent substitutions.

Example 334. (3R)-1-[(3S)-3,4-Dihydro-2H-1-benzopyran-3-carbonyl]-3-{5-methyl-[1,2,4]triazolo[1,5-a]pyrimidin-7-yl}piperidine

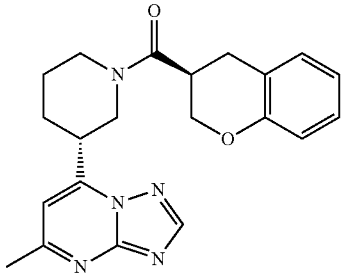 [SMILES: Cc1cc([C@@H]2CCCN(C(=O)[C@@H]3COc4ccccc4C3)C2)n2ncnc2n1]

$^1$H NMR (400 MHz, $CDCl_3$) δ=8.52-8.25 (m, 1H), 7.24-7.05 (m, 2H), 6.97-6.78 (m, 3H), 4.85 (d, J=12.9 Hz, 1H), 4.70-3.99 (m, 3H), 3.73-3.00 (m, 5H), 2.91-2.60 (m, 4H), 2.46-2.26 (m, 1H), 2.09-1.89 (m, 2H), 1.80 (br s, 1H); [M+H]=377.7.

Example 335. (3S)-1-[(3S)-3,4-Dihydro-2H-1-benzopyran-3-carbonyl]-3-{5-methyl-[1,2,4]triazolo[1,5-a]pyrimidin-7-yl}piperidine

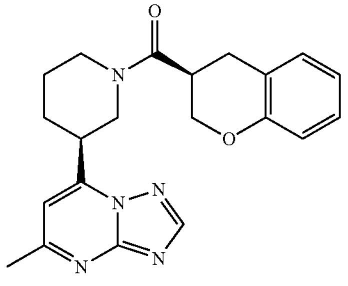 [SMILES: Cc1cc([C@H]2CCCN(C(=O)[C@@H]3COc4ccccc4C3)C2)n2ncnc2n1]

$^1$H NMR (400 MHz, $CDCl_3$) δ=8.51-8.36 (m, 1H), 7.17-6.79 (m, 5H), 4.93-4.74 (m, 1H), 4.71-4.55 (m, 1H), 4.43-4.00 (m, 2H), 3.68-3.54 (m, 1H), 3.42-3.08 (m, 4H), 2.88-2.68 (m, 4H), 2.46-2.25 (m, 1H), 2.10-1.90 (m, 2H), 1.87-1.75 (m, 1H); [M+H]=377.7.

Example 336. (3S)-1-[(3R)-3,4-Dihydro-2H-1-benzopyran-3-carbonyl]-3-{5-methyl-[1,2,4]triazolo[1,5-a]pyrimidin-7-yl}piperidine

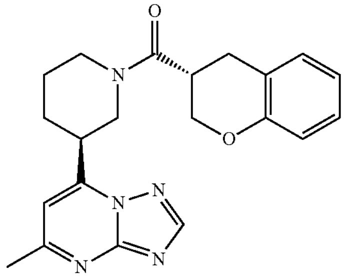 [SMILES: Cc1cc([C@H]2CCCN(C(=O)[C@H]3COc4ccccc4C3)C2)n2ncnc2n1]

$^1$H NMR (400 MHz, $CDCl_3$) δ=8.49-8.25 (m, 1H), 7.23-7.04 (m, 2H), 6.96-6.78 (m, 3H), 4.93-4.77 (m, 0.5H), 4.64 (d, J=12.9 Hz, 1H), 4.48-4.29 (m, 1H), 4.13 (dt, J=3.5, 10.6 Hz, 1H), 4.05 (d, J=13.3 Hz, 0.5H), 3.73-2.99 (m, 5H), 2.91-2.59 (m, 4H), 2.43-2.27 (m, 1H), 2.09-1.89 (m, 2H), 1.80 (br s, 1H); [M+H]=377.7.

Example 337. (2R)-4-[3-Bromo-4-(trifluoromethyl)benzoyl]-2-{5-methyl-[1,2,4]triazolo[1,5-a]pyrimidin-7-yl}morpholine

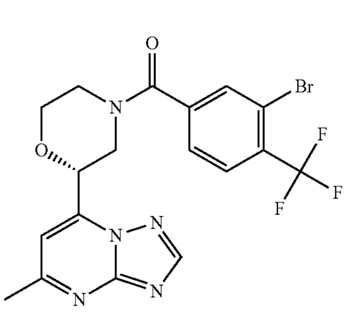 [SMILES: Cc1cc([C@H]2CN(C(=O)c3ccc(C(F)(F)F)c(Br)c3)CCO2)n2ncnc2n1]

$^1$H NMR (400 MHz, DMSO-$d_6$) δ=8.76-8.37 (m, 1H), 8.19-8.01 (m, 1H), 7.93 (d, J=8.2 Hz, 1H), 7.70 (d, J=8.2 Hz, 1H), 7.39-7.13 (m, 1H), 5.55-4.32 (m, 2H), 4.26-4.12 (m, 1H), 4.04-3.35 (m, 2H), 3.19-2.79 (m, 2H), 2.63 (d, J=16.4 Hz, 3H); [M+H]=472.3.

Example 338. (3R)-3-{5-Methyl-[1,2,4]triazolo[1,5-a]pyrimidin-7-yl}-1-[(naphthalen-2-yl)carbonyl]piperidine

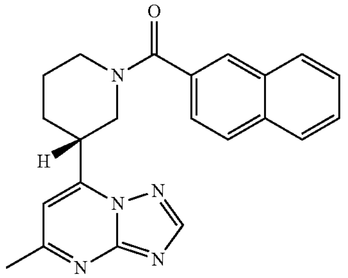 [SMILES: Cc1cc([C@@H]2CCCN(C(=O)c3ccc4ccccc4c3)C2)n2ncnc2n1]

$^1$H NMR (400 MHz, $CD_3OD$) δ=8.40-8.60 (m, 1H), 7.80-8.10 (m, 4H), 7.40-7.60 (m, 3H), 7.05-7.25 (m, 1H), 4.60-5.00 (m, 1H), 4.20-4.35 (m, 1H), 3.70-3.90 (m, 1H), 3.30-3.50 (m, 1H), 3.10-3.25 (m, 1H), 2.55-2.70 (m, 3H), 2.25-2.40 (m, 1H), 1.70-2.20 (m, 3H); [M+H]=372.1.

Examples 339-347 were prepared in a manner analogous to Example 9, with the appropriate starting material and reagent substitutions.

Example 339. 1-[(4-Chloro-3-iodophenyl)carbonyl]-3,3-difluoro-5-{5-methyl-[1,2,4]triazolo[1,5-a]pyrimidin-7-yl}piperidine

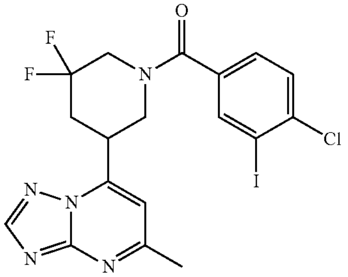 [SMILES: Cc1cc(C2CN(C(=O)c3ccc(Cl)c(I)c3)CC(F)(F)C2)n2ncnc2n1]

$^1$H NMR (400 MHz, $CDCl_3$) δ=8.52-8.65 (m, 1H), 7.95-8.06 (m, 1H), 7.49-7.63 (m, 1H), 7.42 (dd, J=7.83, 1.96 Hz, 1H), 6.92 (br s, 1H), 3.92 (br s, 2H), 3.72 (br s, 3H), 2.61-2.85 (m, 5H); [M+H]=518.1.

Example 340. 3,3-Difluoro-1-[(4-fluoro-3-iodophenyl)carbonyl]-5-{5-methyl-[1,2,4]triazolo[1,5-a]pyrimidin-7-yl}piperidine

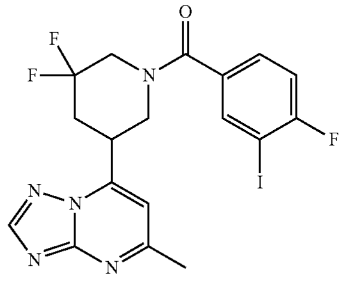 [SMILES: Cc1cc(C2CN(C(=O)c3ccc(F)c(I)c3)CC(F)(F)C2)n2ncnc2n1]

$^1$H NMR (400 MHz, $CDCl_3$) δ=8.56 (s, 1H), 7.93 (d, J=4.30 Hz, 1H), 7.34-7.60 (m, 1H), 7.12-7.26 (m, 1H), 6.92 (br s, 1H), 3.93 (br s, 1H), 3.38 (br s, 5H), 2.64-2.76 (m, 4H); [M+H]=502.1.

Example 341. (5S)-1-(1-Benzofuran-5-carbonyl)-3,3-difluoro-5-{5-methyl-[1,2,4]triazolo[1,5-a]pyrimidin-7-yl}piperidine

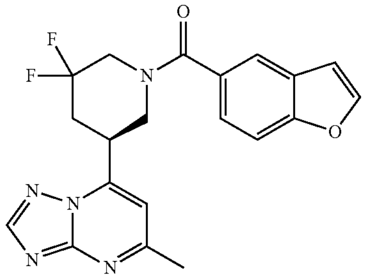 [SMILES: Cc1cc([C@@H]2CN(C(=O)c3ccc4occc4c3)CC(F)(F)C2)n2ncnc2n1]

$^1$H NMR (400 MHz, $CDCl_3$) δ=8.40 (br s, 1H), 7.80 (s, 1H), 7.74-7.69 (m, 1H), 7.57 (d, J=8.2 Hz, 1H), 7.44 (dd, J=1.6, 8.6 Hz, 1H), 6.90-6.82 (m, 2H), 4.75 (br s, 1H), 3.95 (br s, 1H), 3.49 (s, 2H), 2.71 (s, 6H); [M+H]=398.5.

Example 342. (5S)-3,3-Difluoro-1-(4-methoxy-3-methylbenzoyl)-5-{5-methyl-[1,2,4]triazolo[1,5-a]pyrimidin-7-yl}piperidine

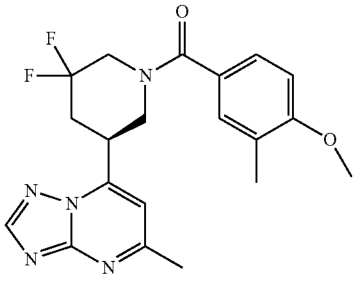 [SMILES: COc1ccc(C(=O)N2C[C@@H](c3cc(C)nc4ncnn34)CC(F)(F)C2)cc1C]

$^1$H NMR (400 MHz, $CDCl_3$) δ=8.43 (s, 1H), 7.36-7.30 (m, 2H), 6.91-6.81 (m, 2H), 4.88-4.29 (m, 2H), 3.95 (d, J=5.1 Hz, 1H), 3.87 (s, 3H), 3.63-3.32 (m, 2H), 2.76-2.56 (m, 5H), 2.57-2.55 (m, 1H), 2.25 (s, 3H); [M+H]=402.58.

Example 343. (2S)-4-(4-Methoxy-3-methylbenzoyl)-2-{5-methyl-[1,2,4]triazolo[1,5-a]pyrimidin-7-yl}morpholine

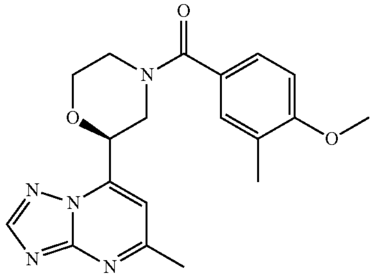 [SMILES: COc1ccc(C(=O)N2CCO[C@H](c3cc(C)nc4ncnn34)C2)cc1C]

$^1$H NMR (400 MHz, $CDCl_3$) δ=8.38 (s, 1H), 7.40 (d, J=6.3 Hz, 2H), 7.16 (s, 1H), 6.88-6.83 (m, 1H), 5.32-5.26 (m, 1H), 4.21 (d, J=11.0 Hz, 2H), 3.95-3.88 (m, 1H), 3.87 (s, 4H), 3.22 (br s, 1H), 2.91 (dd, J=10.2, 12.9 Hz, 1H), 2.72 (s, 3H), 2.29 (s, 3H); [M+H]=368.5.

Example 344. 1-(6-Fluoro-3,4-dihydro-2H-1-benzopyran-3-carbonyl)-3-{5-methyl-[1,2,4]triazolo[1,5-a]pyrimidin-7-yl}piperidine

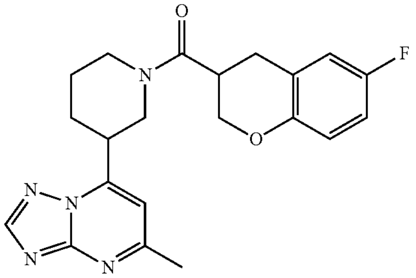 [SMILES: Cc1cc(C2CCCN(C(=O)C3COc4ccc(F)cc4C3)C2)n2ncnc2n1]

$^1$H NMR (400 MHz, $CDCl_3$) δ=8.60-8.29 (m, 1H), 7.04-6.63 (m, 4H), 4.98-3.95 (m, 4H), 3.71-3.53 (m, 1H), 3.47-2.97 (m, 4H), 2.71 (d, J=4.7 Hz, 3H), 2.86-2.62 (m, 1H), 2.45-2.27 (m, 1H), 2.09-1.92 (m, 2H), 1.77 (d, J=10.2 Hz, 1H); [M+H]=396.3.

Example 345. 4-[1-(4-Fluorophenyl)-5-methyl-1H-pyrazole-3-carbonyl]-2-{5-methyl-[1,2,4]triazolo[1,5-a]pyrimidin-7-yl}morpholine

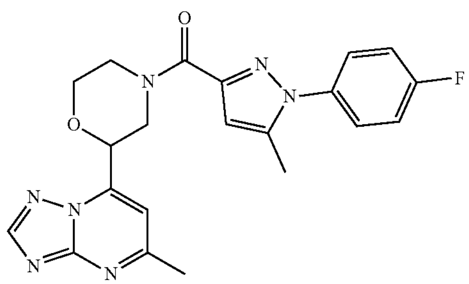 [SMILES: Cc1cc(C2CN(C(=O)c3cc(C)n(-c4ccc(F)cc4)n3)CCO2)n2ncnc2n1]

$^1H$ NMR (400 MHz, $CDCl_3$) δ=8.60-8.13 (m, 1H), 7.49-7.35 (m, 2H), 7.24-7.13 (m, 3H), 6.80-6.69 (m, 1H), 6.06-4.55 (m, 3H), 4.34-3.84 (m, 2H), 3.49 (s, 1H), 3.16 (d, J=12.5 Hz, 1H), 2.73 (s, 3H), 2.41-2.28 (m, 3H); [M+H]=422.1.

Example 346. 1-{5-Methyl-1-[4-(propan-2-yl)phenyl]-1H-pyrazole-3-carbonyl}-3-{5-methyl-[1,2,4]triazolo[1,5-a]pyrimidin-7-yl}piperidine

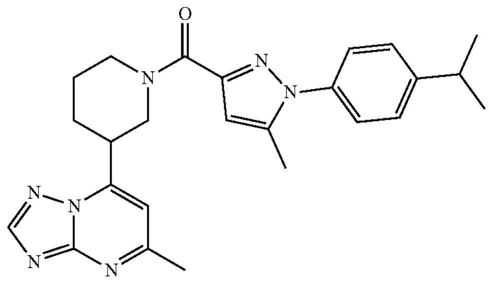 [SMILES: Cc1cc(C2CCCN(C(=O)c3cc(C)n(-c4ccc(C(C)C)cc4)n3)C2)n2ncnc2n1]

$^1H$ NMR (400 MHz, $CDCl_3$) δ=8.53-8.18 (m, 1H), 7.43-7.15 (m, 4H), 6.86 (s, 1H), 6.69-6.49 (m, 1H), 5.15-4.40 (m, 2H), 3.84-2.90 (m, 4H), 2.67 (d, J=16.4 Hz, 3H), 2.32 (d, J=16.4 Hz, 4H), 2.14-1.90 (m, 3H), 1.28 (br s, 6H); [M+H]=444.5.

Example 347. 4-{5-Methyl-1-[4-(propan-2-yl)phenyl]-1H-pyrazole-3-carbonyl}-2-{5-methyl-[1,2,4]triazolo[1,5-a]pyrimidin-7-yl}morpholine

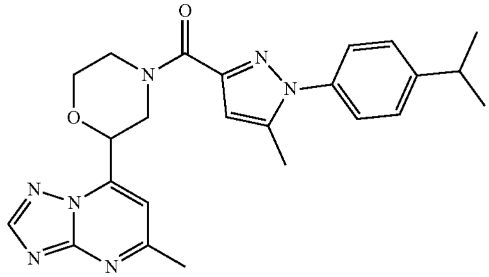 [SMILES: Cc1cc(C2CN(C(=O)c3cc(C)n(-c4ccc(C(C)C)cc4)n3)CCO2)n2ncnc2n1]

$^1H$ NMR (400 MHz, $CDCl_3$) δ=8.51-8.13 (m, 1H), 7.39-7.27 (m, 4H), 7.18 (br s, 1H), 6.70 (s, 1H), 6.10-5.13 (m, 2H), 4.77-3.42 (m, 3H), 3.24-3.08 (m, 1H), 2.96 (td, J=6.7, 13.6 Hz, 1H), 2.71 (s, 3H), 2.38-2.31 (m, 3H), 1.27 (d, J=6.7 Hz, 6H); [M+H]=446.3.

Examples 348-384 were prepared in a manner analogous to Example 5, with the appropriate starting material and reagent substitutions.

Example 348. 1-[(6-Fluoronaphthalen-2-yl)carbonyl]-3-{5-methyl-[1,2,4]triazolo[1,5-a]pyrimidin-7-yl}piperidine

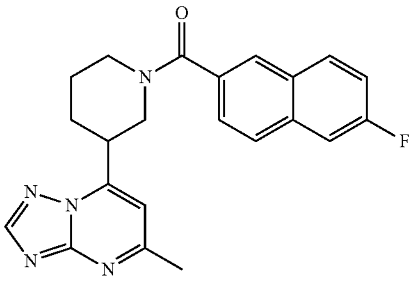 [SMILES: Cc1cc(C2CCCN(C(=O)c3ccc4cc(F)ccc4c3)C2)n2ncnc2n1]

$^1H$ NMR (400 MHz, DMSO-$d_6$) δ=8.26-8.72 (m, 1H), 8.05-8.18 (m, 2H), 7.96 (br s, 1H), 7.76 (br s, 1H), 7.45-7.64 (m, 2H), 7.10-7.39 (m, 1H), 4.42-4.93 (m, 1H), 3.99-4.24 (m, 1H), 3.69 (br s, 2H), 3.17 (s, 1H), 2.88-3.11 (m, 1H), 2.61 (br s, 3H), 2.23 (d, J=10.42 Hz, 1H), 1.98 (br s, 1H), 1.73 (br s, 1H); [M+H]=390.2.

Example 349. 6-[(3-{5-Methyl-[1,2,4]triazolo[1,5-a]pyrimidin-7-yl}piperidin-1-yl)carbonyl]quinoline

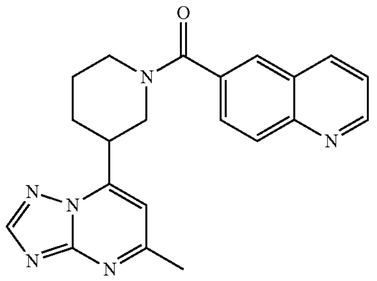 [SMILES: Cc1cc(C2CCCN(C(=O)c3ccc4ncccc4c3)C2)n2ncnc2n1]

$^1H$ NMR (400 MHz, DMSO-$d_6$) δ=9.04 (d, J=3.14 Hz, 1H), 8.59 (d, J=7.78 Hz, 1H), 8.18 (br s, 2H), 8.03-8.14 (m, 1H), 7.77-7.91 (m, 1H), 7.71 (dd, J=8.22, 4.33 Hz, 1H), 7.13-7.37 (m, 1H), 4.77-4.89 (m, 1H), 4.48-4.57 (m, 1H), 4.07 (br s, 1H), 3.57-3.77 (m, 2H), 2.93-3.18 (m, 1H), 2.54-2.70 (m, 3H), 2.23 (d, J=12.30 Hz, 1H), 2.00 (br s, 1H), 1.74 (br s, 1H); [M+H]=373.2.

Example 350. 1-[(2,2-Difluoro-2H-1,3-benzodioxol-5-yl)carbonyl]-3-{5-methyl-[1,2,4]triazolo[1,5-a]pyrimidin-7-yl}piperidine

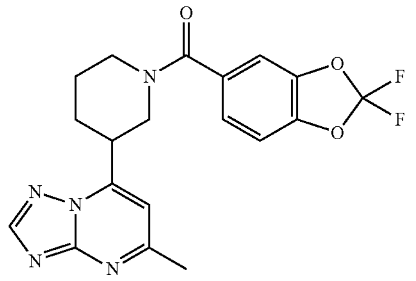 [SMILES: Cc1cc(C2CCCN(C(=O)c3ccc4c(c3)OC(F)(F)O4)C2)n2ncnc2n1]

$^1$H NMR (400 MHz, DMSO-$d_6$) δ=8.37-8.66 (m, 1H), 7.43-7.60 (m, 2H), 7.15-7.36 (m, 2H), 4.71 (br s, 1H), 3.57-4.08 (m, 2H), 3.24 (br s, 2H), 2.86-3.06 (m, 1H), 2.61 (br s, 3H), 2.20 (d, J=10.04 Hz, 1H), 1.97 (d, J=11.04 Hz, 1H), 1.70 (br s, 1H); [M+H]=402.1.

Example 351. 1-[(2,3-Dihydro-1-benzofuran-2-yl) carbonyl]-3-{5-methyl-[1,2,4]triazolo[1,5-a]pyrimidin-7-yl}piperidine

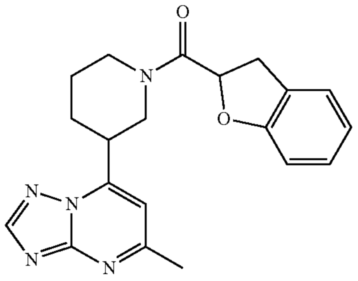 [SMILES: Cc1cc(C2CCCN(C(=O)C3Cc4ccccc4O3)C2)n2ncnc2n1]

$^1$H NMR (400 MHz, DMSO-$d_6$) δ=8.43-8.63 (m, 1H), 7.06-7.37 (m, 3H), 6.71-7.03 (m, 2H), 4.32-4.70 (m, 3H), 3.56-3.85 (m, 1H), 3.34-3.51 (m, 1H), 3.14-3.26 (m, 2H), 2.93-3.05 (m, 1H), 2.54-2.66 (m, 3H), 2.18 (d, J=10.29 Hz, 1H), 1.88-1.96 (m, 1H), 1.53-1.78 (m, 2H); [M+H]=364.2.

Example 352. 1-[(3,4-Dihydro-2H-1-benzopyran-3-yl)carbonyl]-3-{5-methyl-[1,2,4]triazolo[1,5-a]pyrimidin-7-yl}piperidine

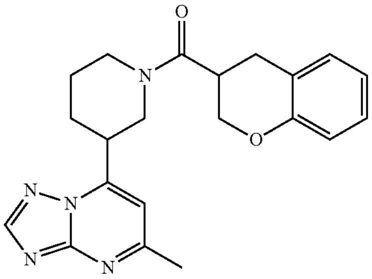 [SMILES: Cc1cc(C2CCCN(C(=O)C3COc4ccccc4C3)C2)n2ncnc2n1]

$^1$H NMR (400 MHz, DMSO-$d_6$) δ=8.48-8.61 (m, 1H), 7.04-7.26 (m, 3H), 6.71-6.91 (m, 2H), 4.26-4.65 (m, 2H), 3.86-4.12 (m, 2H), 3.24-3.62 (m, 3H), 2.68-3.18 (m, 3H), 2.62 (s, 3H), 2.20 (d, J=11.80 Hz, 1H), 1.78-2.01 (m, 2H), 1.45-1.76 (m, 1H); [M+H]=378.2.

Example 353. 1-[(3,4-Dihydro-2H-1-benzopyran-2-yl)carbonyl]-3-{5-methyl-[1,2,4]triazolo[1,5-a]pyrimidin-7-yl}piperidine

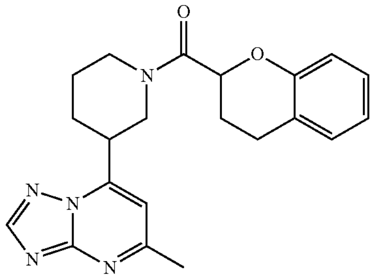 [SMILES: Cc1cc(C2CCCN(C(=O)C3CCc4ccccc4O3)C2)n2ncnc2n1]

$^1$H NMR (400 MHz, DMSO-$d_6$) δ=8.52-8.66 (m, 1H), 7.24 (dd, J=16.00, 10.60 Hz, 1H), 6.98-7.13 (m, 2H), 6.66-6.88 (m, 2H), 5.02-5.16 (m, 1H), 3.96-4.71 (m, 2H), 3.04-3.79 (m, 3H), 2.68-2.87 (m, 2H), 2.54-2.64 (m, 3H), 2.19 (br s, 1H), 1.79-2.04 (m, 4H), 1.55 (br s, 1H); [M+H]=378.2.

Example 354. 1-[(2,3-Dihydro-1,4-benzodioxin-2-yl)carbonyl]-3-{5-methyl-[1,2,4]triazolo[1,5-a]pyrimidin-7-yl}piperidine

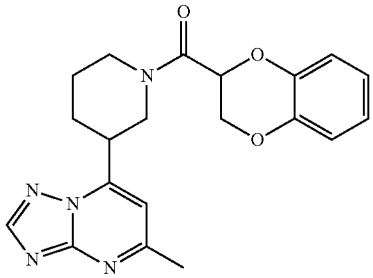 [SMILES: Cc1cc(C2CCCN(C(=O)C3COc4ccccc4O3)C2)n2ncnc2n1]

$^1$H NMR (400 MHz, DMSO-$d_6$) δ=8.49-8.62 (m, 1H), 7.17-7.31 (m, 1H), 6.77-7.01 (m, 4H), 5.18-5.35 (m, 1H), 4.06-4.60 (m, 4H), 3.45 (d, J=11.80 Hz, 1H), 3.17 (s, 1H), 2.67-3.01 (m, 1H), 2.56-2.65 (m, 3H), 2.20 (d, J=12.30 Hz, 1H), 1.83-2.04 (m, 2H), 1.44-1.80 (m, 1H); [M+H]=380.2.

Example 355. 1-[(6-Fluoro-3,4-dihydro-2H-1-benzopyran-2-yl)carbonyl]-3-{5-methyl-[1,2,4]triazolo[1,5-a]pyrimidin-7-yl}piperidine

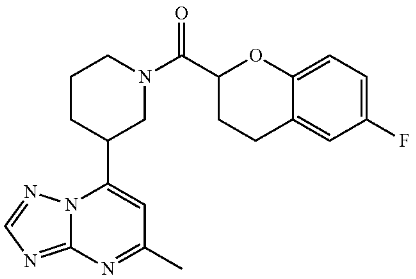 [SMILES: Cc1cc(C2CCCN(C(=O)C3CCc4cc(F)ccc4O3)C2)n2ncnc2n1]

$^1$H NMR (400 MHz, DMSO-$d_6$) δ=8.49-8.62 (m, 1H), 7.13-7.31 (m, 1H), 6.65-7.01 (m, 3H), 4.98-5.16 (m, 1H), 4.29-4.66 (m, 2H), 4.03 (d, J=10.79 Hz, 1H), 3.09-3.67 (m, 2H), 2.67-2.91 (m, 3H), 2.55-2.64 (m, 3H), 2.19 (d, J=8.16 Hz, 1H), 1.79-2.08 (m, 4H); [M+H]=396.2.

Example 356. 2-Methyl-3-[(3-{5-methyl-[1,2,4]triazolo[1,5-a]pyrimidin-7-yl}piperidin-1-yl)carbonyl]-1,2,3,4-tetrahydroisoquinoline

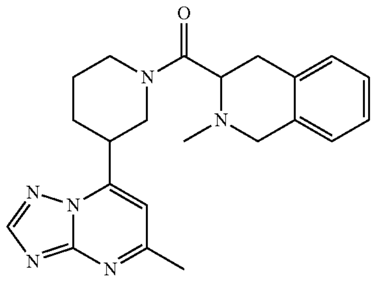 [SMILES: Cc1cc(C2CCCN(C(=O)C3Cc4ccccc4CN3C)C2)n2ncnc2n1]

$^1$H NMR (400 MHz, DMSO-$d_6$) δ=8.30-8.70 (m, 1H), 7.14-7.40 (m, 5H), 4.81-5.06 (m, 1H), 4.45-4.71 (m, 2H), 4.26-4.44 (m, 1H), 3.91-4.06 (m, 1H), 3.52-3.82 (m, 2H), 3.08-3.46 (m, 3H), 2.80-3.02 (m, 4H), 2.63 (s, 3H), 2.58-2.58 (m, 1H), 2.16-2.37 (m, 1H), 1.93 (br s, 2H); [M+H]=391.2.

Example 357. 1-[(3-Iodophenyl)carbonyl]-3-{5-methyl-[1,2,4]triazolo[1,5-a]pyrimidin-7-yl}piperidine

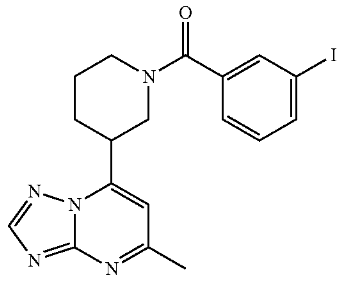 [SMILES: Cc1cc(C2CCCN(C(=O)c3cccc(I)c3)C2)n2ncnc2n1]

$^1$H NMR (400 MHz, DMSO-$d_6$) δ=8.44-8.69 (m, 1H), 7.78 (br s, 2H), 7.45 (br s, 1H), 7.27 (br s, 2H), 4.32-4.86 (m, 1H), 3.64 (t, J=10.67 Hz, 2H), 3.19 (br s, 1H), 2.81-3.06 (m, 1H), 2.62 (br s, 3H), 2.19 (d, J=11.29 Hz, 1H), 1.95 (br s, 1H), 1.71 (br s, 2H); [M+H]=448.1.

Example 358. 1-[(4-Iodophenyl)carbonyl]-3-{5-methyl-[1,2,4]triazolo[1,5-a]pyrimidin-7-yl}piperidine

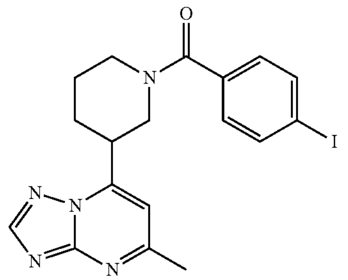 [SMILES: Cc1cc(C2CCCN(C(=O)c3ccc(I)cc3)C2)n2ncnc2n1]

$^1$H NMR (400 MHz, DMSO-$d_6$) δ=8.37-8.61 (m, 1H), 7.75 (br s, 2H), 7.17 (br s, 3H), 4.22-4.78 (m, 1H), 3.43-4.07 (m, 2H), 2.69-3.40 (m, 2H), 2.54 (br s, 3H), 2.13 (d, J=10.29 Hz, 1H), 1.75-1.96 (m, 2H), 1.48-1.73 (m, 1H); [M+H]=448.1.

Example 359. 4-[(3,4-Dihydro-2H-1-benzopyran-3-yl)carbonyl]-2-{5-methyl-[1,2,4]triazolo[1,5-a]pyrimidin-7-yl}morpholine

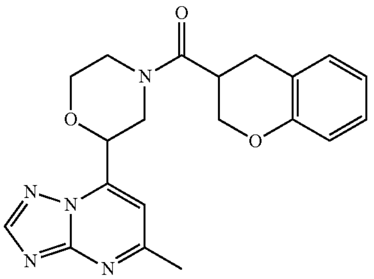 [SMILES: Cc1cc(C2CN(C(=O)C3COc4ccccc4C3)CCO2)n2ncnc2n1]

$^1$H NMR (400 MHz, $CDCl_3$) δ=8.50-8.26 (m, 1H), 7.25-6.80 (m, 5H), 5.43-5.07 (m, 2H), 4.90-4.75 (m, 1H), 4.67 (d, J=11.7 Hz, 1H), 4.37 (d, J=11.7 Hz, 1H), 4.29-4.05 (m, 2H), 3.92-3.75 (m, 1H), 3.62-3.41 (m, 1H), 3.35-2.91 (m, 4H), 2.74 (s, 3H); [M+H]=380.1.

Example 360. 4-[(2,3-Dihydro-1-benzofuran-5-yl)carbonyl]-2-{5-methyl-[1,2,4]triazolo[1,5-a]pyrimidin-7-yl}morpholine

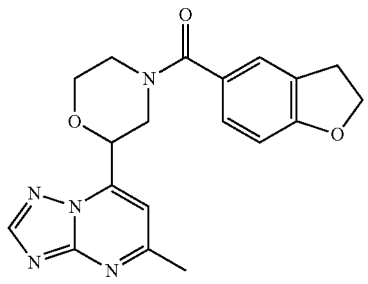 [SMILES: Cc1cc(C2CN(C(=O)c3ccc4c(c3)CCO4)CCO2)n2ncnc2n1]

$^1$H NMR (400 MHz, $CDCl_3$) δ=8.38 (s, 1H), 7.44 (s, 1H), 7.36 (d, J=8.6 Hz, 1H), 7.16 (d, J=0.8 Hz, 1H), 6.82 (d, J=8.2

Hz, 1H), 5.29 (s, 1H), 5.01-4.73 (m, 1H), 4.63 (t, J=8.8 Hz, 2H), 4.39 (br s, 1H), 4.21 (d, J=11.0 Hz, 1H), 3.93-3.84 (m, 1H), 3.26 (t, J=8.8 Hz, 3H), 2.93 (dd, J=10.0, 13.1 Hz, 1H), 2.72 (s, 3H); [M+H]=366.1.

Example 361. 4-[(3,5-Difluoropyridin-2-yl)carbonyl]-2-{5-methyl-[1,2,4]triazolo[1,5-a]pyrimidin-7-yl}morpholine

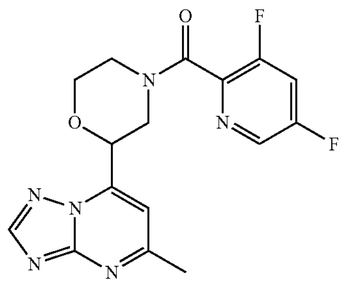 [SMILES: Cc1cc(C2CN(C(=O)c3ncc(F)cc3F)CCO2)n2ncnc2n1]

$^1$H NMR (400 MHz, $CDCl_3$) δ=8.48-8.24 (m, 2H), 7.35 (dtd, J=2.3, 8.4, 14.8 Hz, 1H), 6.98-6.77 (m, 1H), 5.11-3.75 (m, 4H), 3.69-3.31 (m, 2H), 2.96-2.54 (m, 4H); [M+H]=361.1.

Example 362. 1-[(2,3-Dihydro-1-benzofuran-5-yl)carbonyl]-3,3-difluoro-5-{5-methyl-[1,2,4]triazolo[1,5-a]pyrimidin-7-yl}piperidine

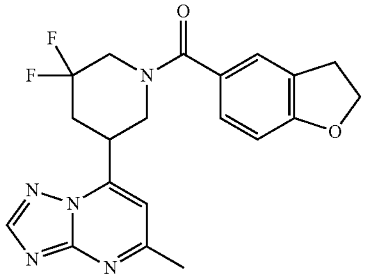 [SMILES: Cc1cc(C2CN(C(=O)c3ccc4c(c3)CCO4)CC(F)(F)C2)n2ncnc2n1]

$^1$H NMR (400 MHz, $CDCl_3$) δ=8.53-8.21 (m, 1H), 7.24-6.74 (m, 4H), 5.23-2.75 (m, 11H), 2.72 (br s, 3H); [M+H]=400.1.

Example 363. 1-[(3,4-Dihydro-2H-1-benzopyran-3-yl)carbonyl]-3,3-difluoro-5-{5-methyl-[1,2,4]triazolo[1,5-a]pyrimidin-7-yl}piperidine

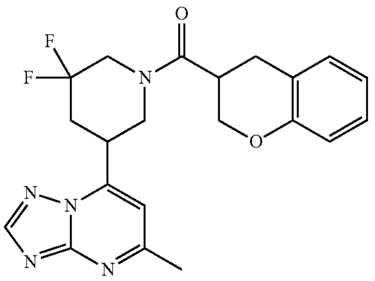

$^1$H NMR (400 MHz, $CDCl_3$) δ=8.49-8.25 (m, 1H), 7.23-6.74 (m, 5H), 5.26-4.60 (m, 2H), 4.54-3.55 (m, 3H), 3.54-3.09 (m, 3H), 2.72 (br s, 6H); [M+H]=414.1.

Example 364. 4-(3,4-Dichlorobenzoyl)-2-{5-methyl-[1,2,4]triazolo[1,5-a]pyrimidin-7-yl}morpholine

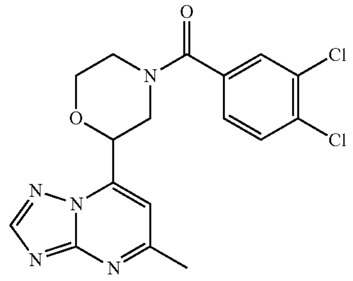 [SMILES: Cc1cc(C2CN(C(=O)c3ccc(Cl)c(Cl)c3)CCO2)n2ncnc2n1]

$^1$H NMR (400 MHz, DMSO-$d_6$) δ=8.76-8.33 (m, 1H), 7.90-7.79 (m, 1H), 7.74 (d, J=8.2 Hz, 1H), 7.54-7.43 (m, 1H), 7.31-7.17 (m, 1H), 5.54-5.14 (m, 1H), 4.54-3.59 (m, 4H), 3.60-3.35 (m, 1H), 3.19-3.04 (m, 1H), 2.63 (br s, 3H); [M+H]=392.2.

Example 365. 3,3-Difluoro-1-(7-methoxy-3,4-dihydro-2H-1-benzopyran-3-carbonyl)-5-{5-methyl-[1,2,4]triazolo[1,5-a]pyrimidin-7-yl}piperidine

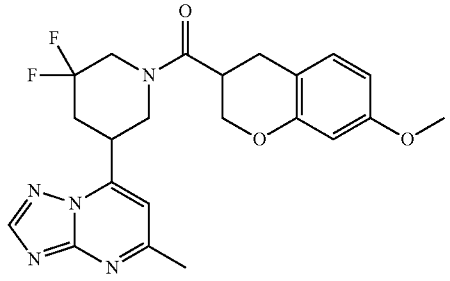 [SMILES: COc1ccc2c(c1)OCC(C(=O)N1CC(c3cc(C)nc4ncnn34)CC(F)(F)C1)C2]

$^1$H NMR (400 MHz, $CDCl_3$) δ=8.50-7.98 (m, 1H), 7.14-6.74 (m, 2H), 6.58-6.30 (m, 2H), 5.21-3.81 (m, 4H), 3.75 (d, J=2.0 Hz, 3H), 3.72-2.75 (m, 6H), 2.70 (s, 4H), 2.14-1.85 (m, 1H); [M+H]=444.1.

Example 366. 1-[(3R)-3,4-Dihydro-2H-1-benzopyran-3-carbonyl]-3-{5-methyl-[1,2,4]triazolo[1,5-a]pyrimidin-7-yl}piperidine

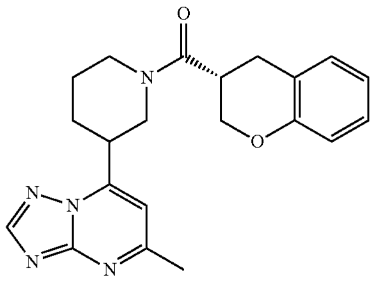 [SMILES: Cc1cc(C2CCCN(C(=O)[C@H]3COc4ccccc4C3)C2)n2ncnc2n1]

$^1$H NMR (400 MHz, $CDCl_3$) δ=8.50-8.22 (m, 1H), 7.24-6.75 (m, 5H), 4.93-4.55 (m, 2H), 4.44-4.02 (m, 2H), 3.68-3.02 (m, 5H), 2.92-2.61 (m, 4H), 2.47-2.19 (m, 1H), 2.08-1.90 (m, 2H), 1.88-1.68 (m, 1H); [M+H]=378.6.

Example 367. 1-[(3S)-3,4-Dihydro-2H-1-benzopyran-3-carbonyl]-3-{5-methyl-[1,2,4]triazolo[1,5-a]pyrimidin-7-yl}piperidine

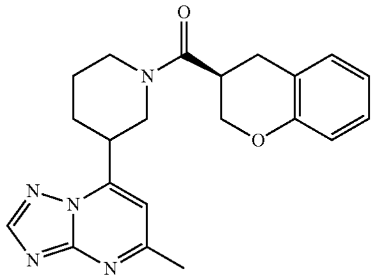 [SMILES: Cc1cc(C2CCCN(C(=O)[C@@H]3COc4ccccc4C3)C2)n2ncnc2n1]

$^1$H NMR (400 MHz, $CDCl_3$) δ=8.54-8.29 (m, 1H), 7.24-6.79 (m, 5H), 4.93-4.56 (m, 2H), 4.47-3.99 (m, 2H), 3.62 (d, J=9.4 Hz, 1H), 3.52-3.01 (m, 4H), 2.90-2.60 (m, 4H), 2.47-2.29 (m, 1H), 2.09-1.90 (m, 2H), 1.86-1.69 (m, 1H); [M+H]=378.5.

Example 368. (2S)-4-[3-Bromo-4-(trifluoromethyl)benzoyl]-2-{5-methyl-[1,2,4]triazolo[1,5-a]pyrimidin-7-yl}morpholine

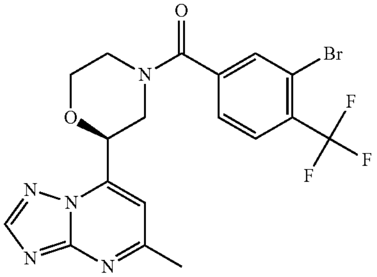 [SMILES: Cc1cc([C@@H]2CN(C(=O)c3ccc(C(F)(F)F)c(Br)c3)CCO2)n2ncnc2n1]

$^1$H NMR (400 MHz, DMSO-$d_6$) δ=8.72-8.40 (m, 1H), 8.18-8.00 (m, 1H), 7.94 (d, J=8.2 Hz, 1H), 7.75-7.62 (m, 1H), 7.35-7.16 (m, 1H), 5.62-4.37 (m, 2H), 4.25-3.85 (m, 2H), 3.56-3.35 (m, 1H), 3.12 (br s, 1H), 2.88 (br s, 1H), 2.63 (d, J=16.8 Hz, 3H); [M+H]=472.2.

Example 369. (2S)-4-(3-Bromo-4,5-difluorobenzoyl)-2-{5-methyl-[1,2,4]triazolo[1,5-a]pyrimidin-7-yl}morpholine

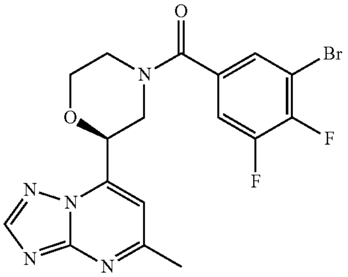 [SMILES: Cc1cc([C@@H]2CN(C(=O)c3cc(F)c(F)c(Br)c3)CCO2)n2ncnc2n1]

$^1$H NMR (400 MHz, DMSO-$d_6$) δ=8.78-8.40 (m, 1H), 7.88-7.59 (m, 2H), 7.27 (d, J=18.8 Hz, 1H), 5.58-4.99 (m, 1H), 4.07-3.82 (m, 3H), 3.64-3.41 (m, 1H), 3.25-2.77 (m, 2H), 2.65 (br s, 3H); [M+H]=438.3.

Example 370. (2S)-2-{5-Methyl-[1,2,4]triazolo[1,5-a]pyrimidin-7-yl}-4-(3,4,5-trichlorobenzoyl)morpholine

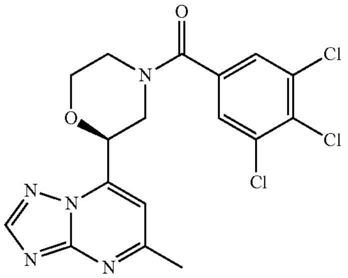 [SMILES: Cc1cc([C@@H]2CN(C(=O)c3cc(Cl)c(Cl)c(Cl)c3)CCO2)n2ncnc2n1]

$^1$H NMR (400 MHz, DMSO-$d_6$) δ=8.81-8.41 (m, 1H), 7.86 (d, J=18.0 Hz, 2H), 7.39-7.16 (m, 1H), 5.53-5.06 (m, 1H), 4.48-3.96 (m, 3H), 3.60-3.42 (m, 1H), 3.10 (br s, 1H), 2.95-2.77 (m, 1H), 2.65 (d, J=11.7 Hz, 3H); [M+H]=426.3.

Example 371. (2S)-4-(3,5-Dichloro-4-fluorobenzoyl)-2-{5-methyl-[1,2,4]triazolo[1,5-a]pyrimidin-7-yl}morpholine

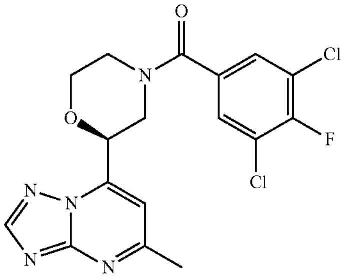 [SMILES: Cc1cc([C@@H]2CN(C(=O)c3cc(Cl)c(F)c(Cl)c3)CCO2)n2ncnc2n1]

$^1$H NMR (400 MHz, DMSO-$d_6$) δ=8.52 (br s, 1H), 7.84 (br s, 2H), 7.64-7.06 (m, 1H), 5.53-5.14 (m, 1H), 4.44-4.17

(m, 2H), 4.05-3.85 (m, 1H), 3.61-3.33 (m, 1H), 3.16-3.01 (m, 1H), 2.91-2.78 (m, 1H), 2.64 (br s, 3H); [M+H]=410.3.

Example 372. (2S)-4-(1-Benzofuran-5-carbonyl)-2-{5-methyl-[1,2,4]triazolo[1,5-a]pyrimidin-7-yl}morpholine

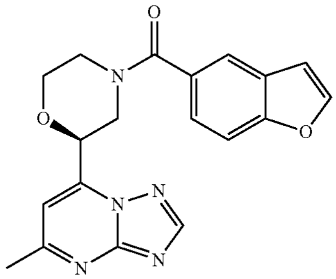 [SMILES: Cc1cc([C@@H]2CN(C(=O)c3ccc4occc4c3)CCO2)n2ncnc2n1]

$^1$H NMR (400 MHz, $CDCl_3$, $CD_3OD$) δ=8.29 (br s, 1H), 7.82 (br s, 1H), 7.73-7.64 (m, 1H), 7.58-7.51 (m, 1H), 7.46 (d, J=8.6 Hz, 1H), 7.16 (s, 1H), 6.84 (d, J=1.6 Hz, 1H), 5.27 (dd, J=2.0, 10.2 Hz, 1H), 4.93-3.79 (m, 4H), 3.24 (br s, 1H), 3.02-2.82 (m, 1H), 2.70 (s, 4H); [M+H]=364.1.

Example 373. (2S)-4-(2,2-Difluoro-2H-1,3-benzodioxole-5-carbonyl)-2-{5-methyl-[1,2,4]triazolo[1,5-a]pyrimidin-7-yl}morpholine

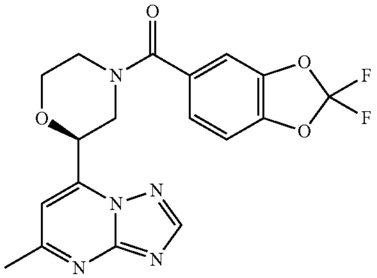 [SMILES: Cc1cc([C@@H]2CN(C(=O)c3ccc4c(c3)OC(F)(F)O4)CCO2)n2ncnc2n1]

$^1$H NMR (400 MHz, $CDCl_3$) δ=8.45 (br s, 1H), 7.38-7.26 (m, 3H), 7.13 (d, J=8.2 Hz, 1H), 5.22 (d, J=9.4 Hz, 1H), 4.81-3.70 (m, 4H), 3.21 (br s, 1H), 3.03-2.86 (m, 1H), 2.73 (s, 3H); [M+H]=404.6.

Example 374. (2S)-4-(1-Methyl-3-phenyl-1H-pyrazole-5-carbonyl)-2-{5-methyl-[1,2,4]triazolo[1,5-a]pyrimidin-7-yl}morpholine

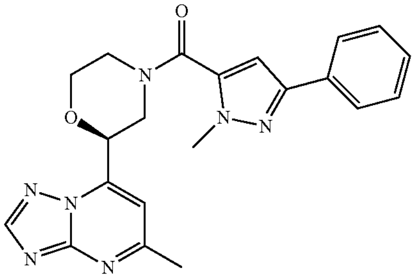 [SMILES: Cc1cc([C@@H]2CN(C(=O)c3cc(-c4ccccc4)nn3C)CCO2)n2ncnc2n1]

$^1$H NMR (400 MHz, $CDCl_3$, $CD_3OD$) δ=8.29 (br s, 1H), 7.75 (br s, 2H), 7.49-7.27 (m, 4H), 7.25-6.92 (m, 1H), 5.23 (d, J=8.2 Hz, 1H), 5.14-4.04 (m, 3H), 3.98 (s, 3H), 3.93-3.76 (m, 1H), 3.08 (br s, 2H), 2.78-2.60 (m, 3H); [M+H]=404.2.

Example 375. (2S)-4-[(3R)-3,4-Dihydro-2H-1-benzopyran-3-carbonyl]-2-{5-methyl-[1,2,4]triazolo[1,5-a]pyrimidin-7-yl}morpholine

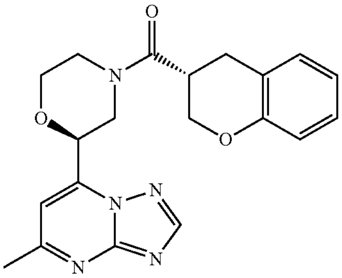 [SMILES: Cc1cc([C@@H]2CN(C(=O)[C@H]3COc4ccccc4C3)CCO2)n2ncnc2n1]

$^1$H NMR (400 MHz, $CDCl_3$) δ=8.51-8.30 (m, 1H), 7.25-7.05 (m, 3H), 6.99-6.81 (m, 2H), 5.41-4.62 (m, 3H), 4.50-3.75 (m, 4H), 3.60-3.45 (m, 1H), 3.26-2.61 (m, 7H); [M+H]=380.1.

Example 376. (2S)-4-[(3S)-3,4-Dihydro-2H-1-benzopyran-3-carbonyl]-2-{5-methyl-[1,2,4]triazolo[1,5-a]pyrimidin-7-yl}morpholine

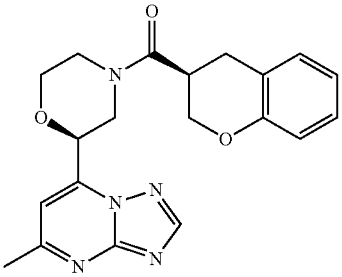 [SMILES: Cc1cc([C@@H]2CN(C(=O)[C@@H]3COc4ccccc4C3)CCO2)n2ncnc2n1]

$^1$H NMR (400 MHz, $CDCl_3$) δ=8.49-8.41 (m, 1H), 7.24-6.99 (m, 3H), 6.94-6.80 (m, 2H), 5.42-4.79 (m, 2H), 4.75-3.77 (m, 5H), 3.54-2.66 (m, 8H); [M+H]=380.6.

Example 377. 1-[(2S)-2,3-Dihydro-1,4-benzodioxine-2-carbonyl]-3-{5-methyl-[1,2,4]triazolo[1,5-a]pyrimidin-7-yl}piperidine

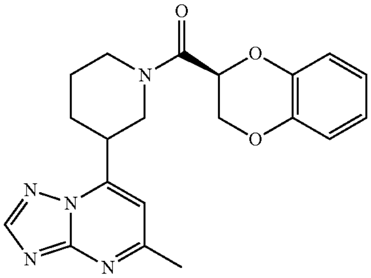

$^1$H NMR (400 MHz, $CDCl_3$) δ=8.52-8.20 (m, 1H), 7.03-6.70 (m, 5H), 5.16-3.09 (m, 7H), 2.94-2.57 (m, 4H), 2.44-2.23 (m, 1H), 2.12-1.70 (m, 3H); [M+H]=380.4.

Example 378. 1-(2,3-Dihydro-1-benzofuran-6-carbonyl)-3-{5-methyl-[1,2,4]triazolo[1,5-a]pyrimidin-7-yl}piperidine

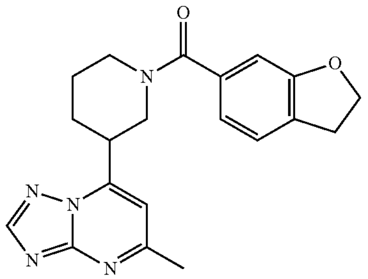

$^1$H NMR (400 MHz, $CDCl_3$) δ=8.41 (br s, 1H), 7.25-7.08 (m, 1H), 6.96-6.68 (m, 3H), 4.93-2.83 (m, 9H), 2.69 (s, 3H), 2.42-1.89 (m, 4H); [M+H]=364.4.

Example 379. 1-[(2R)-2,3-Dihydro-1,4-benzodioxine-2-carbonyl]-3-{5-methyl-[1,2,4]triazolo[1,5-a]pyrimidin-7-yl}piperidine

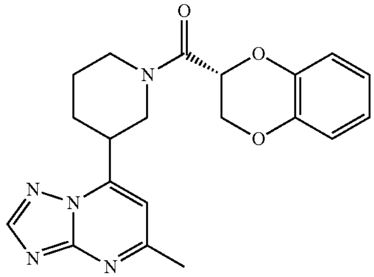

$^1$H NMR (400 MHz, $CDCl_3$) δ=8.51-8.13 (m, 1H), 7.02-6.69 (m, 5H), 5.16-2.75 (m, 8H), 2.72 (s, 3H), 2.46-2.24 (m, 1H), 2.11-1.70 (m, 3H); [M+H]=380.1.

Example 380.4-[1-(2-Fluorophenyl)-1H-pyrazole-3-carbonyl]-2-{5-methyl-[1,2,4]triazolo[1,5-a]pyrimidin-7-yl}morpholine

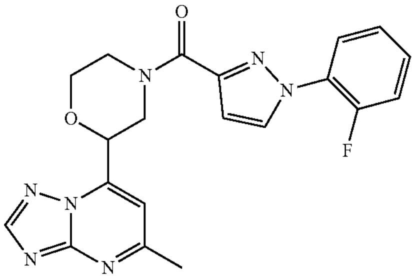 [SMILES: Cc1cc(C2CN(C(=O)c3ccn(-c4ccccc4F)n3)CCO2)n2ncnc2n1]

$^1$H NMR (400 MHz, $CDCl_3$, $D_2O$) δ=8.53-8.15 (m, 1H), 8.10-7.75 (m, 2H), 7.42-7.17 (m, 4H), 7.02 (d, J=2.7 Hz, 1H), 6.11-5.11 (m, 2H), 4.35-4.14 (m, 1H), 4.03-3.89 (m, 1H), 3.64-2.79 (m, 3H), 2.74 (s, 3H); [M+H]=408.1.

Example 381. 4-[1-(2-Chlorophenyl)-1H-pyrazole-3-carbonyl]-2-{5-methyl-[1,2,4]triazolo[1,5-a]pyrimidin-7-yl}morpholine

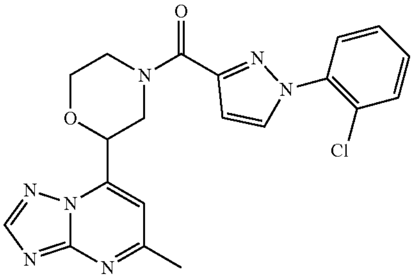 [SMILES: Cc1cc(C2CN(C(=O)c3ccn(-c4ccccc4Cl)n3)CCO2)n2ncnc2n1]

$^1$H NMR (400 MHz, $CDCl_3$, $D_2O$) δ=8.58-8.14 (m, 1H), 7.93-7.80 (m, 1H), 7.64-7.32 (m, 4H), 7.21 (s, 1H), 7.01 (d, J=2.0 Hz, 1H), 5.99-5.11 (m, 2H), 4.74 (d, J=14.1 Hz, 1H), 4.33-4.10 (m, 1H), 4.04-3.82 (m, 1H), 3.64-2.80 (m, 2H), 2.73 (br s, 3H); [M+H]=424.0.

Example 382. 4-[1-(3-Bromophenyl)-1H-pyrazole-3-carbonyl]-2-{5-methyl-[1,2,4]triazolo[1,5-a]pyrimidin-7-yl}morpholine

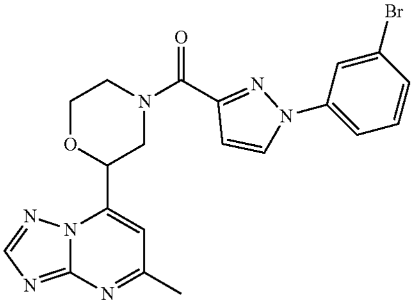 [SMILES: Cc1cc(C2CN(C(=O)c3ccn(-c4cccc(Br)c4)n3)CCO2)n2ncnc2n1]

$^1$H NMR (400 MHz, $CDCl_3$, $D_2O$) δ=8.55-8.23 (m, 1H), 7.99-7.83 (m, 2H), 7.71-7.57 (m, 1H), 7.52-7.45 (m, 1H), 7.35 (q, J=8.1 Hz, 1H), 7.25-7.17 (m, 1H), 7.09-6.96 (m, 1H), 6.06-5.11 (m, 2H), 4.71 (br s, 1H), 4.35-4.15 (m, 1H), 4.03-3.89 (m, 1H), 3.67-2.81 (m, 2H), 2.74 (s, 3H); [M+H]=468.0.

Example 383. 4-[1-(4-Chlorophenyl)-5-methyl-1H-pyrazole-3-carbonyl]-2-{5-methyl-[1,2,4]triazolo[1,5-a]pyrimidin-7-yl}morpholine

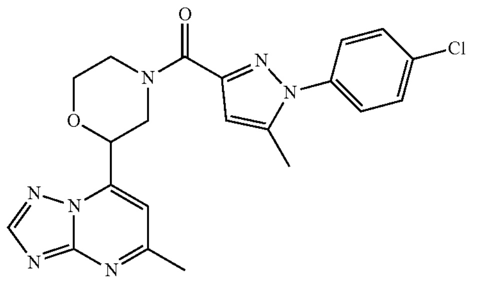 [SMILES: Cc1cc(C2CN(C(=O)c3cc(C)n(-c4ccc(Cl)cc4)n3)CCO2)n2ncnc2n1]

$^1$H NMR (400 MHz, $CDCl_3$ and $D_2O$) δ=8.54-8.14 (m, 1H), 7.55-7.35 (m, 4H), 7.21 (br s, 1H), 6.74 (s, 1H), 6.06-4.65 (m, 3H), 4.69 (br s, 1H), 4.35-2.78 (m, 5H), 2.73 (s, 3H), 2.41-2.33 (m, 3H); [M+H]=438.1.

Example 384. 4-[1-(3-Fluorophenyl)-1H-pyrazole-3-carbonyl]-2-{5-methyl-[1,2,4]triazolo[1,5-a]pyrimidin-7-yl}morpholine

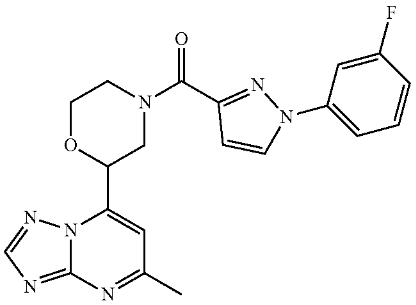 [SMILES: Cc1cc(C2CN(C(=O)c3ccn(-c4cccc(F)c4)n3)CCO2)n2ncnc2n1]

$^1$H NMR (400 MHz, $CDCl_3$, $D_2O$) δ=8.57-8.32 (m, 1H), 7.95 (d, J=2.7 Hz, 1H), 7.75-7.37 (m, 3H), 7.30-7.00 (m, 3H), 6.23-5.14 (m, 2H), 4.73 (d, J=14.5 Hz, 1H), 4.40-4.14 (m, 1H), 4.03-3.88 (m, 1H), 3.72-2.82 (m, 2H), 2.75 (s, 3H); [M+H]=408.2.

Examples 385-564 were prepared in a manner analogous to Example 7, with the appropriate starting material and reagent substitutions.

Example 385. 4-Methyl-2-[(3-{5-methyl-[1,2,4]triazolo[1,5-a]pyrimidin-7-yl}piperidin-1-yl)carbonyl]pyridine

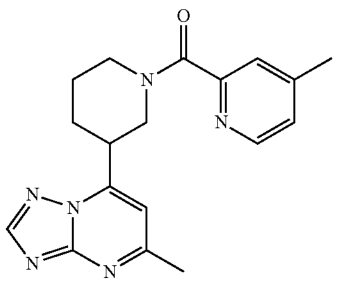 [SMILES: Cc1ccnc(C(=O)N2CCCC(c3cc(C)nc4ncnn34)C2)c1]

[M+H]=337.2.

Example 386. 2-Methoxy-5-[(3-{5-methyl-[1,2,4]triazolo[1,5-a]pyrimidin-7-yl}piperidin-1-yl)carbonyl]pyridine

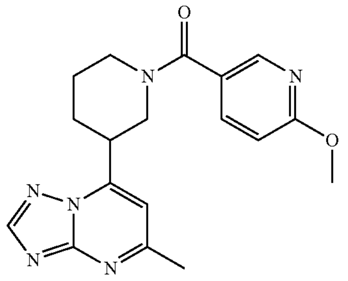 [SMILES: COc1ccc(C(=O)N2CCCC(c3cc(C)nc4ncnn34)C2)cn1]

[M+H]=353.2.

Example 387. 3-[(3-{5-Methyl-[1,2,4]triazolo[1,5-a]pyrimidin-7-yl}piperidin-1-yl)carbonyl]pyridine

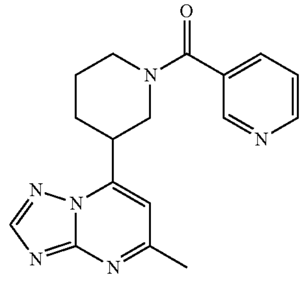

[M+H]=323.2.

Example 388. 2-[(3-{5-Methyl-[1,2,4]triazolo[1,5-a]pyrimidin-7-yl}piperidin-1-yl)carbonyl]-1,6-naphthyridine

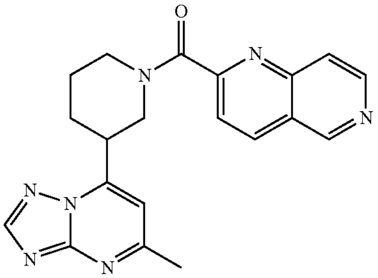 [SMILES: Cc1cc(C2CCCN(C(=O)c3ccc4cnccc4n3)C2)n2ncnc2n1]

[M+H]=374.2.

Example 389. 3-[(3-{5-Methyl-[1,2,4]triazolo[1,5-a]pyrimidin-7-yl}piperidin-1-yl)carbonyl]isoquinoline

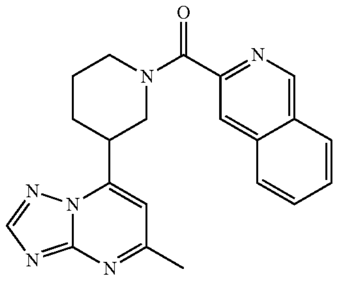 [SMILES: Cc1cc(C2CCCN(C(=O)c3cc4ccccc4cn3)C2)n2ncnc2n1]

[M+H]=373.2.

Example 390. 3-Methyl-4-[(3-{5-methyl-[1,2,4]triazolo[1,5-a]pyrimidin-7-yl}piperidin-1-yl)carbonyl]pyridine

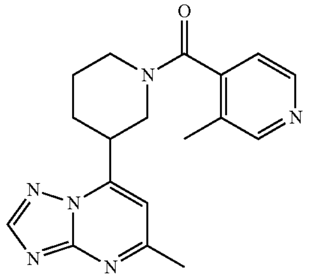 [SMILES: Cc1cc(C2CCCN(C(=O)c3ccncc3C)C2)n2ncnc2n1]

[M+H]=337.2.

Example 391. 2-Methyl-6-[(3-{5-methyl-[1,2,4]triazolo[1,5-a]pyrimidin-7-yl}piperidin-1-yl)carbonyl]pyridine

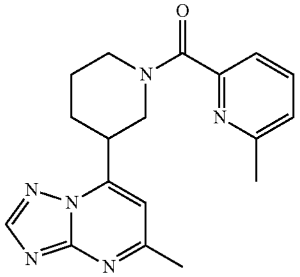 [SMILES: Cc1cccc(C(=O)N2CCCC(c3cc(C)nc4ncnn34)C2)n1]

[M+H]=337.2.

Example 392. 4-[(3-{5-Methyl-[1,2,4]triazolo[1,5-a]pyrimidin-7-yl}piperidin-1-yl)carbonyl]pyridine

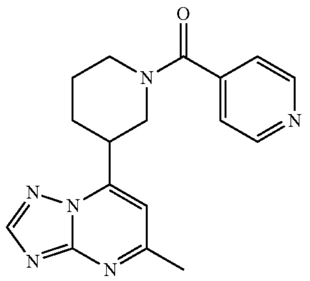 [SMILES: Cc1cc(C2CCCN(C(=O)c3ccncc3)C2)n2ncnc2n1]

[M+H]=323.2.

Example 393. 3-Methyl-5-[(3-{5-methyl-[1,2,4]triazolo[1,5-a]pyrimidin-7-yl}piperidin-1-yl)carbonyl]pyridine

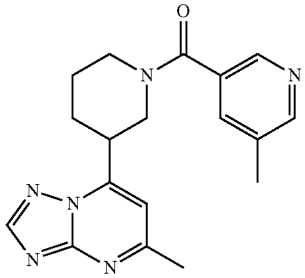 [SMILES: Cc1cncc(C(=O)N2CCCC(c3cc(C)nc4ncnn34)C2)c1]

[M+H]=337.2.

Example 394. 1-({Imidazo[1,2-a]pyridin-6-yl}carbonyl)-3-{5-methyl-[1,2,4]triazolo[1,5-a]pyrimidin-7-yl}piperidine

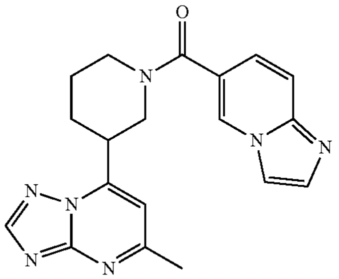 [SMILES: Cc1cc(C2CCCN(C(=O)c3ccc4nccn4c3)C2)n2ncnc2n1]

[M+H]=362.2.

Example 395. 2-[(3-{5-Methyl-[1,2,4]triazolo[1,5-a]pyrimidin-7-yl}piperidin-1-yl)carbonyl]pyridine

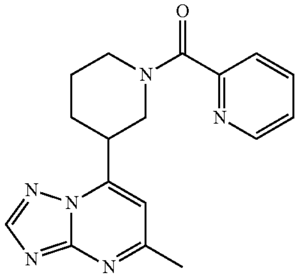 [SMILES: Cc1cc(C2CCCN(C(=O)c3ccccn3)C2)n2ncnc2n1]

[M+H]=323.2.

Example 396. 7-[(3-{5-Methyl-[1,2,4]triazolo[1,5-a]pyrimidin-7-yl}piperidin-1-yl)carbonyl]quinoline

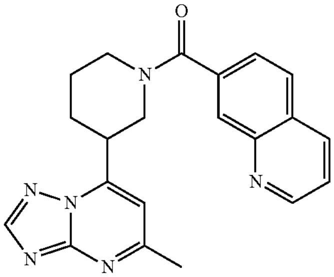 [SMILES: Cc1cc(C2CCCN(C(=O)c3ccc4cccnc4c3)C2)n2ncnc2n1]

[M+H]=373.2.

Example 397. 7-[(3-{5-Methyl-[1,2,4]triazolo[1,5-a]pyrimidin-7-yl}piperidin-1-yl)carbonyl]isoquinoline

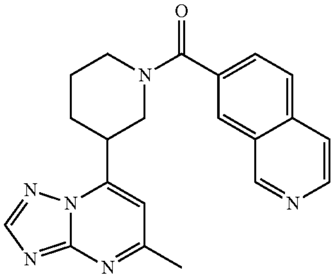 [SMILES: Cc1cc(C2CCCN(C(=O)c3ccc4ccncc4c3)C2)n2ncnc2n1]

[M+H]=373.2.

Example 398. 3-Methyl-2-[(3-{5-methyl-[1,2,4]triazolo[1,5-a]pyrimidin-7-yl}piperidin-1-yl)carbonyl]pyridine

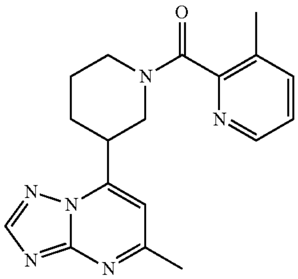

[M+H]=337.2.

Example 399. 1-[(3-{5-Methyl-[1,2,4]triazolo[1,5-a]pyrimidin-7-yl}piperidin-1-yl)carbonyl]isoquinoline

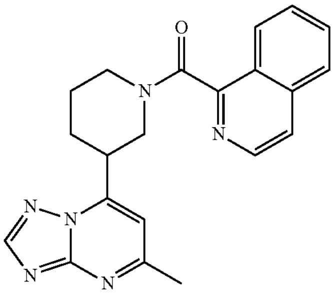 [SMILES: Cc1cc(C2CCCN(C(=O)c3nccc4ccccc34)C2)n2ncnc2n1]

[M+H]=373.2.

Example 400. 2-Methyl-3-[(3-{5-methyl-[1,2,4]triazolo[1,5-a]pyrimidin-7-yl}piperidin-1-yl)carbonyl]pyridine

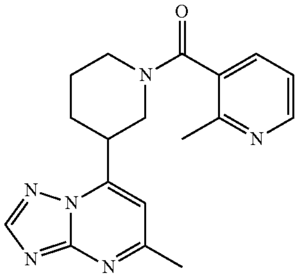 [SMILES: Cc1cc(C2CCCN(C(=O)c3cccnc3C)C2)n2ncnc2n1]

[M+H]=337.2.

Example 401. 3-Chloro-5-[(3-{5-methyl-[1,2,4]triazolo[1,5-a]pyrimidin-7-yl}piperidin-1-yl)carbonyl]pyridine

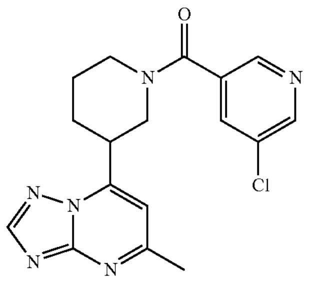 [SMILES: Cc1cc(C2CCCN(C(=O)c3cncc(Cl)c3)C2)n2ncnc2n1]

[M+H]=357.2.

Example 402. 2-Methoxy-4-[(3-{5-methyl-[1,2,4]triazolo[1,5-a]pyrimidin-7-yl}piperidin-1-yl)carbonyl]pyridine

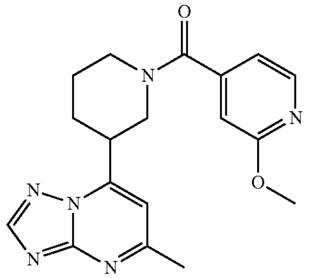 [SMILES: COc1cc(C(=O)N2CCCC(c3cc(C)nc4ncnn34)C2)ccn1]

[M+H]=353.2.

Example 403. 3-Fluoro-5-[(3-{5-methyl-[1,2,4]triazolo[1,5-a]pyrimidin-7-yl}piperidin-1-yl)carbonyl]pyridine

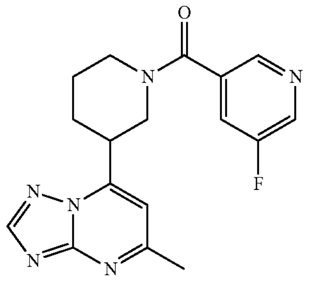 [SMILES: Cc1cc(C2CCCN(C(=O)c3cncc(F)c3)C2)n2ncnc2n1]

[M+H]=341.1.

Example 404. 3-{5-Methyl-[1,2,4]triazolo[1,5-a]pyrimidin-7-yl}-1-({2-methylimidazo[1,2-a]pyridin-3-yl}carbonyl)piperidine

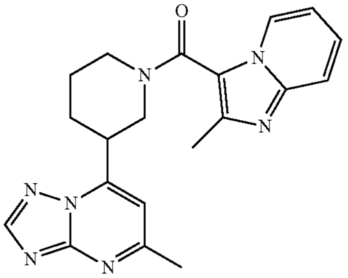 [SMILES: Cc1cc(C2CCCN(C(=O)c3c(C)nc4ccccn34)C2)n2ncnc2n1]

[M+H]=376.2.

Example 405. 3-Chloro-4-[(3-{5-methyl-[1,2,4]triazolo[1,5-a]pyrimidin-7-yl}piperidin-1-yl)carbonyl]pyridine

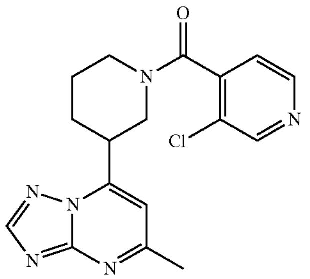 [SMILES: Cc1cc(C2CCCN(C(=O)c3ccncc3Cl)C2)n2ncnc2n1]

[M+H]=357.1.

Example 406. 2-[(3-{5-Methyl-[1,2,4]triazolo[1,5-a]pyrimidin-7-yl}piperidin-1-yl)carbonyl]quinoline

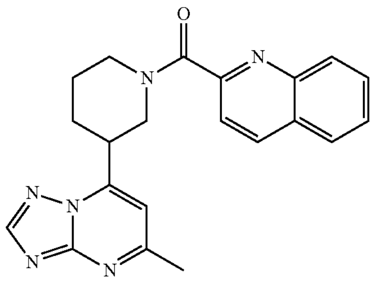 [SMILES: Cc1cc(C2CCCN(C(=O)c3ccc4ccccc4n3)C2)n2ncnc2n1]

[M+H]=373.2.

Example 407. 6-[(3-{5-Methyl-[1,2,4]triazolo[1,5-a]pyrimidin-7-yl}piperidin-1-yl)carbonyl]isoquinoline

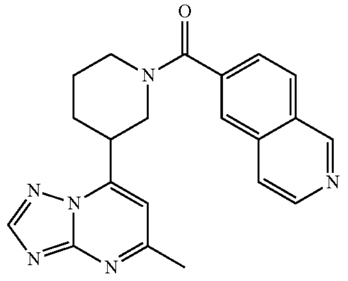 [SMILES: Cc1cc(C2CCCN(C(=O)c3ccc4cnccc4c3)C2)n2ncnc2n1]

[M+H]=373.2.

Example 408. 1-({Imidazo[1,2-a]pyridin-2-yl}carbonyl)-3-{5-methyl-[1,2,4]triazolo[1,5-a]pyrimidin-7-yl}piperidine

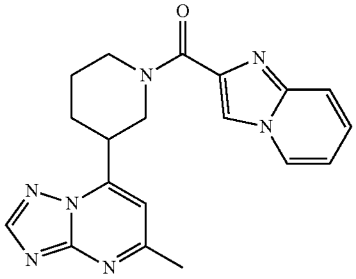 [SMILES: Cc1cc(C2CCCN(C(=O)c3cn4ccccc4n3)C2)n2ncnc2n1]

[M+H]=362.2.

Example 409. 1-[(1-Methyl-1H-pyrrol-2-yl)carbonyl]-3-{5-methyl-[1,2,4]triazolo[1,5-a]pyrimidin-7-yl}piperidine

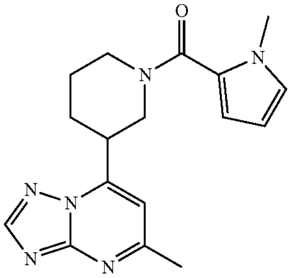 [SMILES: Cc1cc(C2CCCN(C(=O)c3cccn3C)C2)n2ncnc2n1]

[M+H]=325.2.

Example 410. 1-[(2-Methoxy-5-methylphenyl)carbonyl]-3-{5-methyl-[1,2,4]triazolo[1,5-a]pyrimidin-7-yl}piperidine

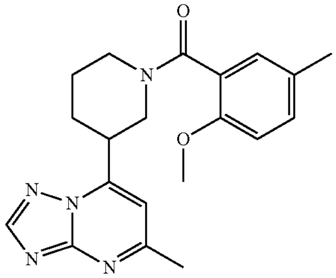 [SMILES: COc1ccc(C)cc1C(=O)N1CCCC(c2cc(C)nc3ncnn23)C1]

[M+H]=366.2.

Example 411. 1-[(1,3-Dimethyl-1H-pyrazol-5-yl)carbonyl]-3-{5-methyl-[1,2,4]triazolo[1,5-a]pyrimidin-7-yl}piperidine

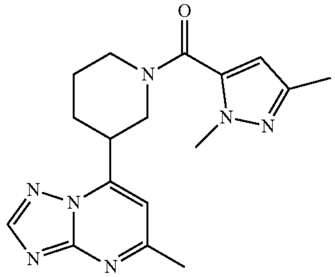 [SMILES: Cc1cc(C2CCCN(C(=O)c3cc(C)nn3C)C2)n2ncnc2n1]

[M+H]=340.2.

Example 412. 1-[(2-Fluoro-3-methylphenyl)carbonyl]-3-{5-methyl-[1,2,4]triazolo[1,5-a]pyrimidin-7-yl}piperidine

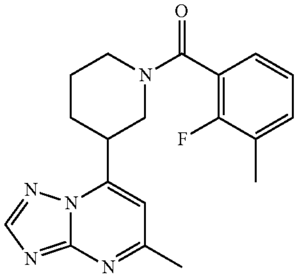

[M+H]=354.2.

Example 413. 3-{5-Methyl-[1,2,4]triazolo[1,5-a]pyrimidin-7-yl}-1-[(naphthalen-1-yl)carbonyl]piperidine

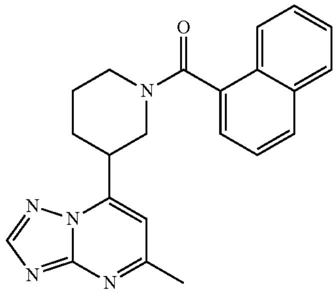 [SMILES: Cc1cc(C2CCCN(C(=O)c3cccc4ccccc34)C2)n2ncnc2n1]

[M+H]=372.2.

Example 414. 1-[(3-Chlorophenyl)carbonyl]-3-{5-methyl-[1,2,4]triazolo[1,5-a]pyrimidin-7-yl}piperidine

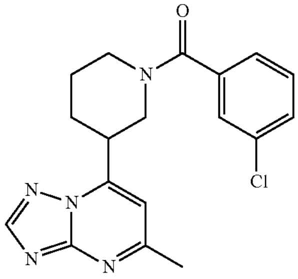 [SMILES: Cc1cc(C2CCCN(C(=O)c3cccc(Cl)c3)C2)n2ncnc2n1]

[M+H]=356.1.

Example 415. 1-[(2-Fluoro-4-methoxyphenyl)carbonyl]-3-{5-methyl-[1,2,4]triazolo[1,5-a]pyrimidin-7-yl}piperidine

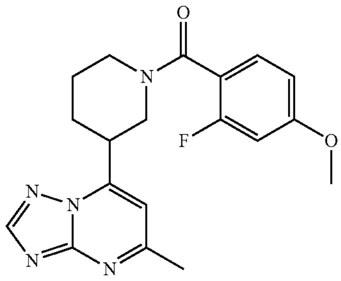 [SMILES: COc1ccc(C(=O)N2CCCC(c3cc(C)nc4ncnn34)C2)c(F)c1]

[M+H]=370.2.

Example 416. 1-[(2-Methoxy-4-methylphenyl)carbonyl]-3-{5-methyl-[1,2,4]triazolo[1,5-a]pyrimidin-7-yl}piperidine

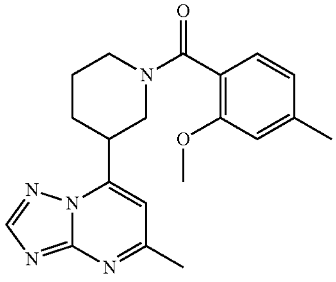 [SMILES: COc1cc(C)ccc1C(=O)N1CCCC(c2cc(C)nc3ncnn23)C1]

[M+H]=366.2.

Example 417. 1-[(3-Fluoro-5-methoxyphenyl)carbonyl]-3-{5-methyl-[1,2,4]triazolo[1,5-a]pyrimidin-7-yl}piperidine

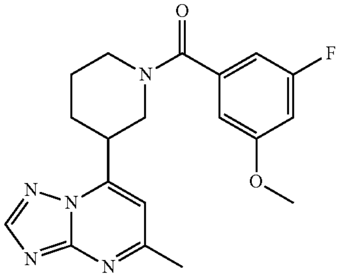 [SMILES: COc1cc(F)cc(C(=O)N2CCCC(c3cc(C)nc4ncnn34)C2)c1]

[M+H]=370.2.

Example 418. 1-[(2-Fluoro-4-methylphenyl)carbonyl]-3-{5-methyl-[1,2,4]triazolo[1,5-a]pyrimidin-7-yl}piperidine

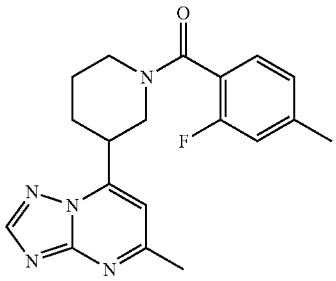

[M+H]=354.2.

Example 419. 2-[(3-{5-Methyl-[1,2,4]triazolo[1,5-a]pyrimidin-7-yl}piperidin-1-yl)carbonyl]quinoxaline

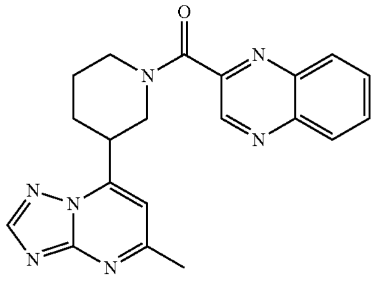 [SMILES: Cc1cc(C2CCCN(C(=O)c3cnc4ccccc4n3)C2)n2ncnc2n1]

[M+H]=374.2.

Example 420. 1-Methyl-3-[(3-{5-methyl-[1,2,4]triazolo[1,5-a]pyrimidin-7-yl}piperidin-1-yl)carbonyl]-1H-indole

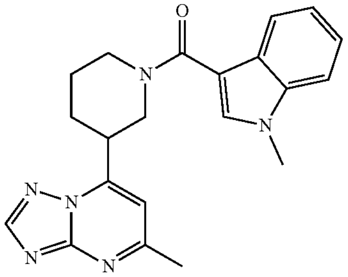 [SMILES: Cc1cc(C2CCCN(C(=O)c3cn(C)c4ccccc34)C2)n2ncnc2n1]

[M+H]=375.2.

Example 421. 6-[(3-{5-Methyl-[1,2,4]triazolo[1,5-a]pyrimidin-7-yl}piperidin-1-yl)carbonyl]-1,3-benzothiazole

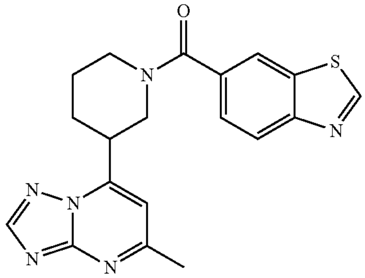 [SMILES: Cc1cc(C2CCCN(C(=O)c3ccc4ncsc4c3)C2)n2ncnc2n1]

[M+H]=379.1.

Example 422. 1-[(3-Methoxy-2-methylphenyl)carbonyl]-3-{5-methyl-[1,2,4]triazolo[1,5-a]pyrimidin-7-yl}piperidine

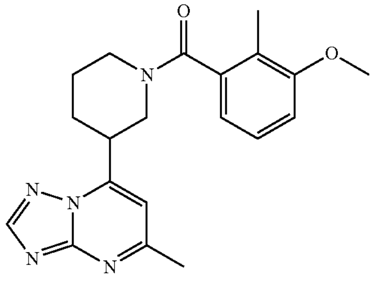 [SMILES: COc1cccc(C(=O)N2CCCC(c3cc(C)nc4ncnn34)C2)c1C]

[M+H]=366.2.

Example 423. 1-[(1-Benzofuran-5-yl)carbonyl]-3-{5-methyl-[1,2,4]triazolo[1,5-a]pyrimidin-7-yl}piperidine

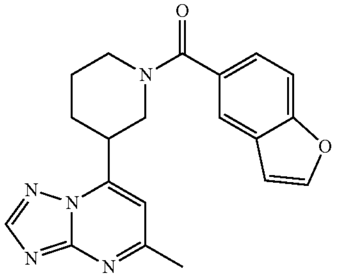 [SMILES: Cc1cc(C2CCCN(C(=O)c3ccc4occc4c3)C2)n2ncnc2n1]

[M+H]=362.2.

Example 424. 3-{5-Methyl-[1,2,4]triazolo[1,5-a]pyrimidin-7-yl}-1-[(5,6,7,8-tetrahydronaphthalen-2-yl)carbonyl]piperidine

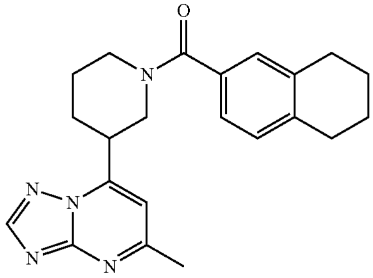 [SMILES: Cc1cc(C2CCCN(C(=O)c3ccc4c(c3)CCCC4)C2)n2ncnc2n1]

[M+H]=376.2.

Example 425. 1-[(3-Cyclopropyl-1,2-oxazol-5-yl)carbonyl]-3-{5-methyl-[1,2,4]triazolo[1,5-a]pyrimidin-7-yl}piperidine

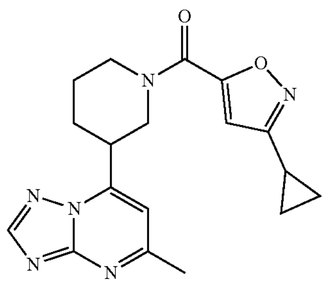 [SMILES: Cc1cc(C2CCCN(C(=O)c3cc(C4CC4)no3)C2)n2ncnc2n1]

[M+H]=353.2.

Example 426. 1-[(2-Chlorophenyl)carbonyl]-3-{5-methyl-[1,2,4]triazolo[1,5-a]pyrimidin-7-yl}piperidine

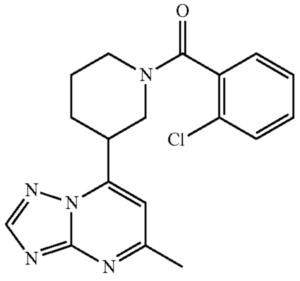

[M+H]=356.1.

Example 427. 3-{5-Methyl-[1,2,4]triazolo[1,5-a]pyrimidin-7-yl}-1-[(2-phenylphenyl)carbonyl]piperidine

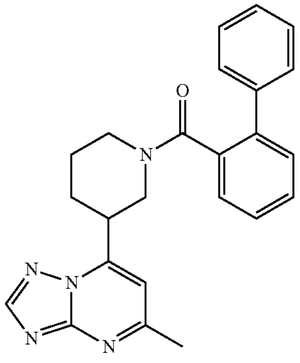 [SMILES: Cc1cc(C2CCCN(C(=O)c3ccccc3-c3ccccc3)C2)n2ncnc2n1]

[M+H]=398.2.

Example 428. 1-[(2,3-Difluorophenyl)carbonyl]-3-{5-methyl-[1,2,4]triazolo[1,5-a]pyrimidin-7-yl}piperidine

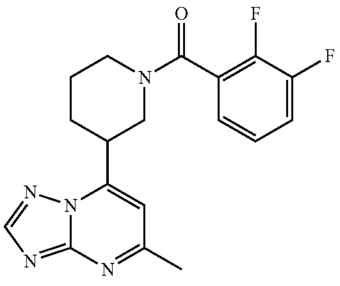

[M+H]=358.1.

Example 429. 1-[(5-Cyclopropyl-1,2-oxazol-4-yl)carbonyl]-3-{5-methyl-[1,2,4]triazolo[1,5-a]pyrimidin-7-yl}piperidine

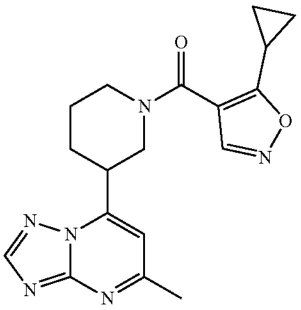 [SMILES: Cc1cc(C2CCCN(C(=O)c3cnoc3C3CC3)C2)n2ncnc2n1]

[M+H]=353.2.

Example 430. 1-[(1-Methyl-5-phenyl-1H-pyrazol-3-yl)carbonyl]-3-{5-methyl-[1,2,4]triazolo[1,5-a]pyrimidin-7-yl}piperidine

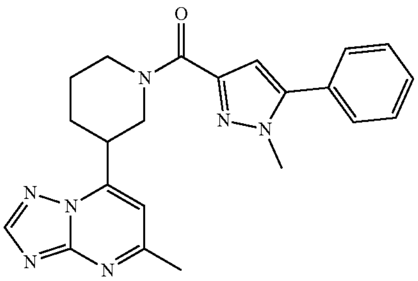 [SMILES: Cc1cc(C2CCCN(C(=O)c3cc(-c4ccccc4)n(C)n3)C2)n2ncnc2n1]

[M+H]=402.2.

Example 431. 1-[(1,5-Dimethyl-1H-pyrazol-4-yl)carbonyl]-3-{5-methyl-[1,2,4]triazolo[1,5-a]pyrimidin-7-yl}piperidine

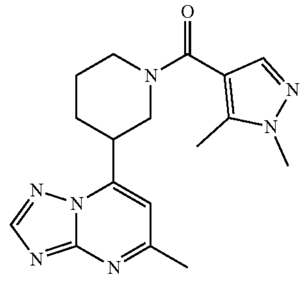 [SMILES: Cc1cc(C2CCCN(C(=O)c3cnn(C)c3C)C2)n2ncnc2n1]

[M+H]=340.2.

Example 432. 1-[(1,5-Dimethyl-1H-pyrazol-3-yl)carbonyl]-3-{5-methyl-[1,2,4]triazolo[1,5-a]pyrimidin-7-yl}piperidine

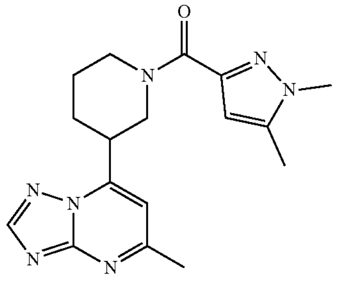 [SMILES: Cc1cc(C2CCCN(C(=O)c3cc(C)n(C)n3)C2)n2ncnc2n1]

[M+H]=340.2.

Example 433. 1-[(2,5-Difluorophenyl)carbonyl]-3-{5-methyl-[1,2,4]triazolo[1,5-a]pyrimidin-7-yl}piperidine

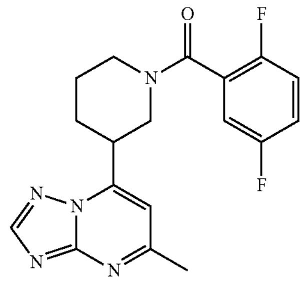

[M+H]=358.1.

Example 434. 1-[(5-Cyclopropyl-1,2-oxazol-3-yl)carbonyl]-3-{5-methyl-[1,2,4]triazolo[1,5-a]pyrimidin-7-yl}piperidine

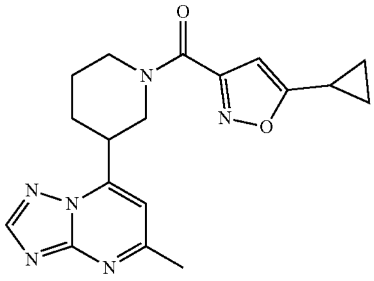 [SMILES: Cc1cc(C2CCCN(C(=O)c3cc(C4CC4)on3)C2)n2ncnc2n1]

[M+H]=353.2.

Example 435. 3-{5-Methyl-[1,2,4]triazolo[1,5-a]pyrimidin-7-yl}-1-{[1-(propan-2-yl)-1H-pyrazol-4-yl]carbonyl}piperidine

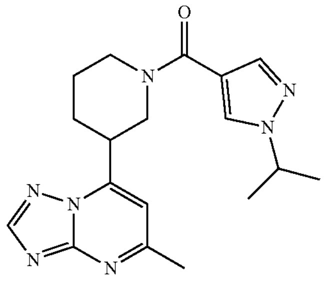 [SMILES: Cc1cc(C2CCCN(C(=O)c3cnn(C(C)C)c3)C2)n2ncnc2n1]

[M+H]=354.2.

Example 436. 1-[(2,4-Dichlorophenyl)carbonyl]-3-{5-methyl-[1,2,4]triazolo[1,5-a]pyrimidin-7-yl}piperidine

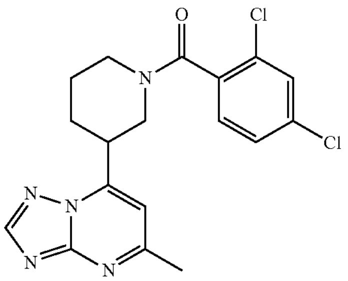 [SMILES: Cc1cc(C2CCCN(C(=O)c3ccc(Cl)cc3Cl)C2)n2ncnc2n1]

[M+H]=390.1.

Example 437. 1-{[1-Methyl-3-(propan-2-yl)-1H-pyrazol-5-yl]carbonyl}-3-{5-methyl-[1,2,4]triazolo[1,5-a]pyrimidin-7-yl}piperidine

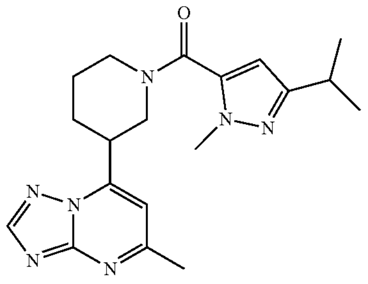 [SMILES: Cc1cc(C2CCCN(C(=O)c3cc(C(C)C)nn3C)C2)n2ncnc2n1]

[M+H]=368.2.

Example 438. 1-[(2,5-Dichlorophenyl)carbonyl]-3-{5-methyl-[1,2,4]triazolo[1,5-a]pyrimidin-7-yl}piperidine

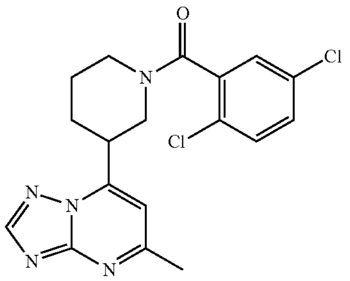 [SMILES: Cc1cc(C2CCCN(C(=O)c3cc(Cl)ccc3Cl)C2)n2ncnc2n1]

[M+H]=390.1.

Example 439. 3-{5-Methyl-[1,2,4]triazolo[1,5-a]pyrimidin-7-yl}-1-[(1-phenyl-1H-pyrazol-4-yl)carbonyl]piperidine

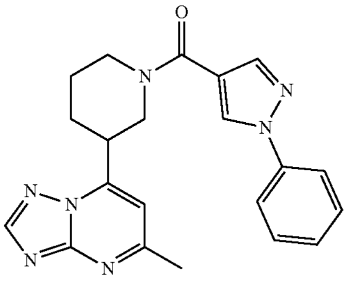 [SMILES: Cc1cc(C2CCCN(C(=O)c3cnn(-c4ccccc4)c3)C2)n2ncnc2n1]

[M+H]=388.2.

Example 440. 1-[(4-Chloro-2-fluorophenyl)carbonyl]-3-{5-methyl-[1,2,4]triazolo[1,5-a]pyrimidin-7-yl}piperidine

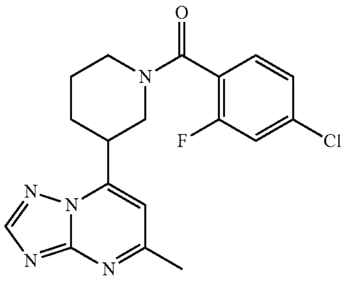 [SMILES: Cc1cc(C2CCCN(C(=O)c3ccc(Cl)cc3F)C2)n2ncnc2n1]

[M+H]=374.1.

Example 441. 1-[(5-Fluoro-2-methylphenyl)carbonyl]-3-{5-methyl-[1,2,4]triazolo[1,5-a]pyrimidin-7-yl}piperidine

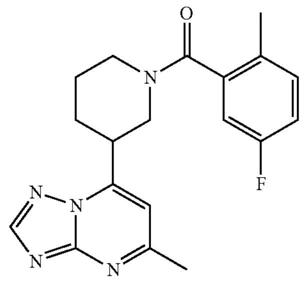

[M+H]=354.2.

Example 442. 1-[(3,4-Dimethoxyphenyl)carbonyl]-3-{5-methyl-[1,2,4]triazolo[1,5-a]pyrimidin-7-yl}piperidine

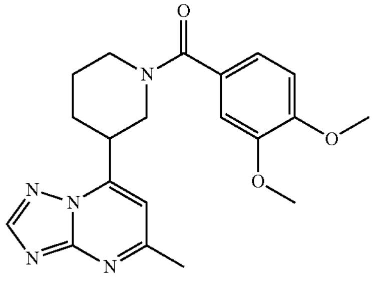 [SMILES: COc1ccc(C(=O)N2CCCC(c3cc(C)nc4ncnn34)C2)cc1OC]

[M+H]=382.2.

Example 443. 1-[(1-Ethyl-1H-pyrazol-5-yl)carbonyl]-3-{5-methyl-[1,2,4]triazolo[1,5-a]pyrimidin-7-yl}piperidine

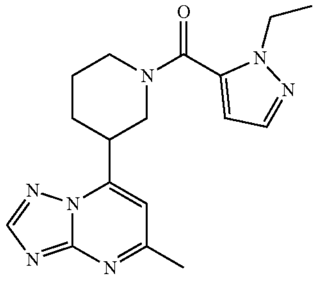 [SMILES: CCn1nccc1C(=O)N1CCCC(c2cc(C)nc3ncnn23)C1]

[M+H]=340.2.

Example 444. 1-[(4-Chlorophenyl)carbonyl]-3-{5-methyl-[1,2,4]triazolo[1,5-a]pyrimidin-7-yl}piperidine

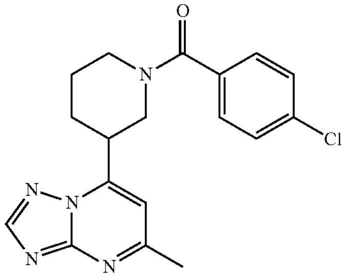 [SMILES: Cc1cc(C2CCCN(C(=O)c3ccc(Cl)cc3)C2)n2ncnc2n1]

[M+H]=356.1.

Example 445. 1-[(1-Methyl-3-phenyl-1H-pyrazol-5-yl)carbonyl]-3-{5-methyl-[1,2,4]triazolo[1,5-a]pyrimidin-7-yl}piperidine

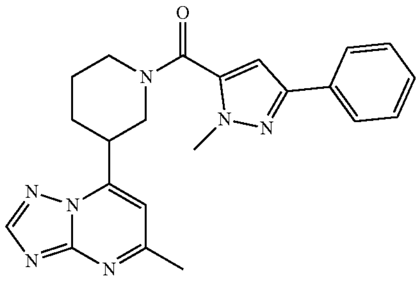

[M+H]=402.2.

Example 446. 1-[(1-Methoxynaphthalen-2-yl)carbonyl]-3-{5-methyl-[1,2,4]triazolo[1,5-a]pyrimidin-7-yl}piperidine

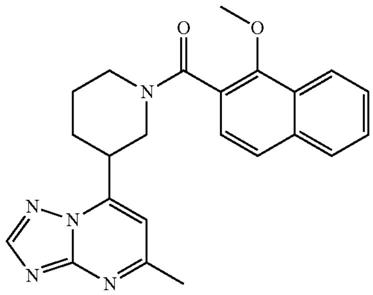 [SMILES: COc1c(C(=O)N2CCCC(c3cc(C)nc4ncnn34)C2)ccc2ccccc12]

[M+H]=402.2.

Example 447. 1-[(6-Methoxynaphthalen-2-yl)carbonyl]-3-{5-methyl-[1,2,4]triazolo[1,5-a]pyrimidin-7-yl}piperidine

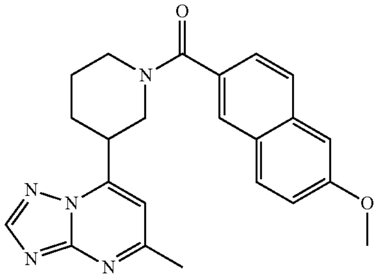 [SMILES: COc1ccc2cc(C(=O)N3CCCC(c4cc(C)nc5ncnn45)C3)ccc2c1]

[M+H]=402.2.

Example 448. 1-[(2H-1,3-Benzodioxol-5-yl)carbonyl]-3-{5-methyl-[1,2,4]triazolo[1,5-a]pyrimidin-7-yl}piperidine

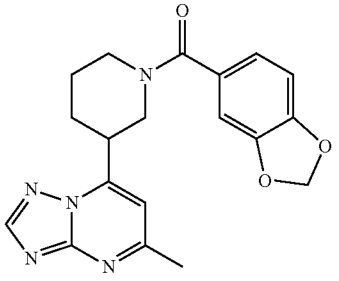

[M+H]=366.1.

Example 449. 1-[(3-Methoxynaphthalen-2-yl)carbonyl]-3-{5-methyl-[1,2,4]triazolo[1,5-a]pyrimidin-7-yl}piperidine

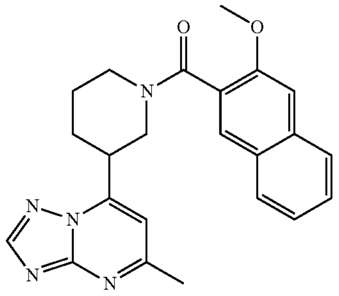 [SMILES: COc1cc2ccccc2cc1C(=O)N1CCCC(c2cc(C)nc3ncnn23)C1]

[M+H]=402.2.

Example 450. 3-{5-Methyl-[1,2,4]triazolo[1,5-a]pyrimidin-7-yl}-1-{[3-(propan-2-yl)phenyl]carbonyl}piperidine

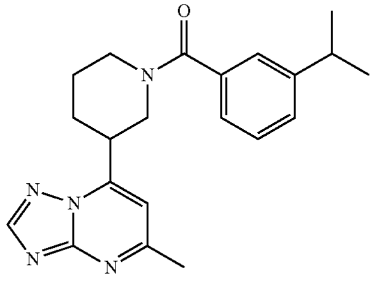

[M+H]=364.2.

Example 451. 1-[(2,3-Dimethoxyphenyl)carbonyl]-3-{5-methyl-[1,2,4]triazolo[1,5-a]pyrimidin-7-yl}piperidine

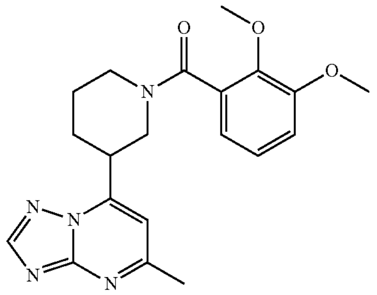 [SMILES: COc1cccc(C(=O)N2CCCC(c3cc(C)nc4ncnn34)C2)c1OC]

[M+H]=382.2.

Example 452. 1-[(1-Benzothiophen-5-yl)carbonyl]-3-{5-methyl-[1,2,4]triazolo[1,5-a]pyrimidin-7-yl}piperidine

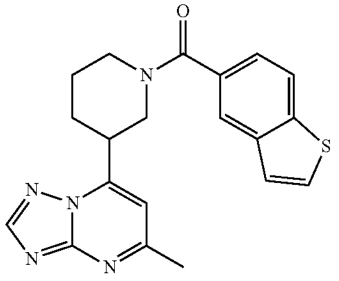 [SMILES: Cc1cc(C2CCCN(C(=O)c3ccc4sccc4c3)C2)n2ncnc2n1]

[M+H]=378.1.

Example 453. 1-[(2,3-Dihydro-1,4-benzodioxin-6-yl)carbonyl]-3-{5-methyl-[1,2,4]triazolo[1,5-a]pyrimidin-7-yl}piperidine

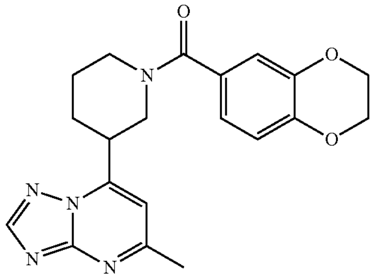 [SMILES: Cc1cc(C2CCCN(C(=O)c3ccc4c(c3)OCCO4)C2)n2ncnc2n1]

[M+H]=380.2.

Example 454. 1-[(2,4-Dimethylphenyl)carbonyl]-3-{5-methyl-[1,2,4]triazolo[1,5-a]pyrimidin-7-yl}piperidine

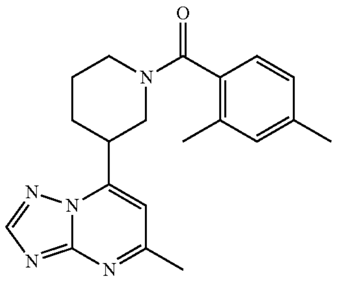 [SMILES: Cc1ccc(C(=O)N2CCCC(c3cc(C)nc4ncnn34)C2)c(C)c1]

[M+H]=350.2.

Example 455. 1-[(2-Methoxyphenyl)carbonyl]-3-{5-methyl-[1,2,4]triazolo[1,5-a]pyrimidin-7-yl}piperidine

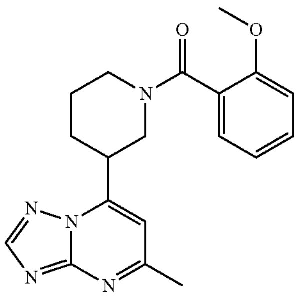 [SMILES: COc1ccccc1C(=O)N1CCCC(c2cc(C)nc3ncnn23)C1]

[M+H]=352.2.

Example 456. 1-[(2-Fluoro-5-methoxyphenyl)carbonyl]-3-{5-methyl-[1,2,4]triazolo[1,5-a]pyrimidin-7-yl}piperidine

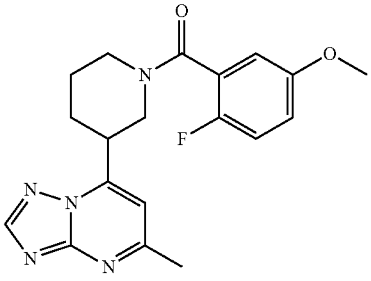 [SMILES: COc1ccc(F)c(C(=O)N2CCCC(c3cc(C)nc4ncnn34)C2)c1]

[M+H]=370.2.

Example 457. 1-[(1-Benzothiophen-2-yl)carbonyl]-3-{5-methyl-[1,2,4]triazolo[1,5-a]pyrimidin-7-yl}piperidine

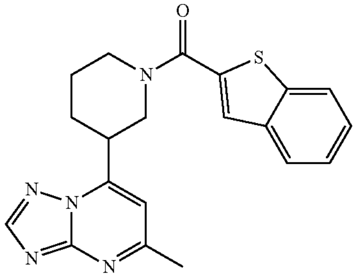 [SMILES: Cc1cc(C2CCCN(C(=O)c3cc4ccccc4s3)C2)n2ncnc2n1]

[M+H]=378.1.

Example 458. 3-{5-Methyl-[1,2,4]triazolo[1,5-a]pyrimidin-7-yl}-1-{[4-(propan-2-yl)phenyl]carbonyl}piperidine

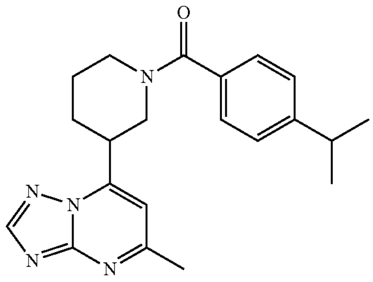 [SMILES: Cc1cc(C2CCCN(C(=O)c3ccc(C(C)C)cc3)C2)n2ncnc2n1]

[M+H]=364.2.

Example 459. 2-[(3-{5-Methyl-[1,2,4]triazolo[1,5-a]pyrimidin-7-yl}piperidin-1-yl)carbonyl]-1,3-benzothiazole

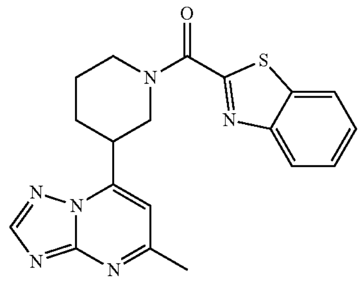 [SMILES: Cc1cc(C2CCCN(C(=O)c3nc4ccccc4s3)C2)n2ncnc2n1]

[M+H]=379.1.

Example 460. 1-[(5-Fluoro-2-methoxyphenyl)carbonyl]-3-{5-methyl-[1,2,4]triazolo[1,5-a]pyrimidin-7-yl}piperidine

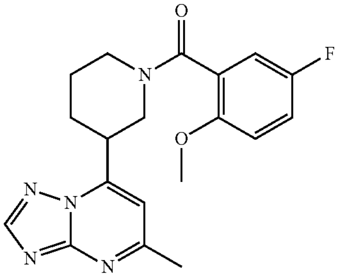 [SMILES: COc1ccc(F)cc1C(=O)N1CCCC(c2cc(C)nc3ncnn23)C1]

[M+H]=370.2.

Example 461. 3-{5-Methyl-[1,2,4]triazolo[1,5-a]pyrimidin-7-yl}-1-[(3-phenylphenyl)carbonyl]piperidine

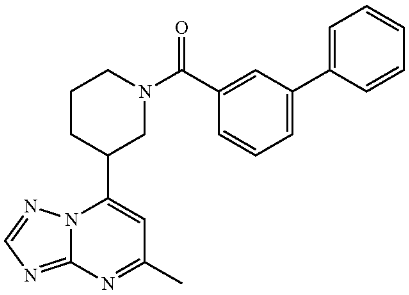 [SMILES: Cc1cc(C2CCCN(C(=O)c3cccc(-c4ccccc4)c3)C2)n2ncnc2n1]

[M+H]=398.2.

Example 462. 1-Methyl-3-[(3-{5-methyl-[1,2,4]triazolo[1,5-a]pyrimidin-7-yl}piperidin-1-yl)carbonyl]-1H-indazole

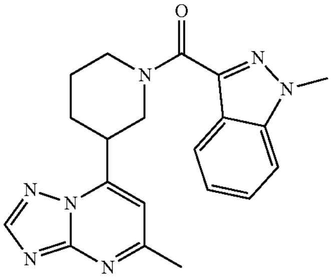 [SMILES: Cc1cc(C2CCCN(C(=O)c3nn(C)c4ccccc34)C2)n2ncnc2n1]

[M+H]=376.2.

Example 463. 1-[(1-Benzofuran-2-yl)carbonyl]-3-{5-methyl-[1,2,4]triazolo[1,5-a]pyrimidin-7-yl}piperidine

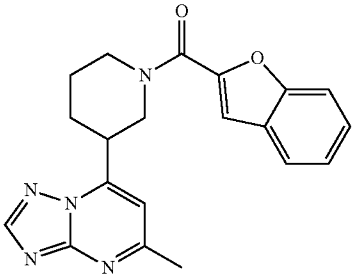 [SMILES: Cc1cc(C2CCCN(C(=O)c3cc4ccccc4o3)C2)n2ncnc2n1]

[M+H]=362.2.

Example 464. 1-[(3-Methoxyphenyl)carbonyl]-3-{5-methyl-[1,2,4]triazolo[1,5-a]pyrimidin-7-yl}piperidine

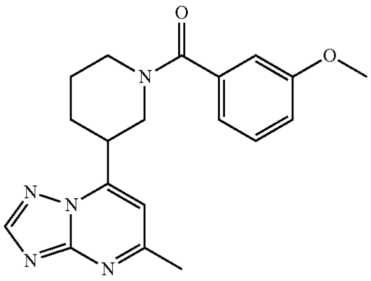 [SMILES: COc1cccc(C(=O)N2CCCC(c3cc(C)nc4ncnn34)C2)c1]

[M+H]=352.2.

Example 465. 1-Methyl-2-[(3-{5-methyl-[1,2,4]triazolo[1,5-a]pyrimidin-7-yl}piperidin-1-yl)carbonyl]-1H-indole

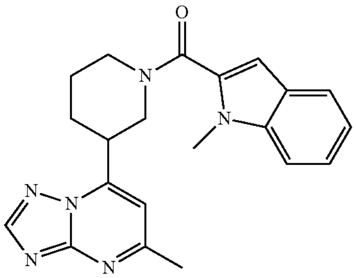 [SMILES: Cc1cc(C2CCCN(C(=O)c3cc4ccccc4n3C)C2)n2ncnc2n1]

[M+H]=375.2.

Example 466. 1-[(2,5-Dimethylphenyl)carbonyl]-3-{5-methyl-[1,2,4]triazolo[1,5-a]pyrimidin-7-yl}piperidine

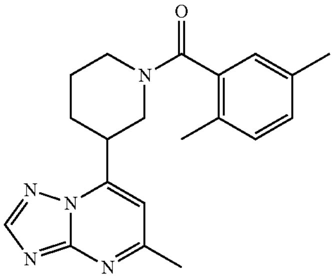 [SMILES: Cc1ccc(C)c(C(=O)N2CCCC(c3cc(C)nc4ncnn34)C2)c1]

[M+H]=350.2.

Example 467. 1-[(4-Fluoro-2-methoxyphenyl)carbonyl]-3-{5-methyl-[1,2,4]triazolo[1,5-a]pyrimidin-7-yl}piperidine

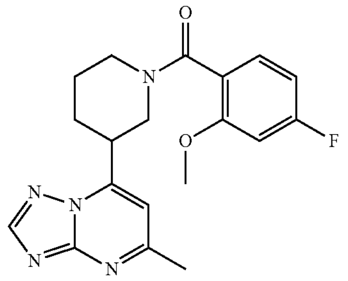 [SMILES: COc1cc(F)ccc1C(=O)N1CCCC(c2cc(C)nc3ncnn23)C1]

[M+H]=370.2.

Example 468. 1-[(3-Fluoro-2-methoxyphenyl)carbonyl]-3-{5-methyl-[1,2,4]triazolo[1,5-a]pyrimidin-7-yl}piperidine

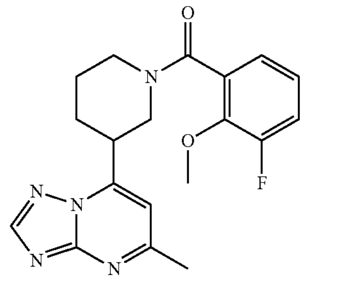

[M+H]=370.2.

Example 469. 1-[(3-Fluoro-2-methylphenyl)carbonyl]-3-{5-methyl-[1,2,4]triazolo[1,5-a]pyrimidin-7-yl}piperidine

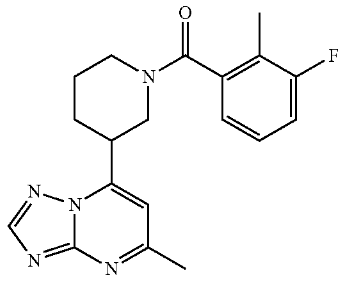 [SMILES: Cc1cc(C2CCCN(C(=O)c3cccc(F)c3C)C2)n2ncnc2n1]

[M+H]=354.2.

Example 470. 1-[(1-Benzothiophen-3-yl)carbonyl]-3-{5-methyl-[1,2,4]triazolo[1,5-a]pyrimidin-7-yl}piperidine

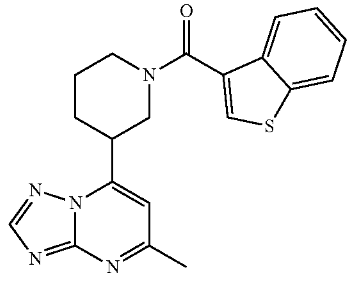 [SMILES: Cc1cc(C2CCCN(C(=O)c3csc4ccccc34)C2)n2ncnc2n1]

[M+H]=378.1.

Example 471. 1-[(3-Chloro-5-fluorophenyl)carbonyl]-3-{5-methyl-[1,2,4]triazolo[1,5-a]pyrimidin-7-yl}piperidine

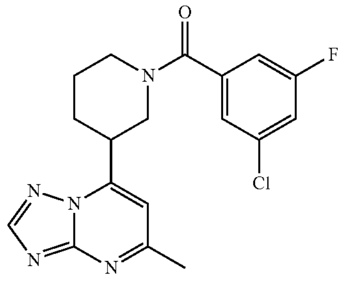 [SMILES: Cc1cc(C2CCCN(C(=O)c3cc(F)cc(Cl)c3)C2)n2ncnc2n1]

[M+H]=374.1.

Example 472. 1-[(2,6-Difluorophenyl)carbonyl]-3-{5-methyl-[1,2,4]triazolo[1,5-a]pyrimidin-7-yl}piperidine

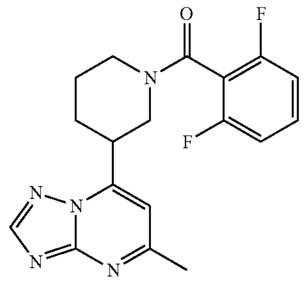 [SMILES: Cc1cc(C2CCCN(C(=O)c3c(F)cccc3F)C2)n2ncnc2n1]

[M+H]=358.1.

Example 473. 1-[(Dimethyl-1,3-thiazol-5-yl)carbonyl]-3-{5-methyl-[1,2,4]triazolo[1,5-a]pyrimidin-7-yl}piperidine

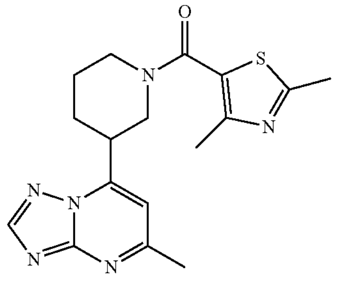 [SMILES: Cc1cc(C2CCCN(C(=O)c3sc(C)nc3C)C2)n2ncnc2n1]

[M+H]=357.1.

Example 474. 1-[(5-Chloro-2-fluorophenyl)carbonyl]-3-{5-methyl-[1,2,4]triazolo[1,5-a]pyrimidin-7-yl}piperidine

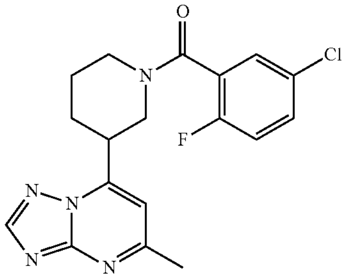 [SMILES: Cc1cc(C2CCCN(C(=O)c3cc(Cl)ccc3F)C2)n2ncnc2n1]

[M+H]=374.1.

Example 475. 1-[(4-Fluoro-3-methylphenyl)carbonyl]-3-{5-methyl-[1,2,4]triazolo[1,5-a]pyrimidin-7-yl}piperidine

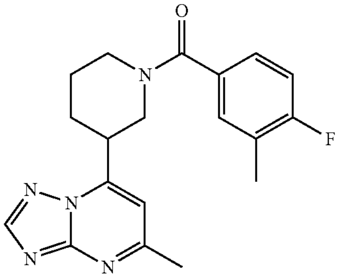 [SMILES: Cc1cc(C2CCCN(C(=O)c3ccc(F)c(C)c3)C2)n2ncnc2n1]

[M+H]=354.2.

Example 476. 2-[(3-{5-Methyl-[1,2,4]triazolo[1,5-a]pyrimidin-7-yl}piperidin-1-yl)carbonyl]benzonitrile

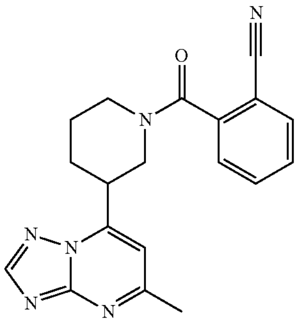 [SMILES: Cc1cc(C2CCCN(C(=O)c3ccccc3C#N)C2)n2ncnc2n1]

[M+H]=347.2.

Example 477. 2-Methyl-3-[(3-{5-methyl-[1,2,4]triazolo[1,5-a]pyrimidin-7-yl}piperidin-1-yl)carbonyl]-2H-indazole

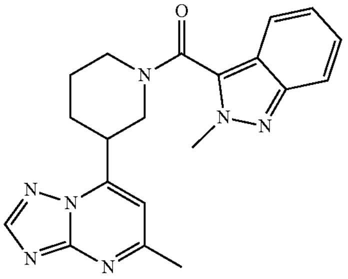 [SMILES: Cc1cc(C2CCCN(C(=O)c3c4ccccc4nn3C)C2)n2ncnc2n1]

[M+H]=376.2.

Example 478. 2-Methyl-5-[(3-{5-methyl-[1,2,4]triazolo[1,5-a]pyrimidin-7-yl}piperidin-1-yl)carbonyl]pyridine

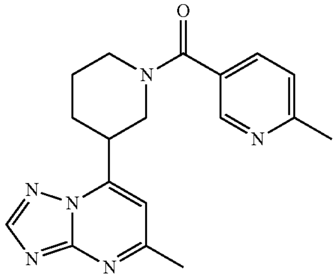 [SMILES: Cc1ccc(C(=O)N2CCCC(c3cc(C)nc4ncnn34)C2)cn1]

[M+H]=337.2.

Example 479. 1-Benzoyl-3-{5-methyl-[1,2,4]triazolo[1,5-a]pyrimidin-7-yl}piperidine

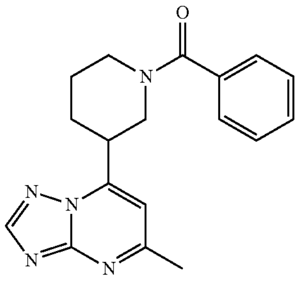 [SMILES: Cc1cc(C2CCCN(C(=O)c3ccccc3)C2)n2ncnc2n1]

[M+H]=322.2.

Example 480. 1-[(4-Chloro-3-fluorophenyl)carbonyl]-3-{5-methyl-[1,2,4]triazolo[1,5-a]pyrimidin-7-yl}piperidine

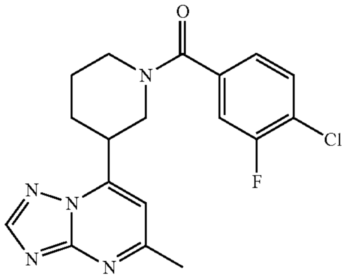 [SMILES: Cc1cc(C2CCCN(C(=O)c3ccc(Cl)c(F)c3)C2)n2ncnc2n1]

[M+H]=374.1.

Example 481. 1-[(4-Methoxy-3-methylphenyl)carbonyl]-3-{5-methyl-[1,2,4]triazolo[1,5-a]pyrimidin-7-yl}piperidine

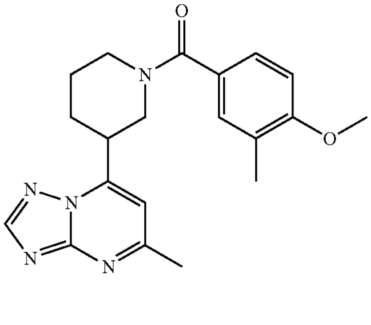 [SMILES: COc1ccc(C(=O)N2CCCC(c3cc(C)nc4ncnn34)C2)cc1C]

Example 482. 1-[(2-Chloro-5-fluorophenyl)carbonyl]-3-{5-methyl-[1,2,4]triazolo[1,5-a]pyrimidin-7-yl}piperidine

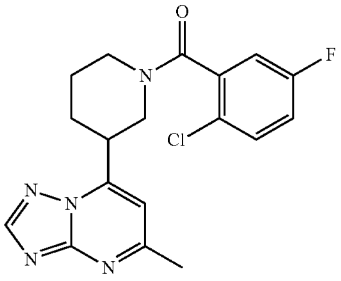 [SMILES: Cc1cc(C2CCCN(C(=O)c3cc(F)ccc3Cl)C2)n2ncnc2n1]

[M+H]=374.1.

Example 483. 1-[(3-Chloro-2-fluorophenyl)carbonyl]-3-{5-methyl-[1,2,4]triazolo[1,5-a]pyrimidin-7-yl}piperidine

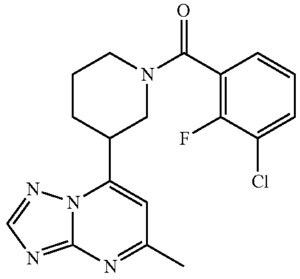 [SMILES: Cc1cc(C2CCCN(C(=O)c3cccc(Cl)c3F)C2)n2ncnc2n1]

[M+H]=374.1.

Example 484. 1-[(4-Fluoro-2-methylphenyl)carbonyl]-3-{5-methyl-[1,2,4]triazolo[1,5-a]pyrimidin-7-yl}piperidine

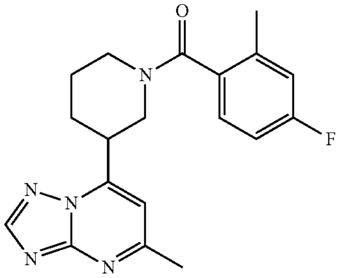 [SMILES: Cc1cc(C2CCCN(C(=O)c3ccc(F)cc3C)C2)n2ncnc2n1]

[M+H]=354.2.

Example 485. 1-[(2,4-Difluorophenyl)carbonyl]-3-{5-methyl-[1,2,4]triazolo[1,5-a]pyrimidin-7-yl}piperidine

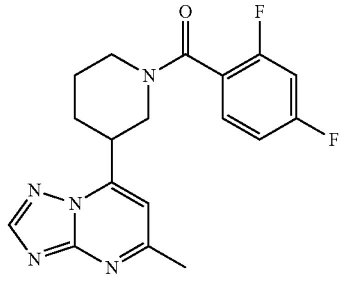 [SMILES: Cc1cc(C2CCCN(C(=O)c3ccc(F)cc3F)C2)n2ncnc2n1]

[M+H]=358.1.

Example 486. 1-[(3,4-Difluorophenyl)carbonyl]-3-{5-methyl-[1,2,4]triazolo[1,5-a]pyrimidin-7-yl}piperidine

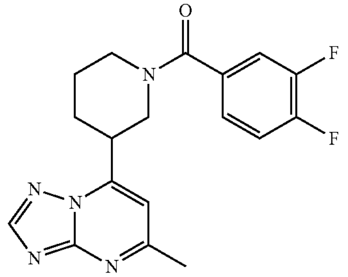 [SMILES: Cc1cc(C2CCCN(C(=O)c3ccc(F)c(F)c3)C2)n2ncnc2n1]

[M+H]=358.1.

Example 487. 1-[(2,3-Dimethylphenyl)carbonyl]-3-{5-methyl-[1,2,4]triazolo[1,5-a]pyrimidin-7-yl}piperidine

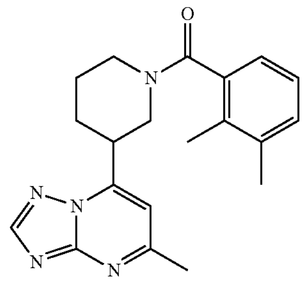 [SMILES: Cc1cc(C2CCCN(C(=O)c3cccc(C)c3C)C2)n2ncnc2n1]

[M+H]=350.2.

Example 488. 1-[(2-Chloro-3-methylphenyl)carbonyl]-3-{5-methyl-[1,2,4]triazolo[1,5-a]pyrimidin-7-yl}piperidine

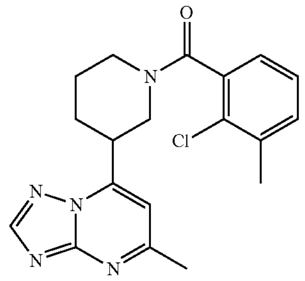 [SMILES: Cc1cc(C2CCCN(C(=O)c3cccc(C)c3Cl)C2)n2ncnc2n1]

[M+H]=370.1

Example 489. 1-{[4-(Difluoromethyl)phenyl]carbonyl}-3-{5-methyl-[1,2,4]triazolo[1,5-a]pyrimidin-7-yl}piperidine

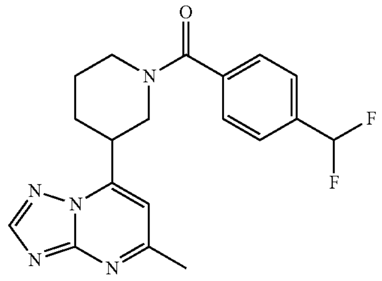 [SMILES: Cc1cc(C2CCCN(C(=O)c3ccc(C(F)F)cc3)C2)n2ncnc2n1]

[M+H]=372.2.

Example 490. 4-[(3-{5-Methyl-[1,2,4]triazolo[1,5-a]pyrimidin-7-yl}piperidin-1-yl)carbonyl]benzonitrile

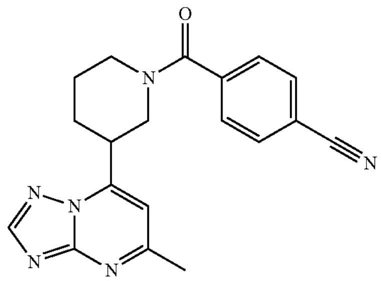 [SMILES: Cc1cc(C2CCCN(C(=O)c3ccc(C#N)cc3)C2)n2ncnc2n1]

[M+H]=347.2.

Example 491. 1-[(4-Methoxy-2-methylphenyl)carbonyl]-3-{5-methyl-[1,2,4]triazolo[1,5-a]pyrimidin-7-yl}piperidine

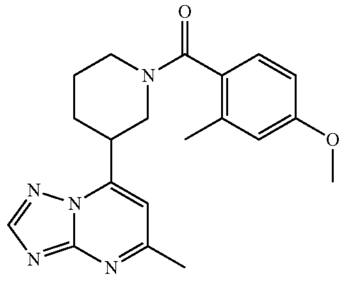 [SMILES: COc1ccc(C(=O)N2CCCC(c3cc(C)nc4ncnn34)C2)c(C)c1]

[M+H]=366.2.

Example 492. 1-[(2-Fluoro-5-methylphenyl)carbonyl]-3-{5-methyl-[1,2,4]triazolo[1,5-a]pyrimidin-7-yl}piperidine

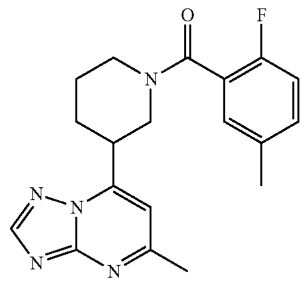 [SMILES: Cc1ccc(F)c(C(=O)N2CCCC(c3cc(C)nc4ncnn34)C2)c1]

[M+H]=354.2.

Example 493. 3-{5-Methyl-[1,2,4]triazolo[1,5-a]pyrimidin-7-yl}-1-[(4-phenylphenyl)carbonyl]piperidine

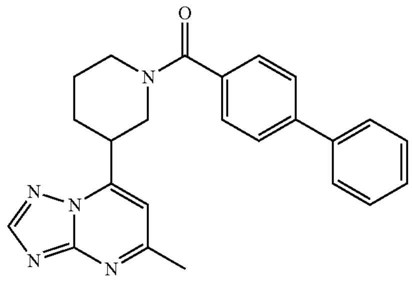 [SMILES: Cc1cc(C2CCCN(C(=O)c3ccc(-c4ccccc4)cc3)C2)n2ncnc2n1]

[M+H]=398.2.

Example 494. 1-[(2,6-Dimethylphenyl)carbonyl]-3-{5-methyl-[1,2,4]triazolo[1,5-a]pyrimidin-7-yl}piperidine

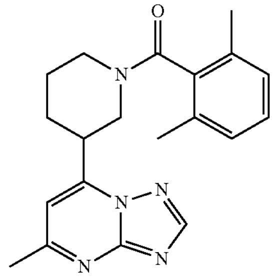 [SMILES: Cc1cc(C2CCCN(C(=O)c3c(C)cccc3C)C2)n2ncnc2n1]

$^1$H NMR (400 MHz, $CDCl_3$) δ=8.27-8.61 (m, 1H), 7.03-7.24 (m, 3H), 6.75-6.97 (m, 1H), 4.80-5.04 (m, 1H), 3.53-4.01 (m, 2H), 2.87-3.52 (m, 2H), 2.66-2.78 (m, 5H), 2.27-2.49 (m, 4H), 2.03-2.25 (m, 3H), 1.60-2.02 (m, 2H); [M+H]= 350.1.

Example 495. 1-[(2-Chloro-6-fluorophenyl)carbonyl]-3-{5-methyl-[1,2,4]triazolo[1,5-a]pyrimidin-7-yl}piperidine

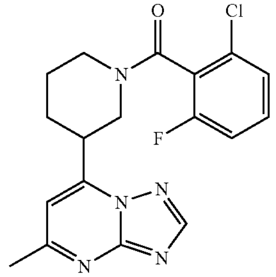

$^1$H NMR (400 MHz, $CDCl_3$) δ=8.23-8.65 (m, 1H), 7.28-7.41 (m, 2H), 7.15 (d, J=11.04 Hz, 1H), 6.80-7.12 (m, 1H), 4.40-4.89 (m, 1H), 3.95-4.21 (m, 1H), 3.59-3.87 (m, 1H), 2.91-3.52 (m, 2H), 2.71-2.76 (m, 4H), 2.31 (br s, 2H), 1.67-1.95 (m, 1H); [M+H]=374.0.

Example 496. 1-[(2-Fluoro-6-methoxyphenyl)carbonyl]-3-{5-methyl-[1,2,4]triazolo[1,5-a]pyrimidin-7-yl}piperidine

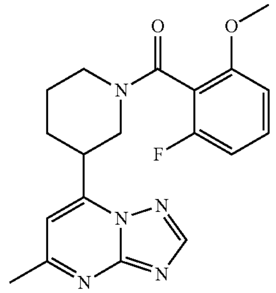

$^1$H NMR (400 MHz, $CDCl_3$) δ=8.22-8.65 (m, 1H), 7.28-7.41 (m, 1H), 6.85-7.20 (m, 1H), 6.58-6.84 (m, 2H), 4.30-4.75 (m, 1H) 3.98-4.27 (m, 1H), 3.60-3.96 (m, 4H), 3.13-3.54 (m, 2H), 2.72-2.76 (m, 4H), 1.81-2.38 (m, 3H), 1.81-2.38 (m, 3H), 1.56-1.78 (m, 1H); [M+H]=370.1.

Example 497. 1-[(2-Chloro-6-methylphenyl)carbonyl]-3-{5-methyl-[1,2,4]triazolo[1,5-a]pyrimidin-7-yl}piperidine

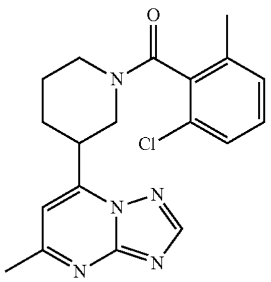 [SMILES: Cc1cc(C2CCCN(C(=O)c3c(C)cccc3Cl)C2)n2ncnc2n1]

$^1$H NMR (400 MHz, $CDCl_3$) δ=8.29-8.67 (m, 1H), 7.27-7.37 (m, 1H), 7.10-7.26 (m, 2H), 6.81-7.10 (m, 1H), 4.43-5.02 (m, 1H) 3.67-4.20 (m, 2H), 3.31-3.64 (m, 1H), 2.91-3.28 (m, 1H), 2.67-2.79 (m, 3H), 2.50 (s, 1H), 2.27-2.42 (m, 3H), 2.17 (s, 1H), 1.81-2.10 (m, 1H), 1.57-1.80 (m, 1H); [M+H]=370.1.

Example 498. 2-(3,3-Difluoro-5-{5-methyl-[1,2,4]triazolo[1,5-a]pyrimidin-7-yl}piperidine-1-carbonyl)-1-methyl-1H-indole

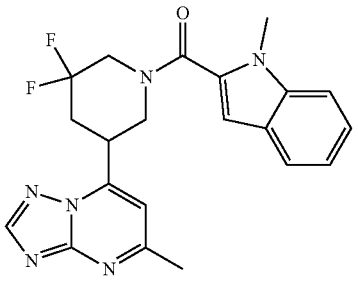 [SMILES: Cc1cc(C2CN(C(=O)c3cc4ccccc4n3C)CC(F)(F)C2)n2ncnc2n1]

[M+H]=411.5.

Example 499. 1-(1-Benzofuran-5-carbonyl)-3,3-difluoro-5-{5-methyl-[1,2,4]triazolo[1,5-a]pyrimidin-7-yl}piperidine

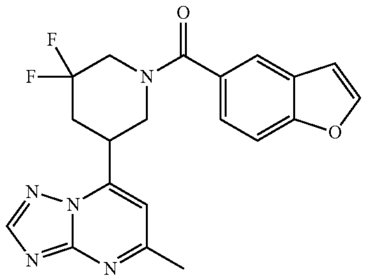 [SMILES: Cc1cc(C2CN(C(=O)c3ccc4occc4c3)CC(F)(F)C2)n2ncnc2n1]

[M+H]=398.4.

Example 500. 3,3-Difluoro-1-(4-methoxy-2-methylbenzoyl)-5-{5-methyl-[1,2,4]triazolo[1,5-a]pyrimidin-7-yl}piperidine

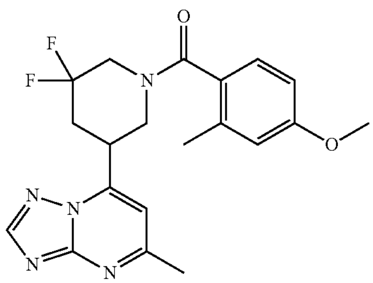 [SMILES: COc1ccc(C(=O)N2CC(c3cc(C)nc4ncnn34)CC(F)(F)C2)c(C)c1]

[M+H]=402.5.

Example 501. 3,3-Difluoro-5-{5-methyl-[1,2,4]triazolo[1,5-a]pyrimidin-7-yl}-1-(5,6,7,8-tetrahydronaphthalene-2-carbonyl)piperidine

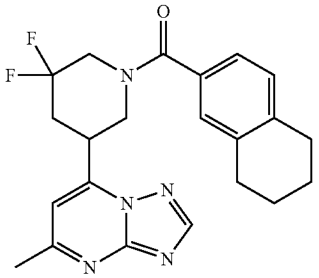 [SMILES: Cc1cc(C2CN(C(=O)c3ccc4c(c3)CCCC4)CC(F)(F)C2)n2ncnc2n1]

[M+H]=412.5.

Example 502. 3-(3,3-Difluoro-5-{5-methyl-[1,2,4]triazolo[1,5-a]pyrimidin-7-yl}piperidine-1-carbonyl)-1-methyl-1H-indole

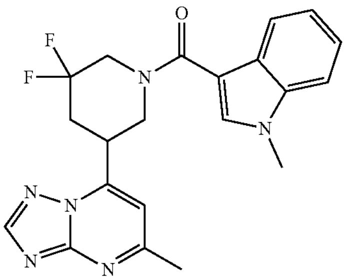 [SMILES: Cc1cc(C2CN(C(=O)c3cn(C)c4ccccc34)CC(F)(F)C2)n2ncnc2n1]

[M+H]=411.4.

Example 503. 1-(1-Benzothiophene-5-carbonyl)-3,3-difluoro-5-{5-methyl-[1,2,4]triazolo[1,5-a]pyrimidin-7-yl}piperidine

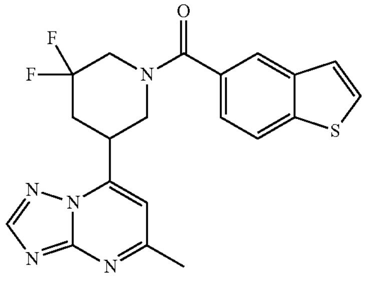 [SMILES: Cc1cc(C2CN(C(=O)c3ccc4sccc4c3)CC(F)(F)C2)n2ncnc2n1]

[M+H]=414.4.

Example 504. 1-(3-Chloro-5-fluorobenzoyl)-3,3-difluoro-5-{5-methyl-[1,2,4]triazolo[1,5-a]pyrimidin-7-yl}piperidine

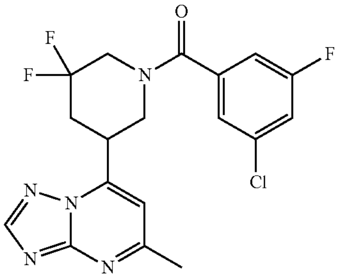 [SMILES: Cc1cc(C2CN(C(=O)c3cc(F)cc(Cl)c3)CC(F)(F)C2)n2ncnc2n1]

[M+H]=410.4.

Example 505. 3,3-Difluoro-5-{5-methyl-[1,2,4]triazolo[1,5-a]pyrimidin-7-yl}-1-(4-phenylbenzoyl)piperidine

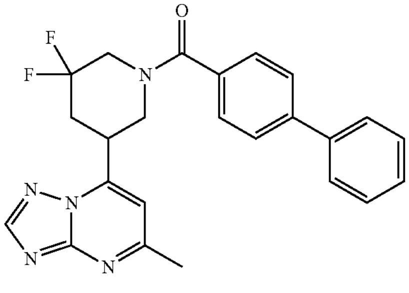 [SMILES: Cc1cc(C2CN(C(=O)c3ccc(-c4ccccc4)cc3)CC(F)(F)C2)n2ncnc2n1]

[M+H]=434.5.

Example 506. 3,3-Difluoro-1-(2-methoxy-4-methylbenzoyl)-5-{5-methyl-[1,2,4]triazolo[1,5-a]pyrimidin-7-yl}piperidine

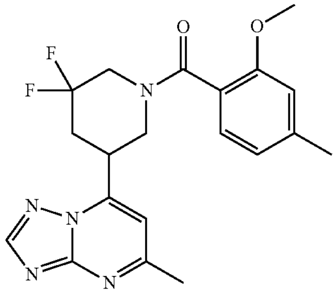 [SMILES: COc1cc(C)ccc1C(=O)N1CC(c2cc(C)nc3ncnn23)CC(F)(F)C1]

[M+H]=402.5.

Example 507. 3,3-Difluoro-1-{imidazo[1,2-a]pyridine-6-carbonyl}-5-{5-methyl-[1,2,4]triazolo[1,5-a]pyrimidin-7-yl}piperidine

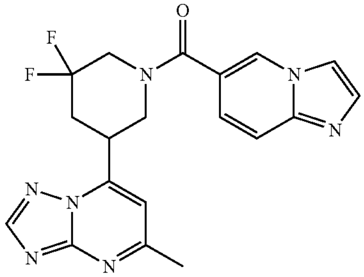 [SMILES: Cc1cc(C2CN(C(=O)c3ccc4nccn4c3)CC(F)(F)C2)n2ncnc2n1]

[M+H]=398.4.

Example 508. 2-(3,3-Difluoro-5-{5-methyl-[1,2,4]triazolo[1,5-a]pyrimidin-7-yl}piperidine-1-carbonyl)quinoxaline

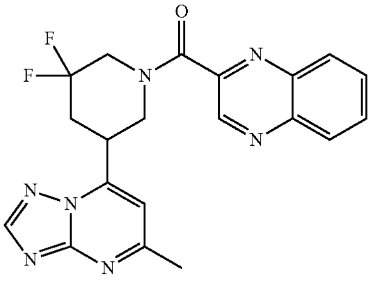 [SMILES: Cc1cc(C2CN(C(=O)c3cnc4ccccc4n3)CC(F)(F)C2)n2ncnc2n1]

[M+H]=410.4.

Example 509. 3,3-Difluoro-1-{imidazo[1,2-a]pyridine-2-carbonyl}-5-{5-methyl-[1,2,4]triazolo[1,5-a]pyrimidin-7-yl}piperidine

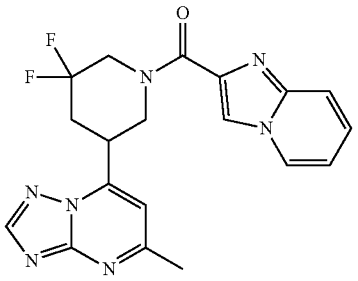 [SMILES: Cc1cc(C2CN(C(=O)c3cn4ccccc4n3)CC(F)(F)C2)n2ncnc2n1]

[M+H]=398.4.

Example 510. 1-(1-Benzothiophene-3-carbonyl)-3,3-difluoro-5-{5-methyl-[1,2,4]triazolo[1,5-a]pyrimidin-7-yl}piperidine

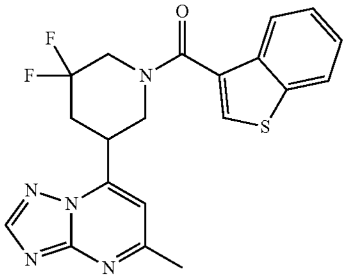 [SMILES: Cc1cc(C2CN(C(=O)c3csc4ccccc34)CC(F)(F)C2)n2ncnc2n1]

[M+H]=414.4.

Example 511. 3,3-Difluoro-1-(2-methoxy-5-methylbenzoyl)-5-{5-methyl-[1,2,4]triazolo[1,5-a]pyrimidin-7-yl}piperidine

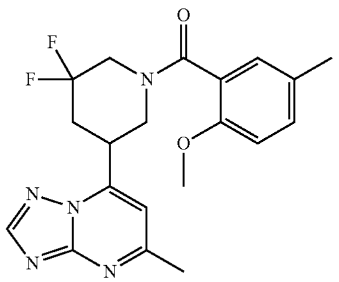 [SMILES: COc1ccc(C)cc1C(=O)N1CC(c2cc(C)nc3ncnn23)CC(F)(F)C1]

[M+H]=402.4.

Example 512. 1-[4-(Difluoromethyl)benzoyl]-3,3-difluoro-5-{5-methyl-[1,2,4]triazolo[1,5-a]pyrimidin-7-yl}piperidine

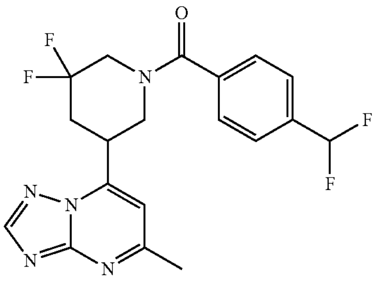 [SMILES: Cc1cc(C2CN(C(=O)c3ccc(C(F)F)cc3)CC(F)(F)C2)n2ncnc2n1]

[M+H]=408.4.

Example 513. 1-(3,4-Dimethoxybenzoyl)-3,3-difluoro-5-{5-methyl-[1,2,4]triazolo[1,5-a]pyrimidin-7-yl}piperidine

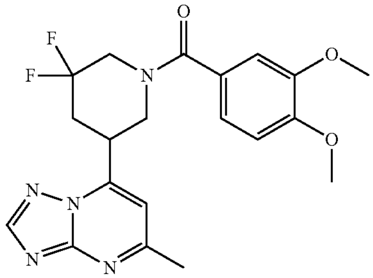 [SMILES: COc1ccc(C(=O)N2CC(c3cc(C)nc4ncnn34)CC(F)(F)C2)cc1OC]

[M+H]=418.5.

Example 514. 1-(5-Chloro-2-fluorobenzoyl)-3,3-difluoro-5-{5-methyl-[1,2,4]triazolo[1,5-a]pyrimidin-7-yl}piperidine

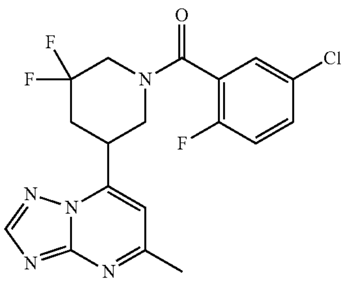 [SMILES: Cc1cc(C2CN(C(=O)c3cc(Cl)ccc3F)CC(F)(F)C2)n2ncnc2n1]

[M+H]=410.4.

Example 515. 3,3-Difluoro-1-(4-fluoro-3-methylbenzoyl)-5-{5-methyl-[1,2,4]triazolo[1,5-a]pyrimidin-7-yl}piperidine

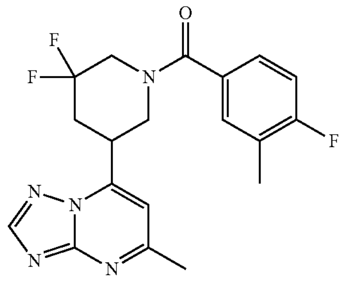 [SMILES: Cc1cc(C2CN(C(=O)c3ccc(F)c(C)c3)CC(F)(F)C2)n2ncnc2n1]

[M+H]=390.4.

Example 516. 3,3-Difluoro-1-(4-methoxy-3-methylbenzoyl)-5-{5-methyl-[1,2,4]triazolo[1,5-a]pyrimidin-7-yl}piperidine

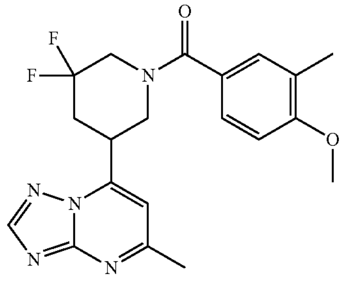

[M+H]=402.5.

Example 517. 3,3-Difluoro-1-(3-methoxybenzoyl)-5-{5-methyl-[1,2,4]triazolo[1,5-a]pyrimidin-7-yl}piperidine

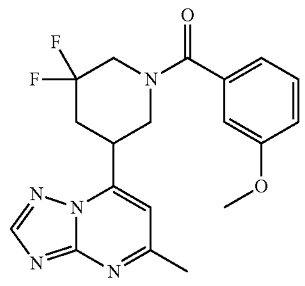 [SMILES: COc1cccc(C(=O)N2CC(c3cc(C)nc4ncnn34)CC(F)(F)C2)c1]

[M+H]=388.4.

Example 518. 1-(2H-1,3-Benzodioxole-5-carbonyl)-3,3-difluoro-5-{5-methyl-[1,2,4]triazolo[1,5-a]pyrimidin-7-yl}piperidine

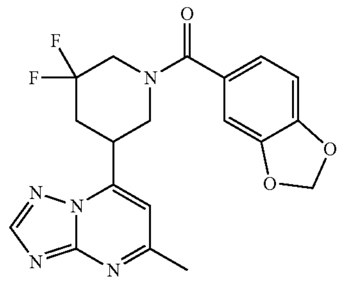 [SMILES: Cc1cc(C2CN(C(=O)c3ccc4c(c3)OCO4)CC(F)(F)C2)n2ncnc2n1]

[M+H]=402.4.

Example 519. 1-(2,3-Dihydro-1,4-benzodioxine-6-carbonyl)-3,3-difluoro-5-{5-methyl-[1,2,4]triazolo[1,5-a]pyrimidin-7-yl}piperidine

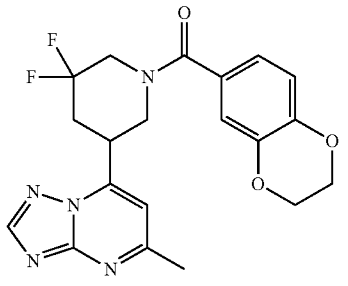 [SMILES: Cc1cc(C2CN(C(=O)c3ccc4c(c3)OCCO4)CC(F)(F)C2)n2ncnc2n1]

[M+H]=416.4.

Example 520. 3,3-Difluoro-1-(3-methoxynaphthalene-2-carbonyl)-5-{5-methyl-[1,2,4]triazolo[1,5-a]pyrimidin-7-yl}piperidine

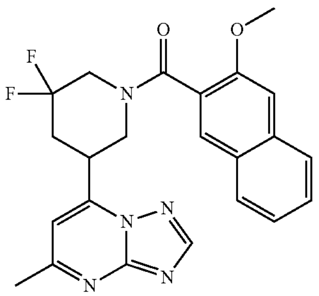 [SMILES: COc1cc2ccccc2cc1C(=O)N1CC(c2cc(C)nc3ncnn23)CC(F)(F)C1]

[M+H]=438.5.

Example 521. 3,3-Difluoro-5-{5-methyl-[1,2,4]triazolo[1,5-a]pyrimidin-7-yl}-1-[4-(propan-2-yl)benzoyl]piperidine

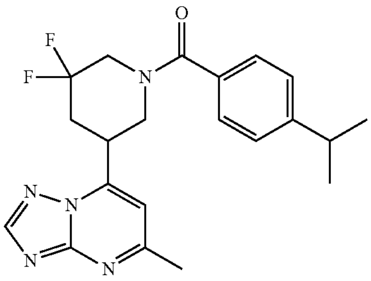 [SMILES: Cc1cc(C2CN(C(=O)c3ccc(C(C)C)cc3)CC(F)(F)C2)n2ncnc2n1]

[M+H]=400.5.

Example 522. 3,3-Difluoro-1-(2-fluoro-5-methylbenzoyl)-5-{5-methyl-[1,2,4]triazolo[1,5-a]pyrimidin-7-yl}piperidine

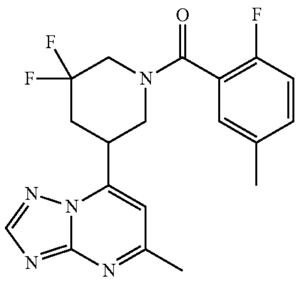 [SMILES: Cc1ccc(F)c(C(=O)N2CC(c3cc(C)nc4ncnn34)CC(F)(F)C2)c1]

[M+H]=390.4.

Example 523. 3,3-Difluoro-1-(3-fluoro-5-methoxybenzoyl)-5-{5-methyl-[1,2,4]triazolo[1,5-a]pyrimidin-7-yl}piperidine

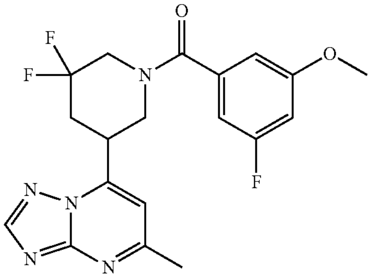 [SMILES: COc1cc(F)cc(C(=O)N2CC(c3cc(C)nc4ncnn34)CC(F)(F)C2)c1]

[M+H]=406.4.

Example 524. 1-(2,3-Dihydro-1H-indene-5-carbonyl)-3,3-difluoro-5-{5-methyl-[1,2,4]triazolo[1,5-a]pyrimidin-7-yl}piperidine

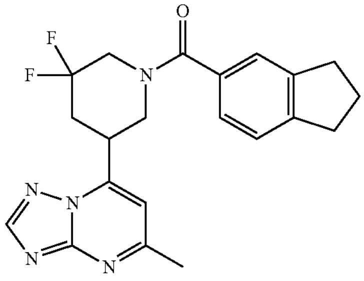 [SMILES: Cc1cc(C2CN(C(=O)c3ccc4c(c3)CCC4)CC(F)(F)C2)n2ncnc2n1]

[M+H]=398.5.

Example 525. 3,3-Difluoro-1-(1-methoxynaphthalene-2-carbonyl)-5-{5-methyl-[1,2,4]triazolo[1,5-a]pyrimidin-7-yl}piperidine

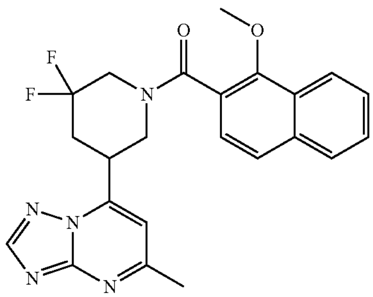 [SMILES: COc1c(C(=O)N2CC(c3cc(C)nc4ncnn34)CC(F)(F)C2)ccc2ccccc12]

[M+H]=438.5.

Example 526. 3,3-Difluoro-1-(6-methoxynaphthalene-2-carbonyl)-5-{5-methyl-[1,2,4]triazolo[1,5-a]pyrimidin-7-yl}piperidine

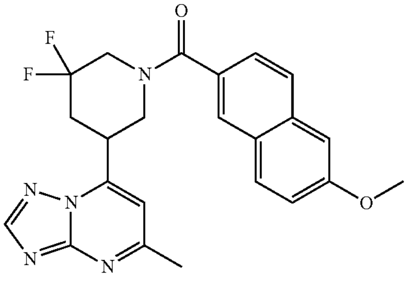 [SMILES: COc1ccc2cc(C(=O)N3CC(c4cc(C)nc5ncnn45)CC(F)(F)C3)ccc2c1]

[M+H]=438.5.

Example 527. 3,3-Difluoro-1-(1-methyl-3-phenyl-1H-pyrazole-5-carbonyl)-5-{5-methyl-[1,2,4]triazolo[1,5-a]pyrimidin-7-yl}piperidine

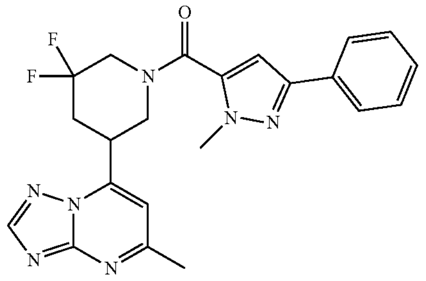 [SMILES: Cc1cc(C2CN(C(=O)c3cc(-c4ccccc4)nn3C)CC(F)(F)C2)n2ncnc2n1]

[M+H]=438.5.

Example 528. 3,3-Difluoro-1-(6-fluoronaphthalene-2-carbonyl)-5-{5-methyl-[1,2,4]triazolo[1,5-a]pyrimidin-7-yl}piperidine

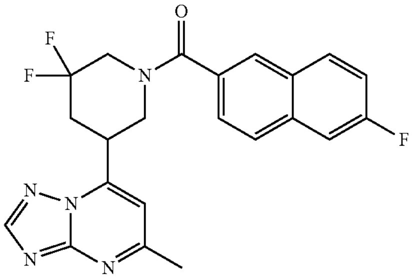 [SMILES: Cc1cc(C2CN(C(=O)c3ccc4cc(F)ccc4c3)CC(F)(F)C2)n2ncnc2n1]

[M+H]=426.5.

Example 529. 2-(3,3-Difluoro-5-{5-methyl-[1,2,4]triazolo[1,5-a]pyrimidin-7-yl}piperidine-1-carbonyl)-1,3-benzothiazole

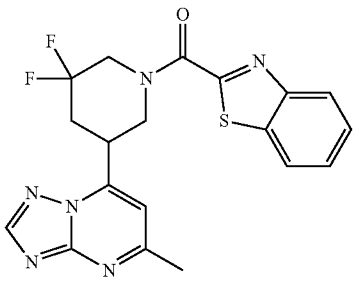 [SMILES: Cc1cc(C2CN(C(=O)c3nc4ccccc4s3)CC(F)(F)C2)n2ncnc2n1]

[M+H]=415.4.

Example 530. 1-(2,2-Difluoro-2H-1,3-benzodioxole-5-carbonyl)-3,3-difluoro-5-{5-methyl-[1,2,4]triazolo[1,5-a]pyrimidin-7-yl}piperidine

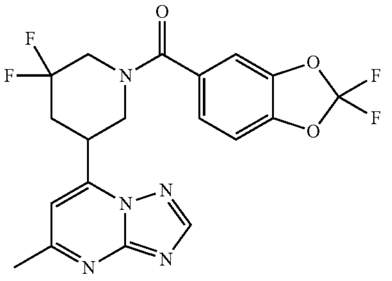 [SMILES: Cc1cc(C2CN(C(=O)c3ccc4c(c3)OC(F)(F)O4)CC(F)(F)C2)n2ncnc2n1]

[M+H]=438.4.

Example 531. 3,3-Difluoro-5-{5-methyl-[1,2,4]triazolo[1,5-a]pyrimidin-7-yl}-1-[3-(propan-2-yl)benzoyl]piperidine

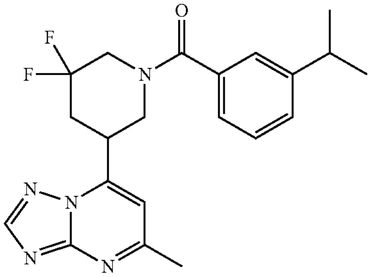 [SMILES: Cc1cc(C2CN(C(=O)c3cccc(C(C)C)c3)CC(F)(F)C2)n2ncnc2n1]

[M+H]=400.5.

Example 532. 3,3-Difluoro-5-{5-methyl-[1,2,4]triazolo[1,5-a]pyrimidin-7-yl}-1-(1-phenyl-1H-pyrazole-4-carbonyl)piperidine

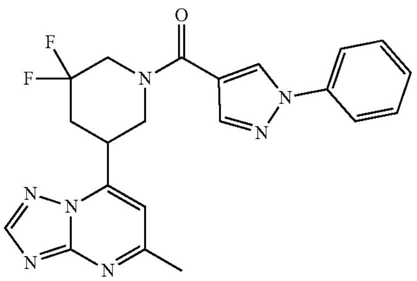 [SMILES: Cc1cc(C2CN(C(=O)c3cnn(-c4ccccc4)c3)CC(F)(F)C2)n2ncnc2n1]

[M+H]=424.5.

Example 533. 1-Methyl-2-(2-{5-methyl-[1,2,4]triazolo[1,5-a]pyrimidin-7-yl}morpholine-4-carbonyl)-1H-indole

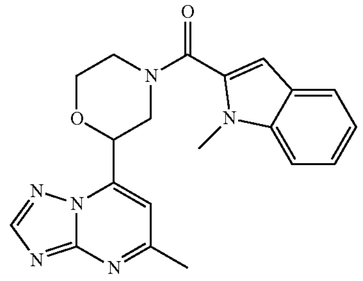

[M+H]=377.4.

Example 534. 4-(1-Benzofuran-5-carbonyl)-2-{5-methyl-[1,2,4]triazolo[1,5-a]pyrimidin-7-yl}morpholine

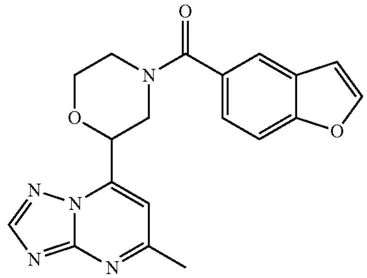

[M+H]=364.4.

Example 535. 4-(1-Benzothiophene-5-carbonyl)-2-{5-methyl-[1,2,4]triazolo[1,5-a]pyrimidin-7-yl}morpholine

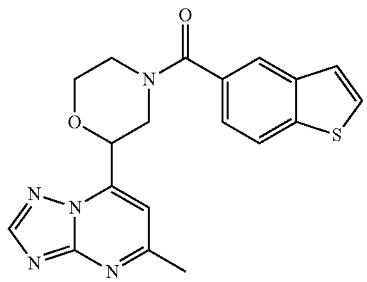 [SMILES: Cc1cc(C2CN(C(=O)c3ccc4sccc4c3)CCO2)n2ncnc2n1]

[M+H]=380.4.

Example 536. 4-(3-Chloro-5-fluorobenzoyl)-2-{5-methyl-[1,2,4]triazolo[1,5-a]pyrimidin-7-yl}morpholine

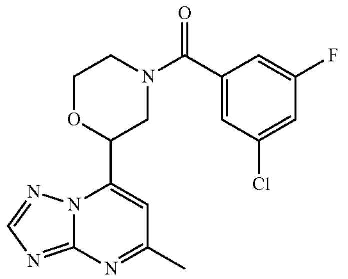

[M+H]=376.4.

Example 537. 4-(2-Methoxy-4-methylbenzoyl)-2-{5-methyl-[1,2,4]triazolo[1,5-a]pyrimidin-7-yl}morpholine

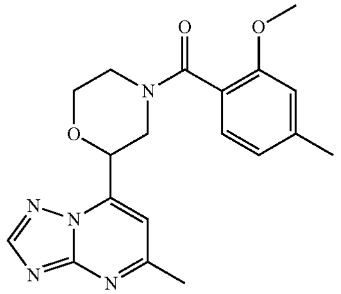 [SMILES: COc1cc(C)ccc1C(=O)N1CCOC(c2cc(C)nc3ncnn23)C1]

[M+H]=368.5.

Example 538. 4-{Imidazo[1,2-a]pyridine-6-carbonyl}-2-{5-methyl-[1,2,4]triazolo[1,5-a]pyrimidin-7-yl}morpholine

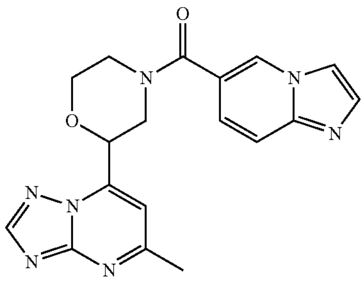 [SMILES: Cc1cc(C2CN(C(=O)c3ccc4nccn4c3)CCO2)n2ncnc2n1]

[M+H]=364.4.

Example 539. 4-(1-Benzofuran-2-carbonyl)-2-{5-methyl-[1,2,4]triazolo[1,5-a]pyrimidin-7-yl}morpholine

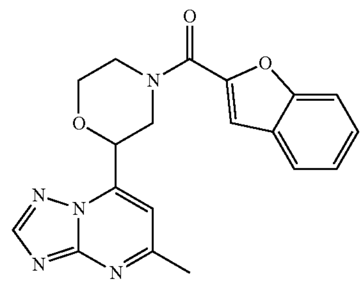 [SMILES: Cc1cc(C2CN(C(=O)c3cc4ccccc4o3)CCO2)n2ncnc2n1]

[M+H]=364.4.

Example 540. 2-(2-{5-Methyl-[1,2,4]triazolo[1,5-a]pyrimidin-7-yl}morpholine-4-carbonyl)quinoxaline

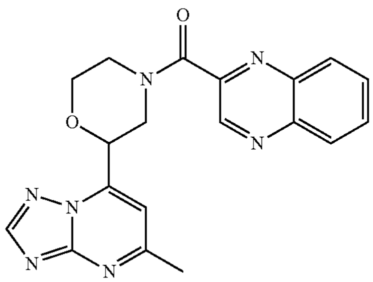 [SMILES: Cc1cc(C2CN(C(=O)c3cnc4ccccc4n3)CCO2)n2ncnc2n1]

[M+H]=376.4.

Example 541. 4-(1-Benzothiophene-3-carbonyl)-2-{5-methyl-[1,2,4]triazolo[1,5-a]pyrimidin-7-yl}morpholine

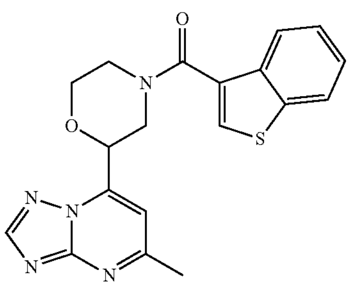 [SMILES: Cc1cc(C2CN(C(=O)c3csc4ccccc34)CCO2)n2ncnc2n1]

[M+H]=380.4.

Example 542. 4-(2-Methoxy-5-methylbenzoyl)-2-{5-methyl-[1,2,4]triazolo[1,5-a]pyrimidin-7-yl}morpholine

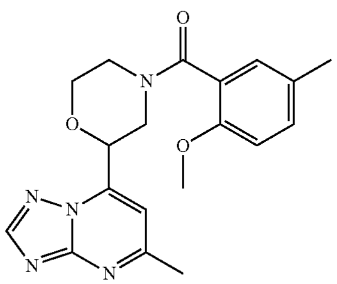

[M+H]=368.4.

Example 543. 4-[4-(Difluoromethyl)benzoyl]-2-{5-methyl-[1,2,4]triazolo[1,5-a]pyrimidin-7-yl}morpholine

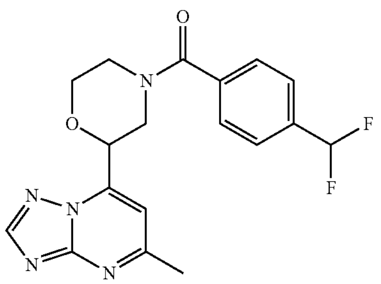

[M+H]=374.4.

Example 544. 4-(3,4-Dimethoxybenzoyl)-2-{5-methyl-[1,2,4]triazolo[1,5-a]pyrimidin-7-yl}morpholine

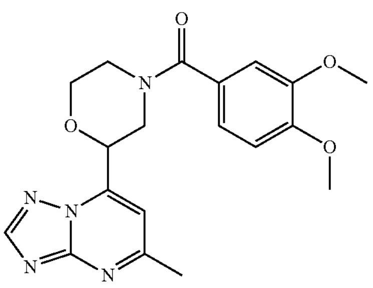 [SMILES: COc1ccc(C(=O)N2CCOC(c3cc(C)nc4ncnn34)C2)cc1OC]

[M+H]=384.4.

Example 545. 4-(5-Chloro-2-fluorobenzoyl)-2-{5-methyl-[1,2,4]triazolo[1,5-a]pyrimidin-7-yl}morpholine

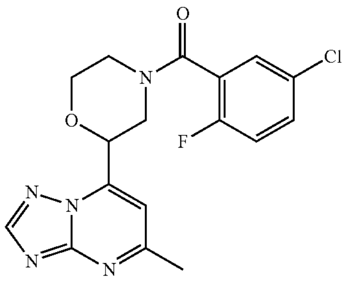

[M+H]=376.4.

Example 546. 4-(4-Fluoro-3-methylbenzoyl)-2-{5-methyl-[1,2,4]triazolo[1,5-a]pyrimidin-7-yl}morpholine

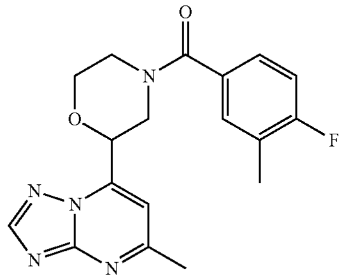 [SMILES: Cc1cc(C2CN(C(=O)c3ccc(F)c(C)c3)CCO2)n2ncnc2n1]

[M+H]=356.4.

Example 547. 4-(4-Methoxy-3-methylbenzoyl)-2-{5-methyl-[1,2,4]triazolo[1,5-a]pyrimidin-7-yl}morpholine

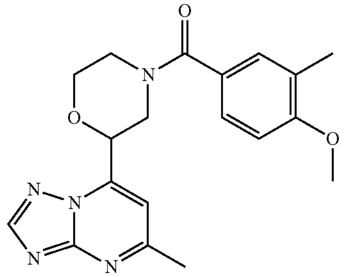 [SMILES: COc1ccc(C(=O)N2CCOC(c3cc(C)nc4ncnn34)C2)cc1C]

[M+H]=368.4.

Example 548. 4-(3-Methoxybenzoyl)-2-{5-methyl-[1,2,4]triazolo[1,5-a]pyrimidin-7-yl}morpholine

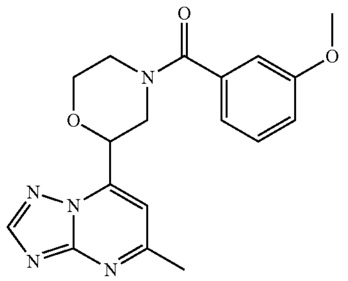 [SMILES: COc1cccc(C(=O)N2CCOC(c3cc(C)nc4ncnn34)C2)c1]

[M+H]=354.4.

Example 549. 4-(2H-1,3-Benzodioxole-5-carbonyl)-2-{5-methyl-[1,2,4]triazolo[1,5-a]pyrimidin-7-yl}morpholine

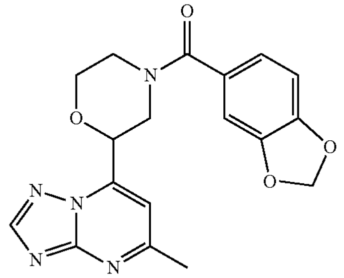 [SMILES: Cc1cc(C2CN(C(=O)c3ccc4c(c3)OCO4)CCO2)n2ncnc2n1]

[M+H]=368.4.

Example 550. 4-(2-Methoxypyridine-4-carbonyl)-2-{5-methyl-[1,2,4]triazolo[1,5-a]pyrimidin-7-yl}morpholine

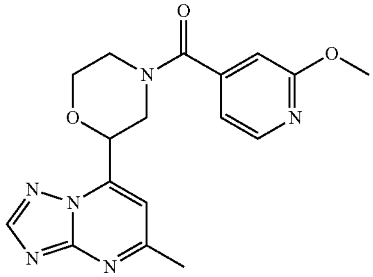 [SMILES: COc1cc(C(=O)N2CCOC(c3cc(C)nc4ncnn34)C2)ccn1]

[M+H]=355.4.

Example 551. 4-(2,3-Dihydro-1,4-benzodioxine-6-carbonyl)-2-{5-methyl-[1,2,4]triazolo[1,5-a]pyrimidin-7-yl}morpholine

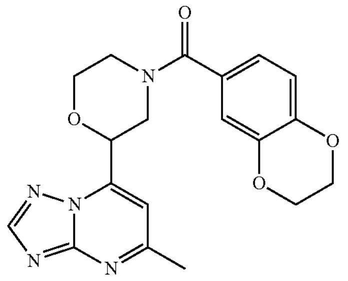 [SMILES: Cc1cc(C2CN(C(=O)c3ccc4c(c3)OCCO4)CCO2)n2ncnc2n1]

[M+H]=382.4.

Example 552. 4-(3-Methoxynaphthalene-2-carbonyl)-2-{5-methyl-[1,2,4]triazolo[1,5-a]pyrimidin-7-yl}morpholine

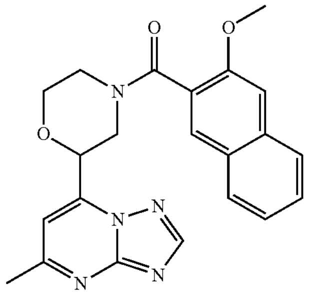 [SMILES: COc1cc2ccccc2cc1C(=O)N1CCOC(c2cc(C)nc3ncnn23)C1]

[M+H]=404.5.

Example 553. 2-{5-Methyl-[1,2,4]triazolo[1,5-a]pyrimidin-7-yl}-4-[4-(propan-2-yl)benzoyl]morpholine

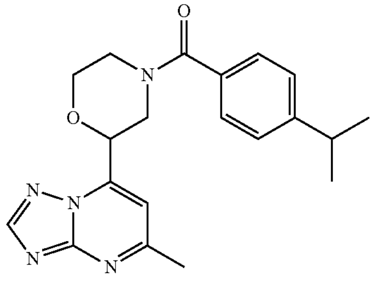 [SMILES: Cc1cc(C2CN(C(=O)c3ccc(C(C)C)cc3)CCO2)n2ncnc2n1]

[M+H]=366.5.

Example 554. 4-(2-Fluoro-5-methylbenzoyl)-2-{5-methyl-[1,2,4]triazolo[1,5-a]pyrimidin-7-yl}morpholine

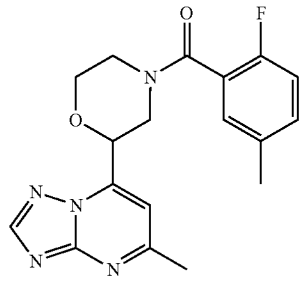

[M+H]=356.4.

Example 555. 4-(3-Fluoro-5-methoxybenzoyl)-2-{5-methyl-[1,2,4]triazolo[1,5-a]pyrimidin-7-yl}morpholine

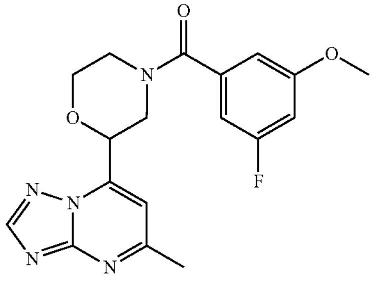 [SMILES: COc1cc(F)cc(C(=O)N2CCOC(c3cc(C)nc4ncnn34)C2)c1]

[M+H]=372.4.

Example 556. 4-(1-Methoxynaphthalene-2-carbonyl)-2-{5-methyl-[1,2,4]triazolo[1,5-a]pyrimidin-7-yl}morpholine

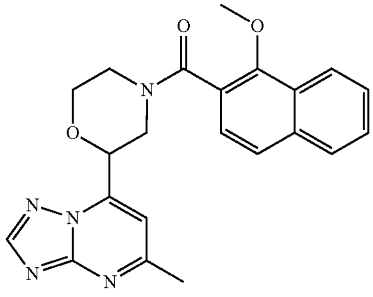

[M+H]=404.5.

Example 557. 4-(6-Methoxynaphthalene-2-carbonyl)-2-{5-methyl-[1,2,4]triazolo[1,5-a]pyrimidin-7-yl}morpholine

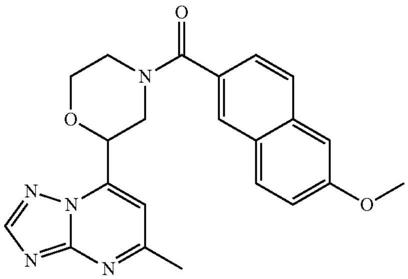 [SMILES: COc1ccc2cc(C(=O)N3CCOC(c4cc(C)nc5ncnn45)C3)ccc2c1]

[M+H]=404.5.

Example 558. 4-(1-Methyl-3-phenyl-1H-pyrazole-5-carbonyl)-2-{5-methyl-[1,2,4]triazolo[1,5-a]pyrimidin-7-yl}morpholine

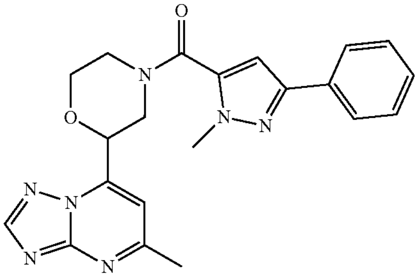 [SMILES: Cc1cc(C2CN(C(=O)c3cc(-c4ccccc4)nn3C)CCO2)n2ncnc2n1]

[M+H]=404.5.

Example 559. 4-(6-Fluoronaphthalene-2-carbonyl)-2-{5-methyl-[1,2,4]triazolo[1,5-a]pyrimidin-7-yl}morpholine

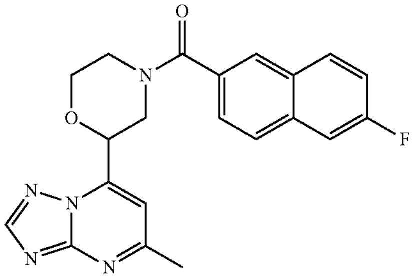 [SMILES: Cc1cc(C2CN(C(=O)c3ccc4cc(F)ccc4c3)CCO2)n2ncnc2n1]

[M+H]=392.4.

Example 560. 4-(2,2-Difluoro-2H-1,3-benzodioxole-5-carbonyl)-2-{5-methyl-[1,2,4]triazolo[1,5-a]pyrimidin-7-yl}morpholine

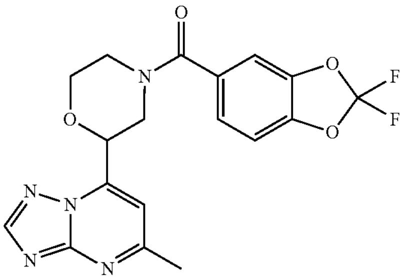 [SMILES: Cc1cc(C2CN(C(=O)c3ccc4c(c3)OC(F)(F)O4)CCO2)n2ncnc2n1]

[M+H]=404.4.

Example 561. 2-{5-Methyl-[1,2,4]triazolo[1,5-a]pyrimidin-7-yl}-4-[3-(propan-2-yl)benzoyl]morpholine

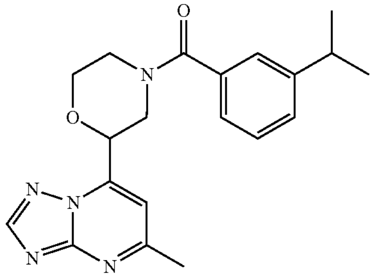 [SMILES: Cc1cc(C2CN(C(=O)c3cccc(C(C)C)c3)CCO2)n2ncnc2n1]

[M+H]=366.5.

Example 562. 3,3-Difluoro-1-(6-fluoro-3,4-dihydro-2H-1-benzopyran-2-carbonyl)-{5-methyl-[1,2,4]triazolo[1,5-a]pyrimidin-7-yl}piperidine

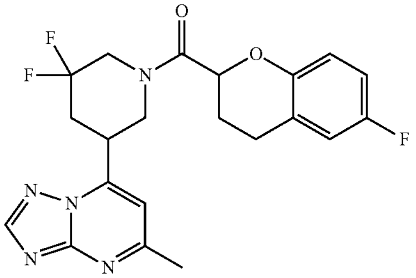 [SMILES: Cc1cc(C2CN(C(=O)C3CCc4cc(F)ccc4O3)CC(F)(F)C2)n2ncnc2n1]

[M+H]=432.5.

Example 563. 1-(3,4-Dihydro-2H-1-benzopyran-2-carbonyl)-3,3-difluoro-5-{5-methyl-[1,2,4]triazolo[1,5-a]pyrimidin-7-yl}piperidine

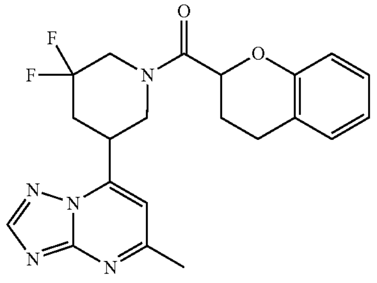 [SMILES: Cc1cc(C2CN(C(=O)C3CCc4ccccc4O3)CC(F)(F)C2)n2ncnc2n1]

[M+H]=414.5.

Example 564. 4-(3,4-Dihydro-2H-1-benzopyran-2-carbonyl)-2-{5-methyl-[1,2,4]triazolo[1,5-a]pyrimidin-7-yl}morpholine

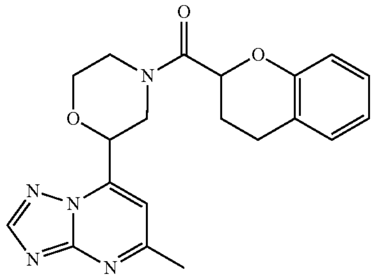 [SMILES: Cc1cc(C2CN(C(=O)C3CCc4ccccc4O3)CCO2)n2ncnc2n1]

[M+H]=380.4.

Example 565. (3,5-Dibromophenyl)(2-(5-methyl-[1,2,4]triazolo[1,5-a]pyrimidin-7-yl)morpholino)methanone-$d_4$

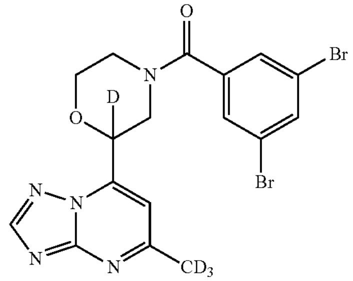

A solution of (3,5-dibromophenyl)(2-(5-methyl-[1,2,4]triazolo[1,5-a]pyrimidin-7-yl)morpholino)methanone (30.00 mg, 0.00 mol) in $CD_3OD$ (0.35 mL, 0.18 mol/L) was treated with DIEA (5.44 μL) at 65° C. for 4 days. The solution was cooled to room temperature. The solid was filtered and washed with heptane. $^1H$ NMR (400 MHz, DMSO-$d_6$) ppm 2.61-2.68 (m, 1H) 3.06-3.16 (m, 1H) 3.40-3.55 (m, 1H) 3.86-4.02 (m, 1H) 4.13-4.47 (m, 2H) 7.16-7.36 (m, 1H) 7.72-7.87 (m, 2H) 7.97-8.03 (m, 1H) 8.48-8.72 (m, 1H); [M+H]=486.1.

Example 566 was made in a manner analogous to Example 565.

Example 566. (3-Bromo-4-fluorophenyl)(3,3-difluoro-5-(5-methyl-[1,2,4]triazolo[1,5-a]pyrimidin-7-yl)piperidin-1-yl)methanone-$d_4$

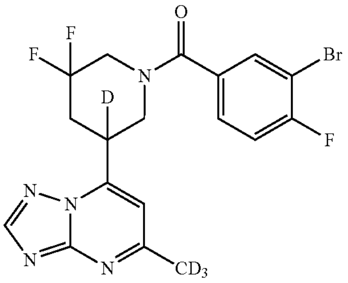

$^1H$ NMR (400 MHz, $CD_3OD$) ppm 2.64-2.76 (m, 2H) 3.34-3.60 (m, 2H) 4.56 (s, 2H) 7.14-7.30 (m, 1H) 7.34-7.46 (m, 1H) 7.52-7.62 (m, 1H) 7.79-7.91 (m, 1H) 8.43-8.63 (m, 1H); [M+H]=459.1.

PHARMACOLOGICAL EXAMPLES

The present disclosure will be further illustrated by the following pharmacological examples. These examples are understood to be exemplary only and are not intended to limit the scope of the invention disclosed herein.

Enzymatic Assay

An IMAP TR-FRET-based phosphodiesterase assay was developed using the PDE2A isoform. IMAP technology is based on high-affinity binding of phosphate by immobilized metal (MIII) coordination complexes on nanoparticles. The IMAP "binding reagent" recognizes phosphate groups on AMP or GMP generated from cAMP or cGMP in a PDE reaction. Cyclic nucleotides that carry a phosphodiester bond and not a free phosphate are not recognized by the binding reagent. The time resolved fluorescence resonance energy transfer (TR-FRET) is afforded by a Terbium (Tb)-Donor pre-bound to the nanoparticles. FRET occurs when the fluorescent-labeled AMP or GMP product of a PDE reaction binds and comes into close proximity to the Tb-Donor complex. Due to the long lifetime of Tb fluorescence, detection can be run in time-resolved mode to reduce or eliminate interference from auto-fluorescent compounds.

The IMAP TR-FRET PDE2A assay was performed in 1536-well white plates. A total of 250 μg per well of FLAG-tagged PDE2A1 (amino acids 2-941) was dispensed in 2.5 μL IMAP assay buffer consisting of 10 mM Tris pH 7.2, 10 mM $MgCl_2$, 1 mM DTT, and 0.1% fatty acid free BSA. 30 nL of compound was then added from 1 mM stocks in DMSO using a Kalypsys Pintool. Plates were incubated for 5 min at room temperature before dispensing 1.5 μL of 533 nM FAM-cAMP substrate for a final concentration of 200 nM. Following a brief centrifugation, plates were incubated for 30 min at room temperature. The assay was terminated by adding 5 μL IMAP binding reagent Tb complex to each well which was prepared according to manufacturer's recommendations (Molecular Devices). Plates were incubated an additional 90 minutes at room temperature and read on a Viewlux plate reader. All compounds were solvated at a concentration of 10 mM in DMSO and tested in 11-point half-log dose-response. Curve fitting and $IC_{50}$ values were determined using a standard four parameter fit.

TABLE 1

| PDE2 ($pIC_{50}$) | Example Numbers |
|---|---|
| >7 | 1, 4, 5, 6, 9, 83, 109, 120, 134, 139, 141, 150, 174, 178, 179, 182, 184, 186, 190, 195, 196, 197, 200, 207, 208, 209, 210, 211, 225, 232, 233, 234, 235, 239, 242, 253, 254, 257, 258, 259, 262, 263, 268, 269, 270, 271, 273, 274, 275, 276, 277, 278, 279, 280, 281, 282, 283, 285, 286, 287, 289, 290, 291, 292, 293, 294, 295, 296, 299, 301, 302, 303, 304, 305, 306, 307, 308, 309, 310, 312, 313, 314, 315, 316, 317, 319, 321, 322, 327, 329, 330, 331, 335, 336, 338, 339, 340, 341, 342, 343, 344, 346, 348, 349, 350, 352, 353, 355, 357, 358, 362, 363, 365, 366, 367, 368, 370, 372, 374, 375, 377, 378, 382, 384, 389, 394, 396, 397, 406, 407, 414, 419, 420, 421, 423, 424, 439, 442, 445, 446, 447, 448, 449, 452, 453, 457, 461, 463, 465, 475, 481, 493, 498, 499, 501, 502, 503, 504, 505, 507, 508, 509, 510, 511, 513, 514, 515, 516, 517, 518, 519, 520, 521, 522, 523, 524, 525, 526, 527, 528, 529, 530, 532, 534, 535, 547, 552, 557, 558, 559, 562, 563 |
| 6-7 | 2, 3, 7, 8, 12, 13, 14, 15, 16, 17, 18, 20, 21, 23, 29, 31, 34, 36, 38, 41, 45, 56, 57, 60, 68, 69, 76, 77, 91, 92, 93, 95, 104, 106, 110, 125, 127, 129, 132, 135, 136, 137, 140, 142, 143, 144, 145, 147, 148, 154, 155, 159, 160, 161, 165, 166, 168, 169, 170, 172, 173, 180, 181, 183, 185, 187, 188, 189, 191, 193, 201, 202, 205, 214, 217, 218, 219, 220, 222, 226, 228, 230, 231, 236, 237, 238, 240, 241, 243, 244, 245, 246, 248, 249, 252, 256, 260, 265, 266, 297, 298, 300, 311, 318, 320, 323, 325, 328, 332, 333, 351, 354, 356, 359, 360, 364, 369, 371, 373, 379, 380, 381, 383, 385, 386, 388, 393, 401, 402, 408, 409, 410, 411, 412, 413, 415, 416, 417, 418, 425, 430, 434, 435, 436, 437, 438, 440, 444, 450, 454, 455, 456, 458, 459, 462, 464, 466, 467, 470, 471, 474, 479, 480, 489, 491, 492, 500, 506, 512, 531, 533, 536, 538, 539, 540, 541, 542, 544, 546, 549, 551, 556, 561, 564 |
| 5-6 | 10, 11, 19, 22, 24, 25, 26, 27, 28, 30, 32, 33, 35, 37, 39, 49, 53, 66, 79, 86, 88, 94, 98, 100, 101, 102, 103, 112, 113, 114, 116, 117, 118, 124, 126, 130, 133, 138, 146, 149, 151, 152, 153, 156, 157, 158, 162, 163, 164, 167, 171, 175, 176, 177, 192, 194, 198, 199, 203, 204, 206, 212, 213, 215, 216, 221, 227, 229, 247, 251, 261, 264, 272, 288, 324, 326, 334, 345, 347, 376, 387, 392, 403, 422, 427, 428, 431, 432, 433, 443, 451, 460, 468, 469, 473, 476, 478, 482, 483, 484, 485, 486, 487, 488, 490, 494, 496, 537, 545, 548, 550, 553, 554, 555, 560 |
| <5 | 40, 42, 43, 44, 46, 47, 48, 50, 51, 52, 54, 55, 58, 59, 61, 62, 63, 64, 65, 67, 70, 71, 72, 73, 74, 75, 78, 80, 81, 82, 84, 85, 87, 89, 90, 96, 97, 99, 105, 107, 108, 111, 115, 119, 121, 122, 123, 128, 131, 223, 224, 250, 255, 267, 284, 337, 361, 390, 391, 395, 398, 399, 400, 404, 405, 426, 429, 441, 472, 477, 495, 497, 543 |

BIOLOGICAL EXAMPLES

The present disclosure will be further illustrated by the following biological examples. These examples are understood to be exemplary only and are not intended to limit the scope of the invention disclosed herein.

Behavioral Assays

Numerous behavioral assays are available to assess the ability of a candidate compound to enhance memory formation, including contextual conditioning (e.g., fear conditioning), temporal conditioning (e.g., trace conditioning), and object recognition. Other non-limiting examples of appropriate assays to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The behavioral assays can also be used in accordance with the present invention, as will be understood by those of ordinary skill in the art. These assays can be directed towards the evaluation of, without limitation, hippocampus-, cortex, and/or amygdala-dependent memory formation or cognitive performance.

Biological Example 1

Effect of Pde2 Inhibitors on Contextual Memory

Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. The percent of time during the test that the animal exhibits such freezing provides a quantitative measure of the contextual associative memory (e.g., Fanselow, *Behav. Neurosci.* 1984, 98, 269-277; Fanselow, *Behav. Neurosci.* 1984, 98, 79-95; and Phillips and LeDoux, *Behav. Neurosci.* 1992, 106, 274-285).

Contextual conditioning has been extensively used to investigate the neural substrates mediating fear-motivated learning (e.g., Phillips and LeDoux, *Behav. Neurosci.* 1992, 106, 274-285; Kim et al., *Behav. Neurosci.* 1993, 107, 1093-1098; and Bourtchouladze et al., *Learn. Mem.* 1998, 5, 365-374). Studies in mice and rats provided evidence for functional interaction between hippocampal and nonhippocampal systems during contextual conditioning training (e.g., Maren et al., *Behav. Brain Res.* 1997, 88, 261-274; Maren et al., *Neurobiol. Learn. Mem.* 1997, 67, 142-149; and Frankland et al., *Behav. Neurosci.* 1998, 112, 863-874). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, nonhippocampal systems can support contextual conditioning.

Contextual conditioning has been extensively used to study the impact of various mutations on hippocampus-dependent learning, as well as strain and genetic background differences in mice (e.g., Bourtchouladze et al., *Cell* 1994, 79, 59-68; Bourtchouladze et al., *Learn Mem.* 1998, 5, 365-374; Kogan et al., *Current Biology* 1997, 7, 1-11; Silva et al., *Current Biology* 1996, 6, 1509-1518; Abel et al., *Cell* 1997, 88, 615-626; Giese et al., *Science* 1998, 279, 870-873; Logue et al., *Neuroscience* 1997, 80, 1075-1086; Chen et al., *Behav. Neurosci.* 1996, 110, 1177-1180; and Nguyen et al., *Learn Mem.* 2000, 7, 170-179).

Because robust learning can be triggered with a few minutes training session, contextual conditioning has been especially useful to study the biology of temporally distinct processes of short- and long-term memory (e.g., Kim et al., *Behav. Neurosci.* 1993, 107, 1093-1098; Bourtchouladze et al., *Cell* 1994, 79, 59-68; Abel et al., *Cell* 1997, 88, 615-626; Logue et al., *Behav. Neurosci.* 1997, 111, 104-113; Bourtchouladze et al., *Learn. Mem.* 1998, 5, 365-374; and Nguyen et al., *Learn. Mem.* 2000, 7, 170-179). As such, contextual conditioning provides an excellent model to evaluate the effects of novel drug compounds on hippocampal-dependent memory formation.

Procedures

Previous investigations have established that training with 1× or 2× CS-US pairings induces sub-maximal (weak) memory in wild-type mice (e.g., U.S. 2009/0053140; Tully et al., *Nat. Rev. Drug Discov.* 2003, 2, 267-77; and Bourtchouladze et al. *Learn. Mem.* 1998, 5, 365-374). Such sub-maximal memory is facilitated by augmenting CREB, while inhibition of CREB impairs maximal memory induced with 5×CS-US pairings (Barad et al. *Proc Natl Acad Sci.* 1998, 95, 15020-15025; Peters et al. *Genes Brain Behav.* 2009, 8, 320-329). Accordingly, contextual conditioning in this study was performed as described by Barad et al. *Proc Natl Acad Sci.* 1998, 95, 15020-15025 and Peters et al. *Genes Brain Behav.* 2009, 8, 320-329. Young-adult (10-12 weeks old) $C_{57}$BL/6 male mice or Long-Evans male rats were used. Mice and rats were group-housed in standard laboratory and maintained on a 12:12 light-dark cycle. The experiments were always conducted during the light phase of the cycle. With the exception of testing times, the animals had ad libidum access to food and water. To assess contextual memory, a modified contextual fear conditioning task originally developed for evaluation of memory in CREB knock-out mice was used (Bourtchouladze et al., 1994). Training sessions comprised a baseline period in the conditioning chamber (Med Associates, Inc.) followed by presentation of unconditioned stimuli (1-5 footshocks each at 0.2-1.0 mA for 2-sec) spaced at 60-sec intervals. Thirty seconds following the last shock, the animal was returned to its home cage. One to 7 days later, the animals were returned to the chamber and freezing behavior was scored. Freezing (complete immobility except respiration) was scored by Video Freeze software (Med Associates, Inc.) over an 8 minute test period. Treatment with cognition enhancers is expected to significantly increase freezing when compared to controls.

All experiments were designed and performed in a counterbalanced fashion. In each experiment, the experimenter was unaware (blind) to the treatment of the subjects during training and testing. Training and test sessions were recorded as digital video files. Data were analyzed by one-way ANOVA with appropriate post-hoc tests using GraphPad Prism software package.

Results

Exemplary compounds were found to enhance contextual memory in the fear conditioning assay. Significant enhancing effects were seen at several concentrations, including 0.03 mg/kg, 0.1 mg/kg, 0.3 mg/kg, 1 mg/kg, and 3 mg/kg.

Biological Example 2

Effect of Pde2 Inhibitors on Novel Object Recognition

Rationale

Novel Object Recognition (NOR) is an assay of recognition learning and memory retrieval, it takes advantage of the spontaneous preference of rodents to investigate a novel object compared with a familiar one. It is an ethologically relevant task, which in contrast to fear conditioning, does not result from negative reinforcement (foot shock) (e.g., Ennaceur and Delacour, *Behav. Brain Res.* 1988, 31, 47-59).

The NOR test has been employed extensively to assess the potential cognitive-enhancing properties of novel compounds derived from high-throughput screening. In object recognition, the task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze et. al., *Proc. Natl. Acad. Sci. USA* 2003, 100, 10518-10522).

Neuroimaging, pharmacological, and lesion studies have demonstrated that the hippocampus and adjacent perirhinal cortex are critical for object recognition memory in rodents, monkeys, and humans (e.g., Mitchell, *Behav. Brain Res.* 1998, 97, 107-113; Teng et al., *J. Neurosci.* 2000, 20, 3853-3863; Mumby, *Brain Res.* 2001, 127, 159-181; Eichenbaum et al., *Annu. Rev. Neurosci.* 2007, 30, 127-152; Squire et al., *Nat. Rev. Neurosci.* 2007, 8, 872-883; and Vann and Alabasser, *Curr. Opin. Neurobiol.* 2011, 21, 440-445). Hence, object recognition provides an excellent behavioral model to evaluate drug-compound effects on cognitive tasks associated with function of the hippocampus and cortex.

Procedures

Object recognition was tested in young Long-Evans hooded male rats using the following protocol. Animals were briefly handled by the experimenter 2-5 days prior to training. Each compound was administered between 15 minutes and 24-hours prior to, or following, training. Habituation sessions (duration 1-20 min, over 1-3 days) were conducted to familiarize the animal to the arena. During training trials (duration of 1-20 min) the animals were allowed to explore two identical objects. A test trial (duration of 1-20 min) was then performed 1-96 hrs later.

For novel object recognition, one object was replaced with one that is novel. All combinations and locations of objects were used in a balanced manner to reduce potential biases attributable to preference for particular locations or objects. Training and test trials were recorded and scored by video-tracking software (e.g. Noldus Ethovision). An animal was scored as exploring an object when its head was oriented toward the object within a distance of 1-2 cm (rat) or when its nose was touching the object. Turning around, climbing, or sitting on an object was not considered as exploration. If the animal generates a long-term memory for the familiar object, it will spend significantly more time exploring the novel object compared to the familiar object during the retention test (Cognitive enhancers are therefore expected to facilitate this discrimination between the familiar and novel object).

A discrimination index was calculated as previously described (Bourtchouladze et al., *Proc. Natl. Acad. Sci. USA* 2003, 100, 10518-10522). In each experiment, the experimenter was unaware (blind) to the treatment of the subjects during training and testing. Data were analyzed by one-way ANOVA with appropriate post-hoc tests using GraphPad Prism or JMP software package.

Results

Exemplary compounds of Formula (I) were found to significantly enhance 24 hour memory for NOR in rats. Significant enhancing effects were seen at several concentrations, including 0.1 mg/kg, 1 mg/kg, and 3 mg/kg.

The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound, which is (2S)-4-[(3,5-Dichlorophenyl) carbonyl]-2-{5-methyl-[1,2,4]triazolo[1,5-a]pyrimidin-7-yl}morpholine.

2. A compound, which is (2S)-4-[3-Bromo-4-(trifluoromethyl)benzoyl]-2-{5-methyl-[1,2,4]triazolo[1,5-a]pyrimidin-7-yl}morpholine.

3. A compound, which is (2S)-4-(3-Bromo-4,5-difluorobenzoyl)-2-{5-methyl-[1,2,4]triazolo[1,5-a]pyrimidin-7-yl}morpholine.

4. A pharmaceutical composition comprising a pharmaceutically acceptable excipient; and an effective amount of the compound of claim 1.

5. A method of inhibiting PDE2 activity, comprising exposing PDE2 to an effective amount of the compound of claim 1.

6. A pharmaceutical composition comprising a pharmaceutically acceptable excipient; and an effective amount of the compound of claim 2.

7. A method of inhibiting PDE2 activity, comprising exposing PDE2 to an effective amount of the compound of claim 2.

8. A pharmaceutical composition comprising a pharmaceutically acceptable excipient; and an effective amount of the compound of claim 3.

9. A method of inhibiting PDE2 activity, comprising exposing PDE2 to an effective amount of the compound of claim 3.

* * * * *